US010111953B2

(12) United States Patent
Swergold et al.

(10) Patent No.: US 10,111,953 B2
(45) Date of Patent: Oct. 30, 2018

(54) METHODS FOR REDUCING REMNANT CHOLESTEROL AND OTHER LIPOPROTEIN FRACTIONS BY ADMINISTERING AN INHIBITOR OF PROPROTEIN CONVERTASE SUBTILISIN KEXIN-9 (PCSK9)

(71) Applicant: REGENERON PHARMACEUTICALS, INC., Tarrytown, NY (US)

(72) Inventors: Gary Swergold, New Rochelle, NY (US); William J. Sasiela, Bloomingdale, NJ (US); Robert C. Pordy, Ardsley, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 670 days.

(21) Appl. No.: 14/290,544

(22) Filed: May 29, 2014

(65) Prior Publication Data

US 2014/0356371 A1 Dec. 4, 2014

Related U.S. Application Data

(60) Provisional application No. 61/991,738, filed on May 12, 2014, provisional application No. 61/953,959, filed on Mar. 17, 2014, provisional application No. 61/935,358, filed on Feb. 4, 2014, provisional application No. 61/919,836, filed on Dec. 23, 2013, provisional application No. 61/901,705, filed on Nov. 8, 2013, provisional application No. 61/828,753, filed on May 30, 2013.

(51) Int. Cl.

| | |
|---|---|
| ***A61K 39/395*** | (2006.01) |
| ***C07K 16/40*** | (2006.01) |
| ***A61K 31/40*** | (2006.01) |
| *A61K 39/00* | (2006.01) |

(52) U.S. Cl.

CPC .......... *A61K 39/3955* (2013.01); *A61K 31/40* (2013.01); *C07K 16/40* (2013.01); *A61K 2039/505* (2013.01); *C07K 2317/21* (2013.01); *C07K 2317/76* (2013.01)

(58) Field of Classification Search

None

See application file for complete search history.

(56) References Cited

U.S. PATENT DOCUMENTS

| | | | | |
|---|---|---|---|---|
| 5,260,440 | A | 11/1993 | Hirai | |
| 5,273,995 | A | 12/1993 | Roth | |
| 5,399,670 | A | 3/1995 | Bhattacharya | |
| 5,851,999 | A | 12/1998 | Ulrich | |
| 5,939,598 | A | 8/1999 | Kucherlapati | |
| 6,011,003 | A | 1/2000 | Charmock-Jones | |
| 6,171,586 | B1 | 1/2001 | Lam | |
| 6,267,958 | B1 | 7/2001 | Andya | |
| 6,270,993 | B1 | 8/2001 | Shibuya | |
| 6,596,541 | B2 | 7/2003 | Murphy | |
| 6,629,949 | B1 | 10/2003 | Douglas | |
| 6,659,982 | B2 | 12/2003 | Douglas | |
| 6,875,432 | B2 | 4/2005 | Liu | |
| 6,946,548 | B2 | 9/2005 | Sarkar | |
| 7,001,892 | B1 | 2/2006 | Chmielweski | |
| 7,029,895 | B2 | 4/2006 | Glucksmann | |
| 7,060,268 | B2 | 6/2006 | Andya | |
| 7,129,338 | B1 | 10/2006 | Ota | |
| 7,300,754 | B2 | 11/2007 | Fadel | |
| 7,482,147 | B2 | 1/2009 | Glucksmann | |
| 7,572,618 | B2 | 8/2009 | Mintier | |
| 7,608,693 | B2 | 10/2009 | Martin | |
| 7,754,208 | B2 | 7/2010 | Ledbetter | |
| 8,030,457 | B2 | 10/2011 | Jackson | |
| 8,062,640 | B2 | 11/2011 | Sleeman | |
| 8,080,243 | B2 | 12/2011 | Liang | |
| 8,092,803 | B2 | 1/2012 | Furfine | |
| 8,168,762 | B2 | 5/2012 | Jackson | |
| 8,188,233 | B2 | 5/2012 | Condra | |
| 8,188,234 | B2 | 5/2012 | Condra | |
| 8,357,371 | B2 * | 1/2013 | Sleeman | A61K 31/40 424/158.1 |
| 8,501,184 | B2 | 8/2013 | Sleeman | |
| 8,795,669 | B2 | 8/2014 | Dix | |
| 8,829,165 | B2 | 9/2014 | Jackson | |

(Continued)

FOREIGN PATENT DOCUMENTS

| | | |
|---|---|---|
| CN | 101489565 | 7/2009 |
| EP | 0409281 | 1/1991 |

(Continued)

OTHER PUBLICATIONS

Shoji et al. (J Am Soc Nephrol 1998 9:1277-1284).*

Pfizer: 'Safety and Tolerability of Multiple Doses of PF-04950615 (RN316) In Subjects With Hypercholesterolemia.' Nov. 3, 2012, XP002682100. Retrieved from the Internet: URL:http://clinicaltrials.gov/ct2/show?term=rn316&rank=2.

Pearson, William R., 'Using the FASTA program to search protein and DNA sequence databases.' Computer Analysis of Sequence Data. 1994, pp. 307-331.

Powell et al., 'Compendium of Excipients for Parenteral Formulations PDA.' Journal of Pharmaceutical Science and Technology. 1998, vol. 52, No. 5, pp. 238-311.

Qui et al., 'Small antibody mimetics comprising two complementarity-determining regions and a framework region for tumor targeting.' Nature Biotechnology. 2007, vol. 25, No. 8, pp. 921-929.

(Continued)

*Primary Examiner* — Sharon X Wen

(57) ABSTRACT

The present invention provides methods for reducing various lipoprotein fractions in the serum of patients. The methods of the invention include reducing serum remnant cholesterol, and/or the serum concentration of one or more LDL-C subfractions in a patient. The methods of the present invention comprise selecting a patient who exhibits elevated serum lipoproteins, and administering to the patient a pharmaceutical composition comprising a PCSK9 inhibitor. In certain embodiments, the PCSK9 inhibitor is an anti-PCSK9 antibody such as the exemplary antibody referred to herein as mAb316P.

12 Claims, 13 Drawing Sheets

Specification includes a Sequence Listing.

(56) References Cited

U.S. PATENT DOCUMENTS

| | | | | |
|---|---|---|---|---|
| 8,883,157 | B1 | 11/2014 | Clube | |
| 9,034,332 | B1 | 5/2015 | Clube | |
| 9,127,068 | B2 | 9/2015 | Okamoto | |
| 9,193,801 | B2 | 11/2015 | Walsh | |
| 9,358,287 | B2 | 6/2016 | Harp | |
| 9,540,449 | B2 | 1/2017 | Yancopoulos | |
| 9,550,837 | B2 * | 1/2017 | Sleeman ................ | C07K 16/40 |
| 2003/0092606 | A1 | 5/2003 | L'Italien | |
| 2003/0113316 | A1 | 6/2003 | Kaisheva | |
| 2003/0118592 | A1 | 6/2003 | Ledbetter | |
| 2003/0133939 | A1 | 7/2003 | Ledbetter | |
| 2004/0101920 | A1 | 5/2004 | Radziejewski | |
| 2004/0197324 | A1 | 10/2004 | Liu | |
| 2005/0281831 | A1 | 12/2005 | Davis-Smyth | |
| 2006/0147945 | A1 | 7/2006 | Edmonds | |
| 2007/0082345 | A1 | 4/2007 | Ota | |
| 2007/0224663 | A1 | 9/2007 | Rosen | |
| 2008/0008697 | A1 | 1/2008 | Mintier | |
| 2009/0142352 | A1 | 6/2009 | Jackson | |
| 2009/0232795 | A1 | 9/2009 | Condra | |
| 2009/0246192 | A1 | 10/2009 | Condra | |
| 2009/0269350 | A1 | 10/2009 | Glucksmann | |
| 2009/0318536 | A1 | 12/2009 | Freier | |
| 2009/0326202 | A1 | 12/2009 | Jackson | |
| 2010/0040610 | A1 | 2/2010 | Sitlani | |
| 2010/0040611 | A1 | 2/2010 | Sparrow | |
| 2010/0041102 | A1 | 2/2010 | Sitlani | |
| 2010/0068199 | A1 | 3/2010 | Liang | |
| 2010/0136028 | A1 | 6/2010 | Sparrow | |
| 2010/0150937 | A1 | 6/2010 | Sparrow | |
| 2010/0166768 | A1 | 7/2010 | Sleeman | |
| 2010/0233177 | A1 | 9/2010 | Yowe | |
| 2011/0027287 | A1 | 2/2011 | Jackson | |
| 2011/0033465 | A1 | 2/2011 | Hedrick | |
| 2011/0065902 | A1 | 3/2011 | Sleeman | |
| 2011/0098450 | A1 | 4/2011 | Igawa | |
| 2011/0111406 | A1 | 5/2011 | Igawa | |
| 2011/0142849 | A1 | 6/2011 | Rue | |
| 2011/0171241 | A1 | 7/2011 | Dix | |
| 2011/0229489 | A1 | 9/2011 | Pons | |
| 2011/0256148 | A1 * | 10/2011 | Sleeman ................ | A61K 31/40<br>424/158.1 |
| 2012/0014951 | A1 | 1/2012 | Liang | |
| 2012/0015435 | A1 | 1/2012 | Liange | |
| 2012/0020975 | A1 | 1/2012 | Jackson | |
| 2012/0027765 | A1 | 2/2012 | Jackson | |
| 2012/0076799 | A1 | 3/2012 | Sparrow | |
| 2012/0077964 | A1 | 3/2012 | Sparrow | |
| 2012/0082679 | A1 | 4/2012 | Sparrow | |
| 2012/0082680 | A1 | 4/2012 | Sitlani | |
| 2012/0093818 | A1 | 4/2012 | Jackson | |
| 2012/0097565 | A1 | 4/2012 | Dix | |
| 2012/0195910 | A1 | 8/2012 | Wu | |
| 2012/0213794 | A1 | 8/2012 | Luo | |
| 2012/0213797 | A1 | 8/2012 | Jackson | |
| 2012/0219558 | A1 | 8/2012 | Ni | |
| 2012/0231005 | A1 | 9/2012 | Luo | |
| 2012/0251544 | A1 | 10/2012 | Jackson | |
| 2013/0011866 | A1 | 1/2013 | Igawa | |
| 2013/0064825 | A1 | 3/2013 | Chan | |
| 2013/0064834 | A1 | 3/2013 | Sleeman | |
| 2013/0085266 | A1 | 4/2013 | Sleeman | |
| 2013/0243784 | A1 | 9/2013 | Swergold | |
| 2014/0004122 | A1 | 1/2014 | Chan | |
| 2014/0099312 | A1 | 4/2014 | Sleeman | |
| 2014/0161821 | A1 | 6/2014 | Udata | |
| 2014/0356370 | A1 | 12/2014 | Swergold | |
| 2015/0140002 | A1 | 5/2015 | Baccara-Dinet | |
| 2015/0152191 | A1 | 6/2015 | Baccara-Dinet | |
| 2015/0231236 | A1 | 8/2015 | Pordy | |
| 2015/0283236 | A1 | 10/2015 | Baccara-Dinet | |
| 2015/0284473 | A1 | 10/2015 | Bessac | |
| 2016/0032015 | A1 | 2/2016 | Walsh et al. | |
| 2016/0152734 | A1 | 2/2016 | Udata | |
| 2017/0049886 | A1 | 2/2017 | Pordy | |
| 2017/0096496 | A1 | 4/2017 | Sleeman | |
| 2017/0296657 | A1 | 10/2017 | Sleeman et al. | |
| 2018/0044436 | A1 | 2/2018 | Walsh et al. | |

FOREIGN PATENT DOCUMENTS

| | | |
|---|---|---|
| EP | 0521471 | 1/1993 |
| EP | 1067182 | 1/2001 |
| EP | 1514933 | 3/2005 |
| EP | 1317537 | 12/2006 |
| EP | 1618212 | 11/2007 |
| EP | 2 703 008 | 8/2012 |
| EP | 2 703 009 | 8/2012 |
| EP | 2 706 070 | 3/2014 |
| WO | WO 1993/000807 | 1/1993 |
| WO | WO97/035620 | 10/1997 |
| WO | WO 98/22136 | 5/1998 |
| WO | WO 99/38495 | 8/1999 |
| WO | WO 01/57081 | 8/2001 |
| WO | WO 2001/092340 | 12/2001 |
| WO | WO 2004/055164 | 7/2004 |
| WO | WO 2004/097047 | 11/2004 |
| WO | WO 2005/047331 | 5/2005 |
| WO | WO 2005103081 | 11/2005 |
| WO | WO 2007/143315 | 12/2007 |
| WO | WO 2007/149334 | 12/2007 |
| WO | WO 2008/054606 | 5/2008 |
| WO | WO 2008/057457 | 5/2008 |
| WO | WO 2008/057458 | 5/2008 |
| WO | WO 2008/057459 | 5/2008 |
| WO | WO 2008/063382 | 5/2008 |
| WO | 2008066776 A2 | 6/2008 |
| WO | WO 2008/073300 | 6/2008 |
| WO | WO 2008/125623 | 10/2008 |
| WO | 2008138536 A2 | 11/2008 |
| WO | WO 2008/133647 | 11/2008 |
| WO | WO 2009/026558 | 2/2009 |
| WO | WO 2009/042765 | 4/2009 |
| WO | WO 2009/055783 | 4/2009 |
| WO | WO 2009/100297 | 8/2009 |
| WO | WO 2009/100318 | 8/2009 |
| WO | WO 2010/029513 | 3/2010 |
| WO | WO 2010/032220 | 3/2010 |
| WO | WO 2010/077854 | 7/2010 |
| WO | WO 2010/102241 | 9/2010 |
| WO | WO 2010/148337 | 12/2010 |
| WO | WO 2011/028938 | 3/2011 |
| WO | WO 2011/039578 | 4/2011 |
| WO | WO 2011/053759 | 5/2011 |
| WO | WO 2011/061712 | 5/2011 |
| WO | WO 2011/072263 | 6/2011 |
| WO | WO 2011/111007 | 9/2011 |
| WO | WO 2012/054438 | 4/2012 |
| WO | WO 2012/064792 | 5/2012 |
| WO | WO 2012/101251 | 8/2012 |
| WO | WO 2012/101252 | 8/2012 |
| WO | WO 2012/101253 | 8/2012 |
| WO | WO 2012/109530 | 8/2012 |
| WO | WO 2012/146776 | 11/2012 |
| WO | WO2012/154999 | 11/2012 |
| WO | WO 2012/154999 | 11/2012 |
| WO | WO 2013/039958 | 3/2013 |
| WO | WO 2013/039969 | 3/2013 |
| WO | WO 2013158984 | 10/2013 |
| WO | WO 2013/166448 | 11/2013 |
| WO | WO 2014/194111 | 12/2014 |
| WO | WO 2014/197752 | 12/2014 |
| WO | WO 2011/117401 | 3/2015 |
| WO | WO 2015/054619 | 4/2015 |
| WO | WO 2015/073494 | 5/2015 |
| WO | WO 2015/123423 | 8/2015 |
| WO | WO 2015/140079 | 9/2015 |
| WO | WO 2015/142668 | 9/2015 |
| WO | WO 2016/011256 | 1/2016 |
| WO | WO 2016/011260 | 1/2016 |

(56) References Cited

OTHER PUBLICATIONS

Reddy et al., 'Elimination of Fc receptor-dependent effector functions of a modified IgG4 monoclonal antibody to human CD4.' The Journal of Immunology. 2000, vol. 164, No. 4, pp. 1925-1933.
Reineke, Ulrich, 'Antibody epitope mapping using arrays of synthetic peptides.' Antibody Engineering. Humana Press. 2004, pp. 443-463.
Sefton, Michael V., 'Implantable Pumps.' Critical Reviews in Biomedical Engineering. 1986, vol. 14, No. 3, pp. 201-240.
Seidah et al., 'The secretory proprotein convertase neural apoptosis-regulated convertase 1 (NARC-1): liver regeneration and neuronal differentiation.' PNAS. 2003,100(3):928-933.
Shields et al., 'Lack of fucose on human IgG1 N-linked oligosaccharide improves binding to human FcγRIII and antibody-dependent cellular toxicity.' Journal of Biological Chemistry. 2002, vol. 277, No. 30, pp. 26733-26740.
Soutar, Anne, 'Unexpected Roles for PCSK9 in Lipid Metabolism.' Current Opinion in Lipidology. 2011, vol. 22, pp. 192-196.
Tiwari et al., 'Statins therapy: a review on conventional and novel formulation approaches.' Journal of Pharmacy and Pharmacology. 2011, vol. 63, No. 8, pp. 983-998.
Tutt et al., 'Trispecific F (ab') 3 derivatives that use cooperative signaling via the TCR/CD3 complex and CD2 to activate and redirect resting cytotoxic T cells.' The Journal of Immunology. 1991, vol. 147, No. 1, pp. 60-69.
Vajdos et al., 'Comprehensive functional maps of the antigen-binding site of an anti-ErbB2 antibody obtained with shotgun scanning mutagenesis.' Journal of Molecular Biology. 2002, vol. 320, No. 2, pp. 415-428.
Ward et al., 'Binding activities of a repertoire of single immunoglobulin variable domains secreted from *Escherichia coli*.' Nature. 1989, vol. 341, No. 6242, pp. 544-546.
Written Opinion of the International Searching Authority for International Application No. PCT/EP2012/051320, dated Jul. 30, 2013 (16 pages).
Wu et al., 'Receptor-mediated in vitro gene transformation by a soluble DNA carrier system.' Journal of Biological Chemistry. 1987, vol. 262, No. 10, pp. 4429-4432.
Holliger et al., 'Diabodies: small bivalent and bispecific antibody fragments.' Proceedings of the National Academy of Sciences. 1993, vol. 90,No. 14, pp. 6444-6448.
Huston et al. 'Protein engineering of antibody binding sites: recovery of specific activity in an anti-digoxin single-chain Fv analogue produced in *Escherichia coli*.' Proceedings of the National Academy of Sciences. 1988, vol. 85, No. 16, pp. 5879.
International Search Report for International Application No. PCT/EP2012/051320, dated Sep. 21, 2012 (9 pages).
Langer et al., 'New methods of drug delivery.' Science. 1990, vol. 249, No. 4976, pp. 1527-1533.
Langer et al., 'Medical Applications of Controlled Release.' CRC Press, Boca Raton, Florida. 1974, pp. 115-138.
Leuenberger et al., 'A Multilingual Glossary of Biotechnological Terms.' Recueil des Travaux Chimiques des Pays Bas. 1996, vol. 115, No. 7, pp. 382.
Padlan et al., 'Identification of specificity-determining residues in antibodies.' The FASEB Journal. 1995, vol. 9, No. 1, pp. 133-139.
Almagro et al., 'Humanization of antibodies.' Frontiers in Bioscience. 2008, vol. 13, pp. 1619-1633.
Altschul et al., 'Basic local alignment search tool.' Journal of Molecular Biology. 1990, vol. 215, No. 3, pp. 403-410.
Altschul et al., 'Gapped BLAST and PSI-BLAST: a new generation of protein database search programs.' Nucleic Acids Research. 1997, vol. 25, No. 17, pp. 3389-3402.
Amgen: 'Ascending Multiple Dose Study to Evaluate the Safety, Tolerability, Pharmacokinetics and Pharmacodynamics of AMG 145 in Subjects With Hyperlipidemia on Stable Doses of a Statin'. May 27, 2010, XP002682099. Retrieved from the Internet: URL:http://clinicaltrials.gov/ct2/show/nct01133522?term=amg+145&rank=2 Accessed on Aug. 6, 2014.
Angal et al., 'A single amino acid substitution abolishes the heterogeneity of chimeric mouse/human (IgG4) antibody.' Molecular Immunology. 1993, vol. 30, No. 1, pp. 105-108.
Bird et al., 'Single-chain antigen-binding proteins.' Science. 1988, vol. 242, No. 4877, pp. 423-426.
Heap et al., 'Analysis of a 17-amino acid residue, virus-neutralizing microantibody.' Journal of General Virology. 2005, vol. 86, No. 6, pp. 1791-1800.
Colhoun, et al., (2014) BMC Cardiovascular Disorders, Biomed Central 14(1):121, "Efficacy and safety of alirocumab, a fully human PCSK0 monoclonal antibody, in high cardiovascular risk patients with poorly controlled hypercholesterolemia on maximally tolerated doses of statins: rationale and design of the Odyssey Combo I and II trials".
Kastelein et al., (2014) Cardiovascular Drugs and Therapy 28(3):281-289, "Efficacy and Safety of Alirocumab in Patients with Heterozygous Familial Hypercholesterolemia not Adequately Controlled with Current Lipid-Lowering Therapy: Design and Rationale of the Odyssey FH Studies".
Robinson et al., (2014) Clinical Cardiology 37(10):597-604, "Efficacy and Safety of Alirocumab as Add-on Therapy in High-Cardiovascular-Risk Patients with Hypercholesterolemia Not Adequately Controlled with Atorvastatin (20 or 40 mg) or Rosuvastatin (10 or 20 mg): Design and Rationale of the Odyssey Options Studies".
International Search Report dated Aug. 19, 2015 for International Application No. PCT/US2015/015633.
Anthem (Sep. 21, 2015) "Proprotein Convertase Subtilisin Kexin 9 (PCSK9) Inhibitors," Policy No. DRUG.00078. American Medical Association. Accessible on the Internet at URL: https://www.anthem.com/ca/medicalpolicies/policies/mp_pw_c182635.htm. [Last Accessed Apr. 27, 2016].
Defesche et al. (Jun. 2-5, 2013) "Natural history of autosomal dominant hypercholesterolemia caused by gain-of-function mutations in proprotein convertase subtilisin/kexin type 9 (PCSK9) (funded by Regeneron/Sanofi)," Abstract of a presentation presented at the 81st European Atherosclerosis Society (EAS) Congress, Jun. 2-5, 2013, Lyon, France.
Hiriyama et al. (Jan. 1, 2014) "Effects of evolocumab (AMG 145), a monoclonal antibody to PCSK9, in hypercholesterolemic, statin-treated Japanese patients at high cardiovascular risk—primary results from the phase 2 Yukawa study," Circulation Journal. 78(5):1073-1082.
International Search Report with Written Opinion corresponding to International Patent Application No. PCT/EP2012/051321, dated Apr. 19, 2012, 10 pages.
International Search Report with Written Opinion corresponding to International Patent Application No. PCT/EP2012/057890, dated Aug. 28, 2012, 14 pages.
International Search Report with Written Opinion corresponding to International Patent Application No. PCT/US2015/040754, dated Oct. 14, 2015, 15 pages.
International Search Report with Written Opinion corresponding to International Patent Application No. PCT/US2015/040765, dated Nov. 26, 2015, 15 pages.
McKenney et al. (Jun. 2-5, 2013) "Dynamics between the monoclonal antibody SAR236553/REGN727, proprotein convertase subtilisin/kexin type 9 (PCSK9) and low-density lipoprotein cholesterol (LDL-C) levels (funding: Regeneron/Sanofi)," Presented as a poster presentation at the 81st European Atherosclerosis Society (EAS) Congress, Jun. 2-5, 2013, Lyon, France.
Schäfer et al. (Mar. 14-16, 2011) "Cholesterol lowering effect of SAR236553/REGN727, a fully human PCSK9 blocking monoclonal antibody in male Syrian hamster," Presented as a poster at the Drugs Affecting Lipid Metabolism (DALM)—XVII International Symposium, Mar. 14-16, 2011, Doha, Qatar.
McPherson, 2013 Journal of the American College of Cardiology 61(4):437-439, "Remnant Cholesterol: Non-(HDL-C + LDL-C) as a Coronary Artery Disease Risk Factor".

(56) References Cited

OTHER PUBLICATIONS

Varbo, et al., 2013 Journal of the American College of Cardiology 61(4):427-436, "Remnant Cholesterol as a Casual Risk Factor for Ischemic Heart Disease".
Abifadel, et al., 2012 Atherosclerosis 223(2):394-400, "Identification and characterization of new gain-of-function mutations in the PCSK9 gene responsible for autosomal dominant hypercholesterolemia".
Abifadel, et al., 2009 Human Mutation 30(4):520-529, "Mutations and polymorphisms in the proprotein convertase subtilisin kexin 9 (PCSK9) gene in cholesterol metabolism and disease".
Abifadel, et al. (2003) Nature Genetics 34(2):154-156, "Mutations in PCSK9 cause autosomal dominant hypercholesterolemia".
Alborn, et al. (2007) Clinical Chemistry 53(10):1814-1819, "Serum proprotein convertase subtilisin Kexin type 9 is correlated directly with serum LDL cholesterol".
Al-Mashhadi et al., 2013 Science Translation Medicine, American Association for the Advancement of Science 5(166):44-53, "Atherosclerosis: Familial hypercholesterolemia and atherosclerosis in clones minipigs created by DNA transposition of a human PCSK9 gain-of-function mutant".
Attie and Seidah (2005) Cell Metabolism 5:290-292, "Dual regulation of the LDL receptor—Some clarity and new questions".
Annex to Form PCT/ISA/206—Communication Relating to the Results of the Partial International Search for PCT/US2009/068013, dated Mar. 10, 2010.
Benjannet, et al. (2006) J. Biological Chemistry 281(41): 30561-30572, "The Proprotein Convertase (PC) PCSK9 Is Inactivated by Furin and/or PC5/6A".
Chan, et al. (2009) PNAS 106(24):9820-9825, "A proprotein convertase subtilisin/kexin type 9 neutralizing antibody reduces serum cholesterol in mice and nonhuman primates".
Chaparro-Riggers, et al. (2012) J. Biological Chemistry 287(14):11090-11097, "Increasing serum half-life and extending cholesterol lowering in vivo by engineering antibody with pH-sensitive binding to PCSK9".
Fallon, et al. (2000) J. Biological Chemistry 275(10):6790-6797, "Increased endosomal sorting of ligand to recycling enhances potency of an intereukin-2 analog".
Fasano, et al., 2008 NMCD Nutrition Metabolism and Cardiovascular Diseases 18(1):S46, "45 Activity of Gain-of-Function PCSK9 Mutants on LDLR Correlates with Total-Cholesterol Values in ADH patients".
Farnier, 2011 American Journal of Cardiovascular Drugs 11(3):145-152, "The role of proprotein convertase subtilisin/kexin type 9 in hyperlipidemia: Focus on therapeutic implications".
Foote and Winter (1992) J. Mol. Biol. 224:487-499, "Antibody Framework Residues Affecting the Conformation of the Hypervariable Loops".
Grozdanov, et al. (2006) Biochem. Cell. Biol. 84:80-92, "Expression and localization of PCSK9 in rat hepatic cells".
Hopkins, et al., 2011 Journal of Clinical Lipidology 5(3):S9-S17, "Familial Hypercholesterolemias: Prevalence, genetics, diagnosis and screening recommendations from the National Lipid Association Expert Panel on Familial Hypercholesterolemia".
Horton, et al. (2007) Trends Biochem Sci. 32(2): 71-77, "Molecular biology of PCSK9: its role in LDL metabolism".
Igawa, et al. (2010) Nature Biotechnology 28(11):1203-1208, "Antibody recycling by engineered pH-dependent antigen binding improves the duration of antigen neutralization".
Ito, et al. (1992) Federation of European Biochemical Societies 309(1):85-88, "The His-probe method: effects of histidine residues introduced into the complementarity-determining regions of antibodies on antigen-antibody interactions at different pH values".
Lagace, et al. (2006) J Clin Invest Am Soc Clin Invest 116(11):2995-3005, "Secreted PCSK9 decreases the number of LDL receptors in hepatocytes and in liver of parabiotic mice".
Lippi and Guidi (2000) QJ Med 93:75-84, "Lipoprotein(a): from ancestral benefit to modern pathogen?".
Lose, et al., 2013 Pharmacotherapy: The Journal of Human Pharmacology and Drug Therapy 33(4):447-460, "Evaluation of Proprotein Convertase Subtilisin/Kexin Type 9: Focus on Potential Clinical and Therapeutic Implications for Low-Density Lipoprotein Cholesterol Lowering".
Lopez, Dayami (2008) Drug News & Perspectives Abstract 21(6): 323, "Inhibition of PCSK9 as a Novel Strategy for the Treatment of Hypercholesterolemia".
Maeda, et a. (2002) J. Controlled Release 82:71-82, "pH-dependent receptor/ligand dissociation as a determining factor for intracellular sorting of ligands for epidermal growth factor receptors in rat hepatocytes".
Marcovina and Koschinsky (1998) The American Journal of Cardiology 82(12A):57U-66U, "Lipoprotein(a) as a Risk Factor for Coronary Artery Disease".
Maxwell and Breslow (2004) PNAS 101(18):7100-7105, "Adenoviral-mediated expression of Pcsk9 in mice results in a low-density lipoprotein receptor knockout phenotype".
McKenney, et a. (2012) Journal of the American College of Cardiology 59(25):2335-2353, "Safety and Efficacy of a Monoclonal Antibody to Proprotein Convertase Subtilisin/Kexin Type 9 Serine Protease, SAR236553/REGN727, in Patients With Primary Hypercholesterolemia Receiving Ongoing Stable Atorvastatin Therapy".
Nakasako, et a. (1999) J. Mol. Biol. 291:117-134, "The pH-dependent structural variation of complementarity-determining region H3 in the crystal structures of the Fv fragment from an anti-dansyl monoclonal antibody".
Naureckiene, et al. (2003) Archives of Biochemistry and Biophysics 420:55-67, "Functional characterization of Narc 1, a novel proteinase related to proteinase K".
Noguchi, et al., 2010 Atherosclerosis 210(1):166-172, "The E32K variant of PCSK9 exacerbates the phenotype of familial hypercholesterolemia by increasing PCSK9 function and concentration in the circulation".
Nordestgaard, et al. (2010) European Hear Journal 31:2844-2853, "Lipoprotein(s) as cardiovascular risk factor: current status".
Parhofer (2011) Current Pharmaceutical Design 17:871-876, "Lipoprotein(a): Medical Treatment Options for an Elusive Molecule".
Park, et al. (2004) J. Biol. Chem. 279: 50630-50638, "Lipids and Lipoproteins: Post-transcriptional Regulation of Low Density Lipoprotein Receptor Protein by Proprotein Convertase Subtilisin/Kexin Type 9a in Mouse Liver".
Rashid, et al. (2005) PNAS 102(15):5374-5379, "Decreased plasma cholesterol and hypersensitivity to statins in mice lacking Pcsk9".
Rhainds, et al., 2012 Clinical Lipidology 7(6):621-640, "PCSK9 inhibition and LDL cholesterol lowering: The biology of an attractive therapeutic target and critical review of the latest clinical trials".
Sarkar, et al. (2002) Nature Biotechnology 20:908-913, "Rational cytokine design for increased lifetime and enhanced potency using pH-activated histidine switching".
Seidah, et al. (2003) PNAS 100(3):928-933, "The secretory proprotein convertase neural apoptosis-regulated convertase 1 (NARC-1): liver regeneration and neuronal differentiation".
Stein, et al. (2012) New England Journal of Medicine 366:1108-1118, "Effect of a Monoclonal Antibody to PCSK9 on D Cholesterol".
Stein and Swergold, 2013 Current Atherosclerosis Reports 15(310):1-14, "Potential of proprotein Convertase Subtilisin/Kexin Type 9 Based Therapeutics".
Stein, et al., 2012 Obstetrical and Gynecological Survey 67(7):413-414, "Effect of a monoclonal antibody to PCSK9 on LDL cholesterol".
Timms, et al. (2004) Human Genetics 114(4):349-353, "A mutation in PCSK9 causing autosomal-dominant hypercholesterolemia in a Utah pedigree".
Watanabe, et al. (2009) J. Biological Chemistry 284(18):12373-12383, "Optimizing pH response of affinity between protein G and IgG Fc".
Winter and Harris (1993) Immunology Today 14(6):243-246, "Humanized Antibodies".
Bays H, Farnier M, Gaudet D, Weiss R, Lima Ruiz J, Watts GF, Gouni-Berthold I, Robinson J, Jones P, Severance R, Averna M, Steinhagen-Thiessen E, Colhoun HM, Zhao J, Du Y, Hanotin C, Donahue S. Efficacy and safety of combining alirocumab with

(56) References Cited

OTHER PUBLICATIONS atorvastatin or rosuvastatin versus statin intensification or adding ezetimibe in high cardiovascular risk patients: Odyssey Options I and II. Circulation. 2014;130:2105-2126.

Bays H; Gaudet D; Weiss R; Lima Ruiz J; Watts GF; Gouni-Berthold I; Robinson J; Zhao J; Hanotin C; Donahue S. PCSK9 Inhibitor Alirocumab as Add-on to Atorvastatin versus Other Lipid Treatment Strategies in Patients at High CVD Risk: Odyssey Options I. Circulation. 2014;130:A16194.

Cannon CP, Cariou B, Blom D, McKenney JM, Lorenzato C, Pordy R, Chaudhari U, Colhoun HM. Efficacy and safety of alirocumab in high cardiovascular risk patients with inadequately controlled hypercholesterolaemia on maximally tolerated daily statin: results from the Odyssey Combo II study; presented at ESC Congress Aug. 31, 2014, abstract not published.

Cannon CP, Cariou B, Blom D, McKenney JM, Lorenzato C, Pordy R, Chaudhari U, Colhoun HM; for the Odyssey Combo II Investigators. Efficacy and safety of alirocumab in high cardiovascular risk patients with inadequately controlled hypercholesterolaemia on maximally tolerated doses of statins: the Odyssey Combo II randomized controlled trial Eur Heart J. 2015. doi:10.1093/eurheartj/ehv028 [epub ahead of print].

Catapano AL, Papadopoulos N. The safety of therapeutic monoclonal antibodies: implications for cardiovascular disease and targeting the PCSK9 pathway. Atherosclerosis 2013;228(1):18-28.

Duff et al. Biochem Journal, the Biochemical Society, vol. 419, No. 3, May 1, 2009 pp. 577-584.

Dufour R, Moriarty PM, Genestin E, Sasiela WJ, Du Y, Ferrand A-C; Ginsberg HN. Effect of REGN727/SAR236553 PCSK9 fully human monoclonal antibody in patients with elevated triglycerides/low high-density lipoprotein cholesterol: data from three phase 2 studies. Circulation 2012;126:Abstract A16127.

Farnier M, Kastelein JJP, Roth E, Taskinen MR, Ginsberg HN, Colhoun HM, Robinson JG, Merlet L, Brunet A, Pordy R, Baccara-Dinet MT. Relationship between alirocumab, PCSK9 and LDL-C levels: results from the Odyssey Mono Phase 3 trial of alirocumab 75 mg every 2 weeks. Atherosclerosis. 2014;235(2):e34-e35. [Abstract MP02E].

Foody J, Khan I, Lewis B. Attainment of low-density lipoprotein cholesterol goals in patients at high cardiovascular risk: results from a managed care population study. Circulation. 2013;128:A17254.

Gaudet D, Kereiakes D, McKenney J, Roth E, Hanotin C, Gipe D, Du Y, Ferrand A-C, Ginsberg H, Stein E. Alirocumab, a fully human monoclonal antibody to PCSK9, reduces high plasma Lp(a) concentration: pooled analysis of 352 patients from phase 2. J Clin Lipidol 2013:7(3):283-284.

Gaudet D, Kereiakes D, McKenney J, Roth E, Hanotin C, Gipe D, Du Y, Ferrand A-C, Ginsberg H, Stein E. Effect of Alirocumab, a Monoclonal Proprotein Convertase Subtilisin/Kexin 9 Antibody, on Lipoprotein(a) Concentrations (a Pooled Analysis of 150 mg Every 2 Weeks Dosing from Phase 2 Trials). Am J Cardiol. 2014;114(5):711-715.

Gaudet D, Kereiakes D, McKenney J, Roth E, Hanotin C, Gipe D, Du Y, Ferrand A-C, Ginsberg H, Stein E. Effect of SAR236553/REGN727 fully human monoclonal anti-proprotein convertase subtilisin/kexin type 9 antibody on plasma lipoprotein(a) concentrations: pooled analysis from three phase 2 studies (NCT:01266876; 01288469; 01288443). Circulation 2012;126:Abstract A14725.

Ginsberg HN, Rader DJ, Raal H, Guyton JR, Lorenzato C, Pordy R, Baccara-Dinet MT, Stroes E. Odyssey High FH: efficacy and safety of alirocumab in patients with severe heterozygous familial hypercholesterolemia. Circulation. 2014;130:2119.

Gusarova V, Howard VG, Okamoto H, Koehler-Stec EM, Papadopoulos N, Murphy AJ, Yancopoulos GD, Stahl N, Sleeman MW. Reduction of LDL cholesterol by a monoclonal antibody to PCSK9 in rodents and nonhuman primates. Clin Lipidol 2012;7(6):737-743.

Hochleitner et al., Characterization of a discontinuous epitope of the human immunodeficiency virus ~HIV! core protein p24 by epitope excision and differential chemical modification followed by mass spectrometric peptide mapping analysis; Protein Science 2000, 9:487-496. Cambridge University Press.

Hopkins PN, Swergold GD, Mellis S, Bruckert E, Luc G, Mendoza J, Du Y, Krempf M. A randomized placebo-phase clinical trial with the monoclonal antibody alirocumab demonstrates reductions in low-density lipoprotein cholesterol in patients with proprotein convertase subtilisin/kexin type 9 gain-of-function mutations. Circulation. 2013;128:A17156.

Hovingh GK, Davidson MH, Kastelein JJ, O'Connor AM. Diagnosis and treatment of familial hypercholesterolaemia. Eur Heart J 2013;34(13):962-971.

International Preliminary Report on Patentability dated Jul. 30, 2013 for International application No. PCT/EP12/051321, 7 pages.

International Search Report and Written Opinion dated Aug. 19, 2015 for International application No. PCT/US2015/015633, 23 pages.

International Search Report and Written Opinion dated Apr. 16, 2015 for International Application No. PCT/US2014/060109 (19 pages).

International Search Report and Written Opinion dated Feb. 3, 2015 for International Application No. PCT/US2014/065149 (17 pages).

International Search Report and Written Opinion dated Jun. 12, 2015 for International Application No. PCT/US2015/020564 (20 pages).

International Search Report dated Aug. 2, 2012 for International application No. PCT/EP12/051321, (4 pages).

Jones P, Bays H, Chaudhari U, Pordy R, Lorenzato C, Miller K, Robinson J. Pooled safety and adverse events in nine randomized, placebo-controlled, phase 2 and 3 clinical trials of alirocumab. J Am Coll Cardiol 2015;65(10_S):A1363.

Junghans et al.: Anti-Tac-H, a Humanized Antibody to the Interleukin 2 Receptor with New Features for Immunotherapy in Malignant and Immune Disorders; Cancer Research, 50. 1495-1502; Mar. 1, 1990.

Kastelein JJP, Ginsberg HN, Langslet G, Kees Hovingh G, Ceska R, Dufour R, Blom D, Civeira F, Krempf M, Farnier M. Efficacy and safety of alirocumab in patients with heterozygous familial hypercholesterolaemia not adequately controlled with current lipid-lowering therapy: results of Odyssey FH I and FH II studies; presented at ESC Congress Aug. 31, 2014, abstract not published.

Kereiakes DJ, Robinson JG, Cannon CP, Lorenzato C, Pordy R, Chaudhari U, Colhoun HM. Efficacy and safety of alirocumab in high cardiovascular risk patients with suboptimally controlled hypercholesterolemia on maximally tolerated doses of statins: The Odyssey Combo I study. Circulation. 2014;130:2119.

Kereiakes DJ, Robinson JG, Cannon CP, Lorenzato C, Pordy R, Chaudhari U, Colhoun HM. Efficacy and safety of the PCSK9 inhibitor alirocumab among high cardiovascular risk patients on maximally tolerated statin therapy: the Odyssey Combo I study. Am Heart J. 2015. In press. DOI: http://dx.doi.org/10.1016/j.ahj.2015.03.004.

Koren M, Stein E, McKenney JM, Gipe D, Hanotin C, Ferrand A-C, Wu R, Dufour R. Efficacy, safety and tolerability of 150 mg Q2W dose of the anti-PCSK9 mAb, REGN727/SAR236553: data from 3 phase 2 studies. Eur Heart J 2012;33(Abstract Supplement);37. Abstract 429.

Koren MJ, Kereiakes D, Pourfarzib R, Winegar D, Banerjee P, Hamon S, Hanotin C, McKenney JM. Effects of alirocumab, a fully human monoclonal antibody to proprotein convertase subtilisin/kexin type 9, on lipoprotein particle concentrations determined by nuclear magnetic resonance: substudy of a randomized double-blind phase II clinical trial. J Am Coll Cardiol 2014;63(12 Suppl 1): A1373.

Koren MJ, Roth EM, McKenney JM, Gipe D, Hanotin C, Ferrand AC, Wu R, Dufour R. Safety and efficacy of alirocumab 150 mg every 2 weeks, a fully human proprotein convertase subtilisin/kexin type 9 monoclonal antibody: a Phase II pooled analysis. Postgrad Med 2015;22:1-8.

Koren MJ, Stein E, Roth E, McKenney JM, Gipe D, Hanotin C, Ferrand A-C, Wu R, Dufour R. Efficacy, safety and tolerability of alirocumab 150 mg Q2W, a fully human PCSK9 monoclonal antibody: a pooled analysis of 352 patients from phase 2. J Clin Lipidol 2013:7(3)279-280.

(56) References Cited

OTHER PUBLICATIONS

Krauss RM, Banerjee P, Hamon S, Hanotin C, Sasiela B, Koren MJ, McKenney JM. Alirocumab, a fully human monoclonal antibody to proprotein convertase subtilisin/kexin type 9, and its effects on lipoprotein subtractions determined by ion mobility. Circulation. 2014;130:A15525.
Kühnast S, van der Hoorn JW, Pieterman E, Sasiela WJ, Gusarova V, Peyman A, Schafer H-L, Schwahn U, Jukema JW, Princen HM. PCSK-9 monoclonal antibody alirocumab dose-dependently decreases atherosclerosis development and enhances the effects of atorvastatin in APOE*3Leiden.CETP mice. Circulation. 2013;128:A15823.
Kühnast S, van der Hoorn JWA, Pieterman EJ, van den Hoek AM, Sasiela WJ, Gusarova V, Peyman A, Schäfer H-L, Schwahn U, Jukema JW, Princen HMG. Alirocumab inhibits atherosclerosis, improves the plaque morphology, and enhances the effects of a statin. J Lipid Res. 2014;55(10):2103-2112.
Lambert G, Chatelais M, Petrides F, Passard M, Thedrez A, Rye KA, Schwahn U, Gusarova V, Blom DJ, Sasiela W, Marais AD. Normalization of Low-Density Lipoprotein Receptor Expression in Receptor Defective Homozygous Familial Hypercholesterolemia by Inhibition of PCSK9 With Alirocumab. J Am Coll Cardiol. 2014;64(21):2299-2300.
Lambert G, Sjouke B, Choque B, Kastelein JJ, Hovingh GK. The PCSK9 decade. J Lipid Res 2012;53(12):2515-2524.
Lunven C, Paehler T, Lewanczyk P, Poitiers F, Brunet A, Rey J, Hanotin C, Sasiela WJ. A randomized study of the relative bioavailability, pharmacodynamics, and safety of alirocumab, a fully human monoclonal antibody to proprotein convertase subtilisin/ kexin type 9, after single subcutaneous administration at three different injection sites in healthy subjects. J Am Coll Cardiol 2014;63(12 Suppl 1): A1377.
Lunven C, Paehler T, Poitiers F, Brunet A, Rey J, Hanotin C, Sasiela WJ. A randomized study of the relative pharmacokinetics, pharmacodynamics and safety of alirocumab, a fully human monoclonal antibody to PCSK9, after single subcutaneous administration at three different injection sites in healthy subjects. Cardiovasc Ther. Dec. 2014;32(6):297-301.
McKenney J, Koren M, Kereiakes D, Hanotin C, Ferrand A-C. A randomized, double-blind, placebo-controlled trial of the safety and efficacy of a monoclonal antibody to proprotein convertase subtilisin/ kexin type 9 serine protease, REGN727/SAR236553, in patients with primary hypercholesterolemia (NCT: 01288443). Presented as a late-breaking oral presentation at the American College of Cardiology (ACC) Annual Scientific Session, Mar. 24-27, 2012, Chicago, Illinois, USA.
Missouri DU Report, Drug Use Review Newsletter, vol. 8, No. 6, Oct./Nov. 2003 "Statin Therapy" pp. 1-9.
Moriarty PM, Jacobson TA, Bruckert E, Thompson PD, Guyton JR, Baccara-Dinet MT, Gipe D. Efficacy and safety of alirocumab, a monoclonal antibody to PCSK9, in statin-intolerant patients: Design and rationale of Odyssey Alternative, a randomized Phase 3 trial. J Clin Lipidol. 2014;8(6):554-561.
Moriarty PM, Lecorps G, Hanotin C, Pordy R, Roth EM. Homogeneity of treatment effect of REGN727/SAR236553, a fully human monoclonal antibody against PCSK9, in lowering LDL-C: data from three phase 2 studies. Eur Heart J. 2013;34(Suppl 1):doi:10.1093/eurheartj/eht307.142.
Moriarty PM, Thompson PD, Cannon CP, Guyton JR, Bergeron J, Zieve H, Bruckert E, Jacobson TA, BaccaraDinet MT, Zhao J, Pordy R, Gipe R. Odyssey Alternative: Efficacy and safety of the proprotein convertase subtilisin/kexin type 9 monoclonal antibody, alirocumab, versus ezetimibe, in patients with statin intolerance as defined by a placebo run-in and statin rechallenge arm. Circulation. 2014;130:2108.
Pordy R, Lecorps G, Bessac L, Sasiela WJ, Ginsberg H. Alirocumab, a fully human monoclonal antibody to proprotein convertase subtilisin/ kexin type 9: therapeutic dosing in phase 3 studies. J Clin Lipidol 2013:7(3):279.
Ramanathan A, Gusarova V, Kyratsous C. Role of alirocumab (proprotein convertase subtilisin/kexin type 9 antibody) on CD81 levels and hepatitis C virus entry into hepatocytes. Circulation. 2013;128:A12052.
Ray KK, Foody J, Khan I, Lewis BE. Attainment of low-density lipoprotein cholesterol goals in patients at very high cardiovascular risk in the United Kingdom: results from a general practice population study. Value Health 2013;16(7):A513.
Rey J, Poitiers F, Paehler T, Brunet A, Pinquier JL, Hanotin C, Sasiela B. Randomized, partial blind study of the pharmacodynamics, pharmacokinetics and safety of multiple subcutaneous doses of alirocumab, a fully human monoclonal antibody to proprotein convertase subtilisin/kexin type 9, administered every 4 weeks alone or in combination with ezetimibe or fenofibrate in healthy subjects. J Am Coll Cardiol 2014;63(12 Suppl 1):A1375.
Robinson J, Farnier M, Chaudhari U, Sasiela B, Lorenzato C, Miller K, Kastelein JJP. Adverse events in patients with low-density lipoprotein cholesterol levels <25 or <15 mg/dL on at least two consecutive visits in fourteen randomized, controlled, clinical trials of alirocumab. J Am Coll Cardiol 2015;65(10_S):A1350.
Robinson JG, Farnier M, Krempf M, Bergeron J, Luc G, Averna M, Stroes E, Langslet G, Raal FJ, El Shahawy M, Koren MJ, Lepor N, Lorenzato C, Pordy R, Chaudhari U, Kastelein JJP. Long-term safety, tolerability and efficacy of alirocumab versus placebo in high cardiovascular risk patients: first results from the Odyssey Long Term study in 2,341 patients. Circulation. 2014;130:2120.
Robinson JG, Farnier M, Krempf M, Bergeron J, Luc G, Averna M, Stroes ES, Langslet G, Raal FJ, Shahawy ME, Koren MJ, Lepor NE, Lorenzato C, Pordy R, Chaudhari U, Kastelein JJ; Odyssey Long Term Investigators. Efficacy and Safety of Alirocumab in Reducing Lipids and Cardiovascular Events. N Eng J Med. 2015.
Roth E, Taskinen M-R, Ginsberg HN, Kastelein JJP, Colhoun HM, Robinson JG, Merlet L, Pordy R, Baccara-Dinet MT. A 24-week study of alirocumab monotherapy versus ezetimibe: The first phase 3 data of a proprotein convertase subtilisin/kexin type 9 inhibitor. J Am Coll Cardiol 2014;63(12 Suppl 1): A.
Roth EM, McKenney J, Hanotin C, Asset G, Stein E. The effects of co-administering a monoclonal antibody to proprotein convertase subtilisin/kexin type 9 serine protease, REGN727/SAR236553, with 10 and 80 mg atorvastatin compared to 80 mg atorvastatin alone in patients with primary hypercholesterolemia (NCT: 01288469). J Am Coll Cardiol 2012;59:E1620.
Roth EM, McKenney JM, Hanotin C, Asset G, Stein EA. Atorvastatin with or without an antibody to PCSK9 in primary hypercholesterolemia. N Engl J Med. 2012;367(20):1891-1900.
Roth EM, McKenney JM. Odyssey Mono: effect of alirocumab 75 mg subcutaneously every 2 weeks as monotherapy versus ezetimibe over 24 weeks. Future Cardiol 2015;11(1):27-37.
Roth EM, Taskinen M-R, Ginsberg H, Kastelein JJP, Colhoun HM, Robinson JG, Merlet L, Pordy R, Baccara-Dinet MT. Monotherapy with the PCSK9 inhibitor alirocumab versus ezetimibe in patients with hypercholesterolemia: Results of a 24 week, double-blind, randomized Phase 3 trial. Int J Cardiol. 2014;176(1):55-61.
Schwartz GG, Bessac L, Berdan LG, Bhatt DL, Bittner V, Diaz R, Goodman SG, Hanotin C, Harrington RA, Jukema JW, Mahaffey KW, Moryusef A, Pordy R, Roe MT, Rorick T, Sasiela WJ, Shirodaria C, Szarek M, Tamby J-F, Tricoci P, White H, Zeiher A, Steg PG. Effect of alirocumab, a monoclonal antibody to pcsk9, on long-term cardiovascular outcomes following acute coronary syndromes: Rationale and design of the odyssey outcomes trial. Am Heart J. 2014;168(5):682-689.e1.
Steen D, Khan I, Becker L, Gorcyca K, Foody J. Attainment of Lipid Levels in Patients at High Cardiovascular Risk: Results from a U.S. Managed Care Population Study. Circulation. 2014;130:A19949.
Steen D, Khan I, Song X, Sanchez R, Gorcyca K, Hollenbeak CS, Foody J. Cardiovascular Event Rates in a High-Risk Managed Care Population in the United States. J Am Coll Cardiol 2015;65(10_S):A1647.
Stein E, Bergeron J, Gaudet D, Weiss R, Gipe D, Wu R, Dufour R, Pordy R. Safety and efficacy of a monoclonal antibody to PCSK9, REGN727/SAR236553, in statin-treated heterozygous familial hypercholesterolemia patients. Presented as an oral presentation at

(56) References Cited

OTHER PUBLICATIONS the 80th European Atherosclerosis Society (EAS) Congress, May 25-28, 2012, Milan, Italy. Abstract 1398.
Stein EA, Bergeron J, Gaudet D, Weiss R, Dufour R, Du Y, Yang F, Andisik M, Toni A, Pordy R, Gipe D. One year open-label treatment with alirocumab 150 mg every two weeks in heterozygous familial hypercholesterolemic patients. Lancet 2012 380:29-36.
Stroes E, Guyton JR, Farnier M, Rader D, Moriarty PM, Bergeron J, Langslet G, Lepor N, Civeira F, Gaudet D, Watts GF, Manvelian G, Lecorps G, Zhao J, Baccara-Dinet M, Roth EM. Efficacy and safety of different dosing regimens of alirocumab (starting doses of 75 mg every two weeks and 150 mg every four weeks) versus placebo in patients with hypercholesterolemia not treated using statins: the Odyssey Choice II study. J Am Coll Cardiol 2015;65(10_S):A1370.
Sullivan, et al. Effect of a Monoclonal Antibody to PCSK9 on Low-Density Lipoprotein Cholesterol Levels in Statin-Intolerant Patients. JAMA. Dec. 19, 2012. vol. 308, No. 23. pp. 2497-2506.
Swergold G, Biedermann S, Renard R, Du Y, Nadler D, Wu R, Mellis S, Lisbon E. REGN727/SAR236553, a fully-human monoclonal antibody to proprotein convertase subtilisin kexin 9 (PCSK9), decreases ApoB and non-HDL-C when administered intravenously to healthy volunteers. J Clin Lipidol 2011;5(3):219.
Swergold G, Biedermann S, Renard R, Nadler D, Wu R, Lisbon EA, Gutierrez MJ, Mellis S. REGN727/SAR236553, a fully human proprotein convertase subtilisin kexin 9 (PCSK9) monoclonal antibody: effects on safety and lipid and lipoprotein profiles when administered subcutaneously. J Am Coll Cardiol 2011;57(14s1):E2023.
Swergold G, Biedermann S, Renard R, Nadler D, Wu R, Mellis S. Safety, lipid, and lipoprotein effects of REGN727/SAR236553, a fully human proprotein convertase subtilisin kexin 9 (PCSK9) neutralizing monoclonal antibody administered intravenously to healthy volunteers. Circulation 2010;122:Abstract A23251.
Swergold G, Smith W, Mellis S, Logan D, Webb C, Wu R, Du Y, Krans T, Gasparino E, Stein EA. Inhibition of proprotein convertase subtilisin/kexin type 9 with a monoclonal antibody REGN727/SAR236553, effectively reduces low-density-lipoprotein cholesterol, as mono or add-on therapy in heterozygous familial and non-familial hypercholesterolemia. Circulation 2011;124:Abstract A16265.
Teramoto T, Kobayashi M, Uno K, Takagi Y, Matsuoka O, Sugimoto M, Inoue S, Minami F, Baccara-Dinet MT. Efficacy and safety of alirocumab in Japanese patients with hypercholesterolemia on stable statin therapy: first data with the 75 mg every two weeks dose. Circulation. 2014;130:A13651.
Toth PP, Hamon S, Jones SR, Joshi PH, Martin SS, Pordy R, Hanotin C. Alirocumab, a proprotein convertase subtilisin/kexin type 9 monoclonal antibody, reduces cholesterol concentrations of all serum low-density lipoprotein cholesterol fractions. Circulation. 2013;128:A17313.
Toth PP, Hamon S, Jones SR, Martin SS, Joshi PH, Kulkarni K, Banerjee P, Hanotin C. Proprotein convertase subtilisin/kexin 9 monoclonal antibody therapy significantly reduces apoprotein CII and CIII levels in serum. Atherosclerosis. 2014;235(2):e107-e108. [Abstract 593].
Van der Hoorn JWA, Kuhnast S, Pieterman E, van der Hoek AM, Sasiela WJ, Gusarova V, Peyman A, Schafer H-L, Schwahn U, Jukema JW, Princen HMG. Alirocumab, a monoclonal antibody to PCSK-9, dose-dependently decreases atherosclerosis, improves plaque stability and shows additive effects with atorvastatin in APOE*3Leiden. CETP mice. Atherosclerosis. 2014;235(2):e19. [Abstract WS16].
Wong ND, Chuang J. Residual Dyslipidemia According to LDL-C, non-HDL-C and Apolipoprotein B by Cardiovascular Risk Category in Statin Treated US Adults. J Clin Lipidol. 2014;8:323-324. Presented as a poster presentation at the National Lipid Association Scientific Sessions, May 1-4, 2014, Orlando, Florida, USA.
Anonymous: A Randomized, Double-Blind, Placebo-Controlled, Parallel Group Study to Evaluate the Effect of Alirocumab (SAR236553/REGN727) on the Occurrence of Cardiovascular Events in Patients Who Have Recently Experienced an Acute Coronary Syndrome. Archive from ClinicalTrials.gov for NCT01663402 on Mar. 11, 2014 (3 pages).
Anonymous: Long-term Safety and Tolerability of Alirocumab SAR236553 (REGN727) in High Cardiovascular Risk Patients With Hypercholesterolemia Not Adequately Controlled With Their Lipid Modifying Therapy: A Randomized, Double-Blind, Placebo-Controlled Study. Archive from ClinicalTrials.gov for NCT01507831 on Jun. 27, 2013 (3 pages).
Blom, Dirk J. et al.: "A 52-Week Placebo-Controlled Trial of Evolocumab in Hyperlipidemia" vol. 370, No. 19, May 8, 2014 pp. 1809-1819.
Costet. PCSK9 inhibitors as LDL cholesterol-lowering agents: Rationale, concerns and preliminary outcomes. Drugs of the Future. May 1, 2012. vol. 37, No. 5, pp. 331-341.
Gonnet et al.: Exhaustive Matching of the Entire Protein Sequence Database; Science; 1992, vol. 256, pp. 1443-1445.
Gusarova V, Sleeman M, Swergold G, Sasiela B, Stahl N, Yancopoulos G, Murphy A. Fully human antibody that blocks PCSK9 demonstrates reduction in LDL-C preclinically and in early clinical trials. Abstract of oral presentation at the Keystone Symposia on Molecular and Cellular Biology, Mar. 25-30, 2012, Montana, USA.
Haddley et al. Alirocumab Anti-Proprotein Convertase 9 (PCSK9) Mab Treatment of Hypercholesterolemia. Drugs of the Future; Apr. 1, 2013. vol. 38, No. 4. pp. 215-216.
Robinson JG, Farnier M, Krempf M, Bergeron J, Luc G, Averna M, Stroes E, Langslet G, Raal FJ, El Shahawy M, Koren MJ, Lepor N, Lorenzato C, Pordy R, Chaudhari U, Kastelein JJP. Long-term safety, tolerability and efficacy of alirocumab versus placebo in high cardiovascular risk patients: first results from the Odyssey Long Term study in 2,341 patients; presented at ESC Congress Aug. 31, 2014, abstract not published.
Roth et al. Alirocumab for hyperlipidemia: physiology of PCSK9 inhibition, pharmacodynamics and Phase I and II clinical trial results of a PCSK9 monoclonal antibody. Future Cardiology. Mar. 2014; vol. 10, No. 2. pp. 187-197. 183-199.
Shao W. New Therapies for Lowering LDL-C: Targeting PCSK9. Abstract of oral presentation at the Sino-American Pharmaceutical Professionals Association—2014 Scientific Symposium, Apr. 26, 2014, New Jersey, USA.
Swergold GD, et al. Identification and characterization of patients with autosomal dominant hypercholesterolemia caused by gain-of-function mutations in proprotein convertase subtilisin/kexin type 9 and comparison with patients with Familial Hypercholesterolemia (FH) and Familial Defective apolipoprotein B (FDB). Abstract of a poster presentation at the American Society of Human Genetics (ASHG), Oct. 22-26, 2013, Boston, USA.
Chinese Patent Application No. 201280015477.6, Office Action dated Dec. 2, 2014 with English summary, 12 pages.
Chinese Patent Application No. 201280015571.1, Office Action dated Sep. 3, 2014 with English summary, 12 pages.
European Patent Application No. 12701015.5, Communication pursuant to Article 94(3) EPC dated Apr. 24, 2015, 9 pages.
European Patent Application No. 12701015.5, Communication pursuant to Article 94(3) EPC dated May 30, 2014, 8 pages.
European Patent Application No. 12701742.4, Communication pursuant to Article 94(3) EPC dated May 28, 2014, 8 pages.
Dube, et al. (2012) Curr Opin Lipidol 23(2):133-140, "Lipoprotein(a): more interesting than ever after 50 years".
Koschinsky and Boffa (2014) Endocrinology and Metabolism Clinics of North America 43(4): 949-962, "Lipoprotein(a): An Important Cardiovascular Risk Factor and a Clinical Conundrum".
Lamon-Fava, et al. (2011) Journal of Lipid Research 52:1181-1187 "Lipoprotein(a) levels, apo(a) isoform size, and coronary heart disease risk in the Framingham Offspring Study".
Third Party Observation for European Patent Application No. 12761864.3 dated Feb. 24, 2016.
Tsimikas, et al. (2015) The Lancet 386(10002):1472-1483, "Antisense therapy targeting apolipoprotein(a): a randomised, double-blind, placebo-controlled phase 1 study".

(56) References Cited

OTHER PUBLICATIONS

Romagnuolo, et al. (2015) The Journal of Biological Chemistry 290(18):11649-11662, "Lipoprotein(a) Catabolism is Regulated by Proprotein Convertase Subtilisin/Kexin Type 9 through the Low Density Lipoprotein Receptor".
Barbie and Lefranc, 1998 Exp. Clin. Immunogenet. 15:171-183, "The Human Immunoglobulin Kappa Variable (IGKV) Genes and Joining (IGKJ) Segments".
Breen, et al. (2001) Pharmaceutical Research 18(9): 1345-1353, "Effect of moisture on the stability of a lyophilized humanized monoclonal antibody formulation".
Carpenter, 1997 Pharm. Res. 14(8): 969-975, Rational Design of Stable Lyophilized Protein Formulations: Some Practical Advice.
Daugherty, et al., 2006 Advanced Drug Delivery Reviews 58: 686-706, "Formulation and delivery issues for monoclonal antibody therapeutics".
Katayama, et al. 2004 J. Pharm. Sci. 93(10): 2609-2623, "Retrospective statistical analysis of lyophilized Protein Formulations of Progenipoietin Using PLS: Determination of the Critical Parameters for Long-Term Storage Stability".
Lefranc, M.-P., et al., IMGT®, the international ImMunoGeneTics information system®, Nucl. Acids Res, 37, D1006-D1012 (2009).
Majumdar, et al. (2011) Journal of Pharmaceutical Sciences 100(7):2563-2573, "Evaluation of the effect of syringe surfaces on protein formulations".
Meehan et al., 1996, J. Controlled Release 46:107-116, "A microinfusor device for the delivery of therapeutic levels of peptides and macromolecules".
Robinson, N., 2002, *PNAS*, 99(8):5283-5288 "Protein Deamidation".
Scaviner, D. et al., 1999 Exp. Clin. Immunogenet. 16:234-240 "Protein Displays of the Human Immunoglobulin Heavy, Kappa and Lambda Variable and Joining Regions".
Varret, et al., 1999 Am. J. Hum. Genet. 64: 1378-1387, "A third major locus for autosomal dominant hypercholesterolemia Maps to 1p. 34.1-p. 32".
Wang, 1999 International J. Pharmaceutics 185(2): 129-188, "Instability, stabilization, and formulation of liquid protein pharmaceuticals".
Webb, et al. 2002 J. Pharm. Sci. 91(2): 543-558, "A new mechanism for decreasing aggregation of Recombinant Human Interferon-γ by a Surfactant: Slowed Dissolution of Lyophilized Formulations in a Solution Containing 0.03% Polysorbate 20".
Davidson, et al. (2011) Journal of Clinical Lipidology 5:338-367, "Clinical utility of inflammatory markers and advanced lipoprotein testing: Advice from an expert panel of lipid specialists".
Rader, et al. (1995) The Journal of Clinical Investigation, Inc. 95:1403-1408, "The Low Density Lipoprotein Receptor Is Not Required for Normal Catabolism of Lp(a) in Humans".
Kostner, et al. (2013) European Heart Journal 34:3268-3276, "When should we measure lipoprotein (a)?".
Jorgensen et al. (2013) European Heart Journal 34:1826-1833, "Genetically elevated non-fasting triglycerides and calculated remnant cholesterol as casual risk factors for myocardial infarction".
Kawashiri, et al. (2012) Circulation 126(21):13869, "Statin Therapy Improves Fractional Catabolic Rate of LDL without Affecting Impaired VLDL and VLDL Remnant Catabolism in Homozygous FH Patient Due to PCSK9 Gene Mutation: Evidence from Kinetic Study with Stable Isotope".
Toth, et al., (2013) Circulation 128(22):17492, "Alirocumab, a Proprotein Convertase Subtilisin/Kexin Type 9 Monoclonal Antibody, Reduces Cholesterol Concentrations of Serum Remnant Lipoprotein Fractions, Very Low-Density Lipoproteins and Triglycerides".
Varbo, et al., (2013) Journal of the American College of Cardiology 61(4):427-436, "Remnant Cholesterol as a Casual Risk Factor for Ischemic Heart Disease".
Partial International Search Report dated Nov. 6, 2014 for International Application No. PCT/US2014/040163.
Bays et al. (2015) J Clin Lipidol. 9(3):471-472 Abstract 183 "Alirocumab treatment effect on non-HDL-C: pooled analyses of ten Phase 3 trials in the Odyssey program".
Bee et al. (2009) Journal of Pharmaceutical Sciences 98(9): 3290-3301 "Precipitation of a monoclonal antibody by soluble tungsten".
Berthold and Berthold (2013) Atherosclerosis Supplements 14:10-5 "Hyperlipoproteinemia(a): Clinical significance and treatment options".
Cariou et al. (May 23-26, 2015) International Symposium on Atherosclerosis. Abstract No. 1039 "Patient and physician perspectives on administration of the PCSK9 monoclonal antibody alirocumab, an injectable medication to lower LDL-C levels".
clinicaltrials.gov (Dec. 23, 2010) "View of NCT01266876," US National Institutes of Health. [accessible on the internet at: https://clinicaltrials.gov/archive/NCT01266876/2010_12_23].
clinicaltrials.gov (Feb. 1, 2011) "View of NCT01288443," US National Institutes of Health. [accessible on the internet at: https://clinicaltrials.gov/archive/NCT01288443/2011_02_01).
clinicaltrials.gov (First Received: Aug. 8, 2012) "View of NCT01663402," US National Institutes of Health. [accessible on the internet at: https://clinicaltrials.gov/ct2/show/NCT01663402].
clinicaltrials.gov (First Received: Jun. 8, 2012) "View of NCT01617655," US National Institutes of Health. [accessible on the internet at: https://clinicaltrials.gov/ct2/show/NCT01617655?term=NCT01617655&rank=1].
clinicaltrials.gov (First Received: Jan. 6, 2012) "View of NCT01507831," US National Institutes of Health. [accessible on the internet at: https://clinicaltrials.gov/ct2/show/NCT01507831?term=NCT01507831&rank=1].
clinicaltrials.gov (First Received: Feb. 1, 2011) "View of NCT01288469," US National Institutes of Health. [accessible on the internet at: https://clinicaltrials.gov/ct2/show/NCT01288469?term=NCT01288469&rank=1].
clinicaltrials.gov (First Received: Oct. 8, 2012) "View of NCT01709500," US National Institutes of Health. [accessible on the internet at: https://clinicaltrials.gov/ct2/show/NCT01709500?term=NCT01709500&rank=1].
clinicaltrials.gov (First Received: Jul. 16, 2012) "View of NCT01644175," US National Institutes of Health. [accessible on the internet at: https://clinicaltrials.gov/ct2/show/NCT01644175?term=NCT01644175&rank=1].
clinicaltrials.gov (First Received: Jul. 16, 2012) "View of NCT01644188," US National Institutes of Health. [accessible on the internet at: https://clinicaltrials.gov/ct2/show/NCT01644188?term=NCT01644188&rank=1].
clinicaltrials.gov (First Received: Jul. 9, 2010) "View of NCT01161082," US National Institutes of Health. [accessible on the internet at: https://clinicaltrials.gov/ct2/show/NCT01161082?term=NCT01161082&rank=1].
clinicaltrials.gov (First Received: Jul. 17, 2012) "View of NCT01644474," US National Institutes of Health. [accessible on the internet at: https://clinicaltrials.gov/ct2/show/NCT01644474?term=NCT01644474&rank=1].
Dufour et al. (2014) Can J Cardiol 30(10 suppl):S338 Abstract 546 "One year open-label treatment with alirocumab 150 mg every two weeks in heterozygous familial hypercholesterolemic patients".
Gaudet et al. (2017) Am Journal Cardiology 119:40-46 "Effect of Alirocumab on Lipoprotein(a) Over ‡1.5 Years (from the Phase 3 Odyssey Program)".
Gorcyca et al. (2015) J Clin Lipidol. 9(3):424 Abstract 118 "Prevalence of atherosclerotic cardiovascular disease and diabetes in the United States".
Hopkins et al. (Dec. 2015) Circ Cardiovasc Genet. 8(6):823-831 "Characterization of Autosomal Dominant Hypercholesterolemia Caused by PCSK9 Gain of Function Mutations and its Specific Treatment with Alirocumab, a PCSK9 Monoclonal Antibody".
Huang et al. (May 2015) J Clin Lipidol. 9(3):437-438 Abstract 134 "Clinical characteristics and unmet need among real-world atherosclerotic cardiovascular disease (ASCVD) patients stratified by statin use".
ISR with WO for International Patent Application No. PCT/EP2012/051321 dated Apr. 19, 2012.
ISR and WO for International Application No. PCT/US2014/046170 dated Oct. 2, 2014.

(56) References Cited

OTHER PUBLICATIONS

ISR and WO from PCT/US2014/040050 dated Oct. 6, 2014.
ISR with WO for International Patent Application No. PCT/EP2015/055369 dated May 21, 2015.
ISR with WO for International Patent Application No. PCT/US2014/041204 dated Oct. 17, 2014.
ISR for International Application No. PCT/US2013/057898 dated Feb. 13, 2014.
Kolata (2015) The New York Times "Praluent Looks Cheap to Those with Extreme Cholesterol" Website [Online] Available Website: www.nytimes.com/2015/07/28/health/praluent-looks-cheap-to-those-with-extreme-cholesterol.html; Last Update: unknown; Accessed on: Nov. 8, 2016.
Konrad et al. (2011) Lipids in Health and Disease 10(1):38 "Effects of currently prescribed LDL-C-lowering drugs on PCSK9 and implications for the next generation of LDL-C-lowering agents".
Kuiper (2015) Pharma ISA Poster "Statin use and low density lipoprotein cholesterol goal attainment among a high cardiovascular risk population in the Netherlands".
Li et al. (2009) Recent Patents on DNA and Gene Sequences 3(3):201-212 "Recent Patents on PCSK9: A New Target for Treating Hypercholesterolemia".
Miettinen et al. (1971) Circulation 44(5):842-850 "Cholesterol production in obesity".
Moon (2007) Cardiology 108:282-289 "Lipoprotein(a) and LDL Particle Size are Related to the Severity of Coronary Artery Disease".
Moriarty et al. (2015) J Clin Lipidol. 9(6):758-769 "Efficacy and safety of alirocumab versus ezetimibe in statin-intolerant patients, with a statin-re-challenge arm: The Odyssey Alternative randomized trial".
Moriarty (2015) 10th International Society for Apheresis Congress XP55317363, Cancun Mexico "PCSK9 Inhibitors and their Effect on Patients who are Statin Intolerant or Receiving Lipoprotein-apheresis".
Office Action from CN2012-80015477.6 dated Dec. 2, 2014 with English summary.
Office Action from CN2012-80015571.1 dated Sep. 3, 2014 with English summary.
Office Action Article 94(3) EP App No. 12701742.4 dated Jun. 1, 2015.
Ray (2015) Clin Lipidol. 10(1):9-12 "Alirocumab: an investigational treatment for hypercholesterolemia".
Reyes-Soffer et al. (2015) Arterioscler Thromb Vasc Biol 35:A129 "Effects of a proprotein convertase subtilisin/kexin type 9 inhibitor, alirocumab, on lipid and lipoprotein metabolism in normal subjects".
Roth et al. (2015) J. Clin. Lipidol. 37(9):1945-1954 "Patient and physician perspectives on administration of the PCSK9 monoclonal antibody alirocumab, an injectable medication to lower LDL-C levels".
Roth et al. (2015) International Symposium on Atherosclerosis, Abstract No. 254 "Phase 3 Randomized Trial Evaluating Alirocumab Every Four Weeks Dosing as Add-on to Statin or as Monotherapy: Odyssey Choice I".
Saeedi and Frohlich (2016) Clinical Diabetes and Endocrinology 2:7 "Lipoprotein (a), an independent cardiovascular risk marker".
Sahebkar et al. (2013) Clinical Therapeutics 35(8):1082-1098 "New LDL-Cholesterol Lowering Therapies: Pharmacology, Clinical Trials, and Relevance to Acute Coronary Syndromes".
Shields et al. (2002) Journal of Biological Chemistry 277(30):26733-26740 "Lack of fucose on human IgG1 N-linked oligosaccharide improves binding to human FcγRIII and antibody-dependent cellular toxicity".
Stahl (2010) "Early Clinical Development #1 REGN727: anti-PCSK9," Regeneron Pharmaceuticals. Accessible on the Internet at URL: http://files.shareholder.com/downloads/REGN/0x0x387214/534aaeb6-5e66-4e8f-86a9-0f9cac20d72f/REGN%20Investor%20Day%20Early%20Clinical%20Development1.pdf.
Stein et al. (2012) The Lancet 380:29-36 "Effect of a monoclonal antibody to PCSK9, REGN727/SAR236553, to reduce low-density lipoprotein cholesterol in patients with heterozygofamilial hypercholesterolemia on stable statin dose with or without ezetimibe therapy: a phase 2 randomized controlled trial".
Steinberg et al. (2009) Proceedings of the National Academy of Sciences USA 106(24):9546-9547 "Inhibition of PCSK9: a powerful weapon for achieving ideal LDL cholesterol levels".
Stroes et al. (2014) J. Am. Coll. Cardiol. 63(23):2541-2548 "Anti-PCSK9 Antibody Effectively Lowers Cholesterol in Patients With Statin Intolerance".
Wang et al. (2007) Journal of Pharmaceutical Sciences 96(1):1-26 "Antibody Structure, Instability, and Formulation".
Wang et al. (2009) Clin. Pharmacology 49(9):1012-1024.
Westerterp et al. (2006) Vasc Biol 26(11):2552-2559 "Cholesteryl Ester Transfer Protein Decreases High-Density Lipoprotein and Severely Aggravates Atherosclerosis in APOE*3-Leiden Mice, Arterioscler Thromb".
Defesche et al. (Jun. 2-5, 2013) Presentation presented at the 81st European Atherosclerosis Society (EAS) Congress, Lyon, France "Natural history of autosomal dominant hypercholesterolemia caused by gain-of-function mutations in proprotein convertase subtilisin/kexin type 9 (PCSK9) (funded by Regeneron/Sanofi)".
McKenney et al. (2013) Abstract 81st European Atherosclerosis Society (EAS) Congress, Jun. 2-5, 2013, Lyon, France "Dynamics between the monoclonal antibody SAR236553/REGN727, proprotein convertase subtilisin/kexin type 9 and low-density lipoprotein cholesterol (LDL-C) levels (funding: Regeneron/Sanofi)".
Reyes-Soffer et al. (2017) Circulation 135:352-362 "Effects of PCSK9 Inhibition with Alirocumab on Lipoprotein Metabolism in Healthy Humans".
Lalanne, Florent, et al., "Wild-type PCSK9 inhibits LDL clearance but does not affect apoB-containing lipoprotein production in mouse and cultured cells," Journal of Lipid Research, vol. 46, 2005, pp. 1312-1319.
Fasano (2009) Atherosclerosis 203:166-171 "Degradation of LDLR Protein Mediated by 'Gain of Function' PCSK9 Mutants in Normal and ARH Cells".
Voet, et al., "Fundamentals of Biochemistry," Von Hoffmann Press, Inc., 1999, pp. 260-264.
Bendig, Mary M., "Humanization of Rodent Monoclonal Antibodies by CDR Grafting," Methods: A Companion to Methods in Enzymology 8, 83-93 (1995).
Jefferis, Roy, et al., "Human Immunoglobulin Allotypes," Review mAbs 1:4, 1-7; Jul./Aug. 2009.
QSM, "Essential medicines and health products," WHO Drug Information, vol. 26, No. 2, 2012.
Voet, et al., "Fundamentals of Biochemistry," Von Hoffmann Press, Inc., 1999, pp. 80-81.
Todo, Yasuhiro, et al., "Detailed Analysis of Serum Lipids and Lipoproteins from Japanese Type III Hyperlipoproteinemia with Apolipoprotein E2/2 Phenotype," Clinica Chimica Acta 348 (2004) 35-40.
Ason, Brandon, et al., "Improved efficacy for ezetimibe and rosuvastatin by attenuating the induction of PCSK9," Journal of Lipid Research, vol. 52, 2011, pp. 679-687.
Chaudhary, Rahul, et al., "PCSK9 inhibitors: A new era of lipid lowering therapy," World Journal of Cardiology, Feb. 26, 2017; 9(2): 76-91.
Zimmerman, Marj P., "How Do PCSK9 Inhibitors Stack Up to Statins for Low-Density Lipoprotein Cholesterol Control?", American health & Drug benefits, Nov. 1, 2015, p. 436.
Stone, Neil J., et al., "2013 ACC/AHA Guideline on the Treatment of Blood Cholesterol to Reduce Atherosclerotic Cardiovascular Risk in Adults," A report of the American College of Cardiology/American Heart Association Task for on Practice Guidelines, Journal of the American College of cardiology, vol. 63, No. 25, Nov. 12, 2013 (Nov. 12, 2013), pp. 2889-2934.
Rahilly-Tierney, Catherine R., "Low-Density Lipoprotein Reduction and Magnitude of Cardiovascular Risk Reduction," Clinical Study, Preventive Cardiology, Spring 2009, MAVERIC, pp. 80-87.

(56) References Cited

OTHER PUBLICATIONS

McNutt, Markey C., et al., "So Far, PCSK9 Inhibitors Work for All Heterozygous FH Patients," Circ Cardiovasc Genet.2015;8:749-751.
Brouwers, M. C. G. J., et al., "Plasma proprotein convertase subtilisin kexin type 9 levels are related to markers of cholesterol synthesis in familial combined hyperlipidemia," Nutrition, Metabolism & Cardiovascular Diseases (2013) 23, 1115-1121.
Yamashita, Sizuya, "PCSK9 (proprotein convertase subtilisin/kexin type 9)", Prevention of Arteriosclerosis, Feb. 10, 2013, vol. 11, No. 4, p. 101-105 (Lambert, Gilles, et al., "Molecular basis of PCSK9 function," Atherosclerosis 203 (2009) 1-7).
Ned, R.M., et al., Cascade Screening for Familial Hypercholesterolemia (FH), PLOS Currents Evidence on Genomic Tests, Jul. 1, 2011. Edition 1. doi: 10.1371/currents.RRN1238.
Notice of Reason(s) for Rejection for JP 2016-516825, dated Jan. 16, 2018.

* cited by examiner

SEQUENCE LISTING

```
<160> NUMBER OF SEQ ID NOS: 765

<210> SEQ ID NO 1
<211> LENGTH: 351
<212> TYPE: DNA
<213> ORGANISM: Artificial Sequence
<220> FEATURE:
<223> OTHER INFORMATION: Synthetic

<400> SEQUENCE: 1

caggtccagc tggtgcagtc tgggggaggc ttggtacagc ctggggggtc cctgagactc      60

tcctgtgcag cctctggatt tactctaagt agttacgaca tgcactgggt ccgccaatct     120
```

acaggaaaag gtctggagtg ggtctcagct attggttcta ccggtgacac atactatcca 180
ggctccgtga agggccgatt caccatcacc agagaaaaag ccaagaactc cgtgtatctt 240
caaatgaaca gcctgagagc cggggacacg gctgtgtatt actgtgtaag agaggggtgg 300
gaggtaccct ttgactactg gggccaggga accctggtca ctgtctcctc a 351

<210> SEQ ID NO 2
<211> LENGTH: 117
<212> TYPE: PRT
<213> ORGANISM: Artificial Sequence
<220> FEATURE:
<223> OTHER INFORMATION: Synthetic

<400> SEQUENCE: 2

Gln Val Gln Leu Val Gln Ser Gly Gly Gly Leu Val Gln Pro Gly Gly
1 5 10 15

Ser Leu Arg Leu Ser Cys Ala Ala Ser Gly Phe Thr Leu Ser Ser Tyr
20 25 30

Asp Met His Trp Val Arg Gln Ser Thr Gly Lys Gly Leu Glu Trp Val
35 40 45

Ser Ala Ile Gly Ser Thr Gly Asp Thr Tyr Tyr Pro Gly Ser Val Lys
50 55 60

Gly Arg Phe Thr Ile Thr Arg Glu Lys Ala Lys Asn Ser Val Tyr Leu
65 70 75 80

Gln Met Asn Ser Leu Arg Ala Gly Asp Thr Ala Val Tyr Tyr Cys Val
85 90 95

Arg Glu Gly Trp Glu Val Pro Phe Asp Tyr Trp Gly Gln Gly Thr Leu
100 105 110

Val Thr Val Ser Ser
115

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggatttactc taagtagtta cgac 24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Leu Ser Ser Tyr Asp
1 5

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5
attggttcta ccggtgacac a 21

<210> SEQ ID NO 6
<211> LENGTH: 7
<212> TYPE: PRT
<213> ORGANISM: Artificial Sequence
<220> FEATURE:
<223> OTHER INFORMATION: Synthetic

<400> SEQUENCE: 6

Ile Gly Ser Thr Gly Asp Thr
1 5

<210> SEQ ID NO 7
<211> LENGTH: 33
<212> TYPE: DNA
<213> ORGANISM: Artificial Sequence
<220> FEATURE:
<223> OTHER INFORMATION: Synthetic

<400> SEQUENCE: 7
gtaagagagg ggtgggaggt accctttgac tac 33

<210> SEQ ID NO 8
<211> LENGTH: 11
<212> TYPE: PRT
<213> ORGANISM: Artificial Sequence
<220> FEATURE:
<223> OTHER INFORMATION: Synthetic

<400> SEQUENCE: 8

Val Arg Glu Gly Trp Glu Val Pro Phe Asp Tyr
1 5 10

<210> SEQ ID NO 9
<211> LENGTH: 327
<212> TYPE: DNA
<213> ORGANISM: Artificial Sequence
<220> FEATURE:
<223> OTHER INFORMATION: Synthetic

<400> SEQUENCE: 9
gacatccaga tgacccagtc tccagccacc ctgtctgtgt ctccagggga aagagccgcc 60
ctctcctgca gggccagtca gagtgttagc agcaacttag cctggtacca ccagaaacct 120
ggccaggctc ccaggctcct catctatggt gcatccacca gggccactgg tatcccagcc 180
aggttcagtg gcattgggtc tgggacagag ttcactctca ttatcagcag cctgcagtct 240
gaagattttg cattttattt ctgtcagcag tataataact ggcctccatt cactttcggc 300
cctgggacca aggtggagat caaacga 327

<210> SEQ ID NO 10
<211> LENGTH: 109
<212> TYPE: PRT
<213> ORGANISM: Artificial Sequence
<220> FEATURE:
<223> OTHER INFORMATION: Synthetic

<400> SEQUENCE: 10

Asp Ile Gln Met Thr Gln Ser Pro Ala Thr Leu Ser Val Ser Pro Gly
1 5 10 15

Glu Arg Ala Ala Leu Ser Cys Arg Ala Ser Gln Ser Val Ser Ser Asn
20 25 30

Leu Ala Trp Tyr His Gln Lys Pro Gly Gln Ala Pro Arg Leu Leu Ile
35 40 45

```
Tyr Gly Ala Ser Thr Arg Ala Thr Gly Ile Pro Ala Arg Phe Ser Gly
    50                  55                  60

Ile Gly Ser Gly Thr Glu Phe Thr Leu Ile Ile Ser Ser Leu Gln Ser
65                  70                  75                  80

Glu Asp Phe Ala Phe Tyr Phe Cys Gln Gln Tyr Asn Asn Trp Pro Pro
                85                  90                  95

Phe Thr Phe Gly Pro Gly Thr Lys Val Glu Ile Lys Arg
            100                 105


<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11

cagagtgtta gcagcaac                                                    18


<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

Gln Ser Val Ser Ser Asn
 1               5


<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13

ggtgcatcc                                                               9


<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Gly Ala Ser
 1


<210> SEQ ID NO 15
<211> LENGTH: 30
<212> TYPE: DNA
<213> ORGANISM: Artificial Sequence
<220> FEATURE:
<223> OTHER INFORMATION: Synthetic

<400> SEQUENCE: 15

cagcagtata ataactggcc tccattcact                                       30


<210> SEQ ID NO 16
<211> LENGTH: 10
<212> TYPE: PRT
```

<213> ORGANISM: Artificial Sequence
<220> FEATURE:
<223> OTHER INFORMATION: Synthetic

<400> SEQUENCE: 16

Gln Gln Tyr Asn Asn Trp Pro Pro Phe Thr
1 5 10

<210> SEQ ID NO 17
<211> LENGTH: 351
<212> TYPE: DNA
<213> ORGANISM: Artificial Sequence
<220> FEATURE:
<223> OTHER INFORMATION: Synthetic

<400> SEQUENCE: 17
gaggtgcagc tggtggagtc tgggggaggc ttggtacagc ctggggggtc cctgagactc 60
tcctgtgcag cctctggatt tactctaagt agttacgaca tgcactgggt ccgccaatct 120
acaggaaaag gtctggagtg ggtctcagct attggttcta ccggtgacac atactatcca 180
ggctccgtga agggccgatt caccatcacc agagaaaaag ccaagaactc cgtgtatctt 240
caaatgaaca gcctgagagc cggggacacg gctgtgtatt actgtgtaag agaggggtgg 300
gaggtaccct ttgactactg gggccaggga accctggtca ccgtctcctc a 351

<210> SEQ ID NO 18
<211> LENGTH: 117
<212> TYPE: PRT
<213> ORGANISM: Artificial Sequence
<220> FEATURE:
<223> OTHER INFORMATION: Synthetic

<400> SEQUENCE: 18

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Leu Ser Ser Tyr
20 25 30

Asp Met His Trp Val Arg Gln Ser Thr Gly Lys Gly Leu Glu Trp Val
35 40 45

Ser Ala Ile Gly Ser Thr Gly Asp Thr Tyr Tyr Pro Gly Ser Val Lys
50 55 60

Gly Arg Phe Thr Ile Thr Arg Glu Lys Ala Lys Asn Ser Val Tyr Leu
65 70 75 80

Gln Met Asn Ser Leu Arg Ala Gly Asp Thr Ala Val Tyr Tyr Cys Val
85 90 95

Arg Glu Gly Trp Glu Val Pro Phe Asp Tyr Trp Gly Gln Gly Thr Leu
100 105 110

Val Thr Val Ser Ser
115

<210> SEQ ID NO 19
<211> LENGTH: 324
<212> TYPE: DNA
<213> ORGANISM: Artificial Sequence
<220> FEATURE:
<223> OTHER INFORMATION: Synthetic

<400> SEQUENCE: 19
gaaatagtga tgacgcagtc tccagccacc ctgtctgtgt ctccagggga aagagccgcc 60
ctctcctgca gggccagtca gagtgttagc agcaacttag cctggtacca ccagaaacct 120
ggccaggctc ccaggctcct catctatggt gcatccacca gggccactgg tatcccagcc 180
aggttcagtg gcattgggtc tgggacagag ttcactctca ttatcagcag cctgcagtct 240
gaagattttg cattttattt ctgtcagcag tataataact ggcctccatt cactttcggc 300
cctgggacca aagtggatat caaa 324

<210> SEQ ID NO 20
<211> LENGTH: 108
<212> TYPE: PRT
<213> ORGANISM: Artificial Sequence
<220> FEATURE:
<223> OTHER INFORMATION: Synthetic

<400> SEQUENCE: 20

```
Glu Ile Val Met Thr Gln Ser Pro Ala Thr Leu Ser Val Ser Pro Gly
 1               5                  10                  15

Glu Arg Ala Ala Leu Ser Cys Arg Ala Ser Gln Ser Val Ser Ser Asn
            20                  25                  30

Leu Ala Trp Tyr His Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ile Gly Ser Gly Thr Glu Phe Thr Leu Ile Ile Ser Ser Leu Gln Ser
65                  70                  75                  80

Glu Asp Phe Ala Phe Tyr Phe Cys Gln Gln Tyr Asn Asn Trp Pro Pro
                85                  90                  95

Phe Thr Phe Gly Pro Gly Thr Lys Val Asp Ile Lys
            100                 105
```

<210> SEQ ID NO 21
<211> LENGTH: 351
<212> TYPE: DNA
<213> ORGANISM: Artificial Sequence
<220> FEATURE:
<223> OTHER INFORMATION: Synthetic

<400> SEQUENCE: 21
gaggtgcagc tggtggagtc tgggggaggc ttggtacagc ctggggggtc cctgagactc 60
tcctgtgcag cctctggatt tactctaagt agttacgaca tgcactgggt ccgccaagct 120
acaggaaaag gtctggagtg ggtctcagct attggttcta ccggtgacac atactatcca 180
ggctccgtga agggccgatt caccatctcc agagaaaatg ccaagaactc cttgtatctt 240
caaatgaaca gcctgagagc cggggacacg gctgtgtatt actgtgtaag agaggggtgg 300
gaggtaccct ttgactactg gggccaggga accctggtca ccgtctcctc a 351

<210> SEQ ID NO 22
<211> LENGTH: 117
<212> TYPE: PRT
<213> ORGANISM: Artificial Sequence
<220> FEATURE:
<223> OTHER INFORMATION: Synthetic

<400> SEQUENCE: 22

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45
```

```
Ser Ala Ile Gly Ser Thr Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Val
                85                  90                  95

Arg Glu Gly Trp Glu Val Pro Phe Asp Tyr Trp Gly Gln Gly Thr Leu
            100                 105                 110

Val Thr Val Ser Ser
        115
```

<210> SEQ ID NO 23
<211> LENGTH: 324
<212> TYPE: DNA
<213> ORGANISM: Artificial Sequence
<220> FEATURE:
<223> OTHER INFORMATION: Synthetic

<400> SEQUENCE: 23

```
gaaatagtga tgacgcagtc tccagccacc ctgtctgtgt ctccagggga aagagccacc      60

ctctcctgca gggccagtca gagtgttagc agcaacttag cctggtacca gcagaaacct     120

ggccaggctc ccaggctcct catctatggt gcatccacca gggccactgg tatcccagcc     180

aggttcagtg gcagtgggtc tgggacagag ttcactctca ccatcagcag cctgcagtct     240

gaagattttg cagtttatta ctgtcagcag tataataact ggcctccatt cactttcggc     300

cctgggacca aagtggatat caaa                                            324
```

<210> SEQ ID NO 24
<211> LENGTH: 108
<212> TYPE: PRT
<213> ORGANISM: Artificial Sequence
<220> FEATURE:
<223> OTHER INFORMATION: Synthetic

<400> SEQUENCE: 24

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Phe Thr Phe Gly Pro Gly Thr Lys Val Asp Ile Lys
            100                 105
```

<210> SEQ ID NO 25
<211> LENGTH: 342
<212> TYPE: DNA
<213> ORGANISM: Artificial Sequence
<220> FEATURE:
<223> OTHER INFORMATION: Synthetic

<400> SEQUENCE: 25

-continued

```
caggtgcagc tggtgcagtc tgggggaggc gtggtccagc ctgggaggtc cctgagactc     60

tcctgtgcag cgtctggatt caccttcagt agctatggca tgcactgggt ccgccaggct    120

ccaggcaagg ggctggagtg ggtggcgttt ataggatttg atggaagtaa tatacattat    180

ggagactccg tgaggggccg aatcatcata tccagagaca attccgagaa cacgttgtat    240

ctggaaatga acagcctgag agccgaggac acggcaatgt actattgtgc gagagagaag    300

ggtttagact ggggccaggg aaccacggtc accgtctcct ca                       342
```

<210> SEQ ID NO 26
<211> LENGTH: 114
<212> TYPE: PRT
<213> ORGANISM: Artificial Sequence
<220> FEATURE:
<223> OTHER INFORMATION: Synthetic

<400> SEQUENCE: 26

```
Gln Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Gly Phe Asp Gly Ser Asn Ile His Tyr Gly Asp Ser Val
    50                  55                  60

Arg Gly Arg Ile Ile Ile Ser Arg Asp Asn Ser Glu Asn Thr Leu Tyr
65                  70                  75                  80

Leu Glu Met Asn Ser Leu Arg Ala Glu Asp Thr Ala Met Tyr Tyr Cys
                85                  90                  95

Ala Arg Glu Lys Gly Leu Asp Trp Gly Gln Gly Thr Thr Val Thr Val
            100                 105                 110

Ser Ser
```

<210> SEQ ID NO 27
<211> LENGTH: 24
<212> TYPE: DNA
<213> ORGANISM: Artificial Sequence
<220> FEATURE:
<223> OTHER INFORMATION: Synthetic

<400> SEQUENCE: 27

```
ggattcacct tcagtagcta tggc                                            24
```

<210> SEQ ID NO 28
<211> LENGTH: 8
<212> TYPE: PRT
<213> ORGANISM: Artificial Sequence
<220> FEATURE:
<223> OTHER INFORMATION: Synthetic

<400> SEQUENCE: 28

```
Gly Phe Thr Phe Ser Ser Tyr Gly
 1               5
```

<210> SEQ ID NO 29
<211> LENGTH: 24
<212> TYPE: DNA
<213> ORGANISM: Artificial Sequence
<220> FEATURE:
<223> OTHER INFORMATION: Synthetic

<400> SEQUENCE: 29
ataggatttg atggaagtaa tata 24

<210> SEQ ID NO 30
<211> LENGTH: 8
<212> TYPE: PRT
<213> ORGANISM: Artificial Sequence
<220> FEATURE:
<223> OTHER INFORMATION: Synthetic

<400> SEQUENCE: 30

Ile Gly Phe Asp Gly Ser Asn Ile
1 5

<210> SEQ ID NO 31
<211> LENGTH: 21
<212> TYPE: DNA
<213> ORGANISM: Artificial Sequence
<220> FEATURE:
<223> OTHER INFORMATION: Synthetic

<400> SEQUENCE: 31
gcgagagaga agggtttaga c 21

<210> SEQ ID NO 32
<211> LENGTH: 7
<212> TYPE: PRT
<213> ORGANISM: Artificial Sequence
<220> FEATURE:
<223> OTHER INFORMATION: Synthetic

<400> SEQUENCE: 32

Ala Arg Glu Lys Gly Leu Asp
1 5

<210> SEQ ID NO 33
<211> LENGTH: 321
<212> TYPE: DNA
<213> ORGANISM: Artificial Sequence
<220> FEATURE:
<223> OTHER INFORMATION: Synthetic

<400> SEQUENCE: 33
gccatccaga tgacccagtc tccttccacc ctgtctgcat ctgtaggaga cagagtcacc 60
atcacttgcc gggccagtca gagtattagt agctggttgg cctggtatca gcagaaacca 120
gggaaagccc ctaagctcct gatctataag gcgtctagtt tagaaagtgg ggtcccatca 180
aggttcagcg gcagtggatc tgggacagaa ttcactctca ccatcagcag cctgcagcct 240
gatgattttg caacttatta ctgccaacag tataatagtt attacacttt tggccagggg 300
accaaggtgg aaatcaaacg a 321

<210> SEQ ID NO 34
<211> LENGTH: 107
<212> TYPE: PRT
<213> ORGANISM: Artificial Sequence
<220> FEATURE:
<223> OTHER INFORMATION: Synthetic

<400> SEQUENCE: 34

Ala Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

```
Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Tyr Thr
                85                  90                  95

Phe Gly Gln Gly Thr Lys Val Glu Ile Lys Arg
            100                 105


<210> SEQ ID NO 35
<211> LENGTH: 18
<212> TYPE: DNA
<213> ORGANISM: Artificial Sequence
<220> FEATURE:
<223> OTHER INFORMATION: Synthetic

<400> SEQUENCE: 35

cagagtatta gtagctgg                                                18


<210> SEQ ID NO 36
<211> LENGTH: 6
<212> TYPE: PRT
<213> ORGANISM: Artificial Sequence
<220> FEATURE:
<223> OTHER INFORMATION: Synthetic

<400> SEQUENCE: 36

Gln Ser Ile Ser Ser Trp
 1               5


<210> SEQ ID NO 37
<211> LENGTH: 9
<212> TYPE: DNA
<213> ORGANISM: Artificial Sequence
<220> FEATURE:
<223> OTHER INFORMATION: Synthetic

<400> SEQUENCE: 37

aaggcgtct                                                           9


<210> SEQ ID NO 38
<211> LENGTH: 3
<212> TYPE: PRT
<213> ORGANISM: Artificial Sequence
<220> FEATURE:
<223> OTHER INFORMATION: Synthetic

<400> SEQUENCE: 38

Lys Ala Ser
 1


<210> SEQ ID NO 39
<211> LENGTH: 24
<212> TYPE: DNA
<213> ORGANISM: Artificial Sequence
<220> FEATURE:
<223> OTHER INFORMATION: Synthetic

<400> SEQUENCE: 39

caacagtata atagttatta cact                                         24


<210> SEQ ID NO 40
```

<211> LENGTH: 8
<212> TYPE: PRT
<213> ORGANISM: Artificial Sequence
<220> FEATURE:
<223> OTHER INFORMATION: Synthetic

<400> SEQUENCE: 40

Gln Gln Tyr Asn Ser Tyr Tyr Thr
1 5

<210> SEQ ID NO 41
<211> LENGTH: 342
<212> TYPE: DNA
<213> ORGANISM: Artificial Sequence
<220> FEATURE:
<223> OTHER INFORMATION: Synthetic

<400> SEQUENCE: 41
caggtgcagc tggtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcgttt ataggatttg atggaagtaa tatacattat 180
ggagactccg tgaggggccg aatcatcata tccagagaca attccgagaa cacgttgtat 240
ctggaaatga acagcctgag agccgaggac acggcaatgt actattgtgc gagagagaag 300
ggtttagact ggggccaggg aaccctggtc accgtctcct ca 342

<210> SEQ ID NO 42
<211> LENGTH: 114
<212> TYPE: PRT
<213> ORGANISM: Artificial Sequence
<220> FEATURE:
<223> OTHER INFORMATION: Synthetic

<400> SEQUENCE: 42

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Phe Ile Gly Phe Asp Gly Ser Asn Ile His Tyr Gly Asp Ser Val
50 55 60

Arg Gly Arg Ile Ile Ile Ser Arg Asp Asn Ser Glu Asn Thr Leu Tyr
65 70 75 80

Leu Glu Met Asn Ser Leu Arg Ala Glu Asp Thr Ala Met Tyr Tyr Cys
85 90 95

Ala Arg Glu Lys Gly Leu Asp Trp Gly Gln Gly Thr Leu Val Thr Val
100 105 110

Ser Ser

<210> SEQ ID NO 43
<211> LENGTH: 318
<212> TYPE: DNA
<213> ORGANISM: Artificial Sequence
<220> FEATURE:
<223> OTHER INFORMATION: Synthetic

<400> SEQUENCE: 43
gacatccaga tgacccagtc tccttccacc ctgtctgcat ctgtaggaga cagagtcacc 60
atcacttgcc gggccagtca gagtattagt agctggttgg cctggtatca gcagaaacca 120
gggaaagccc ctaagctcct gatctataag gcgtctagtt tagaaagtgg ggtcccatca 180
aggttcagcg gcagtggatc tgggacagaa ttcactctca ccatcagcag cctgcagcct 240
gatgattttg caacttatta ctgccaacag tataatagtt attacacttt tggccagggg 300
accaagctgg agatcaaa 318

<210> SEQ ID NO 44
<211> LENGTH: 106
<212> TYPE: PRT
<213> ORGANISM: Artificial Sequence
<220> FEATURE:
<223> OTHER INFORMATION: Synthetic

<400> SEQUENCE: 44

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Lys Pro Gly Lys Ala Pro Lys Leu Leu Ile
35 40 45

Tyr Lys Ala Ser Ser Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Tyr Asn Ser Tyr Tyr Thr
85 90 95

Phe Gly Gln Gly Thr Lys Leu Glu Ile Lys
100 105

<210> SEQ ID NO 45
<211> LENGTH: 342
<212> TYPE: DNA
<213> ORGANISM: Artificial Sequence
<220> FEATURE:
<223> OTHER INFORMATION: Synthetic

<400> SEQUENCE: 45
caggtgcagc tggtggagtc tgggggaggc gtggtccagc ctgggaggtc cctgagactc 60
tcctgtgcag cctctggatt caccttcagt agctatggca tgcactgggt ccgccaggct 120
ccaggcaagg ggctggagtg ggtggcagtt ataggatttg atggaagtaa tatatactat 180
gcagactccg tgaagggccg attcaccatc tccagagaca attccaagaa cacgctgtat 240
ctgcaaatga acagcctgag agctgaggac acggctgtgt attactgtgc gagagagaag 300
ggtttagact ggggccaggg aaccctggtc accgtctcct ca 342

<210> SEQ ID NO 46
<211> LENGTH: 114
<212> TYPE: PRT
<213> ORGANISM: Artificial Sequence
<220> FEATURE:
<223> OTHER INFORMATION: Synthetic

<400> SEQUENCE: 46

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val

```
        35                  40                  45

Ala Val Ile Gly Phe Asp Gly Ser Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Lys Gly Leu Asp Trp Gly Gln Gly Thr Leu Val Thr Val
            100                 105                 110

Ser Ser


<210> SEQ ID NO 47
<211> LENGTH: 319
<212> TYPE: DNA
<213> ORGANISM: Artificial Sequence
<220> FEATURE:
<223> OTHER INFORMATION: Synthetic

<400> SEQUENCE: 47

gacatccaga tgacccagtc tccttccacc ctgtctgcat ctgtaggaga cagagtcacc      60

atcacttgcc gggccagtca gagtattagt agctggttgg cctggtatca gcagaaacca     120

gggaaagccc ctaagctcct gatctataag gcgtctagtt tagaaagtgg ggtcccatca     180

aggttcagcg gcagtggatc tgggacagaa ttcactctca ccatcagcag cctgcagcct     240

gatgattttg caacttatta ctgccaacag tataatagtt attacacttt tggccagggg     300

accaagctgg agatcaaac                                                  319


<210> SEQ ID NO 48
<211> LENGTH: 106
<212> TYPE: PRT
<213> ORGANISM: Artificial Sequence
<220> FEATURE:
<223> OTHER INFORMATION: Synthetic

<400> SEQUENCE: 48

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Tyr Thr
                85                  90                  95

Phe Gly Gln Gly Thr Lys Leu Glu Ile Lys
            100                 105


<210> SEQ ID NO 49
<211> LENGTH: 342
<212> TYPE: DNA
<213> ORGANISM: Artificial Sequence
<220> FEATURE:
<223> OTHER INFORMATION: Synthetic

<400> SEQUENCE: 49
```

-continued

```
caggtgcagc tgcaggagtc tgggggaggc gtggtccagc ctgggaggtc cctgagactc      60

tcctgtgcag cgtctggatt caccttcagt agctatggca tgcactgggt ccgccaggct     120

ccaggcaagg ggctggagtg ggtggcgttt ataggatttg atggaagtaa tatatattat     180

ggagactccg tgaggggccg aatcatcata tccagagaca attccgagaa cacgttgtat     240

ctggaaatga acagcctgag agccgaggac acggcagtgt attattgtgc gagagagaag     300

ggtttagact ggggccaggg aaccctggtc actgtctcct ca                        342


<210> SEQ ID NO 50
<211> LENGTH: 114
<212> TYPE: PRT
<213> ORGANISM: Artificial Sequence
<220> FEATURE:
<223> OTHER INFORMATION: Synthetic

<400> SEQUENCE: 50

Gln Val Gln Leu Gln Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Gly Phe Asp Gly Ser Asn Ile Tyr Tyr Gly Asp Ser Val
    50                  55                  60

Arg Gly Arg Ile Ile Ile Ser Arg Asp Asn Ser Glu Asn Thr Leu Tyr
65                  70                  75                  80

Leu Glu Met Asn Ser Leu Arg Ala Glu Asp Thr Ala Val Tyr Tyr Cys
                85                  90                  95

Ala Arg Glu Lys Gly Leu Asp Trp Gly Gln Gly Thr Leu Val Thr Val
            100                 105                 110

Ser Ser


<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51

ggattcacct tcagtagcta tggc                                             24


<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

Gly Phe Thr Phe Ser Ser Tyr Gly
 1               5


<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53
```

ataggatttg atggaagtaa tata 24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Ile Gly Phe Asp Gly Ser Asn Ile
1 5

<210> SEQ ID NO 55
<211> LENGTH: 21
<212> TYPE: DNA
<213> ORGANISM: Artificial Sequence
<220> FEATURE:
<223> OTHER INFORMATION: Synthetic

<400> SEQUENCE: 55
gcgagagaga agggtttaga c 21

<210> SEQ ID NO 56
<211> LENGTH: 7
<212> TYPE: PRT
<213> ORGANISM: Artificial Sequence
<220> FEATURE:
<223> OTHER INFORMATION: Synthetic

<400> SEQUENCE: 56

Ala Arg Glu Lys Gly Leu Asp
1 5

<210> SEQ ID NO 57
<211> LENGTH: 342
<212> TYPE: DNA
<213> ORGANISM: Artificial Sequence
<220> FEATURE:
<223> OTHER INFORMATION: Synthetic

<400> SEQUENCE: 57
gccatccaga tgacccagtc tccagactcc ctggctgtgt ctctgggcga gagggccacc 60
atcaactgca agtccagcca gagtgttttt cacacctcca acaataagaa ctacttagtt 120
tggtatcagc agaaaccagg acagcctcct aagttgctcc tttactgggc ctctacccgg 180
gaatccgggg tccctgaccg attcagtggc agcgggtctg ggacagattt cactctcacc 240
atcagcagcc tgcaggctga agatgtggca aattattact gtcaccaata ttacagtatt 300
ccgtggacgt tcggccaagg gaccaaggtg gagatcaaac ga 342

<210> SEQ ID NO 58
<211> LENGTH: 114
<212> TYPE: PRT
<213> ORGANISM: Artificial Sequence
<220> FEATURE:
<223> OTHER INFORMATION: Synthetic

<400> SEQUENCE: 58

Ala Ile Gln Met Thr Gln Ser Pro Asp Ser Leu Ala Val Ser Leu Gly
1 5 10 15

Glu Arg Ala Thr Ile Asn Cys Lys Ser Ser Gln Ser Val Phe His Thr
20 25 30

```
Ser Asn Asn Lys Asn Tyr Leu Val Trp Tyr Gln Gln Lys Pro Gly Gln
        35                  40                  45

Pro Pro Lys Leu Leu Leu Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Asn Tyr Tyr Cys His Gln
                85                  90                  95

Tyr Tyr Ser Ile Pro Trp Thr Phe Gly Gln Gly Thr Lys Val Glu Ile
            100                 105                 110

Lys Arg


<210> SEQ ID NO 59
<211> LENGTH: 36
<212> TYPE: DNA
<213> ORGANISM: Artificial Sequence
<220> FEATURE:
<223> OTHER INFORMATION: Synthetic

<400> SEQUENCE: 59

cagagtgttt ttcacacctc caacaataag aactac                              36


<210> SEQ ID NO 60
<211> LENGTH: 12
<212> TYPE: PRT
<213> ORGANISM: Artificial Sequence
<220> FEATURE:
<223> OTHER INFORMATION: Synthetic

<400> SEQUENCE: 60

Gln Ser Val Phe His Thr Ser Asn Asn Lys Asn Tyr
 1               5                  10


<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61

tgggcctct                                                             9


<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Trp Ala Ser
 1


<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63

caccaatatt acagtattcc gtggacg                                        27
```

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

His Gln Tyr Tyr Ser Ile Pro Trp Thr
1               5

<210> SEQ ID NO 65
<211> LENGTH: 342
<212> TYPE: DNA
<213> ORGANISM: Artificial Sequence
<220> FEATURE:
<223> OTHER INFORMATION: Synthetic

<400> SEQUENCE: 65
caggtgcagc tggtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcgttt ataggatttg atggaagtaa tatatattat 180
ggagactccg tgaggggccg aatcatcata tccagagaca attccgagaa cacgttgtat 240
ctggaaatga acagcctgag agccgaggac acggcagtgt attattgtgc gagagagaag 300
ggtttagact ggggccaggg aaccctggtc accgtctcct ca 342

<210> SEQ ID NO 66
<211> LENGTH: 114
<212> TYPE: PRT
<213> ORGANISM: Artificial Sequence
<220> FEATURE:
<223> OTHER INFORMATION: Synthetic

<400> SEQUENCE: 66

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Gly Phe Asp Gly Ser Asn Ile Tyr Tyr Gly Asp Ser Val
    50                  55                  60

Arg Gly Arg Ile Ile Ile Ser Arg Asp Asn Ser Glu Asn Thr Leu Tyr
65                  70                  75                  80

Leu Glu Met Asn Ser Leu Arg Ala Glu Asp Thr Ala Val Tyr Tyr Cys
                85                  90                  95

Ala Arg Glu Lys Gly Leu Asp Trp Gly Gln Gly Thr Leu Val Thr Val
            100                 105                 110

Ser Ser

<210> SEQ ID NO 67
<211> LENGTH: 339
<212> TYPE: DNA
<213> ORGANISM: Artificial Sequence
<220> FEATURE:
<223> OTHER INFORMATION: Synthetic

<400> SEQUENCE: 67
gacatcgtga tgacccagtc tccagactcc ctggctgtgt ctctgggcga gagggccacc 60

```
atcaactgca agtccagcca gagtgttttt cacacctcca acaataagaa ctacttagtt    120

tggtatcagc agaaaccagg acagcctcct aagttgctcc tttactgggc ctctacccgg    180

gaatccgggg tccctgaccg attcagtggc agcgggtctg ggacagattt cactctcacc    240

atcagcagcc tgcaggctga agatgtggca aattattact gtcaccaata ttacagtatt    300

ccgtggacgt tcggccaagg gaccaaggtg gaaatcaaa                          339
```

```
<210> SEQ ID NO 68
<211> LENGTH: 113
<212> TYPE: PRT
<213> ORGANISM: Artificial Sequence
<220> FEATURE:
<223> OTHER INFORMATION: Synthetic

<400> SEQUENCE: 68

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Phe His Thr
            20                  25                  30

Ser Asn Asn Lys Asn Tyr Leu Val Trp Tyr Gln Gln Lys Pro Gly Gln
        35                  40                  45

Pro Pro Lys Leu Leu Leu Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Asn Tyr Tyr Cys His Gln
                85                  90                  95

Tyr Tyr Ser Ile Pro Trp Thr Phe Gly Gln Gly Thr Lys Val Glu Ile
            100                 105                 110

Lys
```

```
<210> SEQ ID NO 69
<211> LENGTH: 342
<212> TYPE: DNA
<213> ORGANISM: Artificial Sequence
<220> FEATURE:
<223> OTHER INFORMATION: Synthetic

<400> SEQUENCE: 69

caggtgcagc tggtggagtc tgggggaggc gtggtccagc ctgggaggtc cctgagactc     60

tcctgtgcag cctctggatt caccttcagt agctatggca tgcactgggt ccgccaggct    120

ccaggcaagg ggctggagtg ggtggcagtt ataggatttg atggaagtaa tatatactat    180

gcagactccg tgaagggccg attcaccatc tccagagaca attccaagaa cacgctgtat    240

ctgcaaatga acagcctgag agctgaggac acggctgtgt attactgtgc gagagagaag    300

ggtttagact ggggccaggg aaccctggtc accgtctcct ca                       342
```

```
<210> SEQ ID NO 70
<211> LENGTH: 114
<212> TYPE: PRT
<213> ORGANISM: Artificial Sequence
<220> FEATURE:
<223> OTHER INFORMATION: Synthetic

<400> SEQUENCE: 70

Gln Val Gln Leu Val Glu Ser Gly Gly Gly Val Val Gln Pro Gly Arg
 1               5                  10                  15
```

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Gly Phe Asp Gly Ser Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Lys Gly Leu Asp Trp Gly Gln Gly Thr Leu Val Thr Val
            100                 105                 110

Ser Ser


<210> SEQ ID NO 71
<211> LENGTH: 339
<212> TYPE: DNA
<213> ORGANISM: Artificial Sequence
<220> FEATURE:
<223> OTHER INFORMATION: Synthetic

<400> SEQUENCE: 71

gacatcgtga tgacccagtc tccagactcc ctggctgtgt ctctgggcga gagggccacc      60

atcaactgca agtccagcca gagtgttttt cacacctcca acaataagaa ctacttagct     120

tggtaccagc agaaaccagg acagcctcct aagctgctca tttactgggc ctctacccgg     180

gaatccgggg tccctgaccg attcagtggc agcgggtctg ggacagattt cactctcacc     240

atcagcagcc tgcaggctga agatgtggca gtttattact gtcaccaata ttacagtatt     300

ccgtggacgt tcggccaagg gaccaaggtg gaaatcaaa                            339


<210> SEQ ID NO 72
<211> LENGTH: 113
<212> TYPE: PRT
<213> ORGANISM: Artificial Sequence
<220> FEATURE:
<223> OTHER INFORMATION: Synthetic

<400> SEQUENCE: 72

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Phe His Thr
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Tyr Ser Ile Pro Trp Thr Phe Gly Gln Gly Thr Lys Val Glu Ile
            100                 105                 110

Lys


<210> SEQ ID NO 73
<211> LENGTH: 354
<212> TYPE: DNA
```

<213> ORGANISM: Artificial Sequence
<220> FEATURE:
<223> OTHER INFORMATION: Synthetic

<400> SEQUENCE: 73
gaagtgcagc tggtgcagtc tgggggaggc ttggtacagc ctggggggtc cctgagactc 60
tcctgtgcag cctctggatt cacctttaac aactatgcca tgaactgggt ccgccaggct 120
ccaggaaagg gactggactg ggtctcaact attagtggta gcggtggtac tacaaactac 180
gcagactccg tgaagggccg tttcattatt tcccgagaca gttccaaaca cacgctgtat 240
ctgcaaatga acagcctgag agccgaggac acggccgtat attactgtgc gaaagattct 300
aactggggaa atttcgatct ctggggccgt ggcaccacgg tcactgtctc ctca 354

<210> SEQ ID NO 74
<211> LENGTH: 118
<212> TYPE: PRT
<213> ORGANISM: Artificial Sequence
<220> FEATURE:
<223> OTHER INFORMATION: Synthetic

<400> SEQUENCE: 74

Glu Val Gln Leu Val Gln Ser Gly Gly Gly Leu Val Gln Pro Gly Gly
1 5 10 15

Ser Leu Arg Leu Ser Cys Ala Ala Ser Gly Phe Thr Phe Asn Asn Tyr
20 25 30

Ala Met Asn Trp Val Arg Gln Ala Pro Gly Lys Gly Leu Asp Trp Val
35 40 45

Ser Thr Ile Ser Gly Ser Gly Gly Thr Thr Asn Tyr Ala Asp Ser Val
50 55 60

Lys Gly Arg Phe Ile Ile Ser Arg Asp Ser Ser Lys His Thr Leu Tyr
65 70 75 80

Leu Gln Met Asn Ser Leu Arg Ala Glu Asp Thr Ala Val Tyr Tyr Cys
85 90 95

Ala Lys Asp Ser Asn Trp Gly Asn Phe Asp Leu Trp Gly Arg Gly Thr
100 105 110

Thr Val Thr Val Ser Ser
115

<210> SEQ ID NO 75
<211> LENGTH: 24
<212> TYPE: DNA
<213> ORGANISM: Artificial Sequence
<220> FEATURE:
<223> OTHER INFORMATION: Synthetic

<400> SEQUENCE: 75
ggattcacct ttaacaacta tgcc 24

<210> SEQ ID NO 76
<211> LENGTH: 8
<212> TYPE: PRT
<213> ORGANISM: Artificial Sequence
<220> FEATURE:
<223> OTHER INFORMATION: Synthetic

<400> SEQUENCE: 76

Gly Phe Thr Phe Asn Asn Tyr Ala
1 5

<210> SEQ ID NO 77

<211> LENGTH: 24
<212> TYPE: DNA
<213> ORGANISM: Artificial Sequence
<220> FEATURE:
<223> OTHER INFORMATION: Synthetic

<400> SEQUENCE: 77
attagtggta gcggtggtac taca 24

<210> SEQ ID NO 78
<211> LENGTH: 8
<212> TYPE: PRT
<213> ORGANISM: Artificial Sequence
<220> FEATURE:
<223> OTHER INFORMATION: Synthetic

<400> SEQUENCE: 78

Ile Ser Gly Ser Gly Gly Thr Thr
1 5

<210> SEQ ID NO 79
<211> LENGTH: 33
<212> TYPE: DNA
<213> ORGANISM: Artificial Sequence
<220> FEATURE:
<223> OTHER INFORMATION: Synthetic

<400> SEQUENCE: 79
gcgaaagatt ctaactgggg aaatttcgat ctc 33

<210> SEQ ID NO 80
<211> LENGTH: 11
<212> TYPE: PRT
<213> ORGANISM: Artificial Sequence
<220> FEATURE:
<223> OTHER INFORMATION: Synthetic

<400> SEQUENCE: 80

Ala Lys Asp Ser Asn Trp Gly Asn Phe Asp Leu
1 5 10

<210> SEQ ID NO 81
<211> LENGTH: 342
<212> TYPE: DNA
<213> ORGANISM: Artificial Sequence
<220> FEATURE:
<223> OTHER INFORMATION: Synthetic

<400> SEQUENCE: 81
gacatccaga tgacccagtc tccagactcc ctggctgtgt ctctgggcga gagggccacc 60
atcaactgca agtccagcca gagtgtttta tacaggtcca acaataggaa cttcttaggt 120
tggtaccagc agaaaccagg gcagcctcct aatctactca tttactgggc atctacccgg 180
gaatccgggg tccctgaccg attcagtggc agcgggtctg ggacagattt cactctcacc 240
atcagcagcc tgcaggctga agatgtggca gtttattact gtcaacaata ttatactact 300
ccgtacactt ttggccaggg gaccaaggtg gaaatcaaac ga 342

<210> SEQ ID NO 82
<211> LENGTH: 114
<212> TYPE: PRT
<213> ORGANISM: Artificial Sequence
<220> FEATURE:
<223> OTHER INFORMATION: Synthetic

<400> SEQUENCE: 82

```
Asp Ile Gln Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Arg
            20                  25                  30

Ser Asn Asn Arg Asn Phe Leu Gly Trp Tyr Gln Gln Lys Pro Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Tyr Thr Phe Gly Gln Gly Thr Lys Val Glu Ile
            100                 105                 110

Lys Arg


<210> SEQ ID NO 83
<211> LENGTH: 36
<212> TYPE: DNA
<213> ORGANISM: Artificial Sequence
<220> FEATURE:
<223> OTHER INFORMATION: Synthetic

<400> SEQUENCE: 83

cagagtgttt tatacaggtc caacaatagg aacttc                                36


<210> SEQ ID NO 84
<211> LENGTH: 12
<212> TYPE: PRT
<213> ORGANISM: Artificial Sequence
<220> FEATURE:
<223> OTHER INFORMATION: Synthetic

<400> SEQUENCE: 84

Gln Ser Val Leu Tyr Arg Ser Asn Asn Arg Asn Phe
 1               5                  10


<210> SEQ ID NO 85
<211> LENGTH: 9
<212> TYPE: DNA
<213> ORGANISM: Artificial Sequence
<220> FEATURE:
<223> OTHER INFORMATION: Synthetic

<400> SEQUENCE: 85

tgggcatct                                                               9


<210> SEQ ID NO 86
<211> LENGTH: 3
<212> TYPE: PRT
<213> ORGANISM: Artificial Sequence
<220> FEATURE:
<223> OTHER INFORMATION: Synthetic

<400> SEQUENCE: 86

Trp Ala Ser
 1


<210> SEQ ID NO 87
<211> LENGTH: 27
<212> TYPE: DNA
<213> ORGANISM: Artificial Sequence
```

<220> FEATURE:
<223> OTHER INFORMATION: Synthetic

<400> SEQUENCE: 87
caacaatatt atactactcc gtacact 27

<210> SEQ ID NO 88
<211> LENGTH: 9
<212> TYPE: PRT
<213> ORGANISM: Artificial Sequence
<220> FEATURE:
<223> OTHER INFORMATION: Synthetic

<400> SEQUENCE: 88

Gln Gln Tyr Tyr Thr Thr Pro Tyr Thr
1 5

<210> SEQ ID NO 89
<211> LENGTH: 354
<212> TYPE: DNA
<213> ORGANISM: Artificial Sequence
<220> FEATURE:
<223> OTHER INFORMATION: Synthetic

<400> SEQUENCE: 89
gaggtgcagc tggtggagtc tgggggaggc ttggtacagc ctggggggtc cctgagactc 60
tcctgtgcag cctctggatt cacctttaac aactatgcca tgaactgggt ccgccaggct 120
ccaggaaagg gactggactg ggtctcaact attagtggta gcggtggtac tacaaactac 180
gcagactccg tgaagggccg tttcattatt tcccgagaca gttccaaaca cacgctgtat 240
ctgcaaatga acagcctgag agccgaggac acggccgtat attactgtgc gaaagattct 300
aactggggaa atttcgatct ctggggccgt ggcaccctgg tcactgtctc ctca 354

<210> SEQ ID NO 90
<211> LENGTH: 118
<212> TYPE: PRT
<213> ORGANISM: Artificial Sequence
<220> FEATURE:
<223> OTHER INFORMATION: Synthetic

<400> SEQUENCE: 90

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Asn Asn Tyr
20 25 30

Ala Met Asn Trp Val Arg Gln Ala Pro Gly Lys Gly Leu Asp Trp Val
35 40 45

Ser Thr Ile Ser Gly Ser Gly Gly Thr Thr Asn Tyr Ala Asp Ser Val
50 55 60

Lys Gly Arg Phe Ile Ile Ser Arg Asp Ser Ser Lys His Thr Leu Tyr
65 70 75 80

Leu Gln Met Asn Ser Leu Arg Ala Glu Asp Thr Ala Val Tyr Tyr Cys
85 90 95

Ala Lys Asp Ser Asn Trp Gly Asn Phe Asp Leu Trp Gly Arg Gly Thr
100 105 110

Leu Val Thr Val Ser Ser
115

<210> SEQ ID NO 91
<211> LENGTH: 339

<212> TYPE: DNA
<213> ORGANISM: Artificial Sequence
<220> FEATURE:
<223> OTHER INFORMATION: Synthetic

<400> SEQUENCE: 91
gacatcgtga tgacccagtc tccagactcc ctggctgtgt ctctgggcga gagggccacc 60
atcaactgca agtccagcca gagtgtttta tacaggtcca acaataggaa cttcttaggt 120
tggtaccagc agaaaccagg gcagcctcct aatctactca tttactgggc atctacccgg 180
gaatccgggg tccctgaccg attcagtggc agcgggtctg ggacagattt cactctcacc 240
atcagcagcc tgcaggctga agatgtggca gtttattact gtcaacaata ttatactact 300
ccgtacactt ttggccaggg gaccaagctg gagatcaaa 339

<210> SEQ ID NO 92
<211> LENGTH: 113
<212> TYPE: PRT
<213> ORGANISM: Artificial Sequence
<220> FEATURE:
<223> OTHER INFORMATION: Synthetic

<400> SEQUENCE: 92

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Val Leu Tyr Arg
20 25 30

Ser Asn Asn Arg Asn Phe Leu Gly Trp Tyr Gln Gln Lys Pro Gly Gln
35 40 45

Pro Pro Asn Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Tyr Tyr Thr Thr Pro Tyr Thr Phe Gly Gln Gly Thr Lys Leu Glu Ile
100 105 110

Lys

<210> SEQ ID NO 93
<211> LENGTH: 354
<212> TYPE: DNA
<213> ORGANISM: Artificial Sequence
<220> FEATURE:
<223> OTHER INFORMATION: Synthetic

<400> SEQUENCE: 93
gaggtgcagc tggtggagtc tgggggaggc ttggtacagc ctggggggtc cctgagactc 60
tcctgtgcag cctctggatt cacctttaac aactatgcca tgagctgggt ccgccaggct 120
ccagggaagg ggctggagtg ggtctcagct attagtggta gcggtggtac tacatactac 180
gcagactccg tgaagggccg gttcaccatc tccagagaca attccaagaa cacgctgtat 240
ctgcaaatga acagcctgag agccgaggac acggccgtat attactgtgc gaaagattct 300
aactggggaa atttcgatct ctggggccgt ggcaccctgg tcactgtctc ctca 354

<210> SEQ ID NO 94
<211> LENGTH: 118
<212> TYPE: PRT
<213> ORGANISM: Artificial Sequence
<220> FEATURE:
<223> OTHER INFORMATION: Synthetic

<400> SEQUENCE: 94

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Asn Asn Tyr
20 25 30

Ala Met Ser Trp Val Arg Gln Ala Pro Gly Lys Gly Leu Glu Trp Val
35 40 45

Ser Ala Ile Ser Gly Ser Gly Gly Thr Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Ser Asn Trp Gly Asn Phe Asp Leu Trp Gly Arg Gly Thr
100 105 110

Leu Val Thr Val Ser Ser
115

<210> SEQ ID NO 95
<211> LENGTH: 339
<212> TYPE: DNA
<213> ORGANISM: Artificial Sequence
<220> FEATURE:
<223> OTHER INFORMATION: Synthetic

<400> SEQUENCE: 95
gacatcgtga tgacccagtc tccagactcc ctggctgtgt ctctgggcga gagggccacc 60
atcaactgca agtccagcca gagtgtttta tacaggtcca acaataggaa cttcttagct 120
tggtaccagc agaaaccagg acagcctcct aagctgctca tttactgggc atctacccgg 180
gaatccgggg tccctgaccg attcagtggc agcgggtctg ggacagattt cactctcacc 240
atcagcagcc tgcaggctga agatgtggca gtttattact gtcaacaata ttatactact 300
ccgtacactt ttggccaggg gaccaagctg gagatcaaa 339

<210> SEQ ID NO 96
<211> LENGTH: 113
<212> TYPE: PRT
<213> ORGANISM: Artificial Sequence
<220> FEATURE:
<223> OTHER INFORMATION: Synthetic

<400> SEQUENCE: 96

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Val Leu Tyr Arg
20 25 30

Ser Asn Asn Arg Asn Phe Leu Ala Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

```
Tyr Tyr Thr Thr Pro Tyr Thr Phe Gly Gln Gly Thr Lys Leu Glu Ile
            100                 105                 110

Lys


<210> SEQ ID NO 97
<211> LENGTH: 351
<212> TYPE: DNA
<213> ORGANISM: Artificial Sequence
<220> FEATURE:
<223> OTHER INFORMATION: Synthetic

<400> SEQUENCE: 97

caggtgcagc tggtgcagtc tgggggaggc ttggtacagc ctggggggtc cctgagactc      60

tcctgtgcag tctctggatt caccctcagt agctacgata tgcactgggt ccgccaacct     120

acaggaaaag gtctggagtg ggtctcagct attggttcta ctggtgacac atactatcca     180

ggctccgtga agggccgatt caccatctcc agagaaaatg ccaagaactc cttgtatctt     240

caaatgaaca gcctgagagc cggggacacg gctgtgtatt actgtgcaag agagggatgg     300

gacgtaccct ttgacttctg gggccaggga accctggtca ccgtctcctc a              351


<210> SEQ ID NO 98
<211> LENGTH: 117
<212> TYPE: PRT
<213> ORGANISM: Artificial Sequence
<220> FEATURE:
<223> OTHER INFORMATION: Synthetic

<400> SEQUENCE: 98

Gln Val Gln Leu Val Gln Ser Gly Gly Gly Leu Val Gln Pro Gly Gly
1               5                   10                  15

Ser Leu Arg Leu Ser Cys Ala Val Ser Gly Phe Thr Leu Ser Ser Tyr
            20                  25                  30

Asp Met His Trp Val Arg Gln Pro Thr Gly Lys Gly Leu Glu Trp Val
        35                  40                  45

Ser Ala Ile Gly Ser Thr Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Gly Trp Asp Val Pro Phe Asp Phe Trp Gly Gln Gly Thr Leu
            100                 105                 110

Val Thr Val Ser Ser
        115


<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99

ggattcaccc tcagtagcta cgat                                             24


<210> SEQ ID NO 100
<211> LENGTH: 8
<212> TYPE: PRT
<213> ORGANISM: Artificial Sequence
<220> FEATURE:
```

<223> OTHER INFORMATION: Synthetic

<400> SEQUENCE: 100

Gly Phe Thr Leu Ser Ser Tyr Asp
1 5

<210> SEQ ID NO 101
<211> LENGTH: 21
<212> TYPE: DNA
<213> ORGANISM: Artificial Sequence
<220> FEATURE:
<223> OTHER INFORMATION: Synthetic

<400> SEQUENCE: 101
attggttcta ctggtgacac a 21

<210> SEQ ID NO 102
<211> LENGTH: 7
<212> TYPE: PRT
<213> ORGANISM: Artificial Sequence
<220> FEATURE:
<223> OTHER INFORMATION: Synthetic

<400> SEQUENCE: 102

Ile Gly Ser Thr Gly Asp Thr
1 5

<210> SEQ ID NO 103
<211> LENGTH: 33
<212> TYPE: DNA
<213> ORGANISM: Artificial Sequence
<220> FEATURE:
<223> OTHER INFORMATION: Synthetic

<400> SEQUENCE: 103
gcaagagagg gatgggacgt accctttgac ttc 33

<210> SEQ ID NO 104
<211> LENGTH: 11
<212> TYPE: PRT
<213> ORGANISM: Artificial Sequence
<220> FEATURE:
<223> OTHER INFORMATION: Synthetic

<400> SEQUENCE: 104

Ala Arg Glu Gly Trp Asp Val Pro Phe Asp Phe
1 5 10

<210> SEQ ID NO 105
<211> LENGTH: 324
<212> TYPE: DNA
<213> ORGANISM: Artificial Sequence
<220> FEATURE:
<223> OTHER INFORMATION: Synthetic

<400> SEQUENCE: 105
gccatccagt tgacccagtc tccatcctcc ctgtctgcat ctgtaggaga cagagtcacc 60
atcacttgcc gggcaagtca ggacattaga aatgatttag gctggtatca gcagaaacca 120
gggaaagccc ctaagctcct gatctatgct gcatccagtt tacaaagtgg ggtcccatca 180
cggttcagcg gcagtggatc tggcacagat ttcactctca ccatcagcag cctgcagcct 240
gaagattttg caacttatta ctgtctacaa gattacaatt acccgtggac gttcggccaa 300
gggaccaagg tggagatcaa acga 324

<210> SEQ ID NO 106
<211> LENGTH: 108
<212> TYPE: PRT
<213> ORGANISM: Artificial Sequence
<220> FEATURE:
<223> OTHER INFORMATION: Synthetic

<400> SEQUENCE: 106

```
Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys Arg
            100                 105
```

<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107
caggacatta gaaatgat 18

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

```
Gln Asp Ile Arg Asn Asp
 1               5
```

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 gctgcatcc 9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

Ala Ala Ser

1

<210> SEQ ID NO 111
<211> LENGTH: 27
<212> TYPE: DNA
<213> ORGANISM: Artificial Sequence
<220> FEATURE:
<223> OTHER INFORMATION: Synthetic

<400> SEQUENCE: 111
ctacaagatt acaattaccc gtggacg 27

<210> SEQ ID NO 112
<211> LENGTH: 9
<212> TYPE: PRT
<213> ORGANISM: Artificial Sequence
<220> FEATURE:
<223> OTHER INFORMATION: Synthetic

<400> SEQUENCE: 112

Leu Gln Asp Tyr Asn Tyr Pro Trp Thr
1 5

<210> SEQ ID NO 113
<211> LENGTH: 351
<212> TYPE: DNA
<213> ORGANISM: Artificial Sequence
<220> FEATURE:
<223> OTHER INFORMATION: Synthetic

<400> SEQUENCE: 113
gaggtgcagc tggtggagtc tgggggaggc ttggtacagc ctgggggtc cctgagactc 60 tcctgtgcag tctctggatt caccctcagt agctacgata tgcactgggt ccgccaacct 120
acaggaaaag gtctggagtg ggtctcagct attggttcta ctggtgacac atactatcca 180
ggctccgtga agggccgatt caccatctcc agagaaaatg ccaagaactc cttgtatctt 240
caaatgaaca gcctgagagc cggggacacg gctgtgtatt actgtgcaag agagggatgg 300
gacgtaccct ttgacttctg gggccaggga accctggtca ccgtctcctc a 351

<210> SEQ ID NO 114
<211> LENGTH: 117
<212> TYPE: PRT
<213> ORGANISM: Artificial Sequence
<220> FEATURE:
<223> OTHER INFORMATION: Synthetic

<400> SEQUENCE: 114

Glu Val Gln Leu Val Glu Ser Gly Gly Gly Leu Val Gln Pro Gly Gly
1 5 10 15

Ser Leu Arg Leu Ser Cys Ala Val Ser Gly Phe Thr Leu Ser Ser Tyr
20 25 30

Asp Met His Trp Val Arg Gln Pro Thr Gly Lys Gly Leu Glu Trp Val
35 40 45

Ser Ala Ile Gly Ser Thr Gly Asp Thr Tyr Tyr Pro Gly Ser Val Lys
50 55 60

Gly Arg Phe Thr Ile Ser Arg Glu Asn Ala Lys Asn Ser Leu Tyr Leu
65 70 75 80

Gln Met Asn Ser Leu Arg Ala Gly Asp Thr Ala Val Tyr Tyr Cys Ala
85 90 95

Arg Glu Gly Trp Asp Val Pro Phe Asp Phe Trp Gly Gln Gly Thr Leu
100 105 110

Val Thr Val Ser Ser
115

<210> SEQ ID NO 115
<211> LENGTH: 321
<212> TYPE: DNA
<213> ORGANISM: Artificial Sequence
<220> FEATURE:
<223> OTHER INFORMATION: Synthetic

<400> SEQUENCE: 115
gccatccaga tgacccagtc tccatcctcc ctgtctgcat ctgtaggaga cagagtcacc 60
atcacttgcc gggcaagtca ggacattaga aatgatttag gctggtatca gcagaaacca 120
gggaaagccc ctaagctcct gatctatgct gcatccagtt tacaaagtgg ggtcccatca 180
cggttcagcg gcagtggatc tggcacagat ttcactctca ccatcagcag cctgcagcct 240
gaagattttg caacttatta ctgtctacaa gattacaatt acccgtggac gttcggccaa 300
gggaccaagg tggaaatcaa a 321

<210> SEQ ID NO 116
<211> LENGTH: 107
<212> TYPE: PRT
<213> ORGANISM: Artificial Sequence
<220> FEATURE:
<223> OTHER INFORMATION: Synthetic

<400> SEQUENCE: 116

Ala Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Arg Asn Asp
20 25 30

Leu Gly Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Asp Tyr Asn Tyr Pro Trp
85 90 95

Thr Phe Gly Gln Gly Thr Lys Val Glu Ile Lys
100 105

<210> SEQ ID NO 117
<211> LENGTH: 351
<212> TYPE: DNA
<213> ORGANISM: Artificial Sequence
<220> FEATURE:
<223> OTHER INFORMATION: Synthetic

<400> SEQUENCE: 117
gaggtgcagc tggtggagtc tgggggaggc ttggtacagc ctggggggtc cctgagactc 60
tcctgtgcag cctctggatt caccctcagt agctacgata tgcactgggt ccgccaagct 120
acaggaaaag gtctggagtg ggtctcagct attggttcta ctggtgacac atactatcca 180
ggctccgtga agggccgatt caccatctcc agagaaaatg ccaagaactc cttgtatctt 240
caaatgaaca gcctgagagc cggggacacg gctgtgtatt actgtgcaag agagggatgg 300
gacgtaccct ttgacttctg gggccaggga accctggtca ccgtctcctc a 351

<210> SEQ ID NO 118
<211> LENGTH: 117
<212> TYPE: PRT
<213> ORGANISM: Artificial Sequence
<220> FEATURE:
<223> OTHER INFORMATION: Synthetic

<400> SEQUENCE: 118

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Ser Thr Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Gly Trp Asp Val Pro Phe Asp Phe Trp Gly Gln Gly Thr Leu
            100                 105                 110

Val Thr Val Ser Ser
        115
```

<210> SEQ ID NO 119
<211> LENGTH: 321
<212> TYPE: DNA
<213> ORGANISM: Artificial Sequence
<220> FEATURE:
<223> OTHER INFORMATION: Synthetic

<400> SEQUENCE: 119

```
gccatccaga tgacccagtc tccatcctcc ctgtctgcat ctgtaggaga cagagtcacc     60

atcacttgcc gggcaagtca ggacattaga aatgatttag gctggtatca gcagaaacca    120

gggaaagccc ctaagctcct gatctatgct gcatccagtt tacaaagtgg ggtcccatca    180

aggttcagcg gcagtggatc tggcacagat ttcactctca ccatcagcag cctgcagcct    240

gaagattttg caacttatta ctgtctacaa gattacaatt acccgtggac gttcggccaa    300

gggaccaagg tggaaatcaa a                                              321
```

<210> SEQ ID NO 120
<211> LENGTH: 107
<212> TYPE: PRT
<213> ORGANISM: Artificial Sequence
<220> FEATURE:
<223> OTHER INFORMATION: Synthetic

<400> SEQUENCE: 120

```
Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
```

```
65                  70                  75                  80

Glu Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys
            100                 105


<210> SEQ ID NO 121
<211> LENGTH: 384
<212> TYPE: DNA
<213> ORGANISM: Artificial Sequence
<220> FEATURE:
<223> OTHER INFORMATION: Synthetic

<400> SEQUENCE: 121

caggtgcagc tgcaggagtc ggggccagga ctggtgaagc cttcggagac cctgtccctc      60

acctgcactg tctctgggga ctccatcaat acttactact ggagctggtt ccggcagccc     120

ccagggaagg gactggagtg gattgggtat atctattata gtggaaccac caactacaac     180

ccctccctca agagtcgagt caccatatca atagacacgc ccaggaacca gttctccctg     240

aagctgatct ctgtgaccgc agcggacacg gccgtgtatt actgtgcgag agagaggatt     300

actatgattc ggggagttac cctctactat tactcctacg gtatggacgt ctggggccaa     360

gggaccacgg tcaccgtctc ctca                                            384


<210> SEQ ID NO 122
<211> LENGTH: 128
<212> TYPE: PRT
<213> ORGANISM: Artificial Sequence
<220> FEATURE:
<223> OTHER INFORMATION: Synthetic

<400> SEQUENCE: 122

Gln Val Gln Leu Gln Glu Ser Gly Pro Gly Leu Val Lys Pro Ser Glu
 1               5                  10                  15

Thr Leu Ser Leu Thr Cys Thr Val Ser Gly Asp Ser Ile Asn Thr Tyr
            20                  25                  30

Tyr Trp Ser Trp Phe Arg Gln Pro Pro Gly Lys Gly Leu Glu Trp Ile
        35                  40                  45

Gly Tyr Ile Tyr Tyr Ser Gly Thr Thr Asn Tyr Asn Pro Ser Leu Lys
    50                  55                  60

Ser Arg Val Thr Ile Ser Ile Asp Thr Pro Arg Asn Gln Phe Ser Leu
65                  70                  75                  80

Lys Leu Ile Ser Val Thr Ala Ala Asp Thr Ala Val Tyr Tyr Cys Ala
                85                  90                  95

Arg Glu Arg Ile Thr Met Ile Arg Gly Val Thr Leu Tyr Tyr Tyr Ser
            100                 105                 110

Tyr Gly Met Asp Val Trp Gly Gln Gly Thr Thr Val Thr Val Ser Ser
        115                 120                 125


<210> SEQ ID NO 123
<211> LENGTH: 24
<212> TYPE: DNA
<213> ORGANISM: Artificial Sequence
<220> FEATURE:
<223> OTHER INFORMATION: Synthetic

<400> SEQUENCE: 123

ggggactcca tcaatactta ctac                                             24
```

<210> SEQ ID NO 124
<211> LENGTH: 8
<212> TYPE: PRT
<213> ORGANISM: Artificial Sequence
<220> FEATURE:
<223> OTHER INFORMATION: Synthetic

<400> SEQUENCE: 124

Gly Asp Ser Ile Asn Thr Tyr Tyr
1 5

<210> SEQ ID NO 125
<211> LENGTH: 21
<212> TYPE: DNA
<213> ORGANISM: Artificial Sequence
<220> FEATURE:
<223> OTHER INFORMATION: Synthetic

<400> SEQUENCE: 125
atctattata gtggaaccac c 21

<210> SEQ ID NO 126
<211> LENGTH: 7
<212> TYPE: PRT
<213> ORGANISM: Artificial Sequence
<220> FEATURE:
<223> OTHER INFORMATION: Synthetic

<400> SEQUENCE: 126

Ile Tyr Tyr Ser Gly Thr Thr
1 5

<210> SEQ ID NO 127
<211> LENGTH: 66
<212> TYPE: DNA
<213> ORGANISM: Artificial Sequence
<220> FEATURE:
<223> OTHER INFORMATION: Synthetic

<400> SEQUENCE: 127
gcgagagaga ggattactat gattcgggga gttaccctct actattactc ctacggtatg 60
gacgtc 66

<210> SEQ ID NO 128
<211> LENGTH: 22
<212> TYPE: PRT
<213> ORGANISM: Artificial Sequence
<220> FEATURE:
<223> OTHER INFORMATION: Synthetic

<400> SEQUENCE: 128

Ala Arg Glu Arg Ile Thr Met Ile Arg Gly Val Thr Leu Tyr Tyr Tyr
1 5 10 15

Ser Tyr Gly Met Asp Val
20

<210> SEQ ID NO 129
<211> LENGTH: 324
<212> TYPE: DNA
<213> ORGANISM: Artificial Sequence
<220> FEATURE:
<223> OTHER INFORMATION: Synthetic

<400> SEQUENCE: 129
gacatccaga tgacccagtc tccatccttc ctgtctgcat ctgtaggaga cagagtcacc 60

```
atcacttgct gggccagtca ggacattagc agttatttag cctggtatca gcaaaaacca    120

gggatagccc ctaagctcct gatctatgct gcatccactt tgcaaagtgg ggtcccatca    180

aggttcggcg gcagtggatc tgggacagaa ttcactctca caatcagcag cctgcagcct    240

gaagattttg caacttatta ctgtcaacag cttaatagtt accctcggac gttcggccaa    300

gggaccaagg tggaaatcaa acga                                            324


<210> SEQ ID NO 130
<211> LENGTH: 108
<212> TYPE: PRT
<213> ORGANISM: Artificial Sequence
<220> FEATURE:
<223> OTHER INFORMATION: Synthetic

<400> SEQUENCE: 130

Asp Ile Gln Met Thr Gln Ser Pro Ser Phe Leu Ser Ala Ser Val Gly
 1               5                  10                  15

Asp Arg Val Thr Ile Thr Cys Trp Ala Ser Gln Asp Ile Ser Ser Tyr
            20                  25                  30

Leu Ala Trp Tyr Gln Gln Lys Pro Gly Ile Ala Pro Lys Leu Leu Ile
        35                  40                  45

Tyr Ala Ala Ser Thr Leu Gln Ser Gly Val Pro Ser Arg Phe Gly Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Arg
                85                  90                  95

Thr Phe Gly Gln Gly Thr Lys Val Glu Ile Lys Arg
            100                 105


<210> SEQ ID NO 131
<211> LENGTH: 18
<212> TYPE: DNA
<213> ORGANISM: Artificial Sequence
<220> FEATURE:
<223> OTHER INFORMATION: Synthetic

<400> SEQUENCE: 131

caggacatta gcagttat                                                    18


<210> SEQ ID NO 132
<211> LENGTH: 6
<212> TYPE: PRT
<213> ORGANISM: Artificial Sequence
<220> FEATURE:
<223> OTHER INFORMATION: Synthetic

<400> SEQUENCE: 132

Gln Asp Ile Ser Ser Tyr
 1               5


<210> SEQ ID NO 133
<211> LENGTH: 9
<212> TYPE: DNA
<213> ORGANISM: Artificial Sequence
<220> FEATURE:
<223> OTHER INFORMATION: Synthetic

<400> SEQUENCE: 133

gctgcatcc                                                               9
```

<210> SEQ ID NO 134
<211> LENGTH: 3
<212> TYPE: PRT
<213> ORGANISM: Artificial Sequence
<220> FEATURE:
<223> OTHER INFORMATION: Synthetic

<400> SEQUENCE: 134

Ala Ala Ser
1

<210> SEQ ID NO 135
<211> LENGTH: 27
<212> TYPE: DNA
<213> ORGANISM: Artificial Sequence
<220> FEATURE:
<223> OTHER INFORMATION: Synthetic

<400> SEQUENCE: 135
caacagctta atagttaccc tcggacg 27

<210> SEQ ID NO 136
<211> LENGTH: 9
<212> TYPE: PRT
<213> ORGANISM: Artificial Sequence
<220> FEATURE:
<223> OTHER INFORMATION: Synthetic

<400> SEQUENCE: 136

Gln Gln Leu Asn Ser Tyr Pro Arg Thr
1 5

<210> SEQ ID NO 137
<211> LENGTH: 384
<212> TYPE: DNA
<213> ORGANISM: Artificial Sequence
<220> FEATURE:
<223> OTHER INFORMATION: Synthetic

<400> SEQUENCE: 137
caggtgcagc tgcaggagtc ggggccagga ctggtgaagc cttcggagac cctgtccctc 60
acctgcactg tctctgggga ctccatcaat acttactact ggagctggtt ccggcagccc 120
ccagggaagg gactggagtg gattgggtat atctattata gtggaaccac caactacaac 180
ccctccctca agagtcgagt caccatatca atagacacgc ccaggaacca gttctccctg 240
aagctgatct ctgtgaccgc agcggacacg gccgtgtatt actgtgcgag agagaggatt 300
actatgattc ggggagttac cctctactat tactcctacg gtatggacgt ctggggccaa 360
gggaccacgg tcaccgtctc ctca 384

<210> SEQ ID NO 138
<211> LENGTH: 128
<212> TYPE: PRT
<213> ORGANISM: Artificial Sequence
<220> FEATURE:
<223> OTHER INFORMATION: Synthetic

<400> SEQUENCE: 138

Gln Val Gln Leu Gln Glu Ser Gly Pro Gly Leu Val Lys Pro Ser Glu
1 5 10 15

Thr Leu Ser Leu Thr Cys Thr Val Ser Gly Asp Ser Ile Asn Thr Tyr
20 25 30

Tyr Trp Ser Trp Phe Arg Gln Pro Pro Gly Lys Gly Leu Glu Trp Ile
35 40 45

```
Gly Tyr Ile Tyr Tyr Ser Gly Thr Thr Asn Tyr Asn Pro Ser Leu Lys
    50                  55                  60

Ser Arg Val Thr Ile Ser Ile Asp Thr Pro Arg Asn Gln Phe Ser Leu
65                  70                  75                  80

Lys Leu Ile Ser Val Thr Ala Ala Asp Thr Ala Val Tyr Tyr Cys Ala
                85                  90                  95

Arg Glu Arg Ile Thr Met Ile Arg Gly Val Thr Leu Tyr Tyr Tyr Ser
            100                 105                 110

Tyr Gly Met Asp Val Trp Gly Gln Gly Thr Thr Val Thr Val Ser Ser
        115                 120                 125


<210> SEQ ID NO 139
<211> LENGTH: 321
<212> TYPE: DNA
<213> ORGANISM: Artificial Sequence
<220> FEATURE:
<223> OTHER INFORMATION: Synthetic

<400> SEQUENCE: 139

gacatccaga tgacccagtc tccatccttc ctgtctgcat ctgtaggaga cagagtcacc      60

atcacttgct gggccagtca ggacattagc agttatttag cctggtatca gcaaaaacca     120

gggatagccc ctaagctcct gatctatgct gcatccactt tgcaaagtgg ggtcccatca     180

aggttcggcg gcagtggatc tgggacagaa ttcactctca caatcagcag cctgcagcct     240

gaagattttg caacttatta ctgtcaacag cttaatagtt accctcggac gttcggccaa     300

gggaccaagg tggaaatcaa a                                               321


<210> SEQ ID NO 140
<211> LENGTH: 107
<212> TYPE: PRT
<213> ORGANISM: Artificial Sequence
<220> FEATURE:
<223> OTHER INFORMATION: Synthetic

<400> SEQUENCE: 140

Asp Ile Gln Met Thr Gln Ser Pro Ser Phe Leu Ser Ala Ser Val Gly
 1               5                  10                  15

Asp Arg Val Thr Ile Thr Cys Trp Ala Ser Gln Asp Ile Ser Ser Tyr
            20                  25                  30

Leu Ala Trp Tyr Gln Gln Lys Pro Gly Ile Ala Pro Lys Leu Leu Ile
        35                  40                  45

Tyr Ala Ala Ser Thr Leu Gln Ser Gly Val Pro Ser Arg Phe Gly Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Arg
                85                  90                  95

Thr Phe Gly Gln Gly Thr Lys Val Glu Ile Lys
            100                 105


<210> SEQ ID NO 141
<211> LENGTH: 384
<212> TYPE: DNA
<213> ORGANISM: Artificial Sequence
<220> FEATURE:
<223> OTHER INFORMATION: Synthetic

<400> SEQUENCE: 141
```

-continued

```
caggtgcagc tgcaggagtc gggcccagga ctggtgaagc cttcggagac cctgtccctc     60

acctgcactg tctctgggga ctccatcaat acttactact ggagctggat ccggcagccc    120

ccagggaagg gactggagtg gattgggtat atctattata gtggaaccac caactacaac    180

ccctccctca agagtcgagt caccatatca gtagacacgt ccaagaacca gttctccctg    240

aagctgagct ctgtgaccgc tgcggacacg gccgtgtatt actgtgcgag agagaggatt    300

actatgattc ggggagttac cctctactat tactcctacg gtatggacgt ctggggccaa    360

gggaccacgg tcaccgtctc ctca                                           384


<210> SEQ ID NO 142
<211> LENGTH: 128
<212> TYPE: PRT
<213> ORGANISM: Artificial Sequence
<220> FEATURE:
<223> OTHER INFORMATION: Synthetic

<400> SEQUENCE: 142

Gln Val Gln Leu Gln Glu Ser Gly Pro Gly Leu Val Lys Pro Ser Glu
 1               5                  10                  15

Thr Leu Ser Leu Thr Cys Thr Val Ser Gly Asp Ser Ile Asn Thr Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Thr Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Arg Ile Thr Met Ile Arg Gly Val Thr Leu Tyr Tyr Tyr Ser
            100                 105                 110

Tyr Gly Met Asp Val Trp Gly Gln Gly Thr Thr Val Thr Val Ser Ser
        115                 120                 125


<210> SEQ ID NO 143
<211> LENGTH: 321
<212> TYPE: DNA
<213> ORGANISM: Artificial Sequence
<220> FEATURE:
<223> OTHER INFORMATION: Synthetic

<400> SEQUENCE: 143

gacatccaga tgacccagtc tccatcctcc ctgtctgcat ctgtaggaga cagagtcacc     60

atcacttgcc gggcaagtca ggacattagc agttatttag gctggtatca gcagaaacca    120

gggaaagccc ctaagcgcct gatctatgct gcatccagtt tgcaaagtgg ggtcccatca    180

aggttcagcg gcagtggatc tgggacagaa ttcactctca caatcagcag cctgcagcct    240

gaagattttg caacttatta ctgtcaacag cttaatagtt accctcggac gttcggccaa    300

gggaccaagg tggaaatcaa a                                              321


<210> SEQ ID NO 144
<211> LENGTH: 107
<212> TYPE: PRT
<213> ORGANISM: Artificial Sequence
<220> FEATURE:
<223> OTHER INFORMATION: Synthetic

<400> SEQUENCE: 144
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Arg
                85                  90                  95

Thr Phe Gly Gln Gly Thr Lys Val Glu Ile Lys
            100                 105
```

<210> SEQ ID NO 145
<211> LENGTH: 378
<212> TYPE: DNA
<213> ORGANISM: Artificial Sequence
<220> FEATURE:
<223> OTHER INFORMATION: Synthetic

<400> SEQUENCE: 145

```
caggtgcagc tggtgcagtc tggagctgag gtgaagaagc ctggggcctc agtgaaggtc     60

tcctgcaagg cttctggtta cacctttacc aactatggta tcagctgggt gcgacaggcc    120

cctggacaag gacttgagtt aatgggatgg attagtggtt acaatggtaa cacaaactat    180

gcacaagaac tccaggccag agtcaccatg accacagaca catccacgag cacagcctac    240

atggagctga ggaacctgag atctgacgac acggccgtat attactgtgc gagagataga    300

gtcgttgtag cagctgctaa ttactacttt tattctatgg acgtctgggg ccaagggacc    360

acggtcaccg tctcctca                                                  378
```

<210> SEQ ID NO 146
<211> LENGTH: 126
<212> TYPE: PRT
<213> ORGANISM: Artificial Sequence
<220> FEATURE:
<223> OTHER INFORMATION: Synthetic

<400> SEQUENCE: 146

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Leu Met
        35                  40                  45

Gly Trp Ile Ser Gly Tyr Asn Gly Asn Thr Asn Tyr Ala Gln Glu Leu
    50                  55                  60

Gln Ala Arg Val Thr Met Thr Thr Asp Thr Ser Thr Ser Thr Ala Tyr
65                  70                  75                  80

Met Glu Leu Arg Asn Leu Arg Ser Asp Asp Thr Ala Val Tyr Tyr Cys
                85                  90                  95

Ala Arg Asp Arg Val Val Val Ala Ala Ala Asn Tyr Tyr Phe Tyr Ser
            100                 105                 110

Met Asp Val Trp Gly Gln Gly Thr Thr Val Thr Val Ser Ser
        115                 120                 125
```

<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147
ggttacacct ttaccaacta tggt 24

<210> SEQ ID NO 148
<211> LENGTH: 8
<212> TYPE: PRT
<213> ORGANISM: Artificial Sequence
<220> FEATURE:
<223> OTHER INFORMATION: Synthetic

<400> SEQUENCE: 148

Gly Tyr Thr Phe Thr Asn Tyr Gly
1 5

<210> SEQ ID NO 149
<211> LENGTH: 24
<212> TYPE: DNA
<213> ORGANISM: Artificial Sequence
<220> FEATURE:
<223> OTHER INFORMATION: Synthetic

<400> SEQUENCE: 149
attagtggtt acaatggtaa caca 24

<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

Ile Ser Gly Tyr Asn Gly Asn Thr
1 5

<210> SEQ ID NO 151
<211> LENGTH: 57
<212> TYPE: DNA
<213> ORGANISM: Artificial Sequence
<220> FEATURE:
<223> OTHER INFORMATION: Synthetic

<400> SEQUENCE: 151
gcgagagata gagtcgttgt agcagctgct aattactact tttattctat ggacgtc 57

<210> SEQ ID NO 152
<211> LENGTH: 19
<212> TYPE: PRT
<213> ORGANISM: Artificial Sequence
<220> FEATURE:
<223> OTHER INFORMATION: Synthetic

<400> SEQUENCE: 152

Ala Arg Asp Arg Val Val Val Ala Ala Ala Asn Tyr Tyr Phe Tyr Ser
1 5 10 15

Met Asp Val

<210> SEQ ID NO 153
<211> LENGTH: 339
<212> TYPE: DNA
<213> ORGANISM: Artificial Sequence
<220> FEATURE:
<223> OTHER INFORMATION: Synthetic

<400> SEQUENCE: 153
gccatccaga tgacccagtc tccactctcc ctgtccgtca cccttggaca gccggcctcc 60
atctcctgca ggtctagtca aagcctcgta tacagtgatg gagacaccta cttgaattgg 120
tttcagcaga ggccaggcca atctccaagg cgcctaattt ataaggtttc taaccgggac 180
tctggggtcc cagacagatt cagcggcagt gggtcaggca ctgctttcac actgaaaatc 240
agcggggtgg aggccgagga tgttggggtt tactactgca tgcaagctac acactggcct 300
cggacgttcg gccaagggac caaggtggaa atcaaacga 339

<210> SEQ ID NO 154
<211> LENGTH: 113
<212> TYPE: PRT
<213> ORGANISM: Artificial Sequence
<220> FEATURE:
<223> OTHER INFORMATION: Synthetic

<400> SEQUENCE: 154

Ala Ile Gln Met Thr Gln Ser Pro Leu Ser Leu Ser Val Thr Leu Gly
1 5 10 15

Gln Pro Ala Ser Ile Ser Cys Arg Ser Ser Gln Ser Leu Val Tyr Ser
20 25 30

Asp Gly Asp Thr Tyr Leu Asn Trp Phe Gln Gln Arg Pro Gly Gln Ser
35 40 45

Pro Arg Arg Leu Ile Tyr Lys Val Ser Asn Arg Asp Ser Gly Val Pro
50 55 60

Asp Arg Phe Ser Gly Ser Gly Ser Gly Thr Ala Phe Thr Leu Lys Ile
65 70 75 80

Ser Gly Val Glu Ala Glu Asp Val Gly Val Tyr Tyr Cys Met Gln Ala
85 90 95

Thr His Trp Pro Arg Thr Phe Gly Gln Gly Thr Lys Val Glu Ile Lys
100 105 110

Arg

<210> SEQ ID NO 155
<211> LENGTH: 33
<212> TYPE: DNA
<213> ORGANISM: Artificial Sequence
<220> FEATURE:
<223> OTHER INFORMATION: Synthetic

<400> SEQUENCE: 155
caaagcctcg tatacagtga tggagacacc tac 33

<210> SEQ ID NO 156
<211> LENGTH: 11
<212> TYPE: PRT
<213> ORGANISM: Artificial Sequence
<220> FEATURE:
<223> OTHER INFORMATION: Synthetic

<400> SEQUENCE: 156

Gln Ser Leu Val Tyr Ser Asp Gly Asp Thr Tyr
1 5 10

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157 aaggtttct 9

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Lys Val Ser
1

<210> SEQ ID NO 159
<211> LENGTH: 27
<212> TYPE: DNA
<213> ORGANISM: Artificial Sequence
<220> FEATURE:
<223> OTHER INFORMATION: Synthetic

<400> SEQUENCE: 159
atgcaagcta cacactggcc tcggacg 27

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Met Gln Ala Thr His Trp Pro Arg Thr
1 5

<210> SEQ ID NO 161
<211> LENGTH: 378
<212> TYPE: DNA
<213> ORGANISM: Artificial Sequence
<220> FEATURE:
<223> OTHER INFORMATION: Synthetic

<400> SEQUENCE: 161
caggttcagc tggtgcagtc tggagctgag gtgaagaagc ctggggcctc agtgaaggtc 60
tcctgcaagg cttctggtta cacctttacc aactatggta tcagctgggt gcgacaggcc 120
cctggacaag gacttgagtt aatgggatgg attagtggtt acaatggtaa cacaaactat 180
gcacaagaac tccaggccag agtcaccatg accacagaca catccacgag cacagcctac 240
atggagctga ggaacctgag atctgacgac acggccgtat attactgtgc gagagataga 300
gtcgttgtag cagctgctaa ttactacttt tattctatgg acgtctgggg ccaagggacc 360
acggtcaccg tctcctca 378

<210> SEQ ID NO 162
<211> LENGTH: 126
<212> TYPE: PRT
<213> ORGANISM: Artificial Sequence
<220> FEATURE:
<223> OTHER INFORMATION: Synthetic

<400> SEQUENCE: 162

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Tyr
20 25 30

Gly Ile Ser Trp Val Arg Gln Ala Pro Gly Gln Gly Leu Glu Leu Met
35 40 45

Gly Trp Ile Ser Gly Tyr Asn Gly Asn Thr Asn Tyr Ala Gln Glu Leu
50 55 60

Gln Ala Arg Val Thr Met Thr Thr Asp Thr Ser Thr Ser Thr Ala Tyr
65 70 75 80

Met Glu Leu Arg Asn Leu Arg Ser Asp Asp Thr Ala Val Tyr Tyr Cys
85 90 95

Ala Arg Asp Arg Val Val Val Ala Ala Ala Asn Tyr Tyr Phe Tyr Ser
100 105 110

Met Asp Val Trp Gly Gln Gly Thr Thr Val Thr Val Ser Ser
115 120 125

<210> SEQ ID NO 163
<211> LENGTH: 336
<212> TYPE: DNA
<213> ORGANISM: Artificial Sequence
<220> FEATURE:
<223> OTHER INFORMATION: Synthetic

<400> SEQUENCE: 163
gatgttgtga tgactcagtc tccactctcc ctgtccgtca cccttggaca gccggcctcc 60
atctcctgca ggtctagtca aagcctcgta tacagtgatg gagacaccta cttgaattgg 120
tttcagcaga ggccaggcca atctccaagg cgcctaattt ataaggtttc taaccgggac 180
tctggggtcc cagacagatt cagcggcagt gggtcaggca ctgctttcac actgaaaatc 240
agcggggtgg aggccgagga tgttggggtt tactactgca tgcaagctac acactggcct 300
cggacgttcg gccaagggac caaggtggaa atcaaa 336

<210> SEQ ID NO 164
<211> LENGTH: 112
<212> TYPE: PRT
<213> ORGANISM: Artificial Sequence
<220> FEATURE:
<223> OTHER INFORMATION: Synthetic

<400> SEQUENCE: 164

Asp Val Val Met Thr Gln Ser Pro Leu Ser Leu Ser Val Thr Leu Gly
1 5 10 15

Gln Pro Ala Ser Ile Ser Cys Arg Ser Ser Gln Ser Leu Val Tyr Ser
20 25 30

Asp Gly Asp Thr Tyr Leu Asn Trp Phe Gln Gln Arg Pro Gly Gln Ser
35 40 45

Pro Arg Arg Leu Ile Tyr Lys Val Ser Asn Arg Asp Ser Gly Val Pro
50 55 60

Asp Arg Phe Ser Gly Ser Gly Ser Gly Thr Ala Phe Thr Leu Lys Ile
65 70 75 80

Ser Gly Val Glu Ala Glu Asp Val Gly Val Tyr Tyr Cys Met Gln Ala
85 90 95

```
Thr His Trp Pro Arg Thr Phe Gly Gln Gly Thr Lys Val Glu Ile Lys
            100                 105                 110


<210> SEQ ID NO 165
<211> LENGTH: 378
<212> TYPE: DNA
<213> ORGANISM: Artificial Sequence
<220> FEATURE:
<223> OTHER INFORMATION: Synthetic

<400> SEQUENCE: 165

caggttcagc tggtgcagtc tggagctgag gtgaagaagc ctggggcctc agtgaaggtc      60

tcctgcaagg cttctggtta cacctttacc aactatggta tcagctgggt gcgacaggcc     120

cctggacaag ggcttgagtg gatgggatgg attagtggtt acaatggtaa cacaaactat     180

gcacagaagc tccagggcag agtcaccatg accacagaca catccacgag cacagcctac     240

atggagctga ggagcctgag atctgacgac acggccgtgt attactgtgc gagagataga     300

gtcgttgtag cagctgctaa ttactacttt tattctatgg acgtctgggg ccaagggacc     360

acggtcaccg tctcctca                                                   378


<210> SEQ ID NO 166
<211> LENGTH: 126
<212> TYPE: PRT
<213> ORGANISM: Artificial Sequence
<220> FEATURE:
<223> OTHER INFORMATION: Synthetic

<400> SEQUENCE: 166

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Val Val Val Ala Ala Ala Asn Tyr Tyr Phe Tyr Ser
            100                 105                 110

Met Asp Val Trp Gly Gln Gly Thr Thr Val Thr Val Ser Ser
        115                 120                 125


<210> SEQ ID NO 167
<211> LENGTH: 336
<212> TYPE: DNA
<213> ORGANISM: Artificial Sequence
<220> FEATURE:
<223> OTHER INFORMATION: Synthetic

<400> SEQUENCE: 167

gatgttgtga tgactcagtc tccactctcc ctgcccgtca cccttggaca gccggcctcc      60

atctcctgca ggtctagtca aagcctcgta tacagtgatg gagacaccta cttgaattgg     120

tttcagcaga ggccaggcca atctccaagg cgcctaattt ataaggtttc taaccgggac     180

tctggggtcc cagacagatt cagcggcagt gggtcaggca ctgatttcac actgaaaatc     240
```

agcagggtgg aggctgagga tgttggggtt tattactgca tgcaagctac acactggcct  300
cggacgttcg gccaagggac caaggtggaa atcaaa  336

```
<210> SEQ ID NO 168
<211> LENGTH: 112
<212> TYPE: PRT
<213> ORGANISM: Artificial Sequence
<220> FEATURE:
<223> OTHER INFORMATION: Synthetic

<400> SEQUENCE: 168
```

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asp Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr His Trp Pro Arg Thr Phe Gly Gln Gly Thr Lys Val Glu Ile Lys
            100                 105                 110

```
<210> SEQ ID NO 169
<211> LENGTH: 375
<212> TYPE: DNA
<213> ORGANISM: Artificial Sequence
<220> FEATURE:
<223> OTHER INFORMATION: Synthetic

<400> SEQUENCE: 169
```

caggtccact tgaaggagtc tggtcctacg ctggtgaaac ccacacagac cctcacgctg   60
acctgcacct tctctggatt ctcactcatc actagtggag tgggtgtggg ctggattcgt  120
cagccccccg gaaaggccct ggagtggctt gcactcattt attggaatgg tgataagcgc  180
tacagcccat ctctgaagag caggctcacc atcaccaagg acacctccaa aaaccaggtg  240
gtccttacaa tgaccaacat ggaccctgtg gacacagcca catattactg tgcacacagg  300
ataactgaaa ctagttacta cttctactac ggtatggacg tctggggcca agggaccacg  360
gtcaccgtct cctca  375

```
<210> SEQ ID NO 170
<211> LENGTH: 125
<212> TYPE: PRT
<213> ORGANISM: Artificial Sequence
<220> FEATURE:
<223> OTHER INFORMATION: Synthetic

<400> SEQUENCE: 170
```

Gln Val His Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ile Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Gly Asp Lys Arg Tyr Ser Pro Ser

-continued

```
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Ile Thr Glu Thr Ser Tyr Tyr Phe Tyr Tyr Gly Met
            100                 105                 110

Asp Val Trp Gly Gln Gly Thr Thr Val Thr Val Ser Ser
        115                 120                 125


<210> SEQ ID NO 171
<211> LENGTH: 30
<212> TYPE: DNA
<213> ORGANISM: Artificial Sequence
<220> FEATURE:
<223> OTHER INFORMATION: Synthetic

<400> SEQUENCE: 171

ggattctcac tcatcactag tggagtgggt                                    30


<210> SEQ ID NO 172
<211> LENGTH: 10
<212> TYPE: PRT
<213> ORGANISM: Artificial Sequence
<220> FEATURE:
<223> OTHER INFORMATION: Synthetic

<400> SEQUENCE: 172

Gly Phe Ser Leu Ile Thr Ser Gly Val Gly
 1               5                  10


<210> SEQ ID NO 173
<211> LENGTH: 21
<212> TYPE: DNA
<213> ORGANISM: Artificial Sequence
<220> FEATURE:
<223> OTHER INFORMATION: Synthetic

<400> SEQUENCE: 173

atttattgga atggtgataa g                                             21


<210> SEQ ID NO 174
<211> LENGTH: 7
<212> TYPE: PRT
<213> ORGANISM: Artificial Sequence
<220> FEATURE:
<223> OTHER INFORMATION: Synthetic

<400> SEQUENCE: 174

Ile Tyr Trp Asn Gly Asp Lys
 1               5


<210> SEQ ID NO 175
<211> LENGTH: 51
<212> TYPE: DNA
<213> ORGANISM: Artificial Sequence
<220> FEATURE:
<223> OTHER INFORMATION: Synthetic

<400> SEQUENCE: 175

gcacacagga taactgaaac tagttactac ttctactacg gtatggacgt c            51


<210> SEQ ID NO 176
<211> LENGTH: 17
```

<212> TYPE: PRT
<213> ORGANISM: Artificial Sequence
<220> FEATURE:
<223> OTHER INFORMATION: Synthetic

<400> SEQUENCE: 176

```
Ala His Arg Ile Thr Glu Thr Ser Tyr Tyr Phe Tyr Tyr Gly Met Asp
 1               5                  10                  15

Val
```

<210> SEQ ID NO 177
<211> LENGTH: 339
<212> TYPE: DNA
<213> ORGANISM: Artificial Sequence
<220> FEATURE:
<223> OTHER INFORMATION: Synthetic

<400> SEQUENCE: 177

```
gacatccaga tgacccagtc tccactctcc ctgcccgtca cccctggaga gccggcctcc      60

atctcctgca ggtctagtca gagcctcctg catagtcatg gatacgacta tttggattgg     120

tacctgcaga agccagggca gtctccacag ctcctgatct atttgggttc taatcgggcc     180

tccggggtcc ctgacaggtt cagtggcagt ggatcaggca cagattttac actgaaaatc     240

agcagagtgg aggctgagga tgttggggtt tattactgca tgcaagctct acaaactccg     300

ctcactttcg gcggagggac caaggtggaa atcaaacga                            339
```

<210> SEQ ID NO 178
<211> LENGTH: 113
<212> TYPE: PRT
<213> ORGANISM: Artificial Sequence
<220> FEATURE:
<223> OTHER INFORMATION: Synthetic

<400> SEQUENCE: 178

```
Asp Ile Gln Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

His Gly Tyr Asp Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

Arg
```

<210> SEQ ID NO 179
<211> LENGTH: 33
<212> TYPE: DNA
<213> ORGANISM: Artificial Sequence
<220> FEATURE:
<223> OTHER INFORMATION: Synthetic

<400> SEQUENCE: 179

```
cagagcctcc tgcatagtca tggatacgac tat                                   33
```

<210> SEQ ID NO 180
<211> LENGTH: 11
<212> TYPE: PRT
<213> ORGANISM: Artificial Sequence
<220> FEATURE:
<223> OTHER INFORMATION: Synthetic

<400> SEQUENCE: 180

```
Gln Ser Leu Leu His Ser His Gly Tyr Asp Tyr
 1               5                  10
```

<210> SEQ ID NO 181
<211> LENGTH: 9
<212> TYPE: DNA
<213> ORGANISM: Artificial Sequence
<220> FEATURE:
<223> OTHER INFORMATION: Synthetic

<400> SEQUENCE: 181 ttgggttct 9

<210> SEQ ID NO 182
<211> LENGTH: 3
<212> TYPE: PRT
<213> ORGANISM: Artificial Sequence
<220> FEATURE:
<223> OTHER INFORMATION: Synthetic

<400> SEQUENCE: 182

```
Leu Gly Ser
 1
```

<210> SEQ ID NO 183
<211> LENGTH: 27
<212> TYPE: DNA
<213> ORGANISM: Artificial Sequence
<220> FEATURE:
<223> OTHER INFORMATION: Synthetic

<400> SEQUENCE: 183
atgcaagctc tacaaactcc gctcact 27

<210> SEQ ID NO 184
<211> LENGTH: 9
<212> TYPE: PRT
<213> ORGANISM: Artificial Sequence
<220> FEATURE:
<223> OTHER INFORMATION: Synthetic

<400> SEQUENCE: 184

```
Met Gln Ala Leu Gln Thr Pro Leu Thr
 1               5
```

<210> SEQ ID NO 185
<211> LENGTH: 375
<212> TYPE: DNA
<213> ORGANISM: Artificial Sequence
<220> FEATURE:
<223> OTHER INFORMATION: Synthetic

<400> SEQUENCE: 185
cagatcacct tgaaggagtc tggtcctacg ctggtgaaac ccacacagac cctcacgctg 60
acctgcacct tctctggatt ctcactcatc actagtggag tgggtgtggg ctggattcgt 120
cagccccccg gaaaggccct ggagtggctt gcactcattt attggaatgg tgataagcgc 180
tacagcccat ctctgaagag caggctcacc atcaccaagg acacctccaa aaaccaggtg 240
gtccttacaa tgaccaacat ggaccctgtg gacacagcca catattactg tgcacacagg 300
ataactgaaa ctagttacta cttctactac ggtatggacg tctggggcca agggaccacg 360
gtcaccgtct cctca 375

<210> SEQ ID NO 186
<211> LENGTH: 125
<212> TYPE: PRT
<213> ORGANISM: Artificial Sequence
<220> FEATURE:
<223> OTHER INFORMATION: Synthetic

<400> SEQUENCE: 186

Gln Ile Thr Leu Lys Glu Ser Gly Pro Thr Leu Val Lys Pro Thr Gln
1 5 10 15

Thr Leu Thr Leu Thr Cys Thr Phe Ser Gly Phe Ser Leu Ile Thr Ser
20 25 30

Gly Val Gly Val Gly Trp Ile Arg Gln Pro Pro Gly Lys Ala Leu Glu
35 40 45

Trp Leu Ala Leu Ile Tyr Trp Asn Gly Asp Lys Arg Tyr Ser Pro Ser
50 55 60

Leu Lys Ser Arg Leu Thr Ile Thr Lys Asp Thr Ser Lys Asn Gln Val
65 70 75 80

Val Leu Thr Met Thr Asn Met Asp Pro Val Asp Thr Ala Thr Tyr Tyr
85 90 95

Cys Ala His Arg Ile Thr Glu Thr Ser Tyr Tyr Phe Tyr Tyr Gly Met
100 105 110

Asp Val Trp Gly Gln Gly Thr Thr Val Thr Val Ser Ser
115 120 125

<210> SEQ ID NO 187
<211> LENGTH: 336
<212> TYPE: DNA
<213> ORGANISM: Artificial Sequence
<220> FEATURE:
<223> OTHER INFORMATION: Synthetic

<400> SEQUENCE: 187
gatattgtga tgactcagtc tccactctcc ctgcccgtca cccctggaga gccggcctcc 60
atctcctgca ggtctagtca gagcctcctg catagtcatg gatacgacta tttggattgg 120
tacctgcaga agccagggca gtctccacag ctcctgatct atttgggttc taatcgggcc 180
tccggggtcc ctgacaggtt cagtggcagt ggatcaggca cagattttac actgaaaatc 240
agcagagtgg aggctgagga tgttggggtt tattactgca tgcaagctct acaaactccg 300
ctcactttcg gcggagggac caaggtggag atcaaa 336

<210> SEQ ID NO 188
<211> LENGTH: 112
<212> TYPE: PRT
<213> ORGANISM: Artificial Sequence
<220> FEATURE:
<223> OTHER INFORMATION: Synthetic

<400> SEQUENCE: 188

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

His Gly Tyr Asp Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro Leu Thr Phe Gly Gly Gly Thr Lys Val Glu Ile Lys
100 105 110

<210> SEQ ID NO 189
<211> LENGTH: 375
<212> TYPE: DNA
<213> ORGANISM: Artificial Sequence
<220> FEATURE:
<223> OTHER INFORMATION: Synthetic

<400> SEQUENCE: 189
cagatcacct tgaaggagtc tggtcctacg ctggtgaaac ccacacagac cctcacgctg 60
acctgcacct tctctggatt ctcactcatc actagtggag tgggtgtggg ctggatccgt 120
cagcccccag gaaaggccct ggagtggctt gcactcattt attggaatgg tgataagcgc 180
tacagcccat ctctgaagag caggctcacc atcaccaagg acacctccaa aaaccaggtg 240
gtccttacaa tgaccaacat ggaccctgtg gacacagcca catattactg tgcacacagg 300
ataactgaaa ctagttacta cttctactac ggtatggacg tctggggcca agggaccacg 360
gtcaccgtct cctca 375

<210> SEQ ID NO 190
<211> LENGTH: 125
<212> TYPE: PRT
<213> ORGANISM: Artificial Sequence
<220> FEATURE:
<223> OTHER INFORMATION: Synthetic

<400> SEQUENCE: 190

Gln Ile Thr Leu Lys Glu Ser Gly Pro Thr Leu Val Lys Pro Thr Gln
1 5 10 15

Thr Leu Thr Leu Thr Cys Thr Phe Ser Gly Phe Ser Leu Ile Thr Ser
20 25 30

Gly Val Gly Val Gly Trp Ile Arg Gln Pro Pro Gly Lys Ala Leu Glu
35 40 45

Trp Leu Ala Leu Ile Tyr Trp Asn Gly Asp Lys Arg Tyr Ser Pro Ser
50 55 60

Leu Lys Ser Arg Leu Thr Ile Thr Lys Asp Thr Ser Lys Asn Gln Val
65 70 75 80

Val Leu Thr Met Thr Asn Met Asp Pro Val Asp Thr Ala Thr Tyr Tyr
85 90 95

Cys Ala His Arg Ile Thr Glu Thr Ser Tyr Tyr Phe Tyr Tyr Gly Met
100 105 110

Asp Val Trp Gly Gln Gly Thr Thr Val Thr Val Ser Ser
115 120 125

<210> SEQ ID NO 191
<211> LENGTH: 336
<212> TYPE: DNA
<213> ORGANISM: Artificial Sequence
<220> FEATURE:
<223> OTHER INFORMATION: Synthetic

<400> SEQUENCE: 191
gatattgtga tgactcagtc tccactctcc ctgcccgtca cccctggaga gccggcctcc 60
atctcctgca ggtctagtca gagcctcctg catagtcatg gatacgacta tttggattgg 120
tacctgcaga agccagggca gtctccacag ctcctgatct atttgggttc taatcgggcc 180
tccggggtcc ctgacaggtt cagtggcagt ggatcaggca cagattttac actgaaaatc 240
agcagagtgg aggctgagga tgttggggtt tattactgca tgcaagctct acaaactccg 300
ctcactttcg gcggagggac caaggtggag atcaaa 336

<210> SEQ ID NO 192
<211> LENGTH: 112
<212> TYPE: PRT
<213> ORGANISM: Artificial Sequence
<220> FEATURE:
<223> OTHER INFORMATION: Synthetic

<400> SEQUENCE: 192

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

His Gly Tyr Asp Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro Leu Thr Phe Gly Gly Gly Thr Lys Val Glu Ile Lys
100 105 110

<210> SEQ ID NO 193
<211> LENGTH: 375
<212> TYPE: DNA
<213> ORGANISM: Artificial Sequence
<220> FEATURE:
<223> OTHER INFORMATION: Synthetic

<400> SEQUENCE: 193
cagatcacct tgaaggagtc tggtcctact ctggtgaaac cctcacagac cctcacgctg 60
acctgcacct tctctgggtt ctcactcagc actagtggag tgggtgtggg ctggatccgt 120
cagcccccag gaaaggccct ggagtggctt gcactcattt attggaattc tgataagcgc 180
tacagcccat ctctgaagag caggctcacc atcaccaagg acacctccaa aaaccaggta 240
gtccttacaa tgaccaacat ggaccctgtg gacacagcca catattactg tgcacacaga 300
catgacagct cgtcctacta cttctactac ggtatggacg tctggggcca agggatcacg 360
gtcaccgtct cctca 375

<210> SEQ ID NO 194
<211> LENGTH: 125
<212> TYPE: PRT
<213> ORGANISM: Artificial Sequence
<220> FEATURE:
<223> OTHER INFORMATION: Synthetic

<400> SEQUENCE: 194

```
Gln Ile Thr Leu Lys Glu Ser Gly Pro Thr Leu Val Lys Pro Ser Gln
 1               5                  10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Ser Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg His Asp Ser Ser Ser Tyr Tyr Phe Tyr Tyr Gly Met
            100                 105                 110

Asp Val Trp Gly Gln Gly Ile Thr Val Thr Val Ser Ser
        115                 120                 125
```

<210> SEQ ID NO 195
<211> LENGTH: 30
<212> TYPE: DNA
<213> ORGANISM: Artificial Sequence
<220> FEATURE:
<223> OTHER INFORMATION: Synthetic

<400> SEQUENCE: 195

```
gggttctcac tcagcactag tggagtgggt                                        30
```

<210> SEQ ID NO 196
<211> LENGTH: 10
<212> TYPE: PRT
<213> ORGANISM: Artificial Sequence
<220> FEATURE:
<223> OTHER INFORMATION: Synthetic

<400> SEQUENCE: 196

```
Gly Phe Ser Leu Ser Thr Ser Gly Val Gly
 1               5                  10
```

<210> SEQ ID NO 197
<211> LENGTH: 21
<212> TYPE: DNA
<213> ORGANISM: Artificial Sequence
<220> FEATURE:
<223> OTHER INFORMATION: Synthetic

<400> SEQUENCE: 197

```
atttattgga attctgataa g                                                 21
```

<210> SEQ ID NO 198
<211> LENGTH: 7
<212> TYPE: PRT
<213> ORGANISM: Artificial Sequence
<220> FEATURE:
<223> OTHER INFORMATION: Synthetic

<400> SEQUENCE: 198

```
Ile Tyr Trp Asn Ser Asp Lys
 1               5
```

<210> SEQ ID NO 199

<211> LENGTH: 51
<212> TYPE: DNA
<213> ORGANISM: Artificial Sequence
<220> FEATURE:
<223> OTHER INFORMATION: Synthetic

<400> SEQUENCE: 199
gcacacagac atgacagctc gtcctactac ttctactacg gtatggacgt c 51

<210> SEQ ID NO 200
<211> LENGTH: 17
<212> TYPE: PRT
<213> ORGANISM: Artificial Sequence
<220> FEATURE:
<223> OTHER INFORMATION: Synthetic

<400> SEQUENCE: 200

Ala His Arg His Asp Ser Ser Ser Tyr Tyr Phe Tyr Tyr Gly Met Asp
1 5 10 15

Val

<210> SEQ ID NO 201
<211> LENGTH: 339
<212> TYPE: DNA
<213> ORGANISM: Artificial Sequence
<220> FEATURE:
<223> OTHER INFORMATION: Synthetic

<400> SEQUENCE: 201
gacatccaga tgacccagtc tccgctctcc ctgcccgtca cccctggaga gccggcctcc 60
atctcctgca ggtctagtca gagcctcctc catagtcatg gatacaacta tttggattgg 120
tacctgcaga agccagggca gtctccacaa ctcctgatct atttgggttc taatcgggcc 180
tccggggtcc ctgacaggtt cagtggcggt ggatcaggca cagattttac actgaaaatc 240
agcagagtgg aggctgagga tgttgggatt tattactgca tgcaagctct acagactcct 300
ctcactttcg gcggagggac caaggtggag atcaaacga 339

<210> SEQ ID NO 202
<211> LENGTH: 113
<212> TYPE: PRT
<213> ORGANISM: Artificial Sequence
<220> FEATURE:
<223> OTHER INFORMATION: Synthetic

<400> SEQUENCE: 202

Asp Ile Gln Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

His Gly Tyr Asn Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Gly Gly Ser Gly Thr Asp Phe Thr Leu Lys Ile
65 70 75 80

Ser Arg Val Glu Ala Glu Asp Val Gly Ile Tyr Tyr Cys Met Gln Ala
85 90 95

Leu Gln Thr Pro Leu Thr Phe Gly Gly Gly Thr Lys Val Glu Ile Lys
100 105 110

Arg

<210> SEQ ID NO 203
<211> LENGTH: 33
<212> TYPE: DNA
<213> ORGANISM: Artificial Sequence
<220> FEATURE:
<223> OTHER INFORMATION: Synthetic

<400> SEQUENCE: 203
cagagcctcc tccatagtca tggatacaac tat 33

<210> SEQ ID NO 204
<211> LENGTH: 11
<212> TYPE: PRT
<213> ORGANISM: Artificial Sequence
<220> FEATURE:
<223> OTHER INFORMATION: Synthetic

<400> SEQUENCE: 204

Gln Ser Leu Leu His Ser His Gly Tyr Asn Tyr
1 5 10

<210> SEQ ID NO 205
<211> LENGTH: 9
<212> TYPE: DNA
<213> ORGANISM: Artificial Sequence
<220> FEATURE:
<223> OTHER INFORMATION: Synthetic

<400> SEQUENCE: 205 ttgggttct 9

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

Leu Gly Ser
1

<210> SEQ ID NO 207
<211> LENGTH: 27
<212> TYPE: DNA
<213> ORGANISM: Artificial Sequence
<220> FEATURE:
<223> OTHER INFORMATION: Synthetic

<400> SEQUENCE: 207
atgcaagctc tacagactcc tctcact 27

<210> SEQ ID NO 208
<211> LENGTH: 9
<212> TYPE: PRT
<213> ORGANISM: Artificial Sequence
<220> FEATURE:
<223> OTHER INFORMATION: Synthetic

<400> SEQUENCE: 208

Met Gln Ala Leu Gln Thr Pro Leu Thr
1 5

<210> SEQ ID NO 209
<211> LENGTH: 375

-continued

<212> TYPE: DNA
<213> ORGANISM: Artificial Sequence
<220> FEATURE:
<223> OTHER INFORMATION: Synthetic

<400> SEQUENCE: 209
cagatcacct tgaaggagtc tggtcctact ctggtgaaac cctcacagac cctcacgctg 60
acctgcacct tctctgggtt ctcactcagc actagtggag tgggtgtggg ctggatccgt 120
cagcccccag gaaaggccct ggagtggctt gcactcattt attggaattc tgataagcgc 180
tacagcccat ctctgaagag caggctcacc atcaccaagg acacctccaa aaaccaggta 240
gtccttacaa tgaccaacat ggaccctgtg gacacagcca catattactg tgcacacaga 300
catgacagct cgtcctacta cttctactac ggtatggacg tctggggcca agggaccacg 360
gtcaccgtct cctca 375

<210> SEQ ID NO 210
<211> LENGTH: 125
<212> TYPE: PRT
<213> ORGANISM: Artificial Sequence
<220> FEATURE:
<223> OTHER INFORMATION: Synthetic

<400> SEQUENCE: 210

Gln Ile Thr Leu Lys Glu Ser Gly Pro Thr Leu Val Lys Pro Ser Gln
1 5 10 15

Thr Leu Thr Leu Thr Cys Thr Phe Ser Gly Phe Ser Leu Ser Thr Ser
20 25 30

Gly Val Gly Val Gly Trp Ile Arg Gln Pro Pro Gly Lys Ala Leu Glu
35 40 45

Trp Leu Ala Leu Ile Tyr Trp Asn Ser Asp Lys Arg Tyr Ser Pro Ser
50 55 60

Leu Lys Ser Arg Leu Thr Ile Thr Lys Asp Thr Ser Lys Asn Gln Val
65 70 75 80

Val Leu Thr Met Thr Asn Met Asp Pro Val Asp Thr Ala Thr Tyr Tyr
85 90 95

Cys Ala His Arg His Asp Ser Ser Ser Tyr Tyr Phe Tyr Tyr Gly Met
100 105 110

Asp Val Trp Gly Gln Gly Thr Thr Val Thr Val Ser Ser
115 120 125

<210> SEQ ID NO 211
<211> LENGTH: 336
<212> TYPE: DNA
<213> ORGANISM: Artificial Sequence
<220> FEATURE:
<223> OTHER INFORMATION: Synthetic

<400> SEQUENCE: 211
gatattgtga tgactcagtc tccgctctcc ctgcccgtca cccctggaga gccggcctcc 60
atctcctgca ggtctagtca gagcctcctc catagtcatg gatacaacta tttggattgg 120
tacctgcaga agccagggca gtctccacaa ctcctgatct atttgggttc taatcgggcc 180
tccggggtcc ctgacaggtt cagtggcggt ggatcaggca cagattttac actgaaaatc 240
agcagagtgg aggctgagga tgttgggatt tattactgca tgcaagctct acagactcct 300
ctcactttcg gcggagggac caaggtggag atcaaa 336

<210> SEQ ID NO 212

<211> LENGTH: 112
<212> TYPE: PRT
<213> ORGANISM: Artificial Sequence
<220> FEATURE:
<223> OTHER INFORMATION: Synthetic

<400> SEQUENCE: 212

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

His Gly Tyr Asn Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Gly Gly Ser Gly Thr Asp Phe Thr Leu Lys Ile
65 70 75 80

Ser Arg Val Glu Ala Glu Asp Val Gly Ile Tyr Tyr Cys Met Gln Ala
85 90 95

Leu Gln Thr Pro Leu Thr Phe Gly Gly Gly Thr Lys Val Glu Ile Lys
100 105 110

<210> SEQ ID NO 213
<211> LENGTH: 375
<212> TYPE: DNA
<213> ORGANISM: Artificial Sequence
<220> FEATURE:
<223> OTHER INFORMATION: Synthetic

<400> SEQUENCE: 213
cagatcacct tgaaggagtc tggtcctacg ctggtgaaac ccacacagac cctcacgctg 60
acctgcacct tctctgggtt ctcactcagc actagtggag tgggtgtggg ctggatccgt 120
cagcccccag gaaaggccct ggagtggctt gcactcattt attggaattc tgataagcgc 180
tacagcccat ctctgaagag caggctcacc atcaccaagg acacctccaa aaaccaggtg 240
gtccttacaa tgaccaacat ggaccctgtg gacacagcca catattactg tgcacacaga 300
catgacagct cgtcctacta cttctactac ggtatggacg tctggggcca agggaccacg 360
gtcaccgtct cctca 375

<210> SEQ ID NO 214
<211> LENGTH: 125
<212> TYPE: PRT
<213> ORGANISM: Artificial Sequence
<220> FEATURE:
<223> OTHER INFORMATION: Synthetic

<400> SEQUENCE: 214

Gln Ile Thr Leu Lys Glu Ser Gly Pro Thr Leu Val Lys Pro Thr Gln
1 5 10 15

Thr Leu Thr Leu Thr Cys Thr Phe Ser Gly Phe Ser Leu Ser Thr Ser
20 25 30

Gly Val Gly Val Gly Trp Ile Arg Gln Pro Pro Gly Lys Ala Leu Glu
35 40 45

Trp Leu Ala Leu Ile Tyr Trp Asn Ser Asp Lys Arg Tyr Ser Pro Ser
50 55 60

Leu Lys Ser Arg Leu Thr Ile Thr Lys Asp Thr Ser Lys Asn Gln Val
65 70 75 80

Val Leu Thr Met Thr Asn Met Asp Pro Val Asp Thr Ala Thr Tyr Tyr

```
                85                  90                  95

Cys Ala His Arg His Asp Ser Ser Ser Tyr Tyr Phe Tyr Tyr Gly Met
            100                 105                 110

Asp Val Trp Gly Gln Gly Thr Thr Val Thr Val Ser Ser
        115                 120                 125


<210> SEQ ID NO 215
<211> LENGTH: 336
<212> TYPE: DNA
<213> ORGANISM: Artificial Sequence
<220> FEATURE:
<223> OTHER INFORMATION: Synthetic

<400> SEQUENCE: 215

gatattgtga tgactcagtc tccactctcc ctgcccgtca cccctggaga gccggcctcc      60

atctcctgca ggtctagtca gagcctcctc catagtcatg gatacaacta tttggattgg     120

tacctgcaga agccagggca gtctccacag ctcctgatct atttgggttc taatcgggcc     180

tccggggtcc ctgacaggtt cagtggcagt ggatcaggca cagattttac actgaaaatc     240

agcagagtgg aggctgagga tgttggggtt tattactgca tgcaagctct acagactcct     300

ctcactttcg gcggagggac caaggtggag atcaaa                               336


<210> SEQ ID NO 216
<211> LENGTH: 112
<212> TYPE: PRT
<213> ORGANISM: Artificial Sequence
<220> FEATURE:
<223> OTHER INFORMATION: Synthetic

<400> SEQUENCE: 216

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

His Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110


<210> SEQ ID NO 217
<211> LENGTH: 381
<212> TYPE: DNA
<213> ORGANISM: Artificial Sequence
<220> FEATURE:
<223> OTHER INFORMATION: Synthetic

<400> SEQUENCE: 217

gagatgcaac tggtggagtc tgggggaggc ttggtccagc ctgggggggtc cctgagactc      60

tcctgtgcag cctctggatt cacctttagt agtcactgga tgaagtgggt ccgccaggct     120

ccagggaagg ggctggagtg ggtggccaac ataaaccaag atggaagtga gaaatactat     180

gtggactctg tgaagggccg attcaccatc tccagagaca acgccaagaa ctcactgttt     240
```

```
ctgcaaatga acagcctgag agccgaggac acggctgtgt attactgtgc gagagatatt    300

gtactaatgg tctatgatat ggactactac tactacggta tggacgtctg gggccaaggg    360

accacggtca ccgtctcctc a                                              381


<210> SEQ ID NO 218
<211> LENGTH: 127
<212> TYPE: PRT
<213> ORGANISM: Artificial Sequence
<220> FEATURE:
<223> OTHER INFORMATION: Synthetic

<400> SEQUENCE: 218

Glu Met Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser His
            20                  25                  30

Trp Met Lys Trp Val Arg Gln Ala Pro Gly Lys Gly Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Ile Val Leu Met Val Tyr Asp Met Asp Tyr Tyr Tyr Tyr
            100                 105                 110

Gly Met Asp Val Trp Gly Gln Gly Thr Thr Val Thr Val Ser Ser
        115                 120                 125


<210> SEQ ID NO 219
<211> LENGTH: 24
<212> TYPE: DNA
<213> ORGANISM: Artificial Sequence
<220> FEATURE:
<223> OTHER INFORMATION: Synthetic

<400> SEQUENCE: 219

ggattcacct ttagtagtca ctgg                                            24


<210> SEQ ID NO 220
<211> LENGTH: 8
<212> TYPE: PRT
<213> ORGANISM: Artificial Sequence
<220> FEATURE:
<223> OTHER INFORMATION: Synthetic

<400> SEQUENCE: 220

Gly Phe Thr Phe Ser Ser His Trp
 1               5


<210> SEQ ID NO 221
<211> LENGTH: 24
<212> TYPE: DNA
<213> ORGANISM: Artificial Sequence
<220> FEATURE:
<223> OTHER INFORMATION: Synthetic

<400> SEQUENCE: 221

ataaaccaag atggaagtga gaaa                                            24


<210> SEQ ID NO 222
```

<211> LENGTH: 8
<212> TYPE: PRT
<213> ORGANISM: Artificial Sequence
<220> FEATURE:
<223> OTHER INFORMATION: Synthetic

<400> SEQUENCE: 222

Ile Asn Gln Asp Gly Ser Glu Lys
1 5

<210> SEQ ID NO 223
<211> LENGTH: 60
<212> TYPE: DNA
<213> ORGANISM: Artificial Sequence
<220> FEATURE:
<223> OTHER INFORMATION: Synthetic

<400> SEQUENCE: 223
gcgagagata ttgtactaat ggtctatgat atggactact actactacgg tatggacgtc 60

<210> SEQ ID NO 224
<211> LENGTH: 20
<212> TYPE: PRT
<213> ORGANISM: Artificial Sequence
<220> FEATURE:
<223> OTHER INFORMATION: Synthetic

<400> SEQUENCE: 224

Ala Arg Asp Ile Val Leu Met Val Tyr Asp Met Asp Tyr Tyr Tyr Tyr
1 5 10 15

Gly Met Asp Val
20

<210> SEQ ID NO 225
<211> LENGTH: 336
<212> TYPE: DNA
<213> ORGANISM: Artificial Sequence
<220> FEATURE:
<223> OTHER INFORMATION: Synthetic

<400> SEQUENCE: 225
gatattgtga tgactcagtc tccactctcc ctgcccgtca cccctggaga gccggcctcc 60
atctcctgca ggtctagtca gagcctcctg catagtaatg gaaacaacta tttggattgg 120
tacctgcaga agccagggca gtctccacag ctcctgatct atttgggttc taatcgggcc 180
tccggggtcc ctgacaggtt cagtggcagt ggatcaggca cagattttac actgaaaatc 240
agcagagtgg aggctgagga tgttggggtt tattactgca tgcaaactct acaaactccg 300
ctcactttcg gcggagggac caaggtggag atcaaa 336

<210> SEQ ID NO 226
<211> LENGTH: 112
<212> TYPE: PRT
<213> ORGANISM: Artificial Sequence
<220> FEATURE:
<223> OTHER INFORMATION: Synthetic

<400> SEQUENCE: 226

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Asn Asn Tyr Leu Asp Trp Tyr Leu Gln Lys Pro Gly Gln Ser
35 40 45

```
Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Leu Thr Phe Gly Gly Gly Thr Lys Val Glu Ile Lys
            100                 105                 110


<210> SEQ ID NO 227
<211> LENGTH: 33
<212> TYPE: DNA
<213> ORGANISM: Artificial Sequence
<220> FEATURE:
<223> OTHER INFORMATION: Synthetic

<400> SEQUENCE: 227

cagagcctcc tgcatagtaa tggaaacaac tat                                33


<210> SEQ ID NO 228
<211> LENGTH: 11
<212> TYPE: PRT
<213> ORGANISM: Artificial Sequence
<220> FEATURE:
<223> OTHER INFORMATION: Synthetic

<400> SEQUENCE: 228

Gln Ser Leu Leu His Ser Asn Gly Asn Asn Tyr
 1               5                  10


<210> SEQ ID NO 229
<211> LENGTH: 9
<212> TYPE: DNA
<213> ORGANISM: Artificial Sequence
<220> FEATURE:
<223> OTHER INFORMATION: Synthetic

<400> SEQUENCE: 229

ttgggttct                                                            9


<210> SEQ ID NO 230
<211> LENGTH: 3
<212> TYPE: PRT
<213> ORGANISM: Artificial Sequence
<220> FEATURE:
<223> OTHER INFORMATION: Synthetic

<400> SEQUENCE: 230

Leu Gly Ser
 1


<210> SEQ ID NO 231
<211> LENGTH: 27
<212> TYPE: DNA
<213> ORGANISM: Artificial Sequence
<220> FEATURE:
<223> OTHER INFORMATION: Synthetic

<400> SEQUENCE: 231

atgcaaactc tacaaactcc gctcact                                       27


<210> SEQ ID NO 232
<211> LENGTH: 9
<212> TYPE: PRT
```

<213> ORGANISM: Artificial Sequence
<220> FEATURE:
<223> OTHER INFORMATION: Synthetic

<400> SEQUENCE: 232

Met Gln Thr Leu Gln Thr Pro Leu Thr
1 5

<210> SEQ ID NO 233
<211> LENGTH: 381
<212> TYPE: DNA
<213> ORGANISM: Artificial Sequence
<220> FEATURE:
<223> OTHER INFORMATION: Synthetic

<400> SEQUENCE: 233
gaggtgcagc tggtggagtc tgggggaggc ttggtccagc ctggggggtc cctgagactc 60
tcctgtgcag cctctggatt cacctttagt agtcactgga tgaagtgggt ccgccaggct 120
ccagggaagg ggctggagtg ggtggccaac ataaaccaag atggaagtga gaaatactat 180
gtggactctg tgaagggccg attcaccatc tccagagaca acgccaagaa ctcactgttt 240
ctgcaaatga acagcctgag agccgaggac acggctgtgt attactgtgc gagagatatt 300
gtactaatgg tctatgatat ggactactac tactacggta tggacgtctg gggccaaggg 360
accacggtca ccgtctcctc a 381

<210> SEQ ID NO 234
<211> LENGTH: 127
<212> TYPE: PRT
<213> ORGANISM: Artificial Sequence
<220> FEATURE:
<223> OTHER INFORMATION: Synthetic

<400> SEQUENCE: 234

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser His
20 25 30

Trp Met Lys Trp Val Arg Gln Ala Pro Gly Lys Gly Leu Glu Trp Val
35 40 45

Ala Asn Ile Asn Gln Asp Gly Ser Glu Lys Tyr Tyr Val Asp Ser Val
50 55 60

Lys Gly Arg Phe Thr Ile Ser Arg Asp Asn Ala Lys Asn Ser Leu Phe
65 70 75 80

Leu Gln Met Asn Ser Leu Arg Ala Glu Asp Thr Ala Val Tyr Tyr Cys
85 90 95

Ala Arg Asp Ile Val Leu Met Val Tyr Asp Met Asp Tyr Tyr Tyr Tyr
100 105 110

Gly Met Asp Val Trp Gly Gln Gly Thr Thr Val Thr Val Ser Ser
115 120 125

<210> SEQ ID NO 235
<211> LENGTH: 336
<212> TYPE: DNA
<213> ORGANISM: Artificial Sequence
<220> FEATURE:
<223> OTHER INFORMATION: Synthetic

<400> SEQUENCE: 235
gatattgtga tgactcagtc tccactctcc ctgcccgtca cccctggaga gccggcctcc 60

```
atctcctgca ggtctagtca gagcctcctg catagtaatg gaaacaacta tttggattgg    120

tacctgcaga agccagggca gtctccacag ctcctgatct atttgggttc taatcgggcc    180

tccggggtcc ctgacaggtt cagtggcagt ggatcaggca cagattttac actgaaaatc    240

agcagagtgg aggctgagga tgttggggtt tattactgca tgcaaactct acaaactccg    300

ctcactttcg gcggagggac caaggtggag atcaaa                              336


<210> SEQ ID NO 236
<211> LENGTH: 112
<212> TYPE: PRT
<213> ORGANISM: Artificial Sequence
<220> FEATURE:
<223> OTHER INFORMATION: Synthetic

<400> SEQUENCE: 236

Asp Ile Val Met Thr Gln Ser Pro Leu Ser Leu Pro Val Thr Pro Gly
 1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Leu Thr Phe Gly Gly Gly Thr Lys Val Glu Ile Lys
            100                 105                 110


<210> SEQ ID NO 237
<211> LENGTH: 381
<212> TYPE: DNA
<213> ORGANISM: Artificial Sequence
<220> FEATURE:
<223> OTHER INFORMATION: Synthetic

<400> SEQUENCE: 237

gaggtgcagc tggtggagtc tgggggaggc ttggtccagc ctggggggtc cctgagactc     60

tcctgtgcag cctctggatt cacctttagt agtcactgga tgagctgggt ccgccaggct    120

ccagggaagg ggctggagtg ggtggccaac ataaaccaag atggaagtga gaaatactat    180

gtggactctg tgaagggccg attcaccatc tccagagaca acgccaagaa ctcactgtat    240

ctgcaaatga acagcctgag agccgaggac acggctgtgt attactgtgc gagagatatt    300

gtactaatgg tctatgatat ggactactac tactacggta tggacgtctg gggcaaggg     360

accacggtca ccgtctcctc a                                              381


<210> SEQ ID NO 238
<211> LENGTH: 127
<212> TYPE: PRT
<213> ORGANISM: Artificial Sequence
<220> FEATURE:
<223> OTHER INFORMATION: Synthetic

<400> SEQUENCE: 238

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Ser His
```

```
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Val Leu Met Val Tyr Asp Met Asp Tyr Tyr Tyr Tyr
            100                 105                 110

Gly Met Asp Val Trp Gly Gln Gly Thr Thr Val Thr Val Ser Ser
        115                 120                 125


<210> SEQ ID NO 239
<211> LENGTH: 336
<212> TYPE: DNA
<213> ORGANISM: Artificial Sequence
<220> FEATURE:
<223> OTHER INFORMATION: Synthetic

<400> SEQUENCE: 239

gatattgtga tgactcagtc tccactctcc ctgcccgtca cccctggaga gccggcctcc     60

atctcctgca ggtctagtca gagcctcctg catagtaatg gaaacaacta tttggattgg    120

tacctgcaga agccagggca gtctccacag ctcctgatct atttgggttc taatcgggcc    180

tccggggtcc ctgacaggtt cagtggcagt ggatcaggca cagattttac actgaaaatc    240

agcagagtgg aggctgagga tgttggggtt tattactgca tgcaaactct acaaactccg    300

ctcactttcg gcggagggac caaggtggag atcaaa                              336


<210> SEQ ID NO 240
<211> LENGTH: 112
<212> TYPE: PRT
<213> ORGANISM: Artificial Sequence
<220> FEATURE:
<223> OTHER INFORMATION: Synthetic

<400> SEQUENCE: 240

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Leu Thr Phe Gly Gly Gly Thr Lys Val Glu Ile Lys
            100                 105                 110


<210> SEQ ID NO 241
<211> LENGTH: 381
<212> TYPE: DNA
<213> ORGANISM: Artificial Sequence
<220> FEATURE:
```

<223> OTHER INFORMATION: Synthetic

<400> SEQUENCE: 241
caggtgcagc tggtggagtc tgggggaggc gtggtccagc ctgggaggtc cctgagactc 60
tcctgtgcag tctctggatt caccttcagt agctatggca tgcactgggt ccgccaggct 120
ccaggcaagg ggctggagtg ggtggcagct atatcatatg atggaagtaa taaatactat 180
gtagactccg tgaagggccg attcaccatc tccagagaca attccaagaa aacgctgtat 240
ctgcaaatga acagcctgag agctgaggac acggctgtgt ataattgtgc gaaaaatatt 300
gtactagtga tgtatgatat agactatcac tactatggga tggacgtctg gggccaaggg 360
accacggtca ccgtctcctc a 381

<210> SEQ ID NO 242
<211> LENGTH: 127
<212> TYPE: PRT
<213> ORGANISM: Artificial Sequence
<220> FEATURE:
<223> OTHER INFORMATION: Synthetic

<400> SEQUENCE: 242

Gln Val Gln Leu Val Glu Ser Gly Gly Gly Val Val Gln Pro Gly Arg
1 5 10 15

Ser Leu Arg Leu Ser Cys Ala Val Ser Gly Phe Thr Phe Ser Ser Tyr
20 25 30

Gly Met His Trp Val Arg Gln Ala Pro Gly Lys Gly Leu Glu Trp Val
35 40 45

Ala Ala Ile Ser Tyr Asp Gly Ser Asn Lys Tyr Tyr Val Asp Ser Val
50 55 60

Lys Gly Arg Phe Thr Ile Ser Arg Asp Asn Ser Lys Lys Thr Leu Tyr
65 70 75 80

Leu Gln Met Asn Ser Leu Arg Ala Glu Asp Thr Ala Val Tyr Asn Cys
85 90 95

Ala Lys Asn Ile Val Leu Val Met Tyr Asp Ile Asp Tyr His Tyr Tyr
100 105 110

Gly Met Asp Val Trp Gly Gln Gly Thr Thr Val Thr Val Ser Ser
115 120 125

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243
ggattcacct tcagtagcta tggc 24

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

Gly Phe Thr Phe Ser Ser Tyr Gly
1 5

<210> SEQ ID NO 245

<211> LENGTH: 24
<212> TYPE: DNA
<213> ORGANISM: Artificial Sequence
<220> FEATURE:
<223> OTHER INFORMATION: Synthetic

<400> SEQUENCE: 245
atatcatatg atggaagtaa taaa 24

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

Ile Ser Tyr Asp Gly Ser Asn Lys
1 5

<210> SEQ ID NO 247
<211> LENGTH: 60
<212> TYPE: DNA
<213> ORGANISM: Artificial Sequence
<220> FEATURE:
<223> OTHER INFORMATION: Synthetic

<400> SEQUENCE: 247
gcgaaaaata ttgtactagt gatgtatgat atagactatc actactatgg gatggacgtc 60

<210> SEQ ID NO 248
<211> LENGTH: 20
<212> TYPE: PRT
<213> ORGANISM: Artificial Sequence
<220> FEATURE:
<223> OTHER INFORMATION: Synthetic

<400> SEQUENCE: 248

Ala Lys Asn Ile Val Leu Val Met Tyr Asp Ile Asp Tyr His Tyr Tyr
1 5 10 15

Gly Met Asp Val
20

<210> SEQ ID NO 249
<211> LENGTH: 336
<212> TYPE: DNA
<213> ORGANISM: Artificial Sequence
<220> FEATURE:
<223> OTHER INFORMATION: Synthetic

<400> SEQUENCE: 249
gatattgtga tgactcagtc tccactctcc ctgcccgtca cccctggaga gccggcctcc 60
atctcctgca ggtctagtca gagcctcctg catagtaatg gatacaacta tttggattgg 120
tacctgcaga agccagggca gtctccacaa ctcctgatct atttgggttt taatcgggcc 180
tccggggtcc ctgacaggtt cagtggcagt ggatcaggca cagattttac actgaaaatc 240
agcagagtgg aggctgagga tgttggggtt tattactgca tgcaagctct acaaactcct 300
ctcactttcg gcggagggac caaggtggag atcaga 336

<210> SEQ ID NO 250
<211> LENGTH: 112
<212> TYPE: PRT
<213> ORGANISM: Artificial Sequence
<220> FEATURE:

<223> OTHER INFORMATION: Synthetic

<400> SEQUENCE: 250

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Tyr Leu Asp Trp Tyr Leu Gln Lys Pro Gly Gln Ser
35 40 45

Pro Gln Leu Leu Ile Tyr Leu Gly Phe Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro Leu Thr Phe Gly Gly Gly Thr Lys Val Glu Ile Arg
100 105 110

<210> SEQ ID NO 251
<211> LENGTH: 33
<212> TYPE: DNA
<213> ORGANISM: Artificial Sequence
<220> FEATURE:
<223> OTHER INFORMATION: Synthetic

<400> SEQUENCE: 251
cagagcctcc tgcatagtaa tggatacaac tat 33

<210> SEQ ID NO 252
<211> LENGTH: 11
<212> TYPE: PRT
<213> ORGANISM: Artificial Sequence
<220> FEATURE:
<223> OTHER INFORMATION: Synthetic

<400> SEQUENCE: 252

Gln Ser Leu Leu His Ser Asn Gly Tyr Asn Tyr
1 5 10

<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253 ttgggtttt 9

<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

Leu Gly Phe
1

<210> SEQ ID NO 255
<211> LENGTH: 27
<212> TYPE: DNA

<213> ORGANISM: Artificial Sequence
<220> FEATURE:
<223> OTHER INFORMATION: Synthetic

<400> SEQUENCE: 255
atgcaagctc tacaaactcc tctcact 27

<210> SEQ ID NO 256
<211> LENGTH: 9
<212> TYPE: PRT
<213> ORGANISM: Artificial Sequence
<220> FEATURE:
<223> OTHER INFORMATION: Synthetic

<400> SEQUENCE: 256

Met Gln Ala Leu Gln Thr Pro Leu Thr
1 5

<210> SEQ ID NO 257
<211> LENGTH: 381
<212> TYPE: DNA
<213> ORGANISM: Artificial Sequence
<220> FEATURE:
<223> OTHER INFORMATION: Synthetic

<400> SEQUENCE: 257
caggtgcagc tggtggagtc tgggggaggc gtggtccagc ctgggaggtc cctgagactc 60
tcctgtgcag tctctggatt caccttcagt agctatggca tgcactgggt ccgccaggct 120
ccaggcaagg ggctggagtg ggtggcagct atatcatatg atggaagtaa taaatactat 180
gtagactccg tgaagggccg attcaccatc tccagagaca attccaagaa aacgctgtat 240
ctgcaaatga acagcctgag agctgaggac acggctgtgt ataattgtgc gaaaaatatt 300
gtactagtga tgtatgatat agactatcac tactatggga tggacgtctg gggccaaggg 360
accacggtca ccgtctcctc a 381

<210> SEQ ID NO 258
<211> LENGTH: 127
<212> TYPE: PRT
<213> ORGANISM: Artificial Sequence
<220> FEATURE:
<223> OTHER INFORMATION: Synthetic

<400> SEQUENCE: 258

Gln Val Gln Leu Val Glu Ser Gly Gly Gly Val Val Gln Pro Gly Arg
1 5 10 15

Ser Leu Arg Leu Ser Cys Ala Val Ser Gly Phe Thr Phe Ser Ser Tyr
20 25 30

Gly Met His Trp Val Arg Gln Ala Pro Gly Lys Gly Leu Glu Trp Val
35 40 45

Ala Ala Ile Ser Tyr Asp Gly Ser Asn Lys Tyr Tyr Val Asp Ser Val
50 55 60

Lys Gly Arg Phe Thr Ile Ser Arg Asp Asn Ser Lys Lys Thr Leu Tyr
65 70 75 80

Leu Gln Met Asn Ser Leu Arg Ala Glu Asp Thr Ala Val Tyr Asn Cys
85 90 95

Ala Lys Asn Ile Val Leu Val Met Tyr Asp Ile Asp Tyr His Tyr Tyr
100 105 110

Gly Met Asp Val Trp Gly Gln Gly Thr Thr Val Thr Val Ser Ser
115 120 125

<210> SEQ ID NO 259
<211> LENGTH: 336
<212> TYPE: DNA
<213> ORGANISM: Artificial Sequence
<220> FEATURE:
<223> OTHER INFORMATION: Synthetic

<400> SEQUENCE: 259
gatattgtga tgactcagtc tccactctcc ctgcccgtca cccctggaga gccggcctcc 60
atctcctgca ggtctagtca gagcctcctg catagtaatg gatacaacta tttggattgg 120
tacctgcaga agccagggca gtctccacaa ctcctgatct atttgggttt taatcgggcc 180
tccggggtcc ctgacaggtt cagtggcagt ggatcaggca cagattttac actgaaaatc 240
agcagagtgg aggctgagga tgttggggtt tattactgca tgcaagctct acaaactcct 300
ctcactttcg gcggagggac caaggtggag atcaaa 336

<210> SEQ ID NO 260
<211> LENGTH: 112
<212> TYPE: PRT
<213> ORGANISM: Artificial Sequence
<220> FEATURE:
<223> OTHER INFORMATION: Synthetic

<400> SEQUENCE: 260

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Tyr Leu Asp Trp Tyr Leu Gln Lys Pro Gly Gln Ser
35 40 45

Pro Gln Leu Leu Ile Tyr Leu Gly Phe Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro Leu Thr Phe Gly Gly Gly Thr Lys Val Glu Ile Lys
100 105 110

<210> SEQ ID NO 261
<211> LENGTH: 381
<212> TYPE: DNA
<213> ORGANISM: Artificial Sequence
<220> FEATURE:
<223> OTHER INFORMATION: Synthetic

<400> SEQUENCE: 261
caggtgcagc tggtggagtc tgggggaggc gtggtccagc ctgggaggtc cctgagactc 60
tcctgtgcag cctctggatt caccttcagt agctatggca tgcactgggt ccgccaggct 120
ccaggcaagg ggctggagtg ggtggcagtt atatcatatg atggaagtaa taaatactat 180
gcagactccg tgaagggccg attcaccatc tccagagaca attccaagaa cacgctgtat 240
ctgcaaatga acagcctgag agctgaggac acggctgtgt attactgtgc gaaaaatatt 300
gtactagtga tgtatgatat agactatcac tactatggga tggacgtctg ggggcaaggg 360
accacggtca ccgtctcctc a 381

<210> SEQ ID NO 262

<211> LENGTH: 127
<212> TYPE: PRT
<213> ORGANISM: Artificial Sequence
<220> FEATURE:
<223> OTHER INFORMATION: Synthetic

<400> SEQUENCE: 262

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asn Ile Val Leu Val Met Tyr Asp Ile Asp Tyr His Tyr Tyr
100 105 110

Gly Met Asp Val Trp Gly Gln Gly Thr Thr Val Thr Val Ser Ser
115 120 125

<210> SEQ ID NO 263
<211> LENGTH: 336
<212> TYPE: DNA
<213> ORGANISM: Artificial Sequence
<220> FEATURE:
<223> OTHER INFORMATION: Synthetic

<400> SEQUENCE: 263
gatattgtga tgactcagtc tccactctcc ctgcccgtca cccctggaga gccggcctcc 60
atctcctgca ggtctagtca gagcctcctg catagtaatg gatacaacta tttggattgg 120
tacctgcaga agccagggca gtctccacag ctcctgatct atttgggttt taatcgggcc 180
tccggggtcc ctgacaggtt cagtggcagt ggatcaggca cagattttac actgaaaatc 240
agcagagtgg aggctgagga tgttggggtt tattactgca tgcaagctct acaaactcct 300
ctcactttcg gcggagggac caaggtggag atcaaa 336

<210> SEQ ID NO 264
<211> LENGTH: 112
<212> TYPE: PRT
<213> ORGANISM: Artificial Sequence
<220> FEATURE:
<223> OTHER INFORMATION: Synthetic

<400> SEQUENCE: 264

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Tyr Leu Asp Trp Tyr Leu Gln Lys Pro Gly Gln Ser
35 40 45

Pro Gln Leu Leu Ile Tyr Leu Gly Phe Asn Arg Ala Ser Gly Val Pro
50 55 60

Asp Arg Phe Ser Gly Ser Gly Ser Gly Thr Asp Phe Thr Leu Lys Ile
65 70 75 80

```
Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110


<210> SEQ ID NO 265
<211> LENGTH: 381
<212> TYPE: DNA
<213> ORGANISM: Artificial Sequence
<220> FEATURE:
<223> OTHER INFORMATION: Synthetic

<400> SEQUENCE: 265

caggtgcagc tggtggagtc tgggggaggc gtggtccagc ctgggaggtc cctgagactc      60

tcctgtgcag tctctggatt caccttcagt agctatggca tgcactgggt ccgccaggct     120

ccaggcaagg ggctggagtg ggtggcagct atatcatatg atggaagtaa taaatactat     180

gtagactccg tgaagggccg attcaccatc tccagagaca attccaagaa aacgctgtat     240

ctgcaaatga acagcctgag agctgaggac acggctgtgt ataattgtgc gaaaaatatt     300

gtactagtga tgtatgatat agactatcac tactatggga tggacgtctg gggccaaggg     360

accacggtca ccgtctcctc a                                               381


<210> SEQ ID NO 266
<211> LENGTH: 127
<212> TYPE: PRT
<213> ORGANISM: Artificial Sequence
<220> FEATURE:
<223> OTHER INFORMATION: Synthetic

<400> SEQUENCE: 266

Gln Val Gln Leu Val Glu Ser Gly Gly Gly Val Val Gln Pro Gly Arg
 1               5                  10                  15

Ser Leu Arg Leu Ser Cys Ala Val Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Ser Tyr Asp Gly Ser Asn Lys Tyr Tyr Val Asp Ser Val
    50                  55                  60

Lys Gly Arg Phe Thr Ile Ser Arg Asp Asn Ser Lys Lys Thr Leu Tyr
65                  70                  75                  80

Leu Gln Met Asn Ser Leu Arg Ala Glu Asp Thr Ala Val Tyr Asn Cys
                85                  90                  95

Ala Lys Asn Ile Val Leu Val Met Tyr Asp Ile Asp Tyr His Tyr Tyr
            100                 105                 110

Gly Met Asp Val Trp Gly Gln Gly Thr Thr Val Thr Val Ser Ser
        115                 120                 125


<210> SEQ ID NO 267
<211> LENGTH: 24
<212> TYPE: DNA
<213> ORGANISM: Artificial Sequence
<220> FEATURE:
<223> OTHER INFORMATION: Synthetic

<400> SEQUENCE: 267

ggattcacct tcagtagcta tggc                                             24


<210> SEQ ID NO 268
<211> LENGTH: 8
```

<212> TYPE: PRT
<213> ORGANISM: Artificial Sequence
<220> FEATURE:
<223> OTHER INFORMATION: Synthetic

<400> SEQUENCE: 268

Gly Phe Thr Phe Ser Ser Tyr Gly
1 5

<210> SEQ ID NO 269
<211> LENGTH: 24
<212> TYPE: DNA
<213> ORGANISM: Artificial Sequence
<220> FEATURE:
<223> OTHER INFORMATION: Synthetic

<400> SEQUENCE: 269
atatcatatg atggaagtaa taaa 24

<210> SEQ ID NO 270
<211> LENGTH: 8
<212> TYPE: PRT
<213> ORGANISM: Artificial Sequence
<220> FEATURE:
<223> OTHER INFORMATION: Synthetic

<400> SEQUENCE: 270

Ile Ser Tyr Asp Gly Ser Asn Lys
1 5

<210> SEQ ID NO 271
<211> LENGTH: 60
<212> TYPE: DNA
<213> ORGANISM: Artificial Sequence
<220> FEATURE:
<223> OTHER INFORMATION: Synthetic

<400> SEQUENCE: 271
gcgaaaaata ttgtactagt gatgtatgat atagactatc actactatgg gatggacgtc 60

<210> SEQ ID NO 272
<211> LENGTH: 20
<212> TYPE: PRT
<213> ORGANISM: Artificial Sequence
<220> FEATURE:
<223> OTHER INFORMATION: Synthetic

<400> SEQUENCE: 272

Ala Lys Asn Ile Val Leu Val Met Tyr Asp Ile Asp Tyr His Tyr Tyr
1 5 10 15

Gly Met Asp Val
20

<210> SEQ ID NO 273
<211> LENGTH: 336
<212> TYPE: DNA
<213> ORGANISM: Artificial Sequence
<220> FEATURE:
<223> OTHER INFORMATION: Synthetic

<400> SEQUENCE: 273
gatattgtga tgactcagtc tccactctcc ctgcccgtca cccctggaga gccggcctcc 60
atctcctgca ggtctagtca gagcctcctg catagtaatg gatacaacta tttggattgg 120
tacctgcaga agccagggca gtctccacaa ctcctgatct atttgggttt taatcgggcc 180

```
tccggggtcc ctgacaggtt cagtggcagt ggatcaggca cagattttac actgaaaatc    240

agcagagtgg aggctgagga tgttggggtt tattactgca tgcaagctct acaaactcct    300

ctcactttcg gcggagggac caaggtggag atcaga                              336


<210> SEQ ID NO 274
<211> LENGTH: 112
<212> TYPE: PRT
<213> ORGANISM: Artificial Sequence
<220> FEATURE:
<223> OTHER INFORMATION: Synthetic

<400> SEQUENCE: 274

Asp Ile Val Met Thr Gln Ser Pro Leu Ser Leu Pro Val Thr Pro Gly
 1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Phe Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Arg
            100                 105                 110


<210> SEQ ID NO 275
<211> LENGTH: 33
<212> TYPE: DNA
<213> ORGANISM: Artificial Sequence
<220> FEATURE:
<223> OTHER INFORMATION: Synthetic

<400> SEQUENCE: 275

cagagcctcc tgcatagtaa tggatacaac tat                                  33


<210> SEQ ID NO 276
<211> LENGTH: 11
<212> TYPE: PRT
<213> ORGANISM: Artificial Sequence
<220> FEATURE:
<223> OTHER INFORMATION: Synthetic

<400> SEQUENCE: 276

Gln Ser Leu Leu His Ser Asn Gly Tyr Asn Tyr
 1               5                   10


<210> SEQ ID NO 277
<211> LENGTH: 9
<212> TYPE: DNA
<213> ORGANISM: Artificial Sequence
<220> FEATURE:
<223> OTHER INFORMATION: Synthetic

<400> SEQUENCE: 277

ttgggtttt                                                              9


<210> SEQ ID NO 278
<211> LENGTH: 3
<212> TYPE: PRT
<213> ORGANISM: Artificial Sequence
```

<220> FEATURE:
<223> OTHER INFORMATION: Synthetic

<400> SEQUENCE: 278

Leu Gly Phe
1

<210> SEQ ID NO 279
<211> LENGTH: 27
<212> TYPE: DNA
<213> ORGANISM: Artificial Sequence
<220> FEATURE:
<223> OTHER INFORMATION: Synthetic

<400> SEQUENCE: 279
atgcaagctc tacaaactcc tctcact 27

<210> SEQ ID NO 280
<211> LENGTH: 9
<212> TYPE: PRT
<213> ORGANISM: Artificial Sequence
<220> FEATURE:
<223> OTHER INFORMATION: Synthetic

<400> SEQUENCE: 280

Met Gln Ala Leu Gln Thr Pro Leu Thr
1 5

<210> SEQ ID NO 281
<211> LENGTH: 381
<212> TYPE: DNA
<213> ORGANISM: Artificial Sequence
<220> FEATURE:
<223> OTHER INFORMATION: Synthetic

<400> SEQUENCE: 281
caggtgcagc tggtggagtc tgggggaggc gtggtccagc ctgggaggtc cctgagactc 60
tcctgtgcag tctctggatt caccttcagt agctatggca tgcactgggt ccgccaggct 120
ccaggcaagg ggctggagtg ggtggcagct atatcatatg atggaagtaa taaatactat 180
gtagactccg tgaagggccg attcaccatc tccagagaca attccaagaa aacgctgtat 240
ctgcaaatga acagcctgag agctgaggac acggctgtgt ataattgtgc gaaaaatatt 300
gtactagtga tgtatgatat agactatcac tactatggga tggacgtctg gggccaaggg 360
accacggtca ccgtctcctc a 381

<210> SEQ ID NO 282
<211> LENGTH: 127
<212> TYPE: PRT
<213> ORGANISM: Artificial Sequence
<220> FEATURE:
<223> OTHER INFORMATION: Synthetic

<400> SEQUENCE: 282

Gln Val Gln Leu Val Glu Ser Gly Gly Gly Val Val Gln Pro Gly Arg
1 5 10 15

Ser Leu Arg Leu Ser Cys Ala Val Ser Gly Phe Thr Phe Ser Ser Tyr
20 25 30

Gly Met His Trp Val Arg Gln Ala Pro Gly Lys Gly Leu Glu Trp Val
35 40 45

Ala Ala Ile Ser Tyr Asp Gly Ser Asn Lys Tyr Tyr Val Asp Ser Val
50 55 60

```
Lys Gly Arg Phe Thr Ile Ser Arg Asp Asn Ser Lys Lys Thr Leu Tyr
65                  70                  75                  80

Leu Gln Met Asn Ser Leu Arg Ala Glu Asp Thr Ala Val Tyr Asn Cys
                85                  90                  95

Ala Lys Asn Ile Val Leu Val Met Tyr Asp Ile Asp Tyr His Tyr Tyr
            100                 105                 110

Gly Met Asp Val Trp Gly Gln Gly Thr Thr Val Thr Val Ser Ser
        115                 120                 125


<210> SEQ ID NO 283
<211> LENGTH: 336
<212> TYPE: DNA
<213> ORGANISM: Artificial Sequence
<220> FEATURE:
<223> OTHER INFORMATION: Synthetic

<400> SEQUENCE: 283

gatattgtga tgactcagtc tccactctcc ctgcccgtca cccctggaga gccggcctcc      60

atctcctgca ggtctagtca gagcctcctg catagtaatg gatacaacta tttggattgg     120

tacctgcaga agccagggca gtctccacaa ctcctgatct atttgggttt taatcgggcc     180

tccggggtcc ctgacaggtt cagtggcagt ggatcaggca cagattttac actgaaaatc     240

agcagagtgg aggctgagga tgttggggtt tattactgca tgcaagctct acaaactcct     300

ctcactttcg gcggagggac caaggtggag atcaaa                               336


<210> SEQ ID NO 284
<211> LENGTH: 112
<212> TYPE: PRT
<213> ORGANISM: Artificial Sequence
<220> FEATURE:
<223> OTHER INFORMATION: Synthetic

<400> SEQUENCE: 284

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Phe Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110


<210> SEQ ID NO 285
<211> LENGTH: 381
<212> TYPE: DNA
<213> ORGANISM: Artificial Sequence
<220> FEATURE:
<223> OTHER INFORMATION: Synthetic

<400> SEQUENCE: 285

caggtgcagc tggtggagtc tgggggaggc gtggtccagc ctgggaggtc cctgagactc      60

tcctgtgcag cctctggatt caccttcagt agctatggca tgcactgggt ccgccaggct     120
```

ccaggcaagg ggctggagtg ggtggcagtt atatcatatg atggaagtaa taaatactat 180
gcagactccg tgaagggccg attcaccatc tccagagaca attccaagaa cacgctgtat 240
ctgcaaatga acagcctgag agctgaggac acggctgtgt attactgtgc gaaaaatatt 300
gtactagtga tgtatgatat agactatcac tactatggga tggacgtctg ggggcaaggg 360
accacggtca ccgtctcctc a 381

<210> SEQ ID NO 286
<211> LENGTH: 127
<212> TYPE: PRT
<213> ORGANISM: Artificial Sequence
<220> FEATURE:
<223> OTHER INFORMATION: Synthetic

<400> SEQUENCE: 286

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asn Ile Val Leu Val Met Tyr Asp Ile Asp Tyr His Tyr Tyr
100 105 110

Gly Met Asp Val Trp Gly Gln Gly Thr Thr Val Thr Val Ser Ser
115 120 125

<210> SEQ ID NO 287
<211> LENGTH: 336
<212> TYPE: DNA
<213> ORGANISM: Artificial Sequence
<220> FEATURE:
<223> OTHER INFORMATION: Synthetic

<400> SEQUENCE: 287
gatattgtga tgactcagtc tccactctcc ctgcccgtca cccctggaga gccggcctcc 60
atctcctgca ggtctagtca gagcctcctg catagtaatg gatacaacta tttggattgg 120
tacctgcaga agccagggca gtctccacag ctcctgatct atttgggttt taatcgggcc 180
tccggggtcc ctgacaggtt cagtggcagt ggatcaggca cagattttac actgaaaatc 240
agcagagtgg aggctgagga tgttggggtt tattactgca tgcaagctct acaaactcct 300
ctcactttcg gcggagggac caaggtggag atcaaa 336

<210> SEQ ID NO 288
<211> LENGTH: 112
<212> TYPE: PRT
<213> ORGANISM: Artificial Sequence
<220> FEATURE:
<223> OTHER INFORMATION: Synthetic

<400> SEQUENCE: 288

Asp Ile Val Met Thr Gln Ser Pro Leu Ser Leu Pro Val Thr Pro Gly
1 5 10 15

```
Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Phe Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110


<210> SEQ ID NO 289
<211> LENGTH: 372
<212> TYPE: DNA
<213> ORGANISM: Artificial Sequence
<220> FEATURE:
<223> OTHER INFORMATION: Synthetic

<400> SEQUENCE: 289

cagatcacct tgaaggagtc tggtcctacg ctggtaaaac ccacacagac cctcacgctg      60

acctgcacct tctctgggtt ctcactcagc gctagtggag tgggtgtggg ctggttccgt     120

cagcccccag gaaaggccct ggagtggctt gcactcattt attggaatga tgataagcgt     180

tacagcccat ctctaaagaa cagcctcacc atcaccaagg acacctccaa aaaccaggtg     240

gtccttacaa tgaccaacat ggaccctgtg gacacagcca catattactg tgcacacaga     300

atacatctat ggtcctactt ctactacggt atggacgtct ggggccaagg gaccacggtc     360

accgtctcct ca                                                         372


<210> SEQ ID NO 290
<211> LENGTH: 124
<212> TYPE: PRT
<213> ORGANISM: Artificial Sequence
<220> FEATURE:
<223> OTHER INFORMATION: Synthetic

<400> SEQUENCE: 290

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Ala Ser
            20                  25                  30

Gly Val Gly Val Gly Trp Phe Arg Gln Pro Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Asn Ser Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Ile His Leu Trp Ser Tyr Phe Tyr Tyr Gly Met Asp
            100                 105                 110

Val Trp Gly Gln Gly Thr Thr Val Thr Val Ser Ser
        115                 120


<210> SEQ ID NO 291
<211> LENGTH: 30
```

<212> TYPE: DNA
<213> ORGANISM: Artificial Sequence
<220> FEATURE:
<223> OTHER INFORMATION: Synthetic

<400> SEQUENCE: 291
gggttctcac tcagcgctag tggagtgggt 30

<210> SEQ ID NO 292
<211> LENGTH: 10
<212> TYPE: PRT
<213> ORGANISM: Artificial Sequence
<220> FEATURE:
<223> OTHER INFORMATION: Synthetic

<400> SEQUENCE: 292

Gly Phe Ser Leu Ser Ala Ser Gly Val Gly
1 5 10

<210> SEQ ID NO 293
<211> LENGTH: 21
<212> TYPE: DNA
<213> ORGANISM: Artificial Sequence
<220> FEATURE:
<223> OTHER INFORMATION: Synthetic

<400> SEQUENCE: 293
atttattgga atgatgataa g 21

<210> SEQ ID NO 294
<211> LENGTH: 7
<212> TYPE: PRT
<213> ORGANISM: Artificial Sequence
<220> FEATURE:
<223> OTHER INFORMATION: Synthetic

<400> SEQUENCE: 294

Ile Tyr Trp Asn Asp Asp Lys
1 5

<210> SEQ ID NO 295
<211> LENGTH: 48
<212> TYPE: DNA
<213> ORGANISM: Artificial Sequence
<220> FEATURE:
<223> OTHER INFORMATION: Synthetic

<400> SEQUENCE: 295
gcacacagaa tacatctatg gtcctacttc tactacggta tggacgtc 48

<210> SEQ ID NO 296
<211> LENGTH: 16
<212> TYPE: PRT
<213> ORGANISM: Artificial Sequence
<220> FEATURE:
<223> OTHER INFORMATION: Synthetic

<400> SEQUENCE: 296

Ala His Arg Ile His Leu Trp Ser Tyr Phe Tyr Tyr Gly Met Asp Val
1 5 10 15

<210> SEQ ID NO 297
<211> LENGTH: 336
<212> TYPE: DNA
<213> ORGANISM: Artificial Sequence
<220> FEATURE:
<223> OTHER INFORMATION: Synthetic

<400> SEQUENCE: 297
gatattgtga tgactcagtc tccactctcc ctgcccgtca cccctggaga gccggcctcc 60
atctcctgca ggtctagtca gactctcctg catagtaatg gatacaacta tttcgattgg 120
tacctgcaga agccagggca gtctccacag ctcctgatct atttgggttc taatcgggcc 180
tccggggtcc ctgacagatt cagtggcagt ggatcaggca cagattttac actgaaaatc 240
agcagagtgg aggctgagga tgttggaatt tattactgca tgcaagctct acaaactcct 300
ctcactttcg gcggagggac caaggtggag atcaga 336

<210> SEQ ID NO 298
<211> LENGTH: 112
<212> TYPE: PRT
<213> ORGANISM: Artificial Sequence
<220> FEATURE:
<223> OTHER INFORMATION: Synthetic

<400> SEQUENCE: 298

Asp Ile Val Met Thr Gln Ser Pro Leu Ser Leu Pro Val Thr Pro Gly
1 5 10 15

Glu Pro Ala Ser Ile Ser Cys Arg Ser Ser Gln Thr Leu Leu His Ser
20 25 30

Asn Gly Tyr Asn Tyr Phe Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Ile Tyr Tyr Cys Met Gln Ala
85 90 95

Leu Gln Thr Pro Leu Thr Phe Gly Gly Gly Thr Lys Val Glu Ile Arg
100 105 110

<210> SEQ ID NO 299
<211> LENGTH: 33
<212> TYPE: DNA
<213> ORGANISM: Artificial Sequence
<220> FEATURE:
<223> OTHER INFORMATION: Synthetic

<400> SEQUENCE: 299
cagactctcc tgcatagtaa tggatacaac tat 33

<210> SEQ ID NO 300
<211> LENGTH: 11
<212> TYPE: PRT
<213> ORGANISM: Artificial Sequence
<220> FEATURE:
<223> OTHER INFORMATION: Synthetic

<400> SEQUENCE: 300

Gln Thr Leu Leu His Ser Asn Gly Tyr Asn Tyr
1 5 10

<210> SEQ ID NO 301
<211> LENGTH: 9
<212> TYPE: DNA
<213> ORGANISM: Artificial Sequence
<220> FEATURE:
<223> OTHER INFORMATION: Synthetic

<400> SEQUENCE: 301 ttgggttct 9

<210> SEQ ID NO 302
<211> LENGTH: 3
<212> TYPE: PRT
<213> ORGANISM: Artificial Sequence
<220> FEATURE:
<223> OTHER INFORMATION: Synthetic

<400> SEQUENCE: 302

Leu Gly Ser
1

<210> SEQ ID NO 303
<211> LENGTH: 27
<212> TYPE: DNA
<213> ORGANISM: Artificial Sequence
<220> FEATURE:
<223> OTHER INFORMATION: Synthetic

<400> SEQUENCE: 303
atgcaagctc tacaaactcc tctcact 27

<210> SEQ ID NO 304
<211> LENGTH: 9
<212> TYPE: PRT
<213> ORGANISM: Artificial Sequence
<220> FEATURE:
<223> OTHER INFORMATION: Synthetic

<400> SEQUENCE: 304

Met Gln Ala Leu Gln Thr Pro Leu Thr
1 5

<210> SEQ ID NO 305
<211> LENGTH: 372
<212> TYPE: DNA
<213> ORGANISM: Artificial Sequence
<220> FEATURE:
<223> OTHER INFORMATION: Synthetic

<400> SEQUENCE: 305
cagatcacct tgaaggagtc tggtcctacg ctggtaaaac ccacacagac cctcacgctg 60
acctgcacct tctctgggtt ctcactcagc gctagtggag tgggtgtggg ctggttccgt 120
cagcccccag gaaaggccct ggagtggctt gcactcattt attggaatga tgataagcgt 180
tacagcccat ctctaaagaa cagcctcacc atcaccaagg acacctccaa aaaccaggtg 240
gtccttacaa tgaccaacat ggaccctgtg gacacagcca catattactg tgcacacaga 300
atacatctat ggtcctactt ctactacggt atggacgtct ggggccaagg gaccacggtc 360
accgtctcct ca 372

<210> SEQ ID NO 306
<211> LENGTH: 124
<212> TYPE: PRT
<213> ORGANISM: Artificial Sequence
<220> FEATURE:
<223> OTHER INFORMATION: Synthetic

<400> SEQUENCE: 306

Gln Ile Thr Leu Lys Glu Ser Gly Pro Thr Leu Val Lys Pro Thr Gln
1 5 10 15

Thr Leu Thr Leu Thr Cys Thr Phe Ser Gly Phe Ser Leu Ser Ala Ser
20 25 30

Gly Val Gly Val Gly Trp Phe Arg Gln Pro Pro Gly Lys Ala Leu Glu
35 40 45

Trp Leu Ala Leu Ile Tyr Trp Asn Asp Asp Lys Arg Tyr Ser Pro Ser
50 55 60

Leu Lys Asn Ser Leu Thr Ile Thr Lys Asp Thr Ser Lys Asn Gln Val
65 70 75 80

Val Leu Thr Met Thr Asn Met Asp Pro Val Asp Thr Ala Thr Tyr Tyr
85 90 95

Cys Ala His Arg Ile His Leu Trp Ser Tyr Phe Tyr Tyr Gly Met Asp
100 105 110

Val Trp Gly Gln Gly Thr Thr Val Thr Val Ser Ser
115 120

<210> SEQ ID NO 307
<211> LENGTH: 336
<212> TYPE: DNA
<213> ORGANISM: Artificial Sequence
<220> FEATURE:
<223> OTHER INFORMATION: Synthetic

<400> SEQUENCE: 307
gatattgtga tgactcagtc tccactctcc ctgcccgtca cccctggaga gccggcctcc 60
atctcctgca ggtctagtca gactctcctg catagtaatg gatacaacta tttcgattgg 120
tacctgcaga agccagggca gtctccacag ctcctgatct atttgggttc taatcgggcc 180
tccggggtcc ctgacagatt cagtggcagt ggatcaggca cagattttac actgaaaatc 240
agcagagtgg aggctgagga tgttggaatt tattactgca tgcaagctct acaaactcct 300
ctcactttcg gcggagggac caaggtggag atcaaa 336

<210> SEQ ID NO 308
<211> LENGTH: 112
<212> TYPE: PRT
<213> ORGANISM: Artificial Sequence
<220> FEATURE:
<223> OTHER INFORMATION: Synthetic

<400> SEQUENCE: 308

Asp Ile Val Met Thr Gln Ser Pro Leu Ser Leu Pro Val Thr Pro Gly
1 5 10 15

Glu Pro Ala Ser Ile Ser Cys Arg Ser Ser Gln Thr Leu Leu His Ser
20 25 30

Asn Gly Tyr Asn Tyr Phe Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Ile Tyr Tyr Cys Met Gln Ala
85 90 95

Leu Gln Thr Pro Leu Thr Phe Gly Gly Gly Thr Lys Val Glu Ile Lys
100 105 110

<210> SEQ ID NO 309
<211> LENGTH: 372
<212> TYPE: DNA
<213> ORGANISM: Artificial Sequence
<220> FEATURE:
<223> OTHER INFORMATION: Synthetic

<400> SEQUENCE: 309
cagatcacct tgaaggagtc tggtcctacg ctggtgaaac ccacacagac cctcacgctg 60
acctgcacct tctctgggtt ctcactcagc gctagtggag tgggtgtggg ctggatccgt 120
cagcccccag gaaaggccct ggagtggctt gcactcattt attggaatga tgataagcgc 180
tacagcccat ctctgaagag caggctcacc atcaccaagg acacctccaa aaaccaggtg 240
gtccttacaa tgaccaacat ggaccctgtg gacacagcca catattactg tgcacacaga 300
atacatctat ggtcctactt ctactacggt atggacgtct gggggcaagg gaccacggtc 360
accgtctcct ca 372

<210> SEQ ID NO 310
<211> LENGTH: 124
<212> TYPE: PRT
<213> ORGANISM: Artificial Sequence
<220> FEATURE:
<223> OTHER INFORMATION: Synthetic

<400> SEQUENCE: 310

Gln Ile Thr Leu Lys Glu Ser Gly Pro Thr Leu Val Lys Pro Thr Gln
1 5 10 15

Thr Leu Thr Leu Thr Cys Thr Phe Ser Gly Phe Ser Leu Ser Ala Ser
20 25 30

Gly Val Gly Val Gly Trp Ile Arg Gln Pro Pro Gly Lys Ala Leu Glu
35 40 45

Trp Leu Ala Leu Ile Tyr Trp Asn Asp Asp Lys Arg Tyr Ser Pro Ser
50 55 60

Leu Lys Ser Arg Leu Thr Ile Thr Lys Asp Thr Ser Lys Asn Gln Val
65 70 75 80

Val Leu Thr Met Thr Asn Met Asp Pro Val Asp Thr Ala Thr Tyr Tyr
85 90 95

Cys Ala His Arg Ile His Leu Trp Ser Tyr Phe Tyr Tyr Gly Met Asp
100 105 110

Val Trp Gly Gln Gly Thr Thr Val Thr Val Ser Ser
115 120

<210> SEQ ID NO 311
<211> LENGTH: 336
<212> TYPE: DNA
<213> ORGANISM: Artificial Sequence
<220> FEATURE:
<223> OTHER INFORMATION: Synthetic

<400> SEQUENCE: 311
gatattgtga tgactcagtc tccactctcc ctgcccgtca cccctggaga gccggcctcc 60
atctcctgca ggtctagtca gactctcctg catagtaatg gatacaacta tttggattgg 120
tacctgcaga agccagggca gtctccacag ctcctgatct atttgggttc taatcgggcc 180
tccggggtcc ctgacaggtt cagtggcagt ggatcaggca cagattttac actgaaaatc 240
agcagagtgg aggctgagga tgttggggtt tattactgca tgcaagctct acaaactcct 300
ctcactttcg gcggagggac caaggtggag atcaaa 336

<210> SEQ ID NO 312
<211> LENGTH: 112
<212> TYPE: PRT

<213> ORGANISM: Artificial Sequence
<220> FEATURE:
<223> OTHER INFORMATION: Synthetic

<400> SEQUENCE: 312

Asp Ile Val Met Thr Gln Ser Pro Leu Ser Leu Pro Val Thr Pro Gly
1 5 10 15

Glu Pro Ala Ser Ile Ser Cys Arg Ser Ser Gln Thr Leu Leu His Ser
20 25 30

Asn Gly Tyr Asn Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro Leu Thr Phe Gly Gly Gly Thr Lys Val Glu Ile Lys
100 105 110

<210> SEQ ID NO 313
<211> LENGTH: 381
<212> TYPE: DNA
<213> ORGANISM: Artificial Sequence
<220> FEATURE:
<223> OTHER INFORMATION: Synthetic

<400> SEQUENCE: 313
caggttcagc tggtgcagtc tggacctgag gtgaagaacc ctggggcctc agtgaaggtc 60
tcctgcaagg cttctggtta cacctttacc acctatggta tcagttgggt acgacaggcc 120
cctggacaag ggcttgagtg gatgggatgg atcagcggtt acaatggtaa aacaaacgat 180
gcacagaagt tccaggacag agtcgccatg accacagaca catccacgag cacagcctac 240
atggagctga ggagcctgag atctgacgac acggccattt attactgttc gagagatcgt 300
ttagtagtac cacctgccct taattattcc tactacgtta tggacgtctg ggccaaggg 360 accacggtca ccgtctcctc a 381

<210> SEQ ID NO 314
<211> LENGTH: 127
<212> TYPE: PRT
<213> ORGANISM: Artificial Sequence
<220> FEATURE:
<223> OTHER INFORMATION: Synthetic

<400> SEQUENCE: 314

Gln Val Gln Leu Val Gln Ser Gly Pro Glu Val Lys Asn Pro Gly Ala
1 5 10 15

Ser Val Lys Val Ser Cys Lys Ala Ser Gly Tyr Thr Phe Thr Thr Tyr
20 25 30

Gly Ile Ser Trp Val Arg Gln Ala Pro Gly Gln Gly Leu Glu Trp Met
35 40 45

Gly Trp Ile Ser Gly Tyr Asn Gly Lys Thr Asn Asp Ala Gln Lys Phe
50 55 60

Gln Asp Arg Val Ala Met Thr Thr Asp Thr Ser Thr Ser Thr Ala Tyr
65 70 75 80

Met Glu Leu Arg Ser Leu Arg Ser Asp Asp Thr Ala Ile Tyr Tyr Cys
85 90 95

```
Ser Arg Asp Arg Leu Val Val Pro Pro Ala Leu Asn Tyr Ser Tyr Tyr
            100                 105                 110

Val Met Asp Val Trp Gly Gln Gly Thr Thr Val Thr Val Ser Ser
        115                 120                 125


<210> SEQ ID NO 315
<211> LENGTH: 24
<212> TYPE: DNA
<213> ORGANISM: Artificial Sequence
<220> FEATURE:
<223> OTHER INFORMATION: Synthetic

<400> SEQUENCE: 315

ggttacacct ttaccaccta tggt                                          24


<210> SEQ ID NO 316
<211> LENGTH: 8
<212> TYPE: PRT
<213> ORGANISM: Artificial Sequence
<220> FEATURE:
<223> OTHER INFORMATION: Synthetic

<400> SEQUENCE: 316

Gly Tyr Thr Phe Thr Thr Tyr Gly
 1               5


<210> SEQ ID NO 317
<211> LENGTH: 24
<212> TYPE: DNA
<213> ORGANISM: Artificial Sequence
<220> FEATURE:
<223> OTHER INFORMATION: Synthetic

<400> SEQUENCE: 317

atcagcggtt acaatggtaa aaca                                          24


<210> SEQ ID NO 318
<211> LENGTH: 8
<212> TYPE: PRT
<213> ORGANISM: Artificial Sequence
<220> FEATURE:
<223> OTHER INFORMATION: Synthetic

<400> SEQUENCE: 318

Ile Ser Gly Tyr Asn Gly Lys Thr
 1               5


<210> SEQ ID NO 319
<211> LENGTH: 60
<212> TYPE: DNA
<213> ORGANISM: Artificial Sequence
<220> FEATURE:
<223> OTHER INFORMATION: Synthetic

<400> SEQUENCE: 319

tcgagagatc gtttagtagt accacctgcc cttaattatt cctactacgt tatggacgtc     60


<210> SEQ ID NO 320
<211> LENGTH: 20
<212> TYPE: PRT
<213> ORGANISM: Artificial Sequence
<220> FEATURE:
<223> OTHER INFORMATION: Synthetic

<400> SEQUENCE: 320

Ser Arg Asp Arg Leu Val Val Pro Pro Ala Leu Asn Tyr Ser Tyr Tyr
```

```
 1               5                  10                  15

Val Met Asp Val
            20


<210> SEQ ID NO 321
<211> LENGTH: 336
<212> TYPE: DNA
<213> ORGANISM: Artificial Sequence
<220> FEATURE:
<223> OTHER INFORMATION: Synthetic

<400> SEQUENCE: 321

gatgttgtga tgactcagtc tccactctcc ctgcccgtca cccttggaca gccggcctcc      60

atctcctgca ggtctagtca aagcctcgta tacagtgatg gaaacaccta cttgaattgg     120

tctcagcaga ggccaggtca atctccaagg cgcctaattt ataaggtttc taaccgggac     180

tctggggtcc cagacagatt cagcggcagt gggtcaggca ctgatttcac actgaaaatc     240

agcagggtgg aggctgagga tgttggggtt tattactgca tgcaaggtac acactggccg     300

tacacttttg gccaggggac caagctggag atcaaa                               336


<210> SEQ ID NO 322
<211> LENGTH: 112
<212> TYPE: PRT
<213> ORGANISM: Artificial Sequence
<220> FEATURE:
<223> OTHER INFORMATION: Synthetic

<400> SEQUENCE: 322

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
            20                  25                  30

Asp Gly Asn Thr Tyr Leu Asn Trp Ser Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110


<210> SEQ ID NO 323
<211> LENGTH: 33
<212> TYPE: DNA
<213> ORGANISM: Artificial Sequence
<220> FEATURE:
<223> OTHER INFORMATION: Synthetic

<400> SEQUENCE: 323

caaagcctcg tatacagtga tggaaacacc tac                                   33


<210> SEQ ID NO 324
<211> LENGTH: 11
<212> TYPE: PRT
<213> ORGANISM: Artificial Sequence
<220> FEATURE:
<223> OTHER INFORMATION: Synthetic

<400> SEQUENCE: 324
```

Gln Ser Leu Val Tyr Ser Asp Gly Asn Thr Tyr
1 5 10

<210> SEQ ID NO 325
<211> LENGTH: 9
<212> TYPE: DNA
<213> ORGANISM: Artificial Sequence
<220> FEATURE:
<223> OTHER INFORMATION: Synthetic

<400> SEQUENCE: 325 aaggtttct 9

<210> SEQ ID NO 326
<211> LENGTH: 3
<212> TYPE: PRT
<213> ORGANISM: Artificial Sequence
<220> FEATURE:
<223> OTHER INFORMATION: Synthetic

<400> SEQUENCE: 326

Lys Val Ser
1

<210> SEQ ID NO 327
<211> LENGTH: 27
<212> TYPE: DNA
<213> ORGANISM: Artificial Sequence
<220> FEATURE:
<223> OTHER INFORMATION: Synthetic

<400> SEQUENCE: 327
atgcaaggta cacactggcc gtacact 27

<210> SEQ ID NO 328
<211> LENGTH: 9
<212> TYPE: PRT
<213> ORGANISM: Artificial Sequence
<220> FEATURE:
<223> OTHER INFORMATION: Synthetic

<400> SEQUENCE: 328

Met Gln Gly Thr His Trp Pro Tyr Thr
1 5

<210> SEQ ID NO 329
<211> LENGTH: 381
<212> TYPE: DNA
<213> ORGANISM: Artificial Sequence
<220> FEATURE:
<223> OTHER INFORMATION: Synthetic

<400> SEQUENCE: 329
caggttcagc tggtgcagtc tggacctgag gtgaagaacc ctggggcctc agtgaaggtc 60
tcctgcaagg cttctggtta cacctttacc acctatggta tcagttgggt acgacaggcc 120
cctggacaag ggcttgagtg gatgggatgg atcagcggtt acaatggtaa aacaaacgat 180
gcacagaagt tccaggacag agtcgccatg accacagaca catccacgag cacagcctac 240
atggagctga ggagcctgag atctgacgac acggccattt attactgttc gagagatcgt 300
ttagtagtac cacctgccct taattattcc tactacgtta tggacgtctg gggccaaggg 360
accacggtca ccgtctcctc a 381

<210> SEQ ID NO 330
<211> LENGTH: 127
<212> TYPE: PRT
<213> ORGANISM: Artificial Sequence
<220> FEATURE:
<223> OTHER INFORMATION: Synthetic

<400> SEQUENCE: 330

```
Gln Val Gln Leu Val Gln Ser Gly Pro Glu Val Lys Asn Pro Gly Ala
 1               5                  10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Asp Ala Gln Lys Phe
    50                  55                  60

Gln Asp Arg Val Ala Met Thr Thr Asp Thr Ser Thr Ser Thr Ala Tyr
65                  70                  75                  80

Met Glu Leu Arg Ser Leu Arg Ser Asp Asp Thr Ala Ile Tyr Tyr Cys
                85                  90                  95

Ser Arg Asp Arg Leu Val Val Pro Pro Ala Leu Asn Tyr Ser Tyr Tyr
            100                 105                 110

Val Met Asp Val Trp Gly Gln Gly Thr Thr Val Thr Val Ser Ser
        115                 120                 125
```

<210> SEQ ID NO 331
<211> LENGTH: 336
<212> TYPE: DNA
<213> ORGANISM: Artificial Sequence
<220> FEATURE:
<223> OTHER INFORMATION: Synthetic

<400> SEQUENCE: 331

```
gatgttgtga tgactcagtc tccactctcc ctgcccgtca cccttggaca gccggcctcc      60

atctcctgca ggtctagtca aagcctcgta tacagtgatg gaaacaccta cttgaattgg     120

tctcagcaga ggccaggtca atctccaagg cgcctaattt ataaggtttc taaccgggac     180

tctggggtcc cagacagatt cagcggcagt gggtcaggca ctgatttcac actgaaaatc     240

agcagggtgg aggctgagga tgttggggtt tattactgca tgcaaggtac acactggccg     300

tacacttttg gccaggggac caagctggag atcaaa                               336
```

<210> SEQ ID NO 332
<211> LENGTH: 112
<212> TYPE: PRT
<213> ORGANISM: Artificial Sequence
<220> FEATURE:
<223> OTHER INFORMATION: Synthetic

<400> SEQUENCE: 332

```
Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
            20                  25                  30

Asp Gly Asn Thr Tyr Leu Asn Trp Ser Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110


<210> SEQ ID NO 333
<211> LENGTH: 381
<212> TYPE: DNA
<213> ORGANISM: Artificial Sequence
<220> FEATURE:
<223> OTHER INFORMATION: Synthetic

<400> SEQUENCE: 333

caggttcagc tggtgcagtc tggagctgag gtgaagaagc ctggggcctc agtgaaggtc     60

tcctgcaagg cttctggtta cacctttacc acctatggta tcagctgggt gcgacaggcc    120

cctggacaag ggcttgagtg gatgggatgg atcagcggtt acaatggtaa aacaaactat    180

gcacagaagc tccagggcag agtcaccatg accacagaca catccacgag cacagcctac    240

atggagctga ggagcctgag atctgacgac acggccgtgt attactgttc gagagatcgt    300

ttagtagtac cacctgccct taattattcc tactacgtta tggacgtctg gggcaagggg    360

accacggtca ccgtctcctc a                                              381


<210> SEQ ID NO 334
<211> LENGTH: 127
<212> TYPE: PRT
<213> ORGANISM: Artificial Sequence
<220> FEATURE:
<223> OTHER INFORMATION: Synthetic

<400> SEQUENCE: 334

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ser Arg Asp Arg Leu Val Val Pro Pro Ala Leu Asn Tyr Ser Tyr Tyr
            100                 105                 110

Val Met Asp Val Trp Gly Gln Gly Thr Thr Val Thr Val Ser Ser
        115                 120                 125


<210> SEQ ID NO 335
<211> LENGTH: 336
<212> TYPE: DNA
<213> ORGANISM: Artificial Sequence
<220> FEATURE:
<223> OTHER INFORMATION: Synthetic

<400> SEQUENCE: 335

gatgttgtga tgactcagtc tccactctcc ctgcccgtca cccttggaca gccggcctcc     60

atctcctgca ggtctagtca aagcctcgta tacagtgatg gaaacaccta cttgaattgg    120
```

```
tttcagcaga ggccaggcca atctccaagg cgcctaattt ataaggtttc taaccgggac    180

tctggggtcc cagacagatt cagcggcagt gggtcaggca ctgatttcac actgaaaatc    240

agcagggtgg aggctgagga tgttggggtt tattactgca tgcaaggtac acactggccg    300

tacacttttg gccaggggac caagctggag atcaaa                              336


<210> SEQ ID NO 336
<211> LENGTH: 112
<212> TYPE: PRT
<213> ORGANISM: Artificial Sequence
<220> FEATURE:
<223> OTHER INFORMATION: Synthetic

<400> SEQUENCE: 336

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110


<210> SEQ ID NO 337
<211> LENGTH: 354
<212> TYPE: DNA
<213> ORGANISM: Artificial Sequence
<220> FEATURE:
<223> OTHER INFORMATION: Synthetic

<400> SEQUENCE: 337

gaggtgcagc tggtggagtc tgggggaggc ctggtcaagc ctggggggtc cctgagactc     60

tcctgtgcag cctctggatt caccttcagt agctatagca tggactgggt ccgccaggct    120

ccagggaagg ggctggagtg ggtctcatcc attagtagta gtagtagtta catatactac    180

gcagactctg tgaagggccg attcaccatc tccagagaca ccgccaagaa ctcactgtat    240

ctgcaaatga acagcctgag agacgaggac acggctgttt attactgtgc gagagagggc    300

agtagcagac tttttgacta ctggggccag ggaaccctgg tcaccgtctc ctca          354


<210> SEQ ID NO 338
<211> LENGTH: 118
<212> TYPE: PRT
<213> ORGANISM: Artificial Sequence
<220> FEATURE:
<223> OTHER INFORMATION: Synthetic

<400> SEQUENCE: 338

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asp Trp Val Arg Gln Ala Pro Gly Lys Gly Leu Glu Trp Val
        35                  40                  45
```

```
Ser Ser Ile Ser Ser Ser Ser Ser Tyr Ile Tyr Tyr Ala Asp Ser Val
    50                  55                  60

Lys Gly Arg Phe Thr Ile Ser Arg Asp Thr Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Gly Ser Ser Arg Leu Phe Asp Tyr Trp Gly Gln Gly Thr
            100                 105                 110

Leu Val Thr Val Ser Ser
        115


<210> SEQ ID NO 339
<211> LENGTH: 24
<212> TYPE: DNA
<213> ORGANISM: Artificial Sequence
<220> FEATURE:
<223> OTHER INFORMATION: Synthetic

<400> SEQUENCE: 339

ggattcacct tcagtagcta tagc                                            24


<210> SEQ ID NO 340
<211> LENGTH: 8
<212> TYPE: PRT
<213> ORGANISM: Artificial Sequence
<220> FEATURE:
<223> OTHER INFORMATION: Synthetic

<400> SEQUENCE: 340

Gly Phe Thr Phe Ser Ser Tyr Ser
 1               5


<210> SEQ ID NO 341
<211> LENGTH: 24
<212> TYPE: DNA
<213> ORGANISM: Artificial Sequence
<220> FEATURE:
<223> OTHER INFORMATION: Synthetic

<400> SEQUENCE: 341

attagtagta gtagtagtta cata                                            24


<210> SEQ ID NO 342
<211> LENGTH: 8
<212> TYPE: PRT
<213> ORGANISM: Artificial Sequence
<220> FEATURE:
<223> OTHER INFORMATION: Synthetic

<400> SEQUENCE: 342

Ile Ser Ser Ser Ser Ser Tyr Ile
 1               5


<210> SEQ ID NO 343
<211> LENGTH: 33
<212> TYPE: DNA
<213> ORGANISM: Artificial Sequence
<220> FEATURE:
<223> OTHER INFORMATION: Synthetic

<400> SEQUENCE: 343

gcgagagagg gcagtagcag actttttgac tac                                  33
```

<210> SEQ ID NO 344
<211> LENGTH: 11
<212> TYPE: PRT
<213> ORGANISM: Artificial Sequence
<220> FEATURE:
<223> OTHER INFORMATION: Synthetic

<400> SEQUENCE: 344

Ala Arg Glu Gly Ser Ser Arg Leu Phe Asp Tyr
1 5 10

<210> SEQ ID NO 345
<211> LENGTH: 321
<212> TYPE: DNA
<213> ORGANISM: Artificial Sequence
<220> FEATURE:
<223> OTHER INFORMATION: Synthetic

<400> SEQUENCE: 345
gacatccaga tgacccagtc tccttccacc ctgtctgcat ctgtaggaga cagagtcacc 60
atcacttgcc gggccagtca gagtattagt agctggttgg cctggtatca gcagagacca 120
gggaaagccc ctaagctcct gatctataag gcgtctagtt tagaaggtgg agtcccatca 180
aggttcagcg gcagtggatc tgggacagaa ttcactctca ccatcagcag cctgcagcct 240
gaggattttg caacttatta ctgccaacag tataatagtt attggtacac ttttggccag 300
gggaccaagc tggagatcaa a 321

<210> SEQ ID NO 346
<211> LENGTH: 107
<212> TYPE: PRT
<213> ORGANISM: Artificial Sequence
<220> FEATURE:
<223> OTHER INFORMATION: Synthetic

<400> SEQUENCE: 346

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Arg Pro Gly Lys Ala Pro Lys Leu Leu Ile
35 40 45

Tyr Lys Ala Ser Ser Leu Glu Gly Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln Tyr Asn Ser Tyr Trp Tyr
85 90 95

Thr Phe Gly Gln Gly Thr Lys Leu Glu Ile Lys
100 105

<210> SEQ ID NO 347
<211> LENGTH: 18
<212> TYPE: DNA
<213> ORGANISM: Artificial Sequence
<220> FEATURE:
<223> OTHER INFORMATION: Synthetic

<400> SEQUENCE: 347
cagagtatta gtagctgg 18

<210> SEQ ID NO 348

<211> LENGTH: 6
<212> TYPE: PRT
<213> ORGANISM: Artificial Sequence
<220> FEATURE:
<223> OTHER INFORMATION: Synthetic

<400> SEQUENCE: 348

Gln Ser Ile Ser Ser Trp
1 5

<210> SEQ ID NO 349
<211> LENGTH: 9
<212> TYPE: DNA
<213> ORGANISM: Artificial Sequence
<220> FEATURE:
<223> OTHER INFORMATION: Synthetic

<400> SEQUENCE: 349 aaggcgtct 9

<210> SEQ ID NO 350
<211> LENGTH: 3
<212> TYPE: PRT
<213> ORGANISM: Artificial Sequence
<220> FEATURE:
<223> OTHER INFORMATION: Synthetic

<400> SEQUENCE: 350

Lys Ala Ser
1

<210> SEQ ID NO 351
<211> LENGTH: 27
<212> TYPE: DNA
<213> ORGANISM: Artificial Sequence
<220> FEATURE:
<223> OTHER INFORMATION: Synthetic

<400> SEQUENCE: 351
caacagtata atagttattg gtacact 27

<210> SEQ ID NO 352
<211> LENGTH: 9
<212> TYPE: PRT
<213> ORGANISM: Artificial Sequence
<220> FEATURE:
<223> OTHER INFORMATION: Synthetic

<400> SEQUENCE: 352

Gln Gln Tyr Asn Ser Tyr Trp Tyr Thr
1 5

<210> SEQ ID NO 353
<211> LENGTH: 354
<212> TYPE: DNA
<213> ORGANISM: Artificial Sequence
<220> FEATURE:
<223> OTHER INFORMATION: Synthetic

<400> SEQUENCE: 353
gaggtgcagc tggtggagtc tgggggaggc ctggtcaagc ctgggggtc cctgagactc 60 tcctgtgcag cctctggatt caccttcagt agctatagca tggactgggt ccgccaggct 120
ccagggaagg ggctggagtg ggtctcatcc attagtagta gtagtagtta catatactac 180
gcagactctg tgaagggccg attcaccatc tccagagaca ccgccaagaa ctcactgtat 240
ctgcaaatga acagcctgag agacgaggac acggctgttt attactgtgc gagagagggc 300
agtagcagac tttttgacta ctggggccag ggaaccctgg tcaccgtctc ctca 354

<210> SEQ ID NO 354
<211> LENGTH: 118
<212> TYPE: PRT
<213> ORGANISM: Artificial Sequence
<220> FEATURE:
<223> OTHER INFORMATION: Synthetic

<400> SEQUENCE: 354

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Ser Met Asp Trp Val Arg Gln Ala Pro Gly Lys Gly Leu Glu Trp Val
35 40 45

Ser Ser Ile Ser Ser Ser Ser Ser Tyr Ile Tyr Tyr Ala Asp Ser Val
50 55 60

Lys Gly Arg Phe Thr Ile Ser Arg Asp Thr Ala Lys Asn Ser Leu Tyr
65 70 75 80

Leu Gln Met Asn Ser Leu Arg Asp Glu Asp Thr Ala Val Tyr Tyr Cys
85 90 95

Ala Arg Glu Gly Ser Ser Arg Leu Phe Asp Tyr Trp Gly Gln Gly Thr
100 105 110

Leu Val Thr Val Ser Ser
115

<210> SEQ ID NO 355
<211> LENGTH: 321
<212> TYPE: DNA
<213> ORGANISM: Artificial Sequence
<220> FEATURE:
<223> OTHER INFORMATION: Synthetic

<400> SEQUENCE: 355
gacatccaga tgacccagtc tccttccacc ctgtctgcat ctgtaggaga cagagtcacc 60
atcacttgcc gggccagtca gagtattagt agctggttgg cctggtatca gcagagacca 120
gggaaagccc ctaagctcct gatctataag gcgtctagtt tagaaggtgg agtcccatca 180
aggttcagcg gcagtggatc tgggacagaa ttcactctca ccatcagcag cctgcagcct 240
gaggattttg caacttatta ctgccaacag tataatagtt attggtacac ttttggccag 300
gggaccaagc tggagatcaa a 321

<210> SEQ ID NO 356
<211> LENGTH: 107
<212> TYPE: PRT
<213> ORGANISM: Artificial Sequence
<220> FEATURE:
<223> OTHER INFORMATION: Synthetic

<400> SEQUENCE: 356

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Arg Pro Gly Lys Ala Pro Lys Leu Leu Ile
35 40 45

-continued

```
Tyr Lys Ala Ser Ser Leu Glu Gly Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Ser Tyr Trp Tyr
                85                  90                  95

Thr Phe Gly Gln Gly Thr Lys Leu Glu Ile Lys
            100                 105
```

<210> SEQ ID NO 357
<211> LENGTH: 354
<212> TYPE: DNA
<213> ORGANISM: Artificial Sequence
<220> FEATURE:
<223> OTHER INFORMATION: Synthetic

<400> SEQUENCE: 357

```
gaggtgcagc tggtggagtc tgggggaggc ctggtcaagc ctgggggtc cctgagactc      60

tcctgtgcag cctctggatt caccttcagt agctatagca tgaactgggt ccgccaggct    120

ccagggaagg ggctggagtg ggtctcatcc attagtagta gtagtagtta catatactac    180

gcagactcag tgaagggccg attcaccatc tccagagaca acgccaagaa ctcactgtat    240

ctgcaaatga acagcctgag agccgaggac acggctgtgt attactgtgc gagagagggc    300

agtagcagac tttttgacta ctggggccaa ggaaccctgg tcaccgtctc ctca          354
```

<210> SEQ ID NO 358
<211> LENGTH: 118
<212> TYPE: PRT
<213> ORGANISM: Artificial Sequence
<220> FEATURE:
<223> OTHER INFORMATION: Synthetic

<400> SEQUENCE: 358

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ser Ser Arg Leu Phe Asp Tyr Trp Gly Gln Gly Thr
            100                 105                 110

Leu Val Thr Val Ser Ser
        115
```

<210> SEQ ID NO 359
<211> LENGTH: 321
<212> TYPE: DNA
<213> ORGANISM: Artificial Sequence
<220> FEATURE:
<223> OTHER INFORMATION: Synthetic

<400> SEQUENCE: 359

```
gacatccaga tgacccagtc tccttccacc ctgtctgcat ctgtaggaga cagagtcacc      60
```

```
atcacttgcc gggccagtca gagtattagt agctggttgg cctggtatca gcagaaacca    120

gggaaagccc ctaagctcct gatctataag gcgtctagtt tagaaagtgg ggtcccatca    180

aggttcagcg gcagtggatc tgggacagaa ttcactctca ccatcagcag cctgcagcct    240

gatgattttg caacttatta ctgccaacag tataatagtt attggtacac ttttggccag    300

gggaccaagc tggagatcaa a                                              321
```

<210> SEQ ID NO 360
<211> LENGTH: 107
<212> TYPE: PRT
<213> ORGANISM: Artificial Sequence
<220> FEATURE:
<223> OTHER INFORMATION: Synthetic

<400> SEQUENCE: 360

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Trp Tyr
                85                  90                  95

Thr Phe Gly Gln Gly Thr Lys Leu Glu Ile Lys
            100                 105
```

<210> SEQ ID NO 361
<211> LENGTH: 384
<212> TYPE: DNA
<213> ORGANISM: Artificial Sequence
<220> FEATURE:
<223> OTHER INFORMATION: Synthetic

<400> SEQUENCE: 361

```
caggtgcacc tggtggagtc tgggggaggc ttggtcaagc ctggagggtc cctgagactc     60

tcctgtgcag cctctggatt caccttcagt gaccactaca tgagctggat ccgccaggct    120

ccagggaagg ggctggagtg gatttcatac attagtaatg atggtggtac caaatactat    180

gtggactctg tggagggccg attcatcatt tccagggaca acgccaagaa ctcattgtat    240

ctacatatga acagcctcag agccgacgac acggccgtgt attactgtgc gagagatcag    300

ggatatattg gctacgactc gtattattac tattcctacg gtatggacgt ctggggccaa    360

gggaccacgg tcaccgtcgc ctca                                           384
```

<210> SEQ ID NO 362
<211> LENGTH: 128
<212> TYPE: PRT
<213> ORGANISM: Artificial Sequence
<220> FEATURE:
<223> OTHER INFORMATION: Synthetic

<400> SEQUENCE: 362

```
Gln Val His Leu Val Glu Ser Gly Gly Gly Leu Val Lys Pro Gly Gly
1               5                   10                  15
```

-continued

```
Ser Leu Arg Leu Ser Cys Ala Ala Ser Gly Phe Thr Phe Ser Asp His
            20                  25                  30

Tyr Met Ser Trp Ile Arg Gln Ala Pro Gly Lys Gly Leu Glu Trp Ile
        35                  40                  45

Ser Tyr Ile Ser Asn Asp Gly Gly Thr Lys Tyr Tyr Val Asp Ser Val
    50                  55                  60

Glu Gly Arg Phe Ile Ile Ser Arg Asp Asn Ala Lys Asn Ser Leu Tyr
65                  70                  75                  80

Leu His Met Asn Ser Leu Arg Ala Asp Asp Thr Ala Val Tyr Tyr Cys
                85                  90                  95

Ala Arg Asp Gln Gly Tyr Ile Gly Tyr Asp Ser Tyr Tyr Tyr Tyr Ser
            100                 105                 110

Tyr Gly Met Asp Val Trp Gly Gln Gly Thr Thr Val Thr Val Ala Ser
        115                 120                 125
```

<210> SEQ ID NO 363
<211> LENGTH: 24
<212> TYPE: DNA
<213> ORGANISM: Artificial Sequence
<220> FEATURE:
<223> OTHER INFORMATION: Synthetic

<400> SEQUENCE: 363
ggattcacct tcagtgacca ctac 24

<210> SEQ ID NO 364
<211> LENGTH: 8
<212> TYPE: PRT
<213> ORGANISM: Artificial Sequence
<220> FEATURE:
<223> OTHER INFORMATION: Synthetic

<400> SEQUENCE: 364

```
Gly Phe Thr Phe Ser Asp His Tyr
1               5
```

<210> SEQ ID NO 365
<211> LENGTH: 24
<212> TYPE: DNA
<213> ORGANISM: Artificial Sequence
<220> FEATURE:
<223> OTHER INFORMATION: Synthetic

<400> SEQUENCE: 365
attagtaatg atggtggtac caaa 24

<210> SEQ ID NO 366
<211> LENGTH: 8
<212> TYPE: PRT
<213> ORGANISM: Artificial Sequence
<220> FEATURE:
<223> OTHER INFORMATION: Synthetic

<400> SEQUENCE: 366

```
Ile Ser Asn Asp Gly Gly Thr Lys
1               5
```

<210> SEQ ID NO 367
<211> LENGTH: 63
<212> TYPE: DNA
<213> ORGANISM: Artificial Sequence
<220> FEATURE:
<223> OTHER INFORMATION: Synthetic

<400> SEQUENCE: 367
gcgagagatc agggatatat tggctacgac tcgtattatt actattccta cggtatggac 60
gtc 63

<210> SEQ ID NO 368
<211> LENGTH: 21
<212> TYPE: PRT
<213> ORGANISM: Artificial Sequence
<220> FEATURE:
<223> OTHER INFORMATION: Synthetic

<400> SEQUENCE: 368

Ala Arg Asp Gln Gly Tyr Ile Gly Tyr Asp Ser Tyr Tyr Tyr Tyr Ser
1 5 10 15

Tyr Gly Met Asp Val
20

<210> SEQ ID NO 369
<211> LENGTH: 321
<212> TYPE: DNA
<213> ORGANISM: Artificial Sequence
<220> FEATURE:
<223> OTHER INFORMATION: Synthetic

<400> SEQUENCE: 369
aaaattgtgt tgacgcagtc tccaggcacc ctgcctttgt ttccagggga aagagccacc 60
ctctcctgta gggccagtca gagtgttaac aacaaattct tagcctggta ccagcagaaa 120
tctggccagg ctcccaggct cctcatctat ggtgcatcca gcagggccac tggcatccca 180
gacaggttca gtggcagtgg gtctgggacc gacttcactc tcaccatcag cggactggag 240
cctgaagatt ttgaagtgta ttattgtcaa gtatatggta actcactcac tctcggcgga 300
gggaccaagg tggagatcaa g 321

<210> SEQ ID NO 370
<211> LENGTH: 107
<212> TYPE: PRT
<213> ORGANISM: Artificial Sequence
<220> FEATURE:
<223> OTHER INFORMATION: Synthetic

<400> SEQUENCE: 370

Lys Ile Val Leu Thr Gln Ser Pro Gly Thr Leu Pro Leu Phe Pro Gly
1 5 10 15

Glu Arg Ala Thr Leu Ser Cys Arg Ala Ser Gln Ser Val Asn Asn Lys
20 25 30

Phe Leu Ala Trp Tyr Gln Gln Lys Ser Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Gly Leu Glu
65 70 75 80

Pro Glu Asp Phe Glu Val Tyr Tyr Cys Gln Val Tyr Gly Asn Ser Leu
85 90 95

Thr Leu Gly Gly Gly Thr Lys Val Glu Ile Lys
100 105

<210> SEQ ID NO 371
<211> LENGTH: 21
<212> TYPE: DNA

<213> ORGANISM: Artificial Sequence
<220> FEATURE:
<223> OTHER INFORMATION: Synthetic

<400> SEQUENCE: 371
cagagtgtta acaacaaatt c 21

<210> SEQ ID NO 372
<211> LENGTH: 7
<212> TYPE: PRT
<213> ORGANISM: Artificial Sequence
<220> FEATURE:
<223> OTHER INFORMATION: Synthetic

<400> SEQUENCE: 372

Gln Ser Val Asn Asn Lys Phe
1 5

<210> SEQ ID NO 373
<211> LENGTH: 9
<212> TYPE: DNA
<213> ORGANISM: Artificial Sequence
<220> FEATURE:
<223> OTHER INFORMATION: Synthetic

<400> SEQUENCE: 373 ggtgcatcc 9

<210> SEQ ID NO 374
<211> LENGTH: 3
<212> TYPE: PRT
<213> ORGANISM: Artificial Sequence
<220> FEATURE:
<223> OTHER INFORMATION: Synthetic

<400> SEQUENCE: 374

Gly Ala Ser
1

<210> SEQ ID NO 375
<211> LENGTH: 24
<212> TYPE: DNA
<213> ORGANISM: Artificial Sequence
<220> FEATURE:
<223> OTHER INFORMATION: Synthetic

<400> SEQUENCE: 375
caagtatatg gtaactcact cact 24

<210> SEQ ID NO 376
<211> LENGTH: 8
<212> TYPE: PRT
<213> ORGANISM: Artificial Sequence
<220> FEATURE:
<223> OTHER INFORMATION: Synthetic

<400> SEQUENCE: 376

Gln Val Tyr Gly Asn Ser Leu Thr
1 5

<210> SEQ ID NO 377
<211> LENGTH: 384
<212> TYPE: DNA
<213> ORGANISM: Artificial Sequence
<220> FEATURE:
<223> OTHER INFORMATION: Synthetic

<400> SEQUENCE: 377
caggtgcagc tggtggagtc tgggggaggc ttggtcaagc ctggagggtc cctgagactc 60
tcctgtgcag cctctggatt caccttcagt gaccactaca tgagctggat ccgccaggct 120
ccagggaagg ggctggagtg gatttcatac attagtaatg atggtggtac caaatactat 180
gtggactctg tggagggccg attcatcatt tccagggaca acgccaagaa ctcattgtat 240
ctacatatga acagcctcag agccgacgac acggccgtgt attactgtgc gagagatcag 300
ggatatattg gctacgactc gtattattac tattcctacg gtatggacgt ctggggccaa 360
gggaccacgg tcaccgtctc ctca 384

<210> SEQ ID NO 378
<211> LENGTH: 128
<212> TYPE: PRT
<213> ORGANISM: Artificial Sequence
<220> FEATURE:
<223> OTHER INFORMATION: Synthetic

<400> SEQUENCE: 378

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp His
20 25 30

Tyr Met Ser Trp Ile Arg Gln Ala Pro Gly Lys Gly Leu Glu Trp Ile
35 40 45

Ser Tyr Ile Ser Asn Asp Gly Gly Thr Lys Tyr Tyr Val Asp Ser Val
50 55 60

Glu Gly Arg Phe Ile Ile Ser Arg Asp Asn Ala Lys Asn Ser Leu Tyr
65 70 75 80

Leu His Met Asn Ser Leu Arg Ala Asp Asp Thr Ala Val Tyr Tyr Cys
85 90 95

Ala Arg Asp Gln Gly Tyr Ile Gly Tyr Asp Ser Tyr Tyr Tyr Tyr Ser
100 105 110

Tyr Gly Met Asp Val Trp Gly Gln Gly Thr Thr Val Thr Val Ser Ser
115 120 125

<210> SEQ ID NO 379
<211> LENGTH: 321
<212> TYPE: DNA
<213> ORGANISM: Artificial Sequence
<220> FEATURE:
<223> OTHER INFORMATION: Synthetic

<400> SEQUENCE: 379
gaaattgtgt tgacgcagtc tccaggcacc ctgcctttgt ttccagggga aagagccacc 60
ctctcctgta gggccagtca gagtgttaac aacaaattct tagcctggta ccagcagaaa 120
tctggccagg ctcccaggct cctcatctat ggtgcatcca gcagggccac tggcatccca 180
gacaggttca gtggcagtgg gtctgggacc gacttcactc tcaccatcag cggactggag 240
cctgaagatt ttgaagtgta ttattgtcaa gtatatggta actcactcac tctcggcgga 300
gggaccaagg tggagatcaa a 321

<210> SEQ ID NO 380
<211> LENGTH: 107
<212> TYPE: PRT
<213> ORGANISM: Artificial Sequence
<220> FEATURE:
<223> OTHER INFORMATION: Synthetic

<400> SEQUENCE: 380

Glu Ile Val Leu Thr Gln Ser Pro Gly Thr Leu Pro Leu Phe Pro Gly
1 5 10 15

Glu Arg Ala Thr Leu Ser Cys Arg Ala Ser Gln Ser Val Asn Asn Lys
20 25 30

Phe Leu Ala Trp Tyr Gln Gln Lys Ser Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Gly Leu Glu
65 70 75 80

Pro Glu Asp Phe Glu Val Tyr Tyr Cys Gln Val Tyr Gly Asn Ser Leu
85 90 95

Thr Leu Gly Gly Gly Thr Lys Val Glu Ile Lys
100 105

<210> SEQ ID NO 381
<211> LENGTH: 384
<212> TYPE: DNA
<213> ORGANISM: Artificial Sequence
<220> FEATURE:
<223> OTHER INFORMATION: Synthetic

<400> SEQUENCE: 381
caggtgcagc tggtggagtc tgggggaggc ttggtcaagc ctggagggtc cctgagactc 60
tcctgtgcag cctctggatt caccttcagt gaccactaca tgagctggat ccgccaggct 120
ccagggaagg ggctggagtg ggtttcatac attagtaatg atggtggtac caaatactac 180
gcagactctg tgaagggccg attcaccatc tccagggaca acgccaagaa ctcactgtat 240
ctgcaaatga acagcctgag agccgaggac acggccgtgt attactgtgc gagagatcag 300
ggatatattg gctacgactc gtattattac tattcctacg gtatggacgt ctgggggcaa 360
gggaccacgg tcaccgtctc ctca 384

<210> SEQ ID NO 382
<211> LENGTH: 128
<212> TYPE: PRT
<213> ORGANISM: Artificial Sequence
<220> FEATURE:
<223> OTHER INFORMATION: Synthetic

<400> SEQUENCE: 382

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp His
20 25 30

Tyr Met Ser Trp Ile Arg Gln Ala Pro Gly Lys Gly Leu Glu Trp Val
35 40 45

Ser Tyr Ile Ser Asn Asp Gly Gly Thr Lys Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Gln Gly Tyr Ile Gly Tyr Asp Ser Tyr Tyr Tyr Tyr Ser
100 105 110

```
Tyr Gly Met Asp Val Trp Gly Gln Gly Thr Thr Val Thr Val Ser Ser
        115                 120                 125


<210> SEQ ID NO 383
<211> LENGTH: 321
<212> TYPE: DNA
<213> ORGANISM: Artificial Sequence
<220> FEATURE:
<223> OTHER INFORMATION: Synthetic

<400> SEQUENCE: 383

gaaattgtgt tgacgcagtc tccaggcacc ctgtctttgt ctccagggga aagagccacc      60

ctctcctgca gggccagtca gagtgttaac aacaaattct tagcctggta ccagcagaaa     120

cctggccagg ctcccaggct cctcatctat ggtgcatcca gcagggccac tggcatccca     180

gacaggttca gtggcagtgg gtctgggaca gacttcactc tcaccatcag cagactggag     240

cctgaagatt ttgcagtgta ttactgtcaa gtatatggta actcactcac tttcggcgga     300

gggaccaagg tggagatcaa a                                               321


<210> SEQ ID NO 384
<211> LENGTH: 107
<212> TYPE: PRT
<213> ORGANISM: Artificial Sequence
<220> FEATURE:
<223> OTHER INFORMATION: Synthetic

<400> SEQUENCE: 384

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Asn Asn Lys
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Val Tyr Gly Asn Ser Leu
                85                  90                  95

Thr Phe Gly Gly Gly Thr Lys Val Glu Ile Lys
            100                 105


<210> SEQ ID NO 385
<211> LENGTH: 360
<212> TYPE: DNA
<213> ORGANISM: Artificial Sequence
<220> FEATURE:
<223> OTHER INFORMATION: Synthetic

<400> SEQUENCE: 385

gaggtgcaga aggtggagtc tgggggaggc ctggtcaagc cggggggggtc cctgagactc      60

tcctgtacag cctctggatt caccttcagt acttataaca tgaattgggt ccgccaggct     120

ccagggaagg gactggagtg ggtctcatcc attaggagta gtagtaatta catatactac     180

gcagactcag tgaagggccg attcaccatc tccagagaca acgccaagaa ttcactgtat     240

ctgcaaatga acagcctgag agccgatgac acggctgtgt attactgtgc gagagatggc     300

agcagttggt acgactactc tgactactgg ggccagggaa ccctggtcac cgtctcctca     360
```

<210> SEQ ID NO 386
<211> LENGTH: 120
<212> TYPE: PRT
<213> ORGANISM: Artificial Sequence
<220> FEATURE:
<223> OTHER INFORMATION: Synthetic

<400> SEQUENCE: 386

```
Glu Val Gln Lys Val Glu Ser Gly Gly Gly Leu Val Lys Pro Gly Gly
 1               5                  10                  15

Ser Leu Arg Leu Ser Cys Thr Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45

Ser Ser Ile Arg Ser Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
        115                 120
```

<210> SEQ ID NO 387
<211> LENGTH: 24
<212> TYPE: DNA
<213> ORGANISM: Artificial Sequence
<220> FEATURE:
<223> OTHER INFORMATION: Synthetic

<400> SEQUENCE: 387
ggattcacct tcagtactta taac 24

<210> SEQ ID NO 388
<211> LENGTH: 8
<212> TYPE: PRT
<213> ORGANISM: Artificial Sequence
<220> FEATURE:
<223> OTHER INFORMATION: Synthetic

<400> SEQUENCE: 388

```
Gly Phe Thr Phe Ser Thr Tyr Asn
 1               5
```

<210> SEQ ID NO 389
<211> LENGTH: 24
<212> TYPE: DNA
<213> ORGANISM: Artificial Sequence
<220> FEATURE:
<223> OTHER INFORMATION: Synthetic

<400> SEQUENCE: 389
attaggagta gtagtaatta cata 24

<210> SEQ ID NO 390
<211> LENGTH: 8
<212> TYPE: PRT
<213> ORGANISM: Artificial Sequence
<220> FEATURE:
<223> OTHER INFORMATION: Synthetic

<400> SEQUENCE: 390

```
Ile Arg Ser Ser Ser Asn Tyr Ile
 1               5


<210> SEQ ID NO 391
<211> LENGTH: 39
<212> TYPE: DNA
<213> ORGANISM: Artificial Sequence
<220> FEATURE:
<223> OTHER INFORMATION: Synthetic

<400> SEQUENCE: 391

gcgagagatg gcagcagttg gtacgactac tctgactac                           39


<210> SEQ ID NO 392
<211> LENGTH: 13
<212> TYPE: PRT
<213> ORGANISM: Artificial Sequence
<220> FEATURE:
<223> OTHER INFORMATION: Synthetic

<400> SEQUENCE: 392

Ala Arg Asp Gly Ser Ser Trp Tyr Asp Tyr Ser Asp Tyr
 1               5                  10


<210> SEQ ID NO 393
<211> LENGTH: 321
<212> TYPE: DNA
<213> ORGANISM: Artificial Sequence
<220> FEATURE:
<223> OTHER INFORMATION: Synthetic

<400> SEQUENCE: 393

gacatccaga tgacccagtc tccttccacc ctgtctgcat ctgtaggaga cagagtcacc     60

atcacttgcc gggccagtca gagtattagt agctggttgg cctggtatca acagatacca    120

gggaaagccc ctaaactcct gatctataag gcgtctagtt tagaaaatgg ggtcccatca    180

aggttcagcg gcagtggatc tgggacagaa ttcactctca tcatcagcag cctgcagcct    240

gatgattttg caacttatta ctgccaacag tatattagtt attctcggac gttcggccaa    300

gggaccaagg tggaaatcaa a                                              321


<210> SEQ ID NO 394
<211> LENGTH: 107
<212> TYPE: PRT
<213> ORGANISM: Artificial Sequence
<220> FEATURE:
<223> OTHER INFORMATION: Synthetic

<400> SEQUENCE: 394

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Ile Pro Gly Lys Ala Pro Lys Leu Leu Ile
        35                  40                  45

Tyr Lys Ala Ser Ser Leu Glu Asn Gly Val Pro Ser Arg Phe Ser Gly
    50                  55                  60

Ser Gly Ser Gly Thr Glu Phe Thr Leu Ile Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95
```

Thr Phe Gly Gln Gly Thr Lys Val Glu Ile Lys
100 105

<210> SEQ ID NO 395
<211> LENGTH: 18
<212> TYPE: DNA
<213> ORGANISM: Artificial Sequence
<220> FEATURE:
<223> OTHER INFORMATION: Synthetic

<400> SEQUENCE: 395
cagagtatta gtagctgg 18

<210> SEQ ID NO 396
<211> LENGTH: 6
<212> TYPE: PRT
<213> ORGANISM: Artificial Sequence
<220> FEATURE:
<223> OTHER INFORMATION: Synthetic

<400> SEQUENCE: 396

Gln Ser Ile Ser Ser Trp
1 5

<210> SEQ ID NO 397
<211> LENGTH: 9
<212> TYPE: DNA
<213> ORGANISM: Artificial Sequence
<220> FEATURE:
<223> OTHER INFORMATION: Synthetic

<400> SEQUENCE: 397 aaggcgtct 9

<210> SEQ ID NO 398
<211> LENGTH: 3
<212> TYPE: PRT
<213> ORGANISM: Artificial Sequence
<220> FEATURE:
<223> OTHER INFORMATION: Synthetic

<400> SEQUENCE: 398

Lys Ala Ser
1

<210> SEQ ID NO 399
<211> LENGTH: 27
<212> TYPE: DNA
<213> ORGANISM: Artificial Sequence
<220> FEATURE:
<223> OTHER INFORMATION: Synthetic

<400> SEQUENCE: 399
caacagtata ttagttattc tcggacg 27

<210> SEQ ID NO 400
<211> LENGTH: 9
<212> TYPE: PRT
<213> ORGANISM: Artificial Sequence
<220> FEATURE:
<223> OTHER INFORMATION: Synthetic

<400> SEQUENCE: 400

Gln Gln Tyr Ile Ser Tyr Ser Arg Thr
1 5

<210> SEQ ID NO 401
<211> LENGTH: 360
<212> TYPE: DNA
<213> ORGANISM: Artificial Sequence
<220> FEATURE:
<223> OTHER INFORMATION: Synthetic

<400> SEQUENCE: 401
gaggtgcagc tggtggagtc tgggggaggc ctggtcaagc cggggggtc cctgagactc 60 tcctgtacag cctctggatt caccttcagt acttataaca tgaattgggt ccgccaggct 120
ccagggaagg gactggagtg ggtctcatcc attaggagta gtagtaatta catatactac 180
gcagactcag tgaagggccg attcaccatc tccagagaca acgccaagaa ttcactgtat 240
ctgcaaatga acagcctgag agccgatgac acggctgtgt attactgtgc gagagatggc 300
agcagttggt acgactactc tgactactgg ggccagggaa ccctggtcac cgtctcctca 360

<210> SEQ ID NO 402
<211> LENGTH: 120
<212> TYPE: PRT
<213> ORGANISM: Artificial Sequence
<220> FEATURE:
<223> OTHER INFORMATION: Synthetic

<400> SEQUENCE: 402

Glu Val Gln Leu Val Glu Ser Gly Gly Gly Leu Val Lys Pro Gly Gly
1 5 10 15

Ser Leu Arg Leu Ser Cys Thr Ala Ser Gly Phe Thr Phe Ser Thr Tyr
20 25 30

Asn Met Asn Trp Val Arg Gln Ala Pro Gly Lys Gly Leu Glu Trp Val
35 40 45

Ser Ser Ile Arg Ser Ser Ser Asn Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Asp Asp Thr Ala Val Tyr Tyr Cys
85 90 95

Ala Arg Asp Gly Ser Ser Trp Tyr Asp Tyr Ser Asp Tyr Trp Gly Gln
100 105 110

Gly Thr Leu Val Thr Val Ser Ser
115 120

<210> SEQ ID NO 403
<211> LENGTH: 321
<212> TYPE: DNA
<213> ORGANISM: Artificial Sequence
<220> FEATURE:
<223> OTHER INFORMATION: Synthetic

<400> SEQUENCE: 403
gacatccaga tgacccagtc tccttccacc ctgtctgcat ctgtaggaga cagagtcacc 60
atcacttgcc gggccagtca gagtattagt agctggttgg cctggtatca acagatacca 120
gggaaagccc ctaaactcct gatctataag gcgtctagtt tagaaaatgg ggtcccatca 180
aggttcagcg gcagtggatc tgggacagaa ttcactctca tcatcagcag cctgcagcct 240
gatgattttg caacttatta ctgccaacag tatattagtt attctcggac gttcggccaa 300
gggaccaagg tggaaatcaa a 321

<210> SEQ ID NO 404

<211> LENGTH: 107
<212> TYPE: PRT
<213> ORGANISM: Artificial Sequence
<220> FEATURE:
<223> OTHER INFORMATION: Synthetic

<400> SEQUENCE: 404

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Ile Pro Gly Lys Ala Pro Lys Leu Leu Ile
35 40 45

Tyr Lys Ala Ser Ser Leu Glu Asn Gly Val Pro Ser Arg Phe Ser Gly
50 55 60

Ser Gly Ser Gly Thr Glu Phe Thr Leu Ile Ile Ser Ser Leu Gln Pro
65 70 75 80

Asp Asp Phe Ala Thr Tyr Tyr Cys Gln Gln Tyr Ile Ser Tyr Ser Arg
85 90 95

Thr Phe Gly Gln Gly Thr Lys Val Glu Ile Lys
100 105

<210> SEQ ID NO 405
<211> LENGTH: 360
<212> TYPE: DNA
<213> ORGANISM: Artificial Sequence
<220> FEATURE:
<223> OTHER INFORMATION: Synthetic

<400> SEQUENCE: 405
gaggtgcagc tggtggagtc tgggggaggc ctggtcaagc ctgggggggtc cctgagactc 60 tcctgtgcag cctctggatt caccttcagt acttataaca tgaactgggt ccgccaggct 120
ccagggaagg ggctggagtg ggtctcatcc attaggagta gtagtaatta catatactac 180
gcagactcag tgaagggccg attcaccatc tccagagaca acgccaagaa ctcactgtat 240
ctgcaaatga acagcctgag agccgaggac acggctgtgt attactgtgc gagagatggc 300
agcagttggt acgactactc tgactactgg ggccaaggaa ccctggtcac cgtctcctca 360

<210> SEQ ID NO 406
<211> LENGTH: 120
<212> TYPE: PRT
<213> ORGANISM: Artificial Sequence
<220> FEATURE:
<223> OTHER INFORMATION: Synthetic

<400> SEQUENCE: 406

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Thr Tyr
20 25 30

Asn Met Asn Trp Val Arg Gln Ala Pro Gly Lys Gly Leu Glu Trp Val
35 40 45

Ser Ser Ile Arg Ser Ser Ser Asn Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

```
Ala Arg Asp Gly Ser Ser Trp Tyr Asp Tyr Ser Asp Tyr Trp Gly Gln
            100                 105                 110

Gly Thr Leu Val Thr Val Ser Ser
        115                 120
```

<210> SEQ ID NO 407
<211> LENGTH: 321
<212> TYPE: DNA
<213> ORGANISM: Artificial Sequence
<220> FEATURE:
<223> OTHER INFORMATION: Synthetic

<400> SEQUENCE: 407

```
gacatccaga tgacccagtc tccttccacc ctgtctgcat ctgtaggaga cagagtcacc     60

atcacttgcc gggccagtca gagtattagt agctggttgg cctggtatca gcagaaacca    120

gggaaagccc ctaagctcct gatctataag gcgtctagtt tagaaagtgg ggtcccatca    180

aggttcagcg gcagtggatc tgggacagaa ttcactctca ccatcagcag cctgcagcct    240

gatgattttg caacttatta ctgccaacag tatattagtt attctcggac gttcggccaa    300

gggaccaagg tggaaatcaa a                                              321
```

<210> SEQ ID NO 408
<211> LENGTH: 107
<212> TYPE: PRT
<213> ORGANISM: Artificial Sequence
<220> FEATURE:
<223> OTHER INFORMATION: Synthetic

<400> SEQUENCE: 408

```
Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105
```

<210> SEQ ID NO 409
<211> LENGTH: 360
<212> TYPE: DNA
<213> ORGANISM: Artificial Sequence
<220> FEATURE:
<223> OTHER INFORMATION: Synthetic

<400> SEQUENCE: 409

```
gaggtgcagc tggtggagtc tgggggaggc ctggtcaagc cgggggggtc cctgagactc     60

tcctgtacag cctctggatt caccttcagt acttataaca tgaattgggt ccgccaggct    120

ccagggaagg gactggagtg ggtctcatcc attaggagta gtagtaatta catatactac    180

gcagactcag tgaagggccg attcaccatc tccagagaca acgccaagaa ttcactgtat    240

ctgcaaatga acagcctgag agccgatgac acggctgtgt attactgtgc gagagatggc    300
```

```
agcagttggt acgactactc tgactactgg ggccagggaa ccctggtcac cgtctcctca    360


<210> SEQ ID NO 410
<211> LENGTH: 120
<212> TYPE: PRT
<213> ORGANISM: Artificial Sequence
<220> FEATURE:
<223> OTHER INFORMATION: Synthetic

<400> SEQUENCE: 410

Glu Val Gln Leu Val Glu Ser Gly Gly Gly Leu Val Lys Pro Gly Gly
 1               5                  10                  15

Ser Leu Arg Leu Ser Cys Thr Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45

Ser Ser Ile Arg Ser Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
        115                 120


<210> SEQ ID NO 411
<211> LENGTH: 24
<212> TYPE: DNA
<213> ORGANISM: Artificial Sequence
<220> FEATURE:
<223> OTHER INFORMATION: Synthetic

<400> SEQUENCE: 411

ggattcacct tcagtactta taac                                            24


<210> SEQ ID NO 412
<211> LENGTH: 8
<212> TYPE: PRT
<213> ORGANISM: Artificial Sequence
<220> FEATURE:
<223> OTHER INFORMATION: Synthetic

<400> SEQUENCE: 412

Gly Phe Thr Phe Ser Thr Tyr Asn
 1               5


<210> SEQ ID NO 413
<211> LENGTH: 24
<212> TYPE: DNA
<213> ORGANISM: Artificial Sequence
<220> FEATURE:
<223> OTHER INFORMATION: Synthetic

<400> SEQUENCE: 413

attaggagta gtagtaatta cata                                            24


<210> SEQ ID NO 414
<211> LENGTH: 8
<212> TYPE: PRT
<213> ORGANISM: Artificial Sequence
<220> FEATURE:
```

<223> OTHER INFORMATION: Synthetic

<400> SEQUENCE: 414

Ile Arg Ser Ser Ser Asn Tyr Ile
1 5

<210> SEQ ID NO 415
<211> LENGTH: 39
<212> TYPE: DNA
<213> ORGANISM: Artificial Sequence
<220> FEATURE:
<223> OTHER INFORMATION: Synthetic

<400> SEQUENCE: 415
gcgagagatg gcagcagttg gtacgactac tctgactac 39

<210> SEQ ID NO 416
<211> LENGTH: 13
<212> TYPE: PRT
<213> ORGANISM: Artificial Sequence
<220> FEATURE:
<223> OTHER INFORMATION: Synthetic

<400> SEQUENCE: 416

Ala Arg Asp Gly Ser Ser Trp Tyr Asp Tyr Ser Asp Tyr
1 5 10

<210> SEQ ID NO 417
<211> LENGTH: 321
<212> TYPE: DNA
<213> ORGANISM: Artificial Sequence
<220> FEATURE:
<223> OTHER INFORMATION: Synthetic

<400> SEQUENCE: 417
gacatccaga tgacccagtc tccttccacc ctgtctgcat ctgtaggaga cagagtcacc 60
atcacttgcc gggccagtca gagtattagt agctggttgg cctggtatca acagatacca 120
gggaaagccc ctaaactcct gatctataag gcgtctagtt tagaaaatgg ggtcccatca 180
aggttcagcg gcagtggatc tgggacagaa ttcactctca tcatcagcag cctgcagcct 240
gatgattttg caacttatta ctgccaacag tatattagtt attctcggac gttcggccaa 300
gggaccaagg tggaaatcaa a 321

<210> SEQ ID NO 418
<211> LENGTH: 107
<212> TYPE: PRT
<213> ORGANISM: Artificial Sequence
<220> FEATURE:
<223> OTHER INFORMATION: Synthetic

<400> SEQUENCE: 418

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Ile Pro Gly Lys Ala Pro Lys Leu Leu Ile
35 40 45

Tyr Lys Ala Ser Ser Leu Glu Asn Gly Val Pro Ser Arg Phe Ser Gly
50 55 60

Ser Gly Ser Gly Thr Glu Phe Thr Leu Ile Ile Ser Ser Leu Gln Pro
65 70 75 80

```
Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105
```

<210> SEQ ID NO 419
<211> LENGTH: 18
<212> TYPE: DNA
<213> ORGANISM: Artificial Sequence
<220> FEATURE:
<223> OTHER INFORMATION: Synthetic

<400> SEQUENCE: 419

```
cagagtatta gtagctgg                                                   18
```

<210> SEQ ID NO 420
<211> LENGTH: 6
<212> TYPE: PRT
<213> ORGANISM: Artificial Sequence
<220> FEATURE:
<223> OTHER INFORMATION: Synthetic

<400> SEQUENCE: 420

```
Gln Ser Ile Ser Ser Trp
 1               5
```

<210> SEQ ID NO 421
<211> LENGTH: 9
<212> TYPE: DNA
<213> ORGANISM: Artificial Sequence
<220> FEATURE:
<223> OTHER INFORMATION: Synthetic

<400> SEQUENCE: 421

```
aaggcgtct                                                              9
```

<210> SEQ ID NO 422
<211> LENGTH: 3
<212> TYPE: PRT
<213> ORGANISM: Artificial Sequence
<220> FEATURE:
<223> OTHER INFORMATION: Synthetic

<400> SEQUENCE: 422

```
Lys Ala Ser
 1
```

<210> SEQ ID NO 423
<211> LENGTH: 27
<212> TYPE: DNA
<213> ORGANISM: Artificial Sequence
<220> FEATURE:
<223> OTHER INFORMATION: Synthetic

<400> SEQUENCE: 423

```
caacagtata ttagttattc tcggacg                                         27
```

<210> SEQ ID NO 424
<211> LENGTH: 9
<212> TYPE: PRT
<213> ORGANISM: Artificial Sequence
<220> FEATURE:
<223> OTHER INFORMATION: Synthetic

<400> SEQUENCE: 424

```
Gln Gln Tyr Ile Ser Tyr Ser Arg Thr
```

1 5

<210> SEQ ID NO 425
<211> LENGTH: 360
<212> TYPE: DNA
<213> ORGANISM: Artificial Sequence
<220> FEATURE:
<223> OTHER INFORMATION: Synthetic

<400> SEQUENCE: 425
gaggtgcagc tggtggagtc tgggggaggc ctggtcaagc cggggggtc cctgagactc 60 tcctgtacag cctctggatt caccttcagt acttataaca tgaattgggt ccgccaggct 120
ccagggaagg gactggagtg ggtctcatcc attaggagta gtagtaatta catatactac 180
gcagactcag tgaagggccg attcaccatc tccagagaca acgccaagaa ttcactgtat 240
ctgcaaatga acagcctgag agccgatgac acggctgtgt attactgtgc gagagatggc 300
agcagttggt acgactactc tgactactgg ggccagggaa ccctggtcac cgtctcctca 360

<210> SEQ ID NO 426
<211> LENGTH: 120
<212> TYPE: PRT
<213> ORGANISM: Artificial Sequence
<220> FEATURE:
<223> OTHER INFORMATION: Synthetic

<400> SEQUENCE: 426

Glu Val Gln Leu Val Glu Ser Gly Gly Gly Leu Val Lys Pro Gly Gly
1 5 10 15

Ser Leu Arg Leu Ser Cys Thr Ala Ser Gly Phe Thr Phe Ser Thr Tyr
20 25 30

Asn Met Asn Trp Val Arg Gln Ala Pro Gly Lys Gly Leu Glu Trp Val
35 40 45

Ser Ser Ile Arg Ser Ser Ser Asn Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Asp Asp Thr Ala Val Tyr Tyr Cys
85 90 95

Ala Arg Asp Gly Ser Ser Trp Tyr Asp Tyr Ser Asp Tyr Trp Gly Gln
100 105 110

Gly Thr Leu Val Thr Val Ser Ser
115 120

<210> SEQ ID NO 427
<211> LENGTH: 321
<212> TYPE: DNA
<213> ORGANISM: Artificial Sequence
<220> FEATURE:
<223> OTHER INFORMATION: Synthetic

<400> SEQUENCE: 427
gacatccaga tgacccagtc tccttccacc ctgtctgcat ctgtaggaga cagagtcacc 60
atcacttgcc gggccagtca gagtattagt agctggttgg cctggtatca acagatacca 120
gggaaagccc ctaaactcct gatctataag gcgtctagtt tagaaaatgg ggtcccatca 180
aggttcagcg gcagtggatc tgggacagaa ttcactctca tcatcagcag cctgcagcct 240
gatgattttg caacttatta ctgccaacag tatattagtt attctcggac gttcggccaa 300
gggaccaagg tggaaatcaa a 321

<210> SEQ ID NO 428
<211> LENGTH: 107
<212> TYPE: PRT
<213> ORGANISM: Artificial Sequence
<220> FEATURE:
<223> OTHER INFORMATION: Synthetic

<400> SEQUENCE: 428

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Ile Pro Gly Lys Ala Pro Lys Leu Leu Ile
35 40 45

Tyr Lys Ala Ser Ser Leu Glu Asn Gly Val Pro Ser Arg Phe Ser Gly
50 55 60

Ser Gly Ser Gly Thr Glu Phe Thr Leu Ile Ile Ser Ser Leu Gln Pro
65 70 75 80

Asp Asp Phe Ala Thr Tyr Tyr Cys Gln Gln Tyr Ile Ser Tyr Ser Arg
85 90 95

Thr Phe Gly Gln Gly Thr Lys Val Glu Ile Lys
100 105

<210> SEQ ID NO 429
<211> LENGTH: 360
<212> TYPE: DNA
<213> ORGANISM: Artificial Sequence
<220> FEATURE:
<223> OTHER INFORMATION: Synthetic

<400> SEQUENCE: 429
gaggtgcagc tggtggagtc tgggggaggc ctggtcaagc ctggggggtc cctgagactc 60
tcctgtgcag cctctggatt caccttcagt acttataaca tgaactgggt ccgccaggct 120
ccagggaagg ggctggagtg ggtctcatcc attaggagta gtagtaatta catatactac 180
gcagactcag tgaagggccg attcaccatc tccagagaca acgccaagaa ctcactgtat 240
ctgcaaatga acagcctgag agccgaggac acggctgtgt attactgtgc gagagatggc 300
agcagttggt acgactactc tgactactgg ggccaaggaa ccctggtcac cgtctcctca 360

<210> SEQ ID NO 430
<211> LENGTH: 120
<212> TYPE: PRT
<213> ORGANISM: Artificial Sequence
<220> FEATURE:
<223> OTHER INFORMATION: Synthetic

<400> SEQUENCE: 430

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Thr Tyr
20 25 30

Asn Met Asn Trp Val Arg Gln Ala Pro Gly Lys Gly Leu Glu Trp Val
35 40 45

Ser Ser Ile Arg Ser Ser Ser Asn Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

```
Leu Gln Met Asn Ser Leu Arg Ala Glu Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
        115                 120
```

<210> SEQ ID NO 431
<211> LENGTH: 321
<212> TYPE: DNA
<213> ORGANISM: Artificial Sequence
<220> FEATURE:
<223> OTHER INFORMATION: Synthetic

<400> SEQUENCE: 431

```
gacatccaga tgacccagtc tccttccacc ctgtctgcat ctgtaggaga cagagtcacc      60

atcacttgcc gggccagtca gagtattagt agctggttgg cctggtatca gcagaaacca     120

gggaaagccc ctaagctcct gatctataag gcgtctagtt tagaaagtgg ggtcccatca     180

aggttcagcg gcagtggatc tgggacagaa ttcactctca ccatcagcag cctgcagcct     240

gatgattttg caacttatta ctgccaacag tatattagtt attctcggac gttcggccaa     300

gggaccaagg tggaaatcaa a                                               321
```

<210> SEQ ID NO 432
<211> LENGTH: 107
<212> TYPE: PRT
<213> ORGANISM: Artificial Sequence
<220> FEATURE:
<223> OTHER INFORMATION: Synthetic

<400> SEQUENCE: 432

```
Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105
```

<210> SEQ ID NO 433
<211> LENGTH: 360
<212> TYPE: DNA
<213> ORGANISM: Artificial Sequence
<220> FEATURE:
<223> OTHER INFORMATION: Synthetic

<400> SEQUENCE: 433

```
gaggtgcagc tggtggagtc tgggggaggc ctggtcaagc cggggggtc cctgagactc      60

tcctgtacag cctctggatt caccttcagt acttataaca tgaattgggt ccgccaggct     120

ccagggaagg gactggagtg ggtctcatcc attaggagta gtagtaatta catatactac     180

gcagactcag tgaagggccg attcaccatc tccagagaca acgccaagag ttcactgtat     240
```

ctgcaaatga acagcctgag agccgaggac acggctgtgt attactgtgc gagagatggc 300
agcagttggt acgactactc tgactactgg ggccagggaa ccctggtcac cgtctcctca 360

<210> SEQ ID NO 434
<211> LENGTH: 120
<212> TYPE: PRT
<213> ORGANISM: Artificial Sequence
<220> FEATURE:
<223> OTHER INFORMATION: Synthetic

<400> SEQUENCE: 434

Glu Val Gln Leu Val Glu Ser Gly Gly Gly Leu Val Lys Pro Gly Gly
1 5 10 15

Ser Leu Arg Leu Ser Cys Thr Ala Ser Gly Phe Thr Phe Ser Thr Tyr
20 25 30

Asn Met Asn Trp Val Arg Gln Ala Pro Gly Lys Gly Leu Glu Trp Val
35 40 45

Ser Ser Ile Arg Ser Ser Ser Asn Tyr Ile Tyr Tyr Ala Asp Ser Val
50 55 60

Lys Gly Arg Phe Thr Ile Ser Arg Asp Asn Ala Lys Ser Ser Leu Tyr
65 70 75 80

Leu Gln Met Asn Ser Leu Arg Ala Glu Asp Thr Ala Val Tyr Tyr Cys
85 90 95

Ala Arg Asp Gly Ser Ser Trp Tyr Asp Tyr Ser Asp Tyr Trp Gly Gln
100 105 110

Gly Thr Leu Val Thr Val Ser Ser
115 120

<210> SEQ ID NO 435
<211> LENGTH: 24
<212> TYPE: DNA
<213> ORGANISM: Artificial Sequence
<220> FEATURE:
<223> OTHER INFORMATION: Synthetic

<400> SEQUENCE: 435
ggattcacct tcagtactta taac 24

<210> SEQ ID NO 436
<211> LENGTH: 8
<212> TYPE: PRT
<213> ORGANISM: Artificial Sequence
<220> FEATURE:
<223> OTHER INFORMATION: Synthetic

<400> SEQUENCE: 436

Gly Phe Thr Phe Ser Thr Tyr Asn
1 5

<210> SEQ ID NO 437
<211> LENGTH: 24
<212> TYPE: DNA
<213> ORGANISM: Artificial Sequence
<220> FEATURE:
<223> OTHER INFORMATION: Synthetic

<400> SEQUENCE: 437
attaggagta gtagtaatta cata 24

<210> SEQ ID NO 438
<211> LENGTH: 8

<212> TYPE: PRT
<213> ORGANISM: Artificial Sequence
<220> FEATURE:
<223> OTHER INFORMATION: Synthetic

<400> SEQUENCE: 438

Ile Arg Ser Ser Ser Asn Tyr Ile
1 5

<210> SEQ ID NO 439
<211> LENGTH: 39
<212> TYPE: DNA
<213> ORGANISM: Artificial Sequence
<220> FEATURE:
<223> OTHER INFORMATION: Synthetic

<400> SEQUENCE: 439
gcgagagatg gcagcagttg gtacgactac tctgactac 39

<210> SEQ ID NO 440
<211> LENGTH: 13
<212> TYPE: PRT
<213> ORGANISM: Artificial Sequence
<220> FEATURE:
<223> OTHER INFORMATION: Synthetic

<400> SEQUENCE: 440

Ala Arg Asp Gly Ser Ser Trp Tyr Asp Tyr Ser Asp Tyr
1 5 10

<210> SEQ ID NO 441
<211> LENGTH: 321
<212> TYPE: DNA
<213> ORGANISM: Artificial Sequence
<220> FEATURE:
<223> OTHER INFORMATION: Synthetic

<400> SEQUENCE: 441
gacatccaga tgacccagtc tccttccacc ctgtctgcat ctgtaggaga cagagtcacc 60
atcacttgcc gggccagtca gagtattagt agctggttgg cctggtatca acaggtacca 120
gggaaagccc ctaaactcct gatctataag gcgtctagtt tagaaaatgg ggtcccatca 180
aggttcagcg gcagtggatc tgggacagaa ttcactctca tcatcagcag cctgcagcct 240
gatgattttg caacttatta ctgccaacag tatattagtt attctcggac gttcggccaa 300
gggaccaagg tggaaatcaa a 321

<210> SEQ ID NO 442
<211> LENGTH: 107
<212> TYPE: PRT
<213> ORGANISM: Artificial Sequence
<220> FEATURE:
<223> OTHER INFORMATION: Synthetic

<400> SEQUENCE: 442

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Val Pro Gly Lys Ala Pro Lys Leu Leu Ile
35 40 45

Tyr Lys Ala Ser Ser Leu Glu Asn Gly Val Pro Ser Arg Phe Ser Gly
50 55 60

```
Ser Gly Ser Gly Thr Glu Phe Thr Leu Ile Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105


<210> SEQ ID NO 443
<211> LENGTH: 18
<212> TYPE: DNA
<213> ORGANISM: Artificial Sequence
<220> FEATURE:
<223> OTHER INFORMATION: Synthetic

<400> SEQUENCE: 443

cagagtatta gtagctgg                                                    18


<210> SEQ ID NO 444
<211> LENGTH: 6
<212> TYPE: PRT
<213> ORGANISM: Artificial Sequence
<220> FEATURE:
<223> OTHER INFORMATION: Synthetic

<400> SEQUENCE: 444

Gln Ser Ile Ser Ser Trp
 1               5


<210> SEQ ID NO 445
<211> LENGTH: 9
<212> TYPE: DNA
<213> ORGANISM: Artificial Sequence
<220> FEATURE:
<223> OTHER INFORMATION: Synthetic

<400> SEQUENCE: 445

aaggcgtct                                                               9


<210> SEQ ID NO 446
<211> LENGTH: 3
<212> TYPE: PRT
<213> ORGANISM: Artificial Sequence
<220> FEATURE:
<223> OTHER INFORMATION: Synthetic

<400> SEQUENCE: 446

Lys Ala Ser
 1


<210> SEQ ID NO 447
<211> LENGTH: 27
<212> TYPE: DNA
<213> ORGANISM: Artificial Sequence
<220> FEATURE:
<223> OTHER INFORMATION: Synthetic

<400> SEQUENCE: 447

caacagtata ttagttattc tcggacg                                          27


<210> SEQ ID NO 448
<211> LENGTH: 9
<212> TYPE: PRT
<213> ORGANISM: Artificial Sequence
<220> FEATURE:
<223> OTHER INFORMATION: Synthetic
```

<400> SEQUENCE: 448

Gln Gln Tyr Ile Ser Tyr Ser Arg Thr
1 5

<210> SEQ ID NO 449
<211> LENGTH: 360
<212> TYPE: DNA
<213> ORGANISM: Artificial Sequence
<220> FEATURE:
<223> OTHER INFORMATION: Synthetic

<400> SEQUENCE: 449
gaggtgcagc tggtggagtc tgggggaggc ctggtcaagc cggggggtc cctgagactc 60 tcctgtacag cctctggatt caccttcagt acttataaca tgaattgggt ccgccaggct 120
ccagggaagg gactggagtg ggtctcatcc attaggagta gtagtaatta catatactac 180
gcagactcag tgaagggccg attcaccatc tccagagaca acgccaagag ttcactgtat 240
ctgcaaatga acagcctgag agccgaggac acggctgtgt attactgtgc gagagatggc 300
agcagttggt acgactactc tgactactgg ggccagggaa ccctggtcac cgtctcctca 360

<210> SEQ ID NO 450
<211> LENGTH: 120
<212> TYPE: PRT
<213> ORGANISM: Artificial Sequence
<220> FEATURE:
<223> OTHER INFORMATION: Synthetic

<400> SEQUENCE: 450

Glu Val Gln Leu Val Glu Ser Gly Gly Gly Leu Val Lys Pro Gly Gly
1 5 10 15

Ser Leu Arg Leu Ser Cys Thr Ala Ser Gly Phe Thr Phe Ser Thr Tyr
20 25 30

Asn Met Asn Trp Val Arg Gln Ala Pro Gly Lys Gly Leu Glu Trp Val
35 40 45

Ser Ser Ile Arg Ser Ser Ser Asn Tyr Ile Tyr Tyr Ala Asp Ser Val
50 55 60

Lys Gly Arg Phe Thr Ile Ser Arg Asp Asn Ala Lys Ser Ser Leu Tyr
65 70 75 80

Leu Gln Met Asn Ser Leu Arg Ala Glu Asp Thr Ala Val Tyr Tyr Cys
85 90 95

Ala Arg Asp Gly Ser Ser Trp Tyr Asp Tyr Ser Asp Tyr Trp Gly Gln
100 105 110

Gly Thr Leu Val Thr Val Ser Ser
115 120

<210> SEQ ID NO 451
<211> LENGTH: 321
<212> TYPE: DNA
<213> ORGANISM: Artificial Sequence
<220> FEATURE:
<223> OTHER INFORMATION: Synthetic

<400> SEQUENCE: 451
gacatccaga tgacccagtc tccttccacc ctgtctgcat ctgtaggaga cagagtcacc 60
atcacttgcc gggccagtca gagtattagt agctggttgg cctggtatca acaggtacca 120
gggaaagccc ctaaactcct gatctataag gcgtctagtt tagaaaatgg ggtcccatca 180
aggttcagcg gcagtggatc tgggacagaa ttcactctca tcatcagcag cctgcagcct 240

```
gatgattttg caacttatta ctgccaacag tatattagtt attctcggac gttcggccaa    300

gggaccaagg tggaaatcaa a                                              321
```

<210> SEQ ID NO 452
<211> LENGTH: 107
<212> TYPE: PRT
<213> ORGANISM: Artificial Sequence
<220> FEATURE:
<223> OTHER INFORMATION: Synthetic

<400> SEQUENCE: 452

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Val Pro Gly Lys Ala Pro Lys Leu Leu Ile
        35                  40                  45

Tyr Lys Ala Ser Ser Leu Glu Asn Gly Val Pro Ser Arg Phe Ser Gly
 50                 55                  60

Ser Gly Ser Gly Thr Glu Phe Thr Leu Ile Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105
```

<210> SEQ ID NO 453
<211> LENGTH: 360
<212> TYPE: DNA
<213> ORGANISM: Artificial Sequence
<220> FEATURE:
<223> OTHER INFORMATION: Synthetic

<400> SEQUENCE: 453

```
gaggtgcagc tggtggagtc tgggggaggc ctggtcaagc ctggggggtc cctgagactc     60

tcctgtgcag cctctggatt caccttcagt acttataaca tgaactgggt ccgccaggct    120

ccagggaagg ggctggagtg ggtctcatcc attaggagta gtagtaatta catatactac    180

gcagactcag tgaagggccg attcaccatc tccagagaca acgccaagaa ctcactgtat    240

ctgcaaatga acagcctgag agccgaggac acggctgtgt attactgtgc gagagatggc    300

agcagttggt acgactactc tgactactgg ggccagggaa ccctggtcac cgtctcctca    360
```

<210> SEQ ID NO 454
<211> LENGTH: 120
<212> TYPE: PRT
<213> ORGANISM: Artificial Sequence
<220> FEATURE:
<223> OTHER INFORMATION: Synthetic

<400> SEQUENCE: 454

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45

Ser Ser Ile Arg Ser Ser Ser Asn Tyr Ile Tyr Tyr Ala Asp Ser Val
 50                 55                  60
```

```
Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
        115                 120


<210> SEQ ID NO 455
<211> LENGTH: 321
<212> TYPE: DNA
<213> ORGANISM: Artificial Sequence
<220> FEATURE:
<223> OTHER INFORMATION: Synthetic

<400> SEQUENCE: 455

gacatccaga tgacccagtc tccttccacc ctgtctgcat ctgtaggaga cagagtcacc     60

atcacttgcc gggccagtca gagtattagt agctggttgg cctggtatca gcagaaacca    120

gggaaagccc ctaagctcct gatctataag gcgtctagtt tagaaagtgg ggtcccatca    180

aggttcagcg gcagtggatc tgggacagaa ttcactctca ccatcagcag cctgcagcct    240

gatgattttg caacttatta ctgccaacag tatattagtt attctcggac gttcggccaa    300

gggaccaagg tggaaatcaa a                                              321


<210> SEQ ID NO 456
<211> LENGTH: 107
<212> TYPE: PRT
<213> ORGANISM: Artificial Sequence
<220> FEATURE:
<223> OTHER INFORMATION: Synthetic

<400> SEQUENCE: 456

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105


<210> SEQ ID NO 457
<211> LENGTH: 360
<212> TYPE: DNA
<213> ORGANISM: Artificial Sequence
<220> FEATURE:
<223> OTHER INFORMATION: Synthetic

<400> SEQUENCE: 457

gaggtgcagc tggtggagtc tgggggaggc ctggtcaagc cggggggtc cctgagactc      60

tcctgtacag cctctggatt caccttcagt acttataaca tgaattgggt ccgccaggct    120
```

```
ccagggaagg gactggagtg ggtctcatcc attaggagta gtagtaatta catatactac    180

gcagactcag tgaagggccg attcaccatc tccagagaca acgccaagaa ttcactgtat    240

ctgcaaatga acagcctgag agccgatgac acggctgtgt attactgtgc gagagatggc    300

agcagttggt acgactactc tgactactgg ggccagggaa ccctggtcac cgtctcctca    360


<210> SEQ ID NO 458
<211> LENGTH: 120
<212> TYPE: PRT
<213> ORGANISM: Artificial Sequence
<220> FEATURE:
<223> OTHER INFORMATION: Synthetic

<400> SEQUENCE: 458

Glu Val Gln Leu Val Glu Ser Gly Gly Gly Leu Val Lys Pro Gly Gly
 1               5                   10                  15

Ser Leu Arg Leu Ser Cys Thr Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45

Ser Ser Ile Arg Ser Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
        115                 120


<210> SEQ ID NO 459
<211> LENGTH: 24
<212> TYPE: DNA
<213> ORGANISM: Artificial Sequence
<220> FEATURE:
<223> OTHER INFORMATION: Synthetic

<400> SEQUENCE: 459

ggattcacct tcagtactta taac                                            24


<210> SEQ ID NO 460
<211> LENGTH: 8
<212> TYPE: PRT
<213> ORGANISM: Artificial Sequence
<220> FEATURE:
<223> OTHER INFORMATION: Synthetic

<400> SEQUENCE: 460

Gly Phe Thr Phe Ser Thr Tyr Asn
 1               5


<210> SEQ ID NO 461
<211> LENGTH: 24
<212> TYPE: DNA
<213> ORGANISM: Artificial Sequence
<220> FEATURE:
<223> OTHER INFORMATION: Synthetic

<400> SEQUENCE: 461

attaggagta gtagtaatta cata                                            24
```

<210> SEQ ID NO 462
<211> LENGTH: 8
<212> TYPE: PRT
<213> ORGANISM: Artificial Sequence
<220> FEATURE:
<223> OTHER INFORMATION: Synthetic

<400> SEQUENCE: 462

Ile Arg Ser Ser Ser Asn Tyr Ile
1               5

<210> SEQ ID NO 463
<211> LENGTH: 39
<212> TYPE: DNA
<213> ORGANISM: Artificial Sequence
<220> FEATURE:
<223> OTHER INFORMATION: Synthetic

<400> SEQUENCE: 463
gcgagagatg gcagcagttg gtacgactac tctgactac 39

<210> SEQ ID NO 464
<211> LENGTH: 13
<212> TYPE: PRT
<213> ORGANISM: Artificial Sequence
<220> FEATURE:
<223> OTHER INFORMATION: Synthetic

<400> SEQUENCE: 464

Ala Arg Asp Gly Ser Ser Trp Tyr Asp Tyr Ser Asp Tyr
1               5                   10

<210> SEQ ID NO 465
<211> LENGTH: 321
<212> TYPE: DNA
<213> ORGANISM: Artificial Sequence
<220> FEATURE:
<223> OTHER INFORMATION: Synthetic

<400> SEQUENCE: 465
gacatccaga tgacccagtc tccttccacc ctgtctgcat ctgtaggaga cagagtcacc 60
atcacttgcc gggccagtca gagtattagt agctggttgg cctggtatca acagatacca 120
gggaaagccc ctaaactcct gatctataag gcgtctagtt tagaaaatgg ggtcccatca 180
aggttcagcg gcagtggatc tgggacagaa ttcactctca tcatcagcag cctgcagcct 240
gatgattttg caacttatta ctgccaacag tatattagtt attctcggac gttcggccaa 300
gggaccaagg tggaaatcaa a 321

<210> SEQ ID NO 466
<211> LENGTH: 107
<212> TYPE: PRT
<213> ORGANISM: Artificial Sequence
<220> FEATURE:
<223> OTHER INFORMATION: Synthetic

<400> SEQUENCE: 466

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Ile Pro Gly Lys Ala Pro Lys Leu Leu Ile
        35                  40                  45

```
Tyr Lys Ala Ser Ser Leu Glu Asn Gly Val Pro Ser Arg Phe Ser Gly
    50                  55                  60

Ser Gly Ser Gly Thr Glu Phe Thr Leu Ile Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105


<210> SEQ ID NO 467
<211> LENGTH: 18
<212> TYPE: DNA
<213> ORGANISM: Artificial Sequence
<220> FEATURE:
<223> OTHER INFORMATION: Synthetic

<400> SEQUENCE: 467

cagagtatta gtagctgg                                                   18


<210> SEQ ID NO 468
<211> LENGTH: 6
<212> TYPE: PRT
<213> ORGANISM: Artificial Sequence
<220> FEATURE:
<223> OTHER INFORMATION: Synthetic

<400> SEQUENCE: 468

Gln Ser Ile Ser Ser Trp
 1               5


<210> SEQ ID NO 469
<211> LENGTH: 9
<212> TYPE: DNA
<213> ORGANISM: Artificial Sequence
<220> FEATURE:
<223> OTHER INFORMATION: Synthetic

<400> SEQUENCE: 469

aaggcgtct                                                              9


<210> SEQ ID NO 470
<211> LENGTH: 3
<212> TYPE: PRT
<213> ORGANISM: Artificial Sequence
<220> FEATURE:
<223> OTHER INFORMATION: Synthetic

<400> SEQUENCE: 470

Lys Ala Ser
 1


<210> SEQ ID NO 471
<211> LENGTH: 27
<212> TYPE: DNA
<213> ORGANISM: Artificial Sequence
<220> FEATURE:
<223> OTHER INFORMATION: Synthetic

<400> SEQUENCE: 471

caacagtata ttagttattc tcggacg                                         27


<210> SEQ ID NO 472
<211> LENGTH: 9
<212> TYPE: PRT
<213> ORGANISM: Artificial Sequence
```

<220> FEATURE:
<223> OTHER INFORMATION: Synthetic

<400> SEQUENCE: 472

Gln Gln Tyr Ile Ser Tyr Ser Arg Thr
1 5

<210> SEQ ID NO 473
<211> LENGTH: 360
<212> TYPE: DNA
<213> ORGANISM: Artificial Sequence
<220> FEATURE:
<223> OTHER INFORMATION: Synthetic

<400> SEQUENCE: 473
gaggtgcagc tggtggagtc tgggggaggc ctggtcaagc cggggggtc cctgagactc 60 tcctgtacag cctctggatt caccttcagt acttataaca tgaattgggt ccgccaggct 120
ccagggaagg gactggagtg ggtctcatcc attaggagta gtagtaatta catatactac 180
gcagactcag tgaagggccg attcaccatc tccagagaca acgccaagaa ttcactgtat 240
ctgcaaatga acagcctgag agccgatgac acggctgtgt attactgtgc gagagatggc 300
agcagttggt acgactactc tgactactgg ggccagggaa ccctggtcac cgtctcctca 360

<210> SEQ ID NO 474
<211> LENGTH: 120
<212> TYPE: PRT
<213> ORGANISM: Artificial Sequence
<220> FEATURE:
<223> OTHER INFORMATION: Synthetic

<400> SEQUENCE: 474

Glu Val Gln Leu Val Glu Ser Gly Gly Gly Leu Val Lys Pro Gly Gly
1 5 10 15

Ser Leu Arg Leu Ser Cys Thr Ala Ser Gly Phe Thr Phe Ser Thr Tyr
20 25 30

Asn Met Asn Trp Val Arg Gln Ala Pro Gly Lys Gly Leu Glu Trp Val
35 40 45

Ser Ser Ile Arg Ser Ser Ser Asn Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Asp Asp Thr Ala Val Tyr Tyr Cys
85 90 95

Ala Arg Asp Gly Ser Ser Trp Tyr Asp Tyr Ser Asp Tyr Trp Gly Gln
100 105 110

Gly Thr Leu Val Thr Val Ser Ser
115 120

<210> SEQ ID NO 475
<211> LENGTH: 321
<212> TYPE: DNA
<213> ORGANISM: Artificial Sequence
<220> FEATURE:
<223> OTHER INFORMATION: Synthetic

<400> SEQUENCE: 475
gacatccaga tgacccagtc tccttccacc ctgtctgcat ctgtaggaga cagagtcacc 60
atcacttgcc gggccagtca gagtattagt agctggttgg cctggtatca acagatacca 120
gggaaagccc ctaaactcct gatctataag gcgtctagtt tagaaaatgg ggtcccatca 180

```
aggttcagcg gcagtggatc tgggacagaa ttcactctca tcatcagcag cctgcagcct    240

gatgattttg caacttatta ctgccaacag tatattagtt attctcggac gttcggccaa    300

gggaccaagg tggaaatcaa a                                              321


<210> SEQ ID NO 476
<211> LENGTH: 107
<212> TYPE: PRT
<213> ORGANISM: Artificial Sequence
<220> FEATURE:
<223> OTHER INFORMATION: Synthetic

<400> SEQUENCE: 476

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Ile Pro Gly Lys Ala Pro Lys Leu Leu Ile
        35                  40                  45

Tyr Lys Ala Ser Ser Leu Glu Asn Gly Val Pro Ser Arg Phe Ser Gly
    50                  55                  60

Ser Gly Ser Gly Thr Glu Phe Thr Leu Ile Ile Ser Ser Leu Gln Pro
65                  70                  75                  80

Asp Asp Phe Ala Thr Tyr Tyr Cys Gln Gln Tyr Ile Ser Tyr Ser Arg
                85                  90                  95

Thr Phe Gly Gln Gly Thr Lys Val Glu Ile Lys
            100                 105


<210> SEQ ID NO 477
<211> LENGTH: 360
<212> TYPE: DNA
<213> ORGANISM: Artificial Sequence
<220> FEATURE:
<223> OTHER INFORMATION: Synthetic

<400> SEQUENCE: 477

gaggtgcagc tggtggagtc tgggggaggc ctggtcaagc ctggggggtc cctgagactc     60

tcctgtgcag cctctggatt caccttcagt acttataaca tgaactgggt ccgccaggct    120

ccagggaagg ggctggagtg ggtctcatcc attaggagta gtagtaatta catatactac    180

gcagactcag tgaagggccg attcaccatc tccagagaca acgccaagaa ctcactgtat    240

ctgcaaatga acagcctgag agccgaggac acggctgtgt attactgtgc gagagatggc    300

agcagttggt acgactactc tgactactgg ggccaaggaa ccctggtcac cgtctcctca    360


<210> SEQ ID NO 478
<211> LENGTH: 120
<212> TYPE: PRT
<213> ORGANISM: Artificial Sequence
<220> FEATURE:
<223> OTHER INFORMATION: Synthetic

<400> SEQUENCE: 478

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Asn Met Asn Trp Val Arg Gln Ala Pro Gly Lys Gly Leu Glu Trp Val
        35                  40                  45
```

```
Ser Ser Ile Arg Ser Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Ser Ser Trp Tyr Asp Tyr Ser Asp Tyr Trp Gly Gln
            100                 105                 110

Gly Thr Leu Val Thr Val Ser Ser
        115                 120
```

<210> SEQ ID NO 479
<211> LENGTH: 321
<212> TYPE: DNA
<213> ORGANISM: Artificial Sequence
<220> FEATURE:
<223> OTHER INFORMATION: Synthetic

<400> SEQUENCE: 479

```
gacatccaga tgacccagtc tccttccacc ctgtctgcat ctgtaggaga cagagtcacc      60
atcacttgcc gggccagtca gagtattagt agctggttgg cctggtatca gcagaaacca    120
gggaaagccc ctaagctcct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgccaacag tatattagtt attctcggac gttcggccaa    300
gggaccaagg tggaaatcaa a                                              321
```

<210> SEQ ID NO 480
<211> LENGTH: 107
<212> TYPE: PRT
<213> ORGANISM: Artificial Sequence
<220> FEATURE:
<223> OTHER INFORMATION: Synthetic

<400> SEQUENCE: 480

```
Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Ile Ser Tyr Ser Arg
                 85                  90                  95

Thr Phe Gly Gln Gly Thr Lys Val Glu Ile Lys
            100                 105
```

<210> SEQ ID NO 481
<211> LENGTH: 354
<212> TYPE: DNA
<213> ORGANISM: Artificial Sequence
<220> FEATURE:
<223> OTHER INFORMATION: Synthetic

<400> SEQUENCE: 481

```
gaggtgcaac tagtggagtc tgggggaggc ttggtacagc ctggggggtc cctgagactc      60
```

```
tcctgtgtag tctctggatt caccttcggt gactacgaca tgcactgggt ccgtcaagct    120

acaggaagag gtctggagtg ggtctcaggt attgctcctg ctggtgacac atcctataca    180

ggctccgtga agggccgatt caccatctcc agagagaatg ccaagaactc cttgcatctt    240

caaatgaaca gcctgacaac cggggacacg gctatatatt attgtgctag agaggatata    300

gcagtgcctg gttttgatta ctggggccag ggaaccctgg tcaccgtctc ctca          354
```

<210> SEQ ID NO 482
<211> LENGTH: 118
<212> TYPE: PRT
<213> ORGANISM: Artificial Sequence
<220> FEATURE:
<223> OTHER INFORMATION: Synthetic

<400> SEQUENCE: 482

```
Glu Val Gln Leu Val Glu Ser Gly Gly Gly Leu Val Gln Pro Gly Gly
 1               5                  10                  15

Ser Leu Arg Leu Ser Cys Val Val Ser Gly Phe Thr Phe Gly Asp Tyr
            20                  25                  30

Asp Met His Trp Val Arg Gln Ala Thr Gly Arg Gly Leu Glu Trp Val
        35                  40                  45

Ser Gly Ile Ala Pro Ala Gly Asp Thr Ser Tyr Thr Gly Ser Val Lys
    50                  55                  60

Gly Arg Phe Thr Ile Ser Arg Glu Asn Ala Lys Asn Ser Leu His Leu
65                  70                  75                  80

Gln Met Asn Ser Leu Thr Thr Gly Asp Thr Ala Ile Tyr Tyr Cys Ala
                85                  90                  95

Arg Glu Asp Ile Ala Val Pro Gly Phe Asp Tyr Trp Gly Gln Gly Thr
            100                 105                 110

Leu Val Thr Val Ser Ser
        115
```

<210> SEQ ID NO 483
<211> LENGTH: 24
<212> TYPE: DNA
<213> ORGANISM: Artificial Sequence
<220> FEATURE:
<223> OTHER INFORMATION: Synthetic

<400> SEQUENCE: 483

```
ggattcacct tcggtgacta cgac                                            24
```

<210> SEQ ID NO 484
<211> LENGTH: 8
<212> TYPE: PRT
<213> ORGANISM: Artificial Sequence
<220> FEATURE:
<223> OTHER INFORMATION: Synthetic

<400> SEQUENCE: 484

```
Gly Phe Thr Phe Gly Asp Tyr Asp
 1               5
```

<210> SEQ ID NO 485
<211> LENGTH: 21
<212> TYPE: DNA
<213> ORGANISM: Artificial Sequence
<220> FEATURE:
<223> OTHER INFORMATION: Synthetic

<400> SEQUENCE: 485
attgctcctg ctggtgacac a 21

<210> SEQ ID NO 486
<211> LENGTH: 7
<212> TYPE: PRT
<213> ORGANISM: Artificial Sequence
<220> FEATURE:
<223> OTHER INFORMATION: Synthetic

<400> SEQUENCE: 486

Ile Ala Pro Ala Gly Asp Thr
1 5

<210> SEQ ID NO 487
<211> LENGTH: 36
<212> TYPE: DNA
<213> ORGANISM: Artificial Sequence
<220> FEATURE:
<223> OTHER INFORMATION: Synthetic

<400> SEQUENCE: 487
gctagagagg atatagcagt gcctggtttt gattac 36

<210> SEQ ID NO 488
<211> LENGTH: 12
<212> TYPE: PRT
<213> ORGANISM: Artificial Sequence
<220> FEATURE:
<223> OTHER INFORMATION: Synthetic

<400> SEQUENCE: 488

Ala Arg Glu Asp Ile Ala Val Pro Gly Phe Asp Tyr
1 5 10

<210> SEQ ID NO 489
<211> LENGTH: 324
<212> TYPE: DNA
<213> ORGANISM: Artificial Sequence
<220> FEATURE:
<223> OTHER INFORMATION: Synthetic

<400> SEQUENCE: 489
gaaatagtga tgacgcagtc tccagccacc ctgtctgtgt ctccagggga acgaggcacc 60
ctctcctgca gggccagtca gagtgttagc agcaacttag cctggtacca gcagaaacct 120
ggccaggctc ccagactcct catctatggt gcatccacga gggccactgg cttcccagcc 180
aggttcagtg gcagtgggtc tgggacagag ttcactctca ccatcagcag cctgcagtct 240
gaagattttg cagtttatta ctgtcagcag tataataagt ggcctccgtt cactttcggc 300
cctgggacca aagtggattt caaa 324

<210> SEQ ID NO 490
<211> LENGTH: 108
<212> TYPE: PRT
<213> ORGANISM: Artificial Sequence
<220> FEATURE:
<223> OTHER INFORMATION: Synthetic

<400> SEQUENCE: 490

Glu Ile Val Met Thr Gln Ser Pro Ala Thr Leu Ser Val Ser Pro Gly
1 5 10 15

Glu Arg Gly Thr Leu Ser Cys Arg Ala Ser Gln Ser Val Ser Ser Asn
20 25 30

```
Leu Ala Trp Tyr Gln Gln Lys Pro Gly Gln Ala Pro Arg Leu Leu Ile
        35                  40                  45

Tyr Gly Ala Ser Thr Arg Ala Thr Gly Phe Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Lys Trp Pro Pro
                85                  90                  95

Phe Thr Phe Gly Pro Gly Thr Lys Val Asp Phe Lys
            100                 105
```

<210> SEQ ID NO 491
<211> LENGTH: 18
<212> TYPE: DNA
<213> ORGANISM: Artificial Sequence
<220> FEATURE:
<223> OTHER INFORMATION: Synthetic

<400> SEQUENCE: 491

```
cagagtgtta gcagcaac                                                    18
```

<210> SEQ ID NO 492
<211> LENGTH: 6
<212> TYPE: PRT
<213> ORGANISM: Artificial Sequence
<220> FEATURE:
<223> OTHER INFORMATION: Synthetic

<400> SEQUENCE: 492

```
Gln Ser Val Ser Ser Asn
 1               5
```

<210> SEQ ID NO 493
<211> LENGTH: 9
<212> TYPE: DNA
<213> ORGANISM: Artificial Sequence
<220> FEATURE:
<223> OTHER INFORMATION: Synthetic

<400> SEQUENCE: 493

```
ggtgcatcc                                                               9
```

<210> SEQ ID NO 494
<211> LENGTH: 3
<212> TYPE: PRT
<213> ORGANISM: Artificial Sequence
<220> FEATURE:
<223> OTHER INFORMATION: Synthetic

<400> SEQUENCE: 494

```
Gly Ala Ser
 1
```

<210> SEQ ID NO 495
<211> LENGTH: 30
<212> TYPE: DNA
<213> ORGANISM: Artificial Sequence
<220> FEATURE:
<223> OTHER INFORMATION: Synthetic

<400> SEQUENCE: 495

```
cagcagtata ataagtggcc tccgttcact                                       30
```

<210> SEQ ID NO 496

<211> LENGTH: 10
<212> TYPE: PRT
<213> ORGANISM: Artificial Sequence
<220> FEATURE:
<223> OTHER INFORMATION: Synthetic

<400> SEQUENCE: 496

Gln Gln Tyr Asn Lys Trp Pro Pro Phe Thr
1 5 10

<210> SEQ ID NO 497
<211> LENGTH: 354
<212> TYPE: DNA
<213> ORGANISM: Artificial Sequence
<220> FEATURE:
<223> OTHER INFORMATION: Synthetic

<400> SEQUENCE: 497
gaggtgcaac tagtggagtc tgggggaggc ttggtacagc ctggggggtc cctgagactc 60
tcctgtgtag tctctggatt caccttcggt gactacgaca tgcactgggt ccgtcaagct 120
acaggaagag gtctggagtg ggtctcaggt attgctcctg ctggtgacac atcctataca 180
ggctccgtga agggccgatt caccatctcc agagagaatg ccaagaactc cttgcatctt 240
caaatgaaca gcctgacaac cggggacacg gctatatatt attgtgctag agaggatata 300
gcagtgcctg gttttgatta ctggggccag ggaaccctgg tcaccgtctc ctca 354

<210> SEQ ID NO 498
<211> LENGTH: 118
<212> TYPE: PRT
<213> ORGANISM: Artificial Sequence
<220> FEATURE:
<223> OTHER INFORMATION: Synthetic

<400> SEQUENCE: 498

Glu Val Gln Leu Val Glu Ser Gly Gly Gly Leu Val Gln Pro Gly Gly
1 5 10 15

Ser Leu Arg Leu Ser Cys Val Val Ser Gly Phe Thr Phe Gly Asp Tyr
20 25 30

Asp Met His Trp Val Arg Gln Ala Thr Gly Arg Gly Leu Glu Trp Val
35 40 45

Ser Gly Ile Ala Pro Ala Gly Asp Thr Ser Tyr Thr Gly Ser Val Lys
50 55 60

Gly Arg Phe Thr Ile Ser Arg Glu Asn Ala Lys Asn Ser Leu His Leu
65 70 75 80

Gln Met Asn Ser Leu Thr Thr Gly Asp Thr Ala Ile Tyr Tyr Cys Ala
85 90 95

Arg Glu Asp Ile Ala Val Pro Gly Phe Asp Tyr Trp Gly Gln Gly Thr
100 105 110

Leu Val Thr Val Ser Ser
115

<210> SEQ ID NO 499
<211> LENGTH: 324
<212> TYPE: DNA
<213> ORGANISM: Artificial Sequence
<220> FEATURE:
<223> OTHER INFORMATION: Synthetic

<400> SEQUENCE: 499
gaaatagtga tgacgcagtc tccagccacc ctgtctgtgt ctccagggga acgaggcacc 60

```
ctctcctgca gggccagtca gagtgttagc agcaacttag cctggtacca gcagaaacct    120

ggccaggctc ccagactcct catctatggt gcatccacga gggccactgg cttcccagcc    180

aggttcagtg gcagtgggtc tgggacagag ttcactctca ccatcagcag cctgcagtct    240

gaagattttg cagtttatta ctgtcagcag tataataagt ggcctccgtt cactttcggc    300

cctgggacca aagtggatat caaa                                           324
```

<210> SEQ ID NO 500
<211> LENGTH: 108
<212> TYPE: PRT
<213> ORGANISM: Artificial Sequence
<220> FEATURE:
<223> OTHER INFORMATION: Synthetic

<400> SEQUENCE: 500

```
Glu Ile Val Met Thr Gln Ser Pro Ala Thr Leu Ser Val Ser Pro Gly
1               5                   10                  15

Glu Arg Gly Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Phe Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Lys Trp Pro Pro
                85                  90                  95

Phe Thr Phe Gly Pro Gly Thr Lys Val Asp Ile Lys
            100                 105
```

<210> SEQ ID NO 501
<211> LENGTH: 354
<212> TYPE: DNA
<213> ORGANISM: Artificial Sequence
<220> FEATURE:
<223> OTHER INFORMATION: Synthetic

<400> SEQUENCE: 501

```
gaggtgcagc tggtggagtc tgggggaggc ttggtacagc ctggggggtc cctgagactc     60

tcctgtgcag cctctggatt caccttcggt gactacgaca tgcactgggt ccgccaagct    120

acaggaaaag gtctggagtg ggtctcagct attgctcctg ctggtgacac atactatcca    180

ggctccgtga agggccgatt caccatctcc agagaaaatg ccaagaactc cttgtatctt    240

caaatgaaca gcctgagagc cggggacacg gctgtgtatt actgtgctag agaggatata    300

gcagtgcctg gttttgatta ctggggccaa ggaaccctgg tcaccgtctc ctca          354
```

<210> SEQ ID NO 502
<211> LENGTH: 118
<212> TYPE: PRT
<213> ORGANISM: Artificial Sequence
<220> FEATURE:
<223> OTHER INFORMATION: Synthetic

<400> SEQUENCE: 502

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Asp Tyr
            20                  25                  30
```

-continued

```
Asp Met His Trp Val Arg Gln Ala Thr Gly Lys Gly Leu Glu Trp Val
        35                  40                  45

Ser Ala Ile Ala Pro Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Asp Ile Ala Val Pro Gly Phe Asp Tyr Trp Gly Gln Gly Thr
            100                 105                 110

Leu Val Thr Val Ser Ser
        115
```

<210> SEQ ID NO 503
<211> LENGTH: 324
<212> TYPE: DNA
<213> ORGANISM: Artificial Sequence
<220> FEATURE:
<223> OTHER INFORMATION: Synthetic

<400> SEQUENCE: 503

```
gaaatagtga tgacgcagtc tccagccacc ctgtctgtgt ctccagggga aagagccacc      60

ctctcctgca gggccagtca gagtgttagc agcaacttag cctggtacca gcagaaacct     120

ggccaggctc ccaggctcct catctatggt gcatccacca gggccactgg tatcccagcc     180

aggttcagtg gcagtgggtc tgggacagag ttcactctca ccatcagcag cctgcagtct     240

gaagattttg cagtttatta ctgtcagcag tataataagt ggcctccgtt cactttcggc     300

cctgggacca aagtggatat caaa                                            324
```

<210> SEQ ID NO 504
<211> LENGTH: 108
<212> TYPE: PRT
<213> ORGANISM: Artificial Sequence
<220> FEATURE:
<223> OTHER INFORMATION: Synthetic

<400> SEQUENCE: 504

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Lys Trp Pro Pro
                85                  90                  95

Phe Thr Phe Gly Pro Gly Thr Lys Val Asp Ile Lys
            100                 105
```

<210> SEQ ID NO 505
<211> LENGTH: 378
<212> TYPE: DNA
<213> ORGANISM: Artificial Sequence
<220> FEATURE:
<223> OTHER INFORMATION: Synthetic

<400> SEQUENCE: 505
caaattctgc tggtgcaatc tggacctgag gtgaaggagc ctggggcctc agtgaaggtc 60
tcctgcaagg cttctggtta cacctttacc aactacgcta tcagctgggt gcgacaggtc 120
cctggacaag ggcttgagtg gatgggatgg gtcagcgctt acaatggtca cacaaactat 180
gcacatgaag tccagggcag agtcaccatg accacagaca catccacgac cacagcctac 240
atggagctga ggagcctgag atctgacgac acggccatgt attactgtgc gagagggggt 300
gtagtcgtgc cagttgctcc ccacttctac aacggtatgg acgtctgggg ccaagggacc 360
acggtcaccg tctcctca 378

<210> SEQ ID NO 506
<211> LENGTH: 126
<212> TYPE: PRT
<213> ORGANISM: Artificial Sequence
<220> FEATURE:
<223> OTHER INFORMATION: Synthetic

<400> SEQUENCE: 506

Gln Ile Leu Leu Val Gln Ser Gly Pro Glu Val Lys Glu Pro Gly Ala
1 5 10 15

Ser Val Lys Val Ser Cys Lys Ala Ser Gly Tyr Thr Phe Thr Asn Tyr
20 25 30

Ala Ile Ser Trp Val Arg Gln Val Pro Gly Gln Gly Leu Glu Trp Met
35 40 45

Gly Trp Val Ser Ala Tyr Asn Gly His Thr Asn Tyr Ala His Glu Val
50 55 60

Gln Gly Arg Val Thr Met Thr Thr Asp Thr Ser Thr Thr Thr Ala Tyr
65 70 75 80

Met Glu Leu Arg Ser Leu Arg Ser Asp Asp Thr Ala Met Tyr Tyr Cys
85 90 95

Ala Arg Gly Gly Val Val Val Pro Val Ala Pro His Phe Tyr Asn Gly
100 105 110

Met Asp Val Trp Gly Gln Gly Thr Thr Val Thr Val Ser Ser
115 120 125

<210> SEQ ID NO 507
<211> LENGTH: 24
<212> TYPE: DNA
<213> ORGANISM: Artificial Sequence
<220> FEATURE:
<223> OTHER INFORMATION: Synthetic

<400> SEQUENCE: 507
ggttacacct ttaccaacta cgct 24

<210> SEQ ID NO 508
<211> LENGTH: 8
<212> TYPE: PRT
<213> ORGANISM: Artificial Sequence
<220> FEATURE:
<223> OTHER INFORMATION: Synthetic

<400> SEQUENCE: 508

Gly Tyr Thr Phe Thr Asn Tyr Ala
1 5

<210> SEQ ID NO 509
<211> LENGTH: 24
<212> TYPE: DNA

<213> ORGANISM: Artificial Sequence
<220> FEATURE:
<223> OTHER INFORMATION: Synthetic

<400> SEQUENCE: 509
gtcagcgctt acaatggtca caca 24

<210> SEQ ID NO 510
<211> LENGTH: 8
<212> TYPE: PRT
<213> ORGANISM: Artificial Sequence
<220> FEATURE:
<223> OTHER INFORMATION: Synthetic

<400> SEQUENCE: 510

Val Ser Ala Tyr Asn Gly His Thr
1 5

<210> SEQ ID NO 511
<211> LENGTH: 57
<212> TYPE: DNA
<213> ORGANISM: Artificial Sequence
<220> FEATURE:
<223> OTHER INFORMATION: Synthetic

<400> SEQUENCE: 511
gcgagagggg gtgtagtcgt gccagttgct ccccacttct acaacggtat ggacgtc 57

<210> SEQ ID NO 512
<211> LENGTH: 19
<212> TYPE: PRT
<213> ORGANISM: Artificial Sequence
<220> FEATURE:
<223> OTHER INFORMATION: Synthetic

<400> SEQUENCE: 512

Ala Arg Gly Gly Val Val Val Pro Val Ala Pro His Phe Tyr Asn Gly
1 5 10 15

Met Asp Val

<210> SEQ ID NO 513
<211> LENGTH: 336
<212> TYPE: DNA
<213> ORGANISM: Artificial Sequence
<220> FEATURE:
<223> OTHER INFORMATION: Synthetic

<400> SEQUENCE: 513
gatattgtga tgactcagtt tccactctcc ctgcccgtca cccctggaga gccggcctcc 60
atctcctgca ggtctagtca gagcctcctg catattaatg aatacaacta tttggattgg 120
tacctaaaga agccagggca gtctccacag ctcctgatct atttgggttt taatcgggcc 180
tccggggtcc ctgacaggtt cagtggcagt ggatcaggca cagattttac actgaaaatc 240
agcagagtgg aggctgagga tgttggggtc tattactgca tgcaagctct tcaaactccg 300
tggacgttag gccaagggac caaggtggaa atcaaa 336

<210> SEQ ID NO 514
<211> LENGTH: 112
<212> TYPE: PRT
<213> ORGANISM: Artificial Sequence
<220> FEATURE:
<223> OTHER INFORMATION: Synthetic

<400> SEQUENCE: 514

```
Asp Ile Val Met Thr Gln Phe Pro Leu Ser Leu Pro Val Thr Pro Gly
 1               5                  10                  15

Glu Pro Ala Ser Ile Ser Cys Arg Ser Ser Gln Ser Leu Leu His Ile
            20                  25                  30

Asn Glu Tyr Asn Tyr Leu Asp Trp Tyr Leu Lys Lys Pro Gly Gln Ser
        35                  40                  45

Pro Gln Leu Leu Ile Tyr Leu Gly Phe Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Leu Gly Gln Gly Thr Lys Val Glu Ile Lys
            100                 105                 110


<210> SEQ ID NO 515
<211> LENGTH: 33
<212> TYPE: DNA
<213> ORGANISM: Artificial Sequence
<220> FEATURE:
<223> OTHER INFORMATION: Synthetic

<400> SEQUENCE: 515

cagagcctcc tgcatattaa tgaatacaac tat                                33


<210> SEQ ID NO 516
<211> LENGTH: 11
<212> TYPE: PRT
<213> ORGANISM: Artificial Sequence
<220> FEATURE:
<223> OTHER INFORMATION: Synthetic

<400> SEQUENCE: 516

Gln Ser Leu Leu His Ile Asn Glu Tyr Asn Tyr
 1               5                  10


<210> SEQ ID NO 517
<211> LENGTH: 9
<212> TYPE: DNA
<213> ORGANISM: Artificial Sequence
<220> FEATURE:
<223> OTHER INFORMATION: Synthetic

<400> SEQUENCE: 517

ttgggtttt                                                            9


<210> SEQ ID NO 518
<211> LENGTH: 3
<212> TYPE: PRT
<213> ORGANISM: Artificial Sequence
<220> FEATURE:
<223> OTHER INFORMATION: Synthetic

<400> SEQUENCE: 518

Leu Gly Phe
 1


<210> SEQ ID NO 519
<211> LENGTH: 27
<212> TYPE: DNA
<213> ORGANISM: Artificial Sequence
<220> FEATURE:
<223> OTHER INFORMATION: Synthetic
```

<400> SEQUENCE: 519
atgcaagctc ttcaaactcc gtggacg 27

<210> SEQ ID NO 520
<211> LENGTH: 9
<212> TYPE: PRT
<213> ORGANISM: Artificial Sequence
<220> FEATURE:
<223> OTHER INFORMATION: Synthetic

<400> SEQUENCE: 520

Met Gln Ala Leu Gln Thr Pro Trp Thr
1 5

<210> SEQ ID NO 521
<211> LENGTH: 378
<212> TYPE: DNA
<213> ORGANISM: Artificial Sequence
<220> FEATURE:
<223> OTHER INFORMATION: Synthetic

<400> SEQUENCE: 521
caggttcagc tggtgcagtc tggacctgag gtgaaggagc ctggggcctc agtgaaggtc 60
tcctgcaagg cttctggtta cacctttacc aactacgcta tcagctgggt gcgacaggtc 120
cctggacaag ggcttgagtg gatgggatgg gtcagcgctt acaatggtca cacaaactat 180
gcacatgaag tccagggcag agtcaccatg accacagaca catccacgac cacagcctac 240
atggagctga ggagcctgag atctgacgac acggccatgt attactgtgc gagagggggt 300
gtagtcgtgc cagttgctcc ccacttctac aacggtatgg acgtctgggg ccaagggacc 360
acggtcaccg tctcctca 378

<210> SEQ ID NO 522
<211> LENGTH: 126
<212> TYPE: PRT
<213> ORGANISM: Artificial Sequence
<220> FEATURE:
<223> OTHER INFORMATION: Synthetic

<400> SEQUENCE: 522

Gln Val Gln Leu Val Gln Ser Gly Pro Glu Val Lys Glu Pro Gly Ala
1 5 10 15

Ser Val Lys Val Ser Cys Lys Ala Ser Gly Tyr Thr Phe Thr Asn Tyr
20 25 30

Ala Ile Ser Trp Val Arg Gln Val Pro Gly Gln Gly Leu Glu Trp Met
35 40 45

Gly Trp Val Ser Ala Tyr Asn Gly His Thr Asn Tyr Ala His Glu Val
50 55 60

Gln Gly Arg Val Thr Met Thr Thr Asp Thr Ser Thr Thr Thr Ala Tyr
65 70 75 80

Met Glu Leu Arg Ser Leu Arg Ser Asp Asp Thr Ala Met Tyr Tyr Cys
85 90 95

Ala Arg Gly Gly Val Val Val Pro Val Ala Pro His Phe Tyr Asn Gly
100 105 110

Met Asp Val Trp Gly Gln Gly Thr Thr Val Thr Val Ser Ser
115 120 125

<210> SEQ ID NO 523
<211> LENGTH: 336

<212> TYPE: DNA
<213> ORGANISM: Artificial Sequence
<220> FEATURE:
<223> OTHER INFORMATION: Synthetic

<400> SEQUENCE: 523
gatattgtga tgactcagtc tccactctcc ctgcccgtca cccctggaga gccggcctcc 60
atctcctgca ggtctagtca gagcctcctg catattaatg aatacaacta tttggattgg 120
tacctaaaga agccagggca gtctccacag ctcctgatct atttgggttt taatcgggcc 180
tccggggtcc ctgacaggtt cagtggcagt ggatcaggca cagattttac actgaaaatc 240
agcagagtgg aggctgagga tgttggggtc tattactgca tgcaagctct tcaaactccg 300
tggacgttag gccaagggac caaggtggaa atcaaa 336

<210> SEQ ID NO 524
<211> LENGTH: 112
<212> TYPE: PRT
<213> ORGANISM: Artificial Sequence
<220> FEATURE:
<223> OTHER INFORMATION: Synthetic

<400> SEQUENCE: 524

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ile
20 25 30

Asn Glu Tyr Asn Tyr Leu Asp Trp Tyr Leu Lys Lys Pro Gly Gln Ser
35 40 45

Pro Gln Leu Leu Ile Tyr Leu Gly Phe Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro Trp Thr Leu Gly Gln Gly Thr Lys Val Glu Ile Lys
100 105 110

<210> SEQ ID NO 525
<211> LENGTH: 378
<212> TYPE: DNA
<213> ORGANISM: Artificial Sequence
<220> FEATURE:
<223> OTHER INFORMATION: Synthetic

<400> SEQUENCE: 525
caggttcagc tggtgcagtc tggagctgag gtgaagaagc ctggggcctc agtgaaggtc 60
tcctgcaagg cttctggtta cacctttacc aactacgcta tcagctgggt gcgacaggcc 120
cctggacaag ggcttgagtg gatgggatgg gtcagcgctt acaatggtca cacaaactat 180
gcacagaagc tccagggcag agtcaccatg accacagaca catccacgag cacagcctac 240
atggagctga ggagcctgag atctgacgac acggccgtgt attactgtgc gagagggggt 300
gtagtcgtgc cagttgctcc ccacttctac aacggtatgg acgtctgggg gcaagggacc 360
acggtcaccg tctcctca 378

<210> SEQ ID NO 526
<211> LENGTH: 126
<212> TYPE: PRT
<213> ORGANISM: Artificial Sequence
<220> FEATURE:
<223> OTHER INFORMATION: Synthetic

<400> SEQUENCE: 526

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
            20                  25                  30

Ala Ile Ser Trp Val Arg Gln Ala Pro Gly Gln Gly Leu Glu Trp Met
        35                  40                  45

Gly Trp Val Ser Ala Tyr Asn Gly His Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Val Val Val Pro Val Ala Pro His Phe Tyr Asn Gly
            100                 105                 110

Met Asp Val Trp Gly Gln Gly Thr Thr Val Thr Val Ser Ser
        115                 120                 125
```

<210> SEQ ID NO 527
<211> LENGTH: 336
<212> TYPE: DNA
<213> ORGANISM: Artificial Sequence
<220> FEATURE:
<223> OTHER INFORMATION: Synthetic

<400> SEQUENCE: 527

```
gatattgtga tgactcagtc tccactctcc ctgcccgtca cccctggaga gccggcctcc      60

atctcctgca ggtctagtca gagcctcctg catattaatg aatacaacta tttggattgg     120

tacctgcaga agccagggca gtctccacag ctcctgatct atttgggttc taatcgggcc     180

tccggggtcc ctgacaggtt cagtggcagt ggatcaggca cagattttac actgaaaatc     240

agcagagtgg aggctgagga tgttggggtt tattactgca tgcaagctct tcaaactccg     300

tggacgttcg gccaagggac caaggtggaa atcaaa                               336
```

<210> SEQ ID NO 528
<211> LENGTH: 112
<212> TYPE: PRT
<213> ORGANISM: Artificial Sequence
<220> FEATURE:
<223> OTHER INFORMATION: Synthetic

<400> SEQUENCE: 528

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ile
            20                  25                  30

Asn Glu Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95
```

Leu Gln Thr Pro Trp Thr Phe Gly Gln Gly Thr Lys Val Glu Ile Lys
100 105 110

<210> SEQ ID NO 529
<211> LENGTH: 351
<212> TYPE: DNA
<213> ORGANISM: Artificial Sequence
<220> FEATURE:
<223> OTHER INFORMATION: Synthetic

<400> SEQUENCE: 529
gaggtgcagc tggtggagtc tgggggaggc ttggtacagc ctggggggtc cctgagactc 60
tcctgtgcag cctctggatt caccctaagt agctacgaca tgcactgggt ccgccaagca 120
acaggaaaag gtctggagtg ggtctcagct attggcagta ctggtgacac atactataca 180
ggctccgtga tgggccgatt caccatctcc agagacgctg ccaaaaactc cttctatctt 240
gaaatgaaca gcctgagagt cggggacacg gctgtatatt actgtgcaag agagggaata 300
agaacaccct atgattattg gggccaggga gcccgggtca ccgtctcctc a 351

<210> SEQ ID NO 530
<211> LENGTH: 117
<212> TYPE: PRT
<213> ORGANISM: Artificial Sequence
<220> FEATURE:
<223> OTHER INFORMATION: Synthetic

<400> SEQUENCE: 530

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Leu Ser Ser Tyr
20 25 30

Asp Met His Trp Val Arg Gln Ala Thr Gly Lys Gly Leu Glu Trp Val
35 40 45

Ser Ala Ile Gly Ser Thr Gly Asp Thr Tyr Tyr Thr Gly Ser Val Met
50 55 60

Gly Arg Phe Thr Ile Ser Arg Asp Ala Ala Lys Asn Ser Phe Tyr Leu
65 70 75 80

Glu Met Asn Ser Leu Arg Val Gly Asp Thr Ala Val Tyr Tyr Cys Ala
85 90 95

Arg Glu Gly Ile Arg Thr Pro Tyr Asp Tyr Trp Gly Gln Gly Ala Arg
100 105 110

Val Thr Val Ser Ser
115

<210> SEQ ID NO 531
<211> LENGTH: 24
<212> TYPE: DNA
<213> ORGANISM: Artificial Sequence
<220> FEATURE:
<223> OTHER INFORMATION: Synthetic

<400> SEQUENCE: 531
ggattcaccc taagtagcta cgac 24

<210> SEQ ID NO 532
<211> LENGTH: 8
<212> TYPE: PRT
<213> ORGANISM: Artificial Sequence
<220> FEATURE:
<223> OTHER INFORMATION: Synthetic

<400> SEQUENCE: 532

Gly Phe Thr Leu Ser Ser Tyr Asp
1 5

<210> SEQ ID NO 533
<211> LENGTH: 21
<212> TYPE: DNA
<213> ORGANISM: Artificial Sequence
<220> FEATURE:
<223> OTHER INFORMATION: Synthetic

<400> SEQUENCE: 533
attggcagta ctggtgacac a 21

<210> SEQ ID NO 534
<211> LENGTH: 7
<212> TYPE: PRT
<213> ORGANISM: Artificial Sequence
<220> FEATURE:
<223> OTHER INFORMATION: Synthetic

<400> SEQUENCE: 534

Ile Gly Ser Thr Gly Asp Thr
1 5

<210> SEQ ID NO 535
<211> LENGTH: 33
<212> TYPE: DNA
<213> ORGANISM: Artificial Sequence
<220> FEATURE:
<223> OTHER INFORMATION: Synthetic

<400> SEQUENCE: 535
gcaagagagg gaataagaac accctatgat tat 33

<210> SEQ ID NO 536
<211> LENGTH: 11
<212> TYPE: PRT
<213> ORGANISM: Artificial Sequence
<220> FEATURE:
<223> OTHER INFORMATION: Synthetic

<400> SEQUENCE: 536

Ala Arg Glu Gly Ile Arg Thr Pro Tyr Asp Tyr
1 5 10

<210> SEQ ID NO 537
<211> LENGTH: 324
<212> TYPE: DNA
<213> ORGANISM: Artificial Sequence
<220> FEATURE:
<223> OTHER INFORMATION: Synthetic

<400> SEQUENCE: 537
gaaatagtga tgacgcagtc tccagccacc ctgtctgtgt ctccagggga aagagccacc 60
ctctcctgca gggccagtca gagtgttagc agcaatgtag cctggtacca gcagaaacct 120
ggccaggctc ccaggctcct catctatggt gcatccacca gggccactgg tatcccagcc 180
aggttcagtg gcagtgggtc tgggacagaa ttcactctca ccatcagcag cctgcagtct 240
gaagattttg cagtttatta ctgtcagcag tataataatt ggcctccatt cactttcggc 300
cctgggacca aagtggatat caaa 324

<210> SEQ ID NO 538

-continued

<211> LENGTH: 108
<212> TYPE: PRT
<213> ORGANISM: Artificial Sequence
<220> FEATURE:
<223> OTHER INFORMATION: Synthetic

<400> SEQUENCE: 538

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Val Ala Trp Tyr Gln Gln Lys Pro Gly Gln Ala Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Asn Asn Trp Pro Pro
85 90 95

Phe Thr Phe Gly Pro Gly Thr Lys Val Asp Ile Lys
100 105

<210> SEQ ID NO 539
<211> LENGTH: 18
<212> TYPE: DNA
<213> ORGANISM: Artificial Sequence
<220> FEATURE:
<223> OTHER INFORMATION: Synthetic

<400> SEQUENCE: 539
cagagtgtta gcagcaat 18

<210> SEQ ID NO 540
<211> LENGTH: 6
<212> TYPE: PRT
<213> ORGANISM: Artificial Sequence
<220> FEATURE:
<223> OTHER INFORMATION: Synthetic

<400> SEQUENCE: 540

Gln Ser Val Ser Ser Asn
1 5

<210> SEQ ID NO 541
<211> LENGTH: 9
<212> TYPE: DNA
<213> ORGANISM: Artificial Sequence
<220> FEATURE:
<223> OTHER INFORMATION: Synthetic

<400> SEQUENCE: 541 ggtgcatcc 9

<210> SEQ ID NO 542
<211> LENGTH: 3
<212> TYPE: PRT
<213> ORGANISM: Artificial Sequence
<220> FEATURE:
<223> OTHER INFORMATION: Synthetic

<400> SEQUENCE: 542

Gly Ala Ser
1

<210> SEQ ID NO 543
<211> LENGTH: 30
<212> TYPE: DNA
<213> ORGANISM: Artificial Sequence
<220> FEATURE:
<223> OTHER INFORMATION: Synthetic

<400> SEQUENCE: 543
cagcagtata ataattggcc tccattcact 30

<210> SEQ ID NO 544
<211> LENGTH: 10
<212> TYPE: PRT
<213> ORGANISM: Artificial Sequence
<220> FEATURE:
<223> OTHER INFORMATION: Synthetic

<400> SEQUENCE: 544

Gln Gln Tyr Asn Asn Trp Pro Pro Phe Thr
1 5 10

<210> SEQ ID NO 545
<211> LENGTH: 351
<212> TYPE: DNA
<213> ORGANISM: Artificial Sequence
<220> FEATURE:
<223> OTHER INFORMATION: Synthetic

<400> SEQUENCE: 545
gaggtgcagc tggtggagtc tgggggaggc ttggtacagc ctggggggtc cctgagactc 60
tcctgtgcag cctctggatt caccctaagt agctacgaca tgcactgggt ccgccaagca 120
acaggaaaag gtctggagtg ggtctcagct attggcagta ctggtgacac atactataca 180
ggctccgtga tgggccgatt caccatctcc agagacgctg ccaaaaactc cttctatctt 240
gaaatgaaca gcctgagagt cggggacacg gctgtatatt actgtgcaag agagggaata 300
agaacaccct atgattattg gggccaggga accctggtca ccgtctcctc a 351

<210> SEQ ID NO 546
<211> LENGTH: 117
<212> TYPE: PRT
<213> ORGANISM: Artificial Sequence
<220> FEATURE:
<223> OTHER INFORMATION: Synthetic

<400> SEQUENCE: 546

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Leu Ser Ser Tyr
20 25 30

Asp Met His Trp Val Arg Gln Ala Thr Gly Lys Gly Leu Glu Trp Val
35 40 45

Ser Ala Ile Gly Ser Thr Gly Asp Thr Tyr Tyr Thr Gly Ser Val Met
50 55 60

Gly Arg Phe Thr Ile Ser Arg Asp Ala Ala Lys Asn Ser Phe Tyr Leu
65 70 75 80

Glu Met Asn Ser Leu Arg Val Gly Asp Thr Ala Val Tyr Tyr Cys Ala
85 90 95

Arg Glu Gly Ile Arg Thr Pro Tyr Asp Tyr Trp Gly Gln Gly Thr Leu
100 105 110

Val Thr Val Ser Ser

115

<210> SEQ ID NO 547
<211> LENGTH: 324
<212> TYPE: DNA
<213> ORGANISM: Artificial Sequence
<220> FEATURE:
<223> OTHER INFORMATION: Synthetic

<400> SEQUENCE: 547
gaaatagtga tgacgcagtc tccagccacc ctgtctgtgt ctccagggga aagagccacc 60
ctctcctgca gggccagtca gagtgttagc agcaatgtag cctggtacca gcagaaacct 120
ggccaggctc ccaggctcct catctatggt gcatccacca gggccactgg tatcccagcc 180
aggttcagtg gcagtgggtc tgggacagaa ttcactctca ccatcagcag cctgcagtct 240
gaagattttg cagtttatta ctgtcagcag tataataatt ggcctccatt cactttcggc 300
cctgggacca aagtggatat caaa 324

<210> SEQ ID NO 548
<211> LENGTH: 108
<212> TYPE: PRT
<213> ORGANISM: Artificial Sequence
<220> FEATURE:
<223> OTHER INFORMATION: Synthetic

<400> SEQUENCE: 548

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Val Ala Trp Tyr Gln Gln Lys Pro Gly Gln Ala Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Asn Asn Trp Pro Pro
85 90 95

Phe Thr Phe Gly Pro Gly Thr Lys Val Asp Ile Lys
100 105

<210> SEQ ID NO 549
<211> LENGTH: 351
<212> TYPE: DNA
<213> ORGANISM: Artificial Sequence
<220> FEATURE:
<223> OTHER INFORMATION: Synthetic

<400> SEQUENCE: 549
gaggtgcagc tggtggagtc tgggggaggc ttggtacagc ctgggggggtc cctgagactc 60 tcctgtgcag cctctggatt caccctaagt agctacgaca tgcactgggt ccgccaagct 120
acaggaaaag gtctggagtg ggtctcagct attggcagta ctggtgacac atactatcca 180
ggctccgtga agggccgatt caccatctcc agagaaaatg ccaagaactc cttgtatctt 240
caaatgaaca gcctgagagc cggggacacg gctgtgtatt actgtgcaag agagggaata 300
agaacaccct atgattattg gggccaagga accctggtca ccgtctcctc a 351

<210> SEQ ID NO 550

<211> LENGTH: 117
<212> TYPE: PRT
<213> ORGANISM: Artificial Sequence
<220> FEATURE:
<223> OTHER INFORMATION: Synthetic

<400> SEQUENCE: 550

```
Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Ser Thr Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Gly Ile Arg Thr Pro Tyr Asp Tyr Trp Gly Gln Gly Thr Leu
            100                 105                 110

Val Thr Val Ser Ser
        115
```

<210> SEQ ID NO 551
<211> LENGTH: 324
<212> TYPE: DNA
<213> ORGANISM: Artificial Sequence
<220> FEATURE:
<223> OTHER INFORMATION: Synthetic

<400> SEQUENCE: 551

```
gaaatagtga tgacgcagtc tccagccacc ctgtctgtgt ctccagggga aagagccacc     60

ctctcctgca gggccagtca gagtgttagc agcaatttag cctggtacca gcagaaacct    120

ggccaggctc ccaggctcct catctatggt gcatccacca gggccactgg tatcccagcc    180

aggttcagtg gcagtgggtc tgggacagag ttcactctca ccatcagcag cctgcagtct    240

gaagattttg cagtttatta ctgtcagcag tataataatt ggcctccatt cactttcggc    300

cctgggacca aagtggatat caaa                                           324
```

<210> SEQ ID NO 552
<211> LENGTH: 108
<212> TYPE: PRT
<213> ORGANISM: Artificial Sequence
<220> FEATURE:
<223> OTHER INFORMATION: Synthetic

<400> SEQUENCE: 552

```
Glu Ile Val Met Thr Gln Ser Pro Ala Thr Leu Ser Val Ser Pro Gly
 1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80
```

```
Glu Asp Phe Ala Val Tyr Tyr Cys Gln Gln Tyr Asn Asn Trp Pro Pro
                85                  90                  95

Phe Thr Phe Gly Pro Gly Thr Lys Val Asp Ile Lys
            100                 105


<210> SEQ ID NO 553
<211> LENGTH: 351
<212> TYPE: DNA
<213> ORGANISM: Artificial Sequence
<220> FEATURE:
<223> OTHER INFORMATION: Synthetic

<400> SEQUENCE: 553

gaggtgcagc tggtggagtc tgggggaggc ttggtacagc ctggggggtc cctgagactc      60

tcctgtgcag cctctggatt caccctaagt agctacgaca tgcactgggt ccgccaagca     120

acaggaaaag gtctggagtg ggtctcagct attggcagta ctggtgacac atactataca     180

ggctccgtga tgggccgatt caccatctcc agagacgctg ccaaaaactc cttctatctt     240

gaaatgaaca gcctgagagt cggggacacg gctgtatatt actgtgcaag agagggaata     300

agaacaccct atgattattg gggccaggga gcccgggtca ccgtctcctc a              351


<210> SEQ ID NO 554
<211> LENGTH: 117
<212> TYPE: PRT
<213> ORGANISM: Artificial Sequence
<220> FEATURE:
<223> OTHER INFORMATION: Synthetic

<400> SEQUENCE: 554

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Ser Thr Gly Asp Thr Tyr Tyr Thr Gly Ser Val Met
    50                  55                  60

Gly Arg Phe Thr Ile Ser Arg Asp Ala Ala Lys Asn Ser Phe Tyr Leu
65                  70                  75                  80

Glu Met Asn Ser Leu Arg Val Gly Asp Thr Ala Val Tyr Tyr Cys Ala
                85                  90                  95

Arg Glu Gly Ile Arg Thr Pro Tyr Asp Tyr Trp Gly Gln Gly Ala Arg
            100                 105                 110

Val Thr Val Ser Ser
        115


<210> SEQ ID NO 555
<211> LENGTH: 24
<212> TYPE: DNA
<213> ORGANISM: Artificial Sequence
<220> FEATURE:
<223> OTHER INFORMATION: Synthetic

<400> SEQUENCE: 555

ggattcaccc taagtagcta cgac                                             24


<210> SEQ ID NO 556
<211> LENGTH: 8
<212> TYPE: PRT
<213> ORGANISM: Artificial Sequence
```

<220> FEATURE:
<223> OTHER INFORMATION: Synthetic

<400> SEQUENCE: 556

Gly Phe Thr Leu Ser Ser Tyr Asp
1 5

<210> SEQ ID NO 557
<211> LENGTH: 21
<212> TYPE: DNA
<213> ORGANISM: Artificial Sequence
<220> FEATURE:
<223> OTHER INFORMATION: Synthetic

<400> SEQUENCE: 557
attggcagta ctggtgacac a 21

<210> SEQ ID NO 558
<211> LENGTH: 7
<212> TYPE: PRT
<213> ORGANISM: Artificial Sequence
<220> FEATURE:
<223> OTHER INFORMATION: Synthetic

<400> SEQUENCE: 558

Ile Gly Ser Thr Gly Asp Thr
1 5

<210> SEQ ID NO 559
<211> LENGTH: 33
<212> TYPE: DNA
<213> ORGANISM: Artificial Sequence
<220> FEATURE:
<223> OTHER INFORMATION: Synthetic

<400> SEQUENCE: 559
gcaagagagg gaataagaac accctatgat tat 33

<210> SEQ ID NO 560
<211> LENGTH: 11
<212> TYPE: PRT
<213> ORGANISM: Artificial Sequence
<220> FEATURE:
<223> OTHER INFORMATION: Synthetic

<400> SEQUENCE: 560

Ala Arg Glu Gly Ile Arg Thr Pro Tyr Asp Tyr
1 5 10

<210> SEQ ID NO 561
<211> LENGTH: 324
<212> TYPE: DNA
<213> ORGANISM: Artificial Sequence
<220> FEATURE:
<223> OTHER INFORMATION: Synthetic

<400> SEQUENCE: 561
gaaatagtga tgacgcagtc tccagccacc ctgtctgtgt ctccagggga aagagccacc 60
ctctcctgca gggccagtca gagtgttagc agcaatgtag cctggtacca gcagaaacct 120
ggccaggctc ccaggctcct catctatggt gcatccacca gggccactgg tatcccagcc 180
aggttcagtg gcagtgggtc tgggacagaa ttcactctca ccatcagcag cctgcagtct 240
gaagattttg cagtttatta ctgtcagcag tataataatt ggcctccatt cactttcggc 300
cctgggacca aagtggatat caaa 324

<210> SEQ ID NO 562
<211> LENGTH: 108
<212> TYPE: PRT
<213> ORGANISM: Artificial Sequence
<220> FEATURE:
<223> OTHER INFORMATION: Synthetic

<400> SEQUENCE: 562

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Val Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Phe Thr Phe Gly Pro Gly Thr Lys Val Asp Ile Lys
            100                 105
```

<210> SEQ ID NO 563
<211> LENGTH: 18
<212> TYPE: DNA
<213> ORGANISM: Artificial Sequence
<220> FEATURE:
<223> OTHER INFORMATION: Synthetic

<400> SEQUENCE: 563
cagagtgtta gcagcaat 18

<210> SEQ ID NO 564
<211> LENGTH: 6
<212> TYPE: PRT
<213> ORGANISM: Artificial Sequence
<220> FEATURE:
<223> OTHER INFORMATION: Synthetic

<400> SEQUENCE: 564

```
Gln Ser Val Ser Ser Asn
 1               5
```

<210> SEQ ID NO 565
<211> LENGTH: 9
<212> TYPE: DNA
<213> ORGANISM: Artificial Sequence
<220> FEATURE:
<223> OTHER INFORMATION: Synthetic

<400> SEQUENCE: 565 ggtgcatcc 9

<210> SEQ ID NO 566
<211> LENGTH: 3
<212> TYPE: PRT
<213> ORGANISM: Artificial Sequence
<220> FEATURE:
<223> OTHER INFORMATION: Synthetic

<400> SEQUENCE: 566

-continued

```
Gly Ala Ser
 1


<210> SEQ ID NO 567
<211> LENGTH: 30
<212> TYPE: DNA
<213> ORGANISM: Artificial Sequence
<220> FEATURE:
<223> OTHER INFORMATION: Synthetic

<400> SEQUENCE: 567

cagcagtata ataattggcc tccattcact                                      30


<210> SEQ ID NO 568
<211> LENGTH: 10
<212> TYPE: PRT
<213> ORGANISM: Artificial Sequence
<220> FEATURE:
<223> OTHER INFORMATION: Synthetic

<400> SEQUENCE: 568

Gln Gln Tyr Asn Asn Trp Pro Pro Phe Thr
 1               5                  10


<210> SEQ ID NO 569
<211> LENGTH: 351
<212> TYPE: DNA
<213> ORGANISM: Artificial Sequence
<220> FEATURE:
<223> OTHER INFORMATION: Synthetic

<400> SEQUENCE: 569

gaggtgcagc tggtggagtc tgggggaggc ttggtacagc ctggggggtc cctgagactc     60

tcctgtgcag cctctggatt caccctaagt agctacgaca tgcactgggt ccgccaagca    120

acaggaaaag gtctggagtg ggtctcagct attggcagta ctggtgacac atactataca    180

ggctccgtga tgggccgatt caccatctcc agagacgctg ccaaaaactc cttctatctt    240

gaaatgaaca gcctgagagt cggggacacg gctgtatatt actgtgcaag agagggaata    300

agaacaccct atgattattg gggccaggga accctggtca ccgtctcctc a             351


<210> SEQ ID NO 570
<211> LENGTH: 117
<212> TYPE: PRT
<213> ORGANISM: Artificial Sequence
<220> FEATURE:
<223> OTHER INFORMATION: Synthetic

<400> SEQUENCE: 570

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Leu Ser Ser Tyr
            20                  25                  30

Asp Met His Trp Val Arg Gln Ala Thr Gly Lys Gly Leu Glu Trp Val
        35                  40                  45

Ser Ala Ile Gly Ser Thr Gly Asp Thr Tyr Tyr Thr Gly Ser Val Met
    50                  55                  60

Gly Arg Phe Thr Ile Ser Arg Asp Ala Ala Lys Asn Ser Phe Tyr Leu
65                  70                  75                  80

Glu Met Asn Ser Leu Arg Val Gly Asp Thr Ala Val Tyr Tyr Cys Ala
                85                  90                  95

Arg Glu Gly Ile Arg Thr Pro Tyr Asp Tyr Trp Gly Gln Gly Thr Leu
```

```
            100                 105                 110

Val Thr Val Ser Ser
        115


<210> SEQ ID NO 571
<211> LENGTH: 324
<212> TYPE: DNA
<213> ORGANISM: Artificial Sequence
<220> FEATURE:
<223> OTHER INFORMATION: Synthetic

<400> SEQUENCE: 571

gaaatagtga tgacgcagtc tccagccacc ctgtctgtgt ctccagggga aagagccacc      60

ctctcctgca gggccagtca gagtgttagc agcaatgtag cctggtacca gcagaaacct     120

ggccaggctc ccaggctcct catctatggt gcatccacca gggccactgg tatcccagcc     180

aggttcagtg gcagtgggtc tgggacagaa ttcactctca ccatcagcag cctgcagtct     240

gaagattttg cagtttatta ctgtcagcag tataataatt ggcctccatt cactttcggc     300

cctgggacca aagtggatat caaa                                            324


<210> SEQ ID NO 572
<211> LENGTH: 108
<212> TYPE: PRT
<213> ORGANISM: Artificial Sequence
<220> FEATURE:
<223> OTHER INFORMATION: Synthetic

<400> SEQUENCE: 572

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Val Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Phe Thr Phe Gly Pro Gly Thr Lys Val Asp Ile Lys
            100                 105


<210> SEQ ID NO 573
<211> LENGTH: 351
<212> TYPE: DNA
<213> ORGANISM: Artificial Sequence
<220> FEATURE:
<223> OTHER INFORMATION: Synthetic

<400> SEQUENCE: 573

gaggtgcagc tggtggagtc tgggggaggc ttggtacagc ctgggggggtc cctgagactc      60

tcctgtgcag cctctggatt caccctaagt agctacgaca tgcactgggt ccgccaagct     120

acaggaaaag gtctggagtg ggtctcagct attggcagta ctggtgacac atactatcca     180

ggctccgtga agggccgatt caccatctcc agagaaaatg ccaagaactc cttgtatctt     240

caaatgaaca gcctgagagc cggggacacg gctgtgtatt actgtgcaag agagggaata     300

agaacaccct atgattattg gggccaagga accctggtca ccgtctcctc a              351
```

<210> SEQ ID NO 574
<211> LENGTH: 117
<212> TYPE: PRT
<213> ORGANISM: Artificial Sequence
<220> FEATURE:
<223> OTHER INFORMATION: Synthetic

<400> SEQUENCE: 574

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Leu Ser Ser Tyr
20 25 30

Asp Met His Trp Val Arg Gln Ala Thr Gly Lys Gly Leu Glu Trp Val
35 40 45

Ser Ala Ile Gly Ser Thr Gly Asp Thr Tyr Tyr Pro Gly Ser Val Lys
50 55 60

Gly Arg Phe Thr Ile Ser Arg Glu Asn Ala Lys Asn Ser Leu Tyr Leu
65 70 75 80

Gln Met Asn Ser Leu Arg Ala Gly Asp Thr Ala Val Tyr Tyr Cys Ala
85 90 95

Arg Glu Gly Ile Arg Thr Pro Tyr Asp Tyr Trp Gly Gln Gly Thr Leu
100 105 110

Val Thr Val Ser Ser
115

<210> SEQ ID NO 575
<211> LENGTH: 324
<212> TYPE: DNA
<213> ORGANISM: Artificial Sequence
<220> FEATURE:
<223> OTHER INFORMATION: Synthetic

<400> SEQUENCE: 575
gaaatagtga tgacgcagtc tccagccacc ctgtctgtgt ctccagggga aagagccacc 60
ctctcctgca gggccagtca gagtgttagc agcaatttag cctggtacca gcagaaacct 120
ggccaggctc ccaggctcct catctatggt gcatccacca gggccactgg tatcccagcc 180
aggttcagtg gcagtgggtc tgggacagag ttcactctca ccatcagcag cctgcagtct 240
gaagattttg cagtttatta ctgtcagcag tataataatt ggcctccatt cactttcggc 300
cctgggacca aagtggatat caaa 324

<210> SEQ ID NO 576
<211> LENGTH: 108
<212> TYPE: PRT
<213> ORGANISM: Artificial Sequence
<220> FEATURE:
<223> OTHER INFORMATION: Synthetic

<400> SEQUENCE: 576

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile
35 40 45

Tyr Gly Ala Ser Thr Arg Ala Thr Gly Ile Pro Ala Arg Phe Ser Gly
50 55 60

-continued

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Asn Asn Trp Pro Pro
85 90 95

Phe Thr Phe Gly Pro Gly Thr Lys Val Asp Ile Lys
100 105

<210> SEQ ID NO 577
<211> LENGTH: 363
<212> TYPE: DNA
<213> ORGANISM: Artificial Sequence
<220> FEATURE:
<223> OTHER INFORMATION: Synthetic

<400> SEQUENCE: 577
gaagtgcagc tggtggagtc tgggggaggc ttggtacagc ctggcaggtc cctgagactc 60
tcctgtgcag cctctggatt cacctttgat gattatgcca tgcactgggt ccggcaagct 120
ccagggaagg gcctggagtg ggtctcaggt attaattgga acagtggtag cataggctat 180
gcggactctg tgaagggccg attcaccatc tccagagaca acgccaagca ctccctgtat 240
ctgcaaatga acagtctgag acctgaggac acggccttgt attactgtgt aaaagaggtg 300
actacgggat actactacgg tatggacgtc tggggccaag ggaccacggt caccgtctcc 360
tca 363

<210> SEQ ID NO 578
<211> LENGTH: 121
<212> TYPE: PRT
<213> ORGANISM: Artificial Sequence
<220> FEATURE:
<223> OTHER INFORMATION: Synthetic

<400> SEQUENCE: 578

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Ala Pro Gly Lys Gly Leu Glu Trp Val
35 40 45

Ser Gly Ile Asn Trp Asn Ser Gly Ser Ile Gly Tyr Ala Asp Ser Val
50 55 60

Lys Gly Arg Phe Thr Ile Ser Arg Asp Asn Ala Lys His Ser Leu Tyr
65 70 75 80

Leu Gln Met Asn Ser Leu Arg Pro Glu Asp Thr Ala Leu Tyr Tyr Cys
85 90 95

Val Lys Glu Val Thr Thr Gly Tyr Tyr Tyr Gly Met Asp Val Trp Gly
100 105 110

Gln Gly Thr Thr Val Thr Val Ser Ser
115 120

<210> SEQ ID NO 579
<211> LENGTH: 24
<212> TYPE: DNA
<213> ORGANISM: Artificial Sequence
<220> FEATURE:
<223> OTHER INFORMATION: Synthetic

<400> SEQUENCE: 579
ggattcacct ttgatgatta tgcc 24

<210> SEQ ID NO 580
<211> LENGTH: 8
<212> TYPE: PRT
<213> ORGANISM: Artificial Sequence
<220> FEATURE:
<223> OTHER INFORMATION: Synthetic

<400> SEQUENCE: 580

Gly Phe Thr Phe Asp Asp Tyr Ala
1 5

<210> SEQ ID NO 581
<211> LENGTH: 24
<212> TYPE: DNA
<213> ORGANISM: Artificial Sequence
<220> FEATURE:
<223> OTHER INFORMATION: Synthetic

<400> SEQUENCE: 581
attaattgga acagtggtag cata 24

<210> SEQ ID NO 582
<211> LENGTH: 8
<212> TYPE: PRT
<213> ORGANISM: Artificial Sequence
<220> FEATURE:
<223> OTHER INFORMATION: Synthetic

<400> SEQUENCE: 582

Ile Asn Trp Asn Ser Gly Ser Ile
1 5

<210> SEQ ID NO 583
<211> LENGTH: 42
<212> TYPE: DNA
<213> ORGANISM: Artificial Sequence
<220> FEATURE:
<223> OTHER INFORMATION: Synthetic

<400> SEQUENCE: 583
gtaaaagagg tgactacggg atactactac ggtatggacg tc 42

<210> SEQ ID NO 584
<211> LENGTH: 14
<212> TYPE: PRT
<213> ORGANISM: Artificial Sequence
<220> FEATURE:
<223> OTHER INFORMATION: Synthetic

<400> SEQUENCE: 584

Val Lys Glu Val Thr Thr Gly Tyr Tyr Tyr Gly Met Asp Val
1 5 10

<210> SEQ ID NO 585
<211> LENGTH: 321
<212> TYPE: DNA
<213> ORGANISM: Artificial Sequence
<220> FEATURE:
<223> OTHER INFORMATION: Synthetic

<400> SEQUENCE: 585
gacatccagt tgacccagtc tccatccttc ctgtctgcat ctgtaggaga cagagtcacc 60
atcacttgct gggccagtca gggcattagc agttatttag cctggtatca gaaaaaacca 120
gggaaagccc ctaacctcct gatctatgat gcatccactt tgcaaagtgg ggtcccatca 180
aggttcagcg gcagtggatc tgggacagaa ttcactctca cactcagcag cctgcagcct 240
gaagattttg caacttatta ctgtcaacag cttaatattt acccattcac tttcggccct 300
gggaccaaag tggatatcaa a 321

<210> SEQ ID NO 586
<211> LENGTH: 107
<212> TYPE: PRT
<213> ORGANISM: Artificial Sequence
<220> FEATURE:
<223> OTHER INFORMATION: Synthetic

<400> SEQUENCE: 586

Asp Ile Gln Leu Thr Gln Ser Pro Ser Phe Leu Ser Ala Ser Val Gly
1 5 10 15

Asp Arg Val Thr Ile Thr Cys Trp Ala Ser Gln Gly Ile Ser Ser Tyr
20 25 30

Leu Ala Trp Tyr Gln Lys Lys Pro Gly Lys Ala Pro Asn Leu Leu Ile
35 40 45

Tyr Asp Ala Ser Thr Leu Gln Ser Gly Val Pro Ser Arg Phe Ser Gly
50 55 60

Ser Gly Ser Gly Thr Glu Phe Thr Leu Thr Leu Ser Ser Leu Gln Pro
65 70 75 80

Glu Asp Phe Ala Thr Tyr Tyr Cys Gln Gln Leu Asn Ile Tyr Pro Phe
85 90 95

Thr Phe Gly Pro Gly Thr Lys Val Asp Ile Lys
100 105

<210> SEQ ID NO 587
<211> LENGTH: 18
<212> TYPE: DNA
<213> ORGANISM: Artificial Sequence
<220> FEATURE:
<223> OTHER INFORMATION: Synthetic

<400> SEQUENCE: 587
cagggcatta gcagttat 18

<210> SEQ ID NO 588
<211> LENGTH: 6
<212> TYPE: PRT
<213> ORGANISM: Artificial Sequence
<220> FEATURE:
<223> OTHER INFORMATION: Synthetic

<400> SEQUENCE: 588

Gln Gly Ile Ser Ser Tyr
1 5

<210> SEQ ID NO 589
<211> LENGTH: 9
<212> TYPE: DNA
<213> ORGANISM: Artificial Sequence
<220> FEATURE:
<223> OTHER INFORMATION: Synthetic

<400> SEQUENCE: 589 gatgcatcc 9

<210> SEQ ID NO 590
<211> LENGTH: 3
<212> TYPE: PRT
<213> ORGANISM: Artificial Sequence
<220> FEATURE:
<223> OTHER INFORMATION: Synthetic

<400> SEQUENCE: 590

Asp Ala Ser
 1

<210> SEQ ID NO 591
<211> LENGTH: 27
<212> TYPE: DNA
<213> ORGANISM: Artificial Sequence
<220> FEATURE:
<223> OTHER INFORMATION: Synthetic

<400> SEQUENCE: 591
caacagctta atatttaccc attcact 27

<210> SEQ ID NO 592
<211> LENGTH: 9
<212> TYPE: PRT
<213> ORGANISM: Artificial Sequence
<220> FEATURE:
<223> OTHER INFORMATION: Synthetic

<400> SEQUENCE: 592

Gln Gln Leu Asn Ile Tyr Pro Phe Thr
 1               5

<210> SEQ ID NO 593
<211> LENGTH: 363
<212> TYPE: DNA
<213> ORGANISM: Artificial Sequence
<220> FEATURE:
<223> OTHER INFORMATION: Synthetic

<400> SEQUENCE: 593
gaagtgcagc tggtggagtc tgggggaggc ttggtacagc ctggcaggtc cctgagactc 60
tcctgtgcag cctctggatt cacctttgat gattatgcca tgcactgggt ccggcaagct 120
ccagggaagg gcctggagtg ggtctcaggt attaattgga acagtggtag cataggctat 180
gcggactctg tgaagggccg attcaccatc tccagagaca acgccaagca ctccctgtat 240
ctgcaaatga acagtctgag acctgaggac acggccttgt attactgtgt aaaagaggtg 300
actacgggat actactacgg tatggacgtc tggggccaag ggaccacggt caccgtctcc 360
tca 363

<210> SEQ ID NO 594
<211> LENGTH: 121
<212> TYPE: PRT
<213> ORGANISM: Artificial Sequence
<220> FEATURE:
<223> OTHER INFORMATION: Synthetic

<400> SEQUENCE: 594

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Asn Trp Asn Ser Gly Ser Ile Gly Tyr Ala Asp Ser Val
    50                  55                  60

-continued

```
Lys Gly Arg Phe Thr Ile Ser Arg Asp Asn Ala Lys His Ser Leu Tyr
65                  70                  75                  80

Leu Gln Met Asn Ser Leu Arg Pro Glu Asp Thr Ala Leu Tyr Tyr Cys
                85                  90                  95

Val Lys Glu Val Thr Thr Gly Tyr Tyr Tyr Gly Met Asp Val Trp Gly
            100                 105                 110

Gln Gly Thr Thr Val Thr Val Ser Ser
        115                 120


<210> SEQ ID NO 595
<211> LENGTH: 321
<212> TYPE: DNA
<213> ORGANISM: Artificial Sequence
<220> FEATURE:
<223> OTHER INFORMATION: Synthetic

<400> SEQUENCE: 595

gacatccagt tgacccagtc tccatccttc ctgtctgcat ctgtaggaga cagagtcacc      60

atcacttgct gggccagtca gggcattagc agttatttag cctggtatca gaaaaaacca     120

gggaaagccc ctaacctcct gatctatgat gcatccactt tgcaaagtgg ggtcccatca     180

aggttcagcg gcagtggatc tgggacagaa ttcactctca cactcagcag cctgcagcct     240

gaagattttg caacttatta ctgtcaacag cttaatattt acccattcac tttcggccct     300

gggaccaaag tggatatcaa a                                               321


<210> SEQ ID NO 596
<211> LENGTH: 107
<212> TYPE: PRT
<213> ORGANISM: Artificial Sequence
<220> FEATURE:
<223> OTHER INFORMATION: Synthetic

<400> SEQUENCE: 596

Asp Ile Gln Leu Thr Gln Ser Pro Ser Phe Leu Ser Ala Ser Val Gly
 1               5                  10                  15

Asp Arg Val Thr Ile Thr Cys Trp Ala Ser Gln Gly Ile Ser Ser Tyr
            20                  25                  30

Leu Ala Trp Tyr Gln Lys Lys Pro Gly Lys Ala Pro Asn Leu Leu Ile
        35                  40                  45

Tyr Asp Ala Ser Thr Leu Gln Ser Gly Val Pro Ser Arg Phe Ser Gly
    50                  55                  60

Ser Gly Ser Gly Thr Glu Phe Thr Leu Thr Leu Ser Ser Leu Gln Pro
65                  70                  75                  80

Glu Asp Phe Ala Thr Tyr Tyr Cys Gln Gln Leu Asn Ile Tyr Pro Phe
                85                  90                  95

Thr Phe Gly Pro Gly Thr Lys Val Asp Ile Lys
            100                 105


<210> SEQ ID NO 597
<211> LENGTH: 363
<212> TYPE: DNA
<213> ORGANISM: Artificial Sequence
<220> FEATURE:
<223> OTHER INFORMATION: Synthetic

<400> SEQUENCE: 597

gaagtgcagc tggtggagtc tgggggaggc ttggtacagc ctggcaggtc cctgagactc      60

tcctgtgcag cctctggatt cacctttgat gattatgcca tgcactgggt ccggcaagct     120
```

```
ccagggaagg gcctggagtg ggtctcaggt attaattgga acagtggtag cataggctat    180

gcggactctg tgaagggccg attcaccatc tccagagaca acgccaagaa ctccctgtat    240

ctgcaaatga acagtctgag agctgaggac acggccttgt attactgtgt aaaagaggtg    300

actacgggat actactacgg tatggacgtc tgggggcaag ggaccacggt caccgtctcc    360

tca                                                                  363


<210> SEQ ID NO 598
<211> LENGTH: 121
<212> TYPE: PRT
<213> ORGANISM: Artificial Sequence
<220> FEATURE:
<223> OTHER INFORMATION: Synthetic

<400> SEQUENCE: 598

Glu Val Gln Leu Val Glu Ser Gly Gly Gly Leu Val Gln Pro Gly Arg
 1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Asn Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Glu Val Thr Thr Gly Tyr Tyr Tyr Gly Met Asp Val Trp Gly
            100                 105                 110

Gln Gly Thr Thr Val Thr Val Ser Ser
        115                 120


<210> SEQ ID NO 599
<211> LENGTH: 321
<212> TYPE: DNA
<213> ORGANISM: Artificial Sequence
<220> FEATURE:
<223> OTHER INFORMATION: Synthetic

<400> SEQUENCE: 599

gacatccagt tgacccagtc tccatccttc ctgtctgcat ctgtaggaga cagagtcacc     60

atcacttgcc gggccagtca gggcattagc agttatttag cctggtatca gcaaaaacca    120

gggaaagccc ctaagctcct gatctatgat gcatccactt tgcaaagtgg ggtcccatca    180

aggttcagcg gcagtggatc tgggacagaa ttcactctca caatcagcag cctgcagcct    240

gaagattttg caacttatta ctgtcaacag cttaatattt acccattcac tttcggccct    300

gggaccaaag tggatatcaa a                                              321


<210> SEQ ID NO 600
<211> LENGTH: 107
<212> TYPE: PRT
<213> ORGANISM: Artificial Sequence
<220> FEATURE:
<223> OTHER INFORMATION: Synthetic

<400> SEQUENCE: 600

Asp Ile Gln Leu Thr Gln Ser Pro Ser Phe Leu Ser Ala Ser Val Gly
 1               5                   10                  15
```

```
Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ile Tyr Pro Phe
                85                  90                  95

Thr Phe Gly Pro Gly Thr Lys Val Asp Ile Lys
            100                 105


<210> SEQ ID NO 601
<211> LENGTH: 366
<212> TYPE: DNA
<213> ORGANISM: Artificial Sequence
<220> FEATURE:
<223> OTHER INFORMATION: Synthetic

<400> SEQUENCE: 601

gaggtgcagt tgttggagtc tgggggaggc ttggtacagc ctggggggtc cctgagactc      60

tcctgtgcag cctctggatt cacgtttagt agctatgcca tgaactgggt ccgccaggct     120

ccagggaagg ggctggattg ggtctcaggt atcagtggta atggtggtag cacctactac     180

gcagactccg tgaagggccg gttcaccatc tccagagaca tttccaagaa cacgctgtat     240

gtgcaaatgc acagcctgag agtcgaggac acggccgttt actactgtgc gaaagcccgt     300

tattacgatt tttggggggg gaatttcgat ctctggggcc gtggcaccca ggtcactgtc     360

tcctca                                                                366


<210> SEQ ID NO 602
<211> LENGTH: 122
<212> TYPE: PRT
<213> ORGANISM: Artificial Sequence
<220> FEATURE:
<223> OTHER INFORMATION: Synthetic

<400> SEQUENCE: 602

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Asp Trp Val
        35                  40                  45

Ser Gly Ile Ser Gly Asn Gly Gly Ser Thr Tyr Tyr Ala Asp Ser Val
    50                  55                  60

Lys Gly Arg Phe Thr Ile Ser Arg Asp Ile Ser Lys Asn Thr Leu Tyr
65                  70                  75                  80

Val Gln Met His Ser Leu Arg Val Glu Asp Thr Ala Val Tyr Tyr Cys
                85                  90                  95

Ala Lys Ala Arg Tyr Tyr Asp Phe Trp Gly Gly Asn Phe Asp Leu Trp
            100                 105                 110

Gly Arg Gly Thr Gln Val Thr Val Ser Ser
        115                 120


<210> SEQ ID NO 603
<211> LENGTH: 24
```

<212> TYPE: DNA
<213> ORGANISM: Artificial Sequence
<220> FEATURE:
<223> OTHER INFORMATION: Synthetic

<400> SEQUENCE: 603
ggattcacgt ttagtagcta tgcc 24

<210> SEQ ID NO 604
<211> LENGTH: 8
<212> TYPE: PRT
<213> ORGANISM: Artificial Sequence
<220> FEATURE:
<223> OTHER INFORMATION: Synthetic

<400> SEQUENCE: 604

Gly Phe Thr Phe Ser Ser Tyr Ala
1 5

<210> SEQ ID NO 605
<211> LENGTH: 24
<212> TYPE: DNA
<213> ORGANISM: Artificial Sequence
<220> FEATURE:
<223> OTHER INFORMATION: Synthetic

<400> SEQUENCE: 605
atcagtggta atggtggtag cacc 24

<210> SEQ ID NO 606
<211> LENGTH: 8
<212> TYPE: PRT
<213> ORGANISM: Artificial Sequence
<220> FEATURE:
<223> OTHER INFORMATION: Synthetic

<400> SEQUENCE: 606

Ile Ser Gly Asn Gly Gly Ser Thr
1 5

<210> SEQ ID NO 607
<211> LENGTH: 45
<212> TYPE: DNA
<213> ORGANISM: Artificial Sequence
<220> FEATURE:
<223> OTHER INFORMATION: Synthetic

<400> SEQUENCE: 607
gcgaaagccc gttattacga tttttggggg gggaatttcg atctc 45

<210> SEQ ID NO 608
<211> LENGTH: 15
<212> TYPE: PRT
<213> ORGANISM: Artificial Sequence
<220> FEATURE:
<223> OTHER INFORMATION: Synthetic

<400> SEQUENCE: 608

Ala Lys Ala Arg Tyr Tyr Asp Phe Trp Gly Gly Asn Phe Asp Leu
1 5 10 15

<210> SEQ ID NO 609
<211> LENGTH: 324
<212> TYPE: DNA
<213> ORGANISM: Artificial Sequence
<220> FEATURE:
<223> OTHER INFORMATION: Synthetic

<400> SEQUENCE: 609
gaaattgtgt tgacgcagtc tccaggcacc ctgtctttgt ctccagggga aagagccacc 60
ctctcctgca gggccagtca gagtgttagc atcaggtact tagcctggta tcagcagaaa 120
cctggccagg ctcccaggct cctcatctat ggtgcatcca gcagggccac tggcatccca 180
gacaggttca gtgtcagtgt gtctgggaca gacttcactc tcaccatcac tagactggag 240
cctgaagatt ttgcagtcta ttactgtcag caatatggta gttcaccgct cactttcggc 300
ggagggacca aggtggagat caaa 324

<210> SEQ ID NO 610
<211> LENGTH: 108
<212> TYPE: PRT
<213> ORGANISM: Artificial Sequence
<220> FEATURE:
<223> OTHER INFORMATION: Synthetic

<400> SEQUENCE: 610

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ile Arg
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Val Ser Val Ser Gly Thr Asp Phe Thr Leu Thr Ile Thr Arg Leu Glu
65 70 75 80

Pro Glu Asp Phe Ala Val Tyr Tyr Cys Gln Gln Tyr Gly Ser Ser Pro
85 90 95

Leu Thr Phe Gly Gly Gly Thr Lys Val Glu Ile Lys
100 105

<210> SEQ ID NO 611
<211> LENGTH: 21
<212> TYPE: DNA
<213> ORGANISM: Artificial Sequence
<220> FEATURE:
<223> OTHER INFORMATION: Synthetic

<400> SEQUENCE: 611
cagagtgtta gcatcaggta c 21

<210> SEQ ID NO 612
<211> LENGTH: 7
<212> TYPE: PRT
<213> ORGANISM: Artificial Sequence
<220> FEATURE:
<223> OTHER INFORMATION: Synthetic

<400> SEQUENCE: 612

Gln Ser Val Ser Ile Arg Tyr
1 5

<210> SEQ ID NO 613
<211> LENGTH: 9
<212> TYPE: DNA
<213> ORGANISM: Artificial Sequence
<220> FEATURE:
<223> OTHER INFORMATION: Synthetic

<400> SEQUENCE: 613 ggtgcatcc 9

<210> SEQ ID NO 614
<211> LENGTH: 3
<212> TYPE: PRT
<213> ORGANISM: Artificial Sequence
<220> FEATURE:
<223> OTHER INFORMATION: Synthetic

<400> SEQUENCE: 614

Gly Ala Ser
1

<210> SEQ ID NO 615
<211> LENGTH: 27
<212> TYPE: DNA
<213> ORGANISM: Artificial Sequence
<220> FEATURE:
<223> OTHER INFORMATION: Synthetic

<400> SEQUENCE: 615
cagcaatatg gtagttcacc gctcact 27

<210> SEQ ID NO 616
<211> LENGTH: 9
<212> TYPE: PRT
<213> ORGANISM: Artificial Sequence
<220> FEATURE:
<223> OTHER INFORMATION: Synthetic

<400> SEQUENCE: 616

Gln Gln Tyr Gly Ser Ser Pro Leu Thr
1 5

<210> SEQ ID NO 617
<211> LENGTH: 366
<212> TYPE: DNA
<213> ORGANISM: Artificial Sequence
<220> FEATURE:
<223> OTHER INFORMATION: Synthetic

<400> SEQUENCE: 617
gaggtgcagt tgttggagtc tgggggaggc ttggtacagc ctggggggtc cctgagactc 60
tcctgtgcag cctctggatt cacgtttagt agctatgcca tgaactgggt ccgccaggct 120
ccagggaagg ggctggattg ggtctcaggt atcagtggta atggtggtag cacctactac 180
gcagactccg tgaagggccg gttcaccatc tccagagaca tttccaagaa cacgctgtat 240
gtgcaaatgc acagcctgag agtcgaggac acggccgttt actactgtgc gaaagcccgt 300
tattacgatt tttggggggg gaatttcgat ctctggggcc gtggcaccct ggtcactgtc 360
tcctca 366

<210> SEQ ID NO 618
<211> LENGTH: 122
<212> TYPE: PRT
<213> ORGANISM: Artificial Sequence
<220> FEATURE:
<223> OTHER INFORMATION: Synthetic

<400> SEQUENCE: 618

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Asn Trp Val Arg Gln Ala Pro Gly Lys Gly Leu Asp Trp Val
35 40 45

Ser Gly Ile Ser Gly Asn Gly Gly Ser Thr Tyr Tyr Ala Asp Ser Val
50 55 60

Lys Gly Arg Phe Thr Ile Ser Arg Asp Ile Ser Lys Asn Thr Leu Tyr
65 70 75 80

Val Gln Met His Ser Leu Arg Val Glu Asp Thr Ala Val Tyr Tyr Cys
85 90 95

Ala Lys Ala Arg Tyr Tyr Asp Phe Trp Gly Gly Asn Phe Asp Leu Trp
100 105 110

Gly Arg Gly Thr Leu Val Thr Val Ser Ser
115 120

<210> SEQ ID NO 619
<211> LENGTH: 324
<212> TYPE: DNA
<213> ORGANISM: Artificial Sequence
<220> FEATURE:
<223> OTHER INFORMATION: Synthetic

<400> SEQUENCE: 619
gaaattgtgt tgacgcagtc tccaggcacc ctgtctttgt ctccagggga aagagccacc 60
ctctcctgca gggccagtca gagtgttagc atcaggtact tagcctggta tcagcagaaa 120
cctggccagg ctcccaggct cctcatctat ggtgcatcca gcagggccac tggcatccca 180
gacaggttca gtgtcagtgt gtctgggaca gacttcactc tcaccatcac tagactggag 240
cctgaagatt ttgcagtcta ttactgtcag caatatggta gttcaccgct cactttcggc 300
ggagggacca aggtggagat caaa 324

<210> SEQ ID NO 620
<211> LENGTH: 108
<212> TYPE: PRT
<213> ORGANISM: Artificial Sequence
<220> FEATURE:
<223> OTHER INFORMATION: Synthetic

<400> SEQUENCE: 620

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ile Arg
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Val Ser Val Ser Gly Thr Asp Phe Thr Leu Thr Ile Thr Arg Leu Glu
65 70 75 80

Pro Glu Asp Phe Ala Val Tyr Tyr Cys Gln Gln Tyr Gly Ser Ser Pro
85 90 95

Leu Thr Phe Gly Gly Gly Thr Lys Val Glu Ile Lys
100 105

<210> SEQ ID NO 621
<211> LENGTH: 366
<212> TYPE: DNA
<213> ORGANISM: Artificial Sequence
<220> FEATURE:
<223> OTHER INFORMATION: Synthetic

<400> SEQUENCE: 621
gaggtgcagc tgttggagtc tgggggaggc ttggtacagc ctggggggtc cctgagactc 60
tcctgtgcag cctctggatt cacgtttagt agctatgcca tgagctgggt ccgccaggct 120
ccagggaagg ggctggagtg ggtctcagct atcagtggta atggtggtag cacctactac 180
gcagactccg tgaagggccg gttcaccatc tccagagaca attccaagaa cacgctgtat 240
ctgcaaatga acagcctgag agccgaggac acggccgtat attactgtgc gaaagcccgt 300
tattacgatt tttggggggg gaatttcgat ctctggggcc gtggcaccct ggtcactgtc 360
tcctca 366

<210> SEQ ID NO 622
<211> LENGTH: 122
<212> TYPE: PRT
<213> ORGANISM: Artificial Sequence
<220> FEATURE:
<223> OTHER INFORMATION: Synthetic

<400> SEQUENCE: 622

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Asn Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Ala Arg Tyr Tyr Asp Phe Trp Gly Gly Asn Phe Asp Leu Trp
100 105 110

Gly Arg Gly Thr Leu Val Thr Val Ser Ser
115 120

<210> SEQ ID NO 623
<211> LENGTH: 324
<212> TYPE: DNA
<213> ORGANISM: Artificial Sequence
<220> FEATURE:
<223> OTHER INFORMATION: Synthetic

<400> SEQUENCE: 623
gaaattgtgt tgacgcagtc tccaggcacc ctgtctttgt ctccagggga aagagccacc 60
ctctcctgca gggccagtca gagtgttagc atcaggtact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag caatatggta gttcaccgct cactttcggc 300
ggagggacca aggtggagat caaa 324

<210> SEQ ID NO 624
<211> LENGTH: 108
<212> TYPE: PRT

<213> ORGANISM: Artificial Sequence
<220> FEATURE:
<223> OTHER INFORMATION: Synthetic

<400> SEQUENCE: 624

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ile Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105
```

<210> SEQ ID NO 625
<211> LENGTH: 381
<212> TYPE: DNA
<213> ORGANISM: Artificial Sequence
<220> FEATURE:
<223> OTHER INFORMATION: Synthetic

<400> SEQUENCE: 625

```
caggttcagc tggtgcagtc tggacctgag gtgaagaacc ctggggcctc agtgaaggtc      60

tcctgcaagg cttctggtta cacctttacc acctatggta tcagttgggt acgacaggcc     120

cctggacaag ggcttgagtg gatgggatgg atcagcggtt acaatggtaa aacaaacgat     180

gcacagaagt tccaggacag agtcgccatg accacagaca catccacgag cacagcctac     240

atggagctga ggagcctgag atctgacgac acggccattt attactgttc gagagatcgt     300

ttagtagtac cacctgccct ttattattcc tactacgtta tggacgtctg gggccaaggg     360

accacggtca ccgtctcctc a                                               381
```

<210> SEQ ID NO 626
<211> LENGTH: 127
<212> TYPE: PRT
<213> ORGANISM: Artificial Sequence
<220> FEATURE:
<223> OTHER INFORMATION: Synthetic

<400> SEQUENCE: 626

```
Gln Val Gln Leu Val Gln Ser Gly Pro Glu Val Lys Asn Pro Gly Ala
 1               5                  10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Asp Ala Gln Lys Phe
    50                  55                  60

Gln Asp Arg Val Ala Met Thr Thr Asp Thr Ser Thr Ser Thr Ala Tyr
65                  70                  75                  80

Met Glu Leu Arg Ser Leu Arg Ser Asp Asp Thr Ala Ile Tyr Tyr Cys
                85                  90                  95
```

```
Ser Arg Asp Arg Leu Val Val Pro Pro Ala Leu Tyr Tyr Ser Tyr Tyr
            100                 105                 110

Val Met Asp Val Trp Gly Gln Gly Thr Thr Val Thr Val Ser Ser
        115                 120                 125


<210> SEQ ID NO 627
<211> LENGTH: 24
<212> TYPE: DNA
<213> ORGANISM: Artificial Sequence
<220> FEATURE:
<223> OTHER INFORMATION: Synthetic

<400> SEQUENCE: 627

ggttacacct ttaccaccta tggt                                            24


<210> SEQ ID NO 628
<211> LENGTH: 8
<212> TYPE: PRT
<213> ORGANISM: Artificial Sequence
<220> FEATURE:
<223> OTHER INFORMATION: Synthetic

<400> SEQUENCE: 628

Gly Tyr Thr Phe Thr Thr Tyr Gly
 1               5


<210> SEQ ID NO 629
<211> LENGTH: 24
<212> TYPE: DNA
<213> ORGANISM: Artificial Sequence
<220> FEATURE:
<223> OTHER INFORMATION: Synthetic

<400> SEQUENCE: 629

atcagcggtt acaatggtaa aaca                                            24


<210> SEQ ID NO 630
<211> LENGTH: 8
<212> TYPE: PRT
<213> ORGANISM: Artificial Sequence
<220> FEATURE:
<223> OTHER INFORMATION: Synthetic

<400> SEQUENCE: 630

Ile Ser Gly Tyr Asn Gly Lys Thr
 1               5


<210> SEQ ID NO 631
<211> LENGTH: 60
<212> TYPE: DNA
<213> ORGANISM: Artificial Sequence
<220> FEATURE:
<223> OTHER INFORMATION: Synthetic

<400> SEQUENCE: 631

tcgagagatc gtttagtagt accacctgcc ctttattatt cctactacgt tatggacgtc     60


<210> SEQ ID NO 632
<211> LENGTH: 20
<212> TYPE: PRT
<213> ORGANISM: Artificial Sequence
<220> FEATURE:
<223> OTHER INFORMATION: Synthetic

<400> SEQUENCE: 632

Ser Arg Asp Arg Leu Val Val Pro Pro Ala Leu Tyr Tyr Ser Tyr Tyr
```

```
 1               5                   10                  15

Val Met Asp Val
            20
```

<210> SEQ ID NO 633
<211> LENGTH: 336
<212> TYPE: DNA
<213> ORGANISM: Artificial Sequence
<220> FEATURE:
<223> OTHER INFORMATION: Synthetic

<400> SEQUENCE: 633

```
gatgttgtga tgactcagtc tccactctcc ctgcccgtca cccttggaca gccggcctcc      60

atctcctgca ggtctagtca aagcctcgta tacagtgatg gaaacaccta cttgaattgg     120

tttcagcaga ggccaggtca atctccaagg cgcctaattt ataaggtttc taaccgggac     180

tctggggtcc cagacagatt cagcggcagt gggtcaggca ctgatttcac actgaaaatc     240

agcagggtgg aggctgagga tgttggggtt tattactgca tgcaaggtac acactggccg     300

tacacttttg gccaggggac caagctggag atcaaa                               336
```

<210> SEQ ID NO 634
<211> LENGTH: 112
<212> TYPE: PRT
<213> ORGANISM: Artificial Sequence
<220> FEATURE:
<223> OTHER INFORMATION: Synthetic

<400> SEQUENCE: 634

```
Asp Val Val Met Thr Gln Ser Pro Leu Ser Leu Pro Val Thr Leu Gly
 1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110
```

<210> SEQ ID NO 635
<211> LENGTH: 33
<212> TYPE: DNA
<213> ORGANISM: Artificial Sequence
<220> FEATURE:
<223> OTHER INFORMATION: Synthetic

<400> SEQUENCE: 635

```
caaagcctcg tatacagtga tggaaacacc tac                                   33
```

<210> SEQ ID NO 636
<211> LENGTH: 11
<212> TYPE: PRT
<213> ORGANISM: Artificial Sequence
<220> FEATURE:
<223> OTHER INFORMATION: Synthetic

<400> SEQUENCE: 636

Gln Ser Leu Val Tyr Ser Asp Gly Asn Thr Tyr
1 5 10

<210> SEQ ID NO 637
<211> LENGTH: 9
<212> TYPE: DNA
<213> ORGANISM: Artificial Sequence
<220> FEATURE:
<223> OTHER INFORMATION: Synthetic

<400> SEQUENCE: 637 aaggtttct 9

<210> SEQ ID NO 638
<211> LENGTH: 3
<212> TYPE: PRT
<213> ORGANISM: Artificial Sequence
<220> FEATURE:
<223> OTHER INFORMATION: Synthetic

<400> SEQUENCE: 638

Lys Val Ser
1

<210> SEQ ID NO 639
<211> LENGTH: 27
<212> TYPE: DNA
<213> ORGANISM: Artificial Sequence
<220> FEATURE:
<223> OTHER INFORMATION: Synthetic

<400> SEQUENCE: 639
atgcaaggta cacactggcc gtacact 27

<210> SEQ ID NO 640
<211> LENGTH: 9
<212> TYPE: PRT
<213> ORGANISM: Artificial Sequence
<220> FEATURE:
<223> OTHER INFORMATION: Synthetic

<400> SEQUENCE: 640

Met Gln Gly Thr His Trp Pro Tyr Thr
1 5

<210> SEQ ID NO 641
<211> LENGTH: 381
<212> TYPE: DNA
<213> ORGANISM: Artificial Sequence
<220> FEATURE:
<223> OTHER INFORMATION: Synthetic

<400> SEQUENCE: 641
caggttcagc tggtgcagtc tggacctgag gtgaagaacc ctggggcctc agtgaaggtc 60
tcctgcaagg cttctggtta cacctttacc acctatggta tcagttgggt acgacaggcc 120
cctggacaag ggcttgagtg gatgggatgg atcagcggtt acaatggtaa aacaaacgat 180
gcacagaagt tccaggacag agtcgccatg accacagaca catccacgag cacagcctac 240
atggagctga ggagcctgag atctgacgac acggccattt attactgttc gagagatcgt 300
ttagtagtac cacctgccct ttattattcc tactacgtta tggacgtctg ggccaagggg 360
accacggtca ccgtctcctc a 381

<210> SEQ ID NO 642
<211> LENGTH: 127
<212> TYPE: PRT
<213> ORGANISM: Artificial Sequence
<220> FEATURE:
<223> OTHER INFORMATION: Synthetic

<400> SEQUENCE: 642

```
Gln Val Gln Leu Val Gln Ser Gly Pro Glu Val Lys Asn Pro Gly Ala
 1               5                  10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Asp Ala Gln Lys Phe
    50                  55                  60

Gln Asp Arg Val Ala Met Thr Thr Asp Thr Ser Thr Ser Thr Ala Tyr
65                  70                  75                  80

Met Glu Leu Arg Ser Leu Arg Ser Asp Asp Thr Ala Ile Tyr Tyr Cys
                85                  90                  95

Ser Arg Asp Arg Leu Val Val Pro Pro Ala Leu Tyr Tyr Ser Tyr Tyr
            100                 105                 110

Val Met Asp Val Trp Gly Gln Gly Thr Thr Val Thr Val Ser Ser
        115                 120                 125
```

<210> SEQ ID NO 643
<211> LENGTH: 336
<212> TYPE: DNA
<213> ORGANISM: Artificial Sequence
<220> FEATURE:
<223> OTHER INFORMATION: Synthetic

<400> SEQUENCE: 643

```
gatgttgtga tgactcagtc tccactctcc ctgcccgtca cccttggaca gccggcctcc     60

atctcctgca ggtctagtca aagcctcgta tacagtgatg gaaacaccta cttgaattgg    120

tttcagcaga ggccaggtca atctccaagg cgcctaattt ataaggtttc taaccgggac    180

tctggggtcc cagacagatt cagcggcagt gggtcaggca ctgatttcac actgaaaatc    240

agcagggtgg aggctgagga tgttggggtt tattactgca tgcaaggtac acactggccg    300

tacacttttg gccaggggac caagctggag atcaaa                              336
```

<210> SEQ ID NO 644
<211> LENGTH: 112
<212> TYPE: PRT
<213> ORGANISM: Artificial Sequence
<220> FEATURE:
<223> OTHER INFORMATION: Synthetic

<400> SEQUENCE: 644

```
Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110


<210> SEQ ID NO 645
<211> LENGTH: 381
<212> TYPE: DNA
<213> ORGANISM: Artificial Sequence
<220> FEATURE:
<223> OTHER INFORMATION: Synthetic

<400> SEQUENCE: 645

caggttcagc tggtgcagtc tggagctgag gtgaagaagc ctggggcctc agtgaaggtc      60

tcctgcaagg cttctggtta cacctttacc acctatggta tcagctgggt gcgacaggcc     120

cctggacaag ggcttgagtg gatgggatgg atcagcggtt acaatggtaa aacaaactat     180

gcacagaagc tccagggcag agtcaccatg accacagaca catccacgag cacagcctac     240

atggagctga ggagcctgag atctgacgac acggccgtgt attactgttc gagagatcgt     300

ttagtagtac cacctgccct ttattattcc tactacgtta tggacgtctg gggcaaggg      360

accacggtca ccgtctcctc a                                               381


<210> SEQ ID NO 646
<211> LENGTH: 127
<212> TYPE: PRT
<213> ORGANISM: Artificial Sequence
<220> FEATURE:
<223> OTHER INFORMATION: Synthetic

<400> SEQUENCE: 646

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ser Arg Asp Arg Leu Val Val Pro Pro Ala Leu Tyr Tyr Ser Tyr Tyr
            100                 105                 110

Val Met Asp Val Trp Gly Gln Gly Thr Thr Val Thr Val Ser Ser
        115                 120                 125


<210> SEQ ID NO 647
<211> LENGTH: 336
<212> TYPE: DNA
<213> ORGANISM: Artificial Sequence
<220> FEATURE:
<223> OTHER INFORMATION: Synthetic

<400> SEQUENCE: 647

gatgttgtga tgactcagtc tccactctcc ctgcccgtca cccttggaca gccggcctcc      60

atctcctgca ggtctagtca aagcctcgta tacagtgatg gaaacaccta cttgaattgg     120
```

-continued

```
tttcagcaga ggccaggcca atctccaagg cgcctaattt ataaggtttc taaccgggac    180

tctggggtcc cagacagatt cagcggcagt gggtcaggca ctgatttcac actgaaaatc    240

agcagggtgg aggctgagga tgttggggtt tattactgca tgcaaggtac acactggccg    300

tacacttttg gccaggggac caagctggag atcaaa                              336
```

<210> SEQ ID NO 648
<211> LENGTH: 112
<212> TYPE: PRT
<213> ORGANISM: Artificial Sequence
<220> FEATURE:
<223> OTHER INFORMATION: Synthetic

<400> SEQUENCE: 648

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110
```

<210> SEQ ID NO 649
<211> LENGTH: 381
<212> TYPE: DNA
<213> ORGANISM: Artificial Sequence
<220> FEATURE:
<223> OTHER INFORMATION: Synthetic

<400> SEQUENCE: 649

```
caggttcagc tggtgcagtc tggacctgag gtgaagaacc ctggggcctc agtgaaggtc     60

tcctgcaagg cttctggtta cacctttacc acctatggta tcagttgggt acgacaggcc    120

cctggacaag ggcttgagtg gatgggatgg atcagcggtt acaatggtaa aacaaacgat    180

gcacagaagt tccaggacag agtcgccatg accacagaca catccacgag cacagcctac    240

atggagctga ggagcctgag atctgacgac acggccattt attactgttc gagagatcgt    300

ttagtagtac cacctgccct taattattac tactacgtta tggacgtctg gggccaaggg    360

accacggtca ccgtctcctc a                                              381
```

<210> SEQ ID NO 650
<211> LENGTH: 127
<212> TYPE: PRT
<213> ORGANISM: Artificial Sequence
<220> FEATURE:
<223> OTHER INFORMATION: Synthetic

<400> SEQUENCE: 650

```
Gln Val Gln Leu Val Gln Ser Gly Pro Glu Val Lys Asn Pro Gly Ala
1               5                   10                  15

Ser Val Lys Val Ser Cys Lys Ala Ser Gly Tyr Thr Phe Thr Thr Tyr
            20                  25                  30
```

```
Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Asp Ala Gln Lys Phe
    50                  55                  60

Gln Asp Arg Val Ala Met Thr Thr Asp Thr Ser Thr Ser Thr Ala Tyr
65                  70                  75                  80

Met Glu Leu Arg Ser Leu Arg Ser Asp Asp Thr Ala Ile Tyr Tyr Cys
                85                  90                  95

Ser Arg Asp Arg Leu Val Val Pro Pro Ala Leu Asn Tyr Tyr Tyr Tyr
            100                 105                 110

Val Met Asp Val Trp Gly Gln Gly Thr Thr Val Thr Val Ser Ser
        115                 120                 125


<210> SEQ ID NO 651
<211> LENGTH: 24
<212> TYPE: DNA
<213> ORGANISM: Artificial Sequence
<220> FEATURE:
<223> OTHER INFORMATION: Synthetic

<400> SEQUENCE: 651

ggttacacct ttaccaccta tggt                                            24


<210> SEQ ID NO 652
<211> LENGTH: 8
<212> TYPE: PRT
<213> ORGANISM: Artificial Sequence
<220> FEATURE:
<223> OTHER INFORMATION: Synthetic

<400> SEQUENCE: 652

Gly Tyr Thr Phe Thr Thr Tyr Gly
 1               5


<210> SEQ ID NO 653
<211> LENGTH: 24
<212> TYPE: DNA
<213> ORGANISM: Artificial Sequence
<220> FEATURE:
<223> OTHER INFORMATION: Synthetic

<400> SEQUENCE: 653

atcagcggtt acaatggtaa aaca                                            24


<210> SEQ ID NO 654
<211> LENGTH: 8
<212> TYPE: PRT
<213> ORGANISM: Artificial Sequence
<220> FEATURE:
<223> OTHER INFORMATION: Synthetic

<400> SEQUENCE: 654

Ile Ser Gly Tyr Asn Gly Lys Thr
 1               5


<210> SEQ ID NO 655
<211> LENGTH: 60
<212> TYPE: DNA
<213> ORGANISM: Artificial Sequence
<220> FEATURE:
<223> OTHER INFORMATION: Synthetic

<400> SEQUENCE: 655

tcgagagatc gtttagtagt accacctgcc cttaattatt actactacgt tatggacgtc     60
```

<210> SEQ ID NO 656
<211> LENGTH: 20
<212> TYPE: PRT
<213> ORGANISM: Artificial Sequence
<220> FEATURE:
<223> OTHER INFORMATION: Synthetic

<400> SEQUENCE: 656

```
Ser Arg Asp Arg Leu Val Val Pro Pro Ala Leu Asn Tyr Tyr Tyr Tyr
 1               5                  10                  15

Val Met Asp Val
            20
```

<210> SEQ ID NO 657
<211> LENGTH: 336
<212> TYPE: DNA
<213> ORGANISM: Artificial Sequence
<220> FEATURE:
<223> OTHER INFORMATION: Synthetic

<400> SEQUENCE: 657

```
gatgttgtga tgactcagtc tccactctcc ctgcccgtca cccttggaca gccggcctcc      60

atctcctgca ggtctagtca aagcctcgta tacagtgatg gaaacaccta cttgaattgg     120

tttcagcaga ggccaggtca atctccaagg cgcctaattt ataaggtttc taaccgggac     180

tctggggtcc cagacagatt cagcggcagt gggtcaggca ctgatttcac actgaaaatc     240

agcagggtgg aggctgagga tgttggggtt tattactgca tgcaaggtac acactggccg     300

tacacttttg gccaggggac caagctggag atcaaa                               336
```

<210> SEQ ID NO 658
<211> LENGTH: 112
<212> TYPE: PRT
<213> ORGANISM: Artificial Sequence
<220> FEATURE:
<223> OTHER INFORMATION: Synthetic

<400> SEQUENCE: 658

```
Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110
```

<210> SEQ ID NO 659
<211> LENGTH: 33
<212> TYPE: DNA
<213> ORGANISM: Artificial Sequence
<220> FEATURE:
<223> OTHER INFORMATION: Synthetic

<400> SEQUENCE: 659
caaagcctcg tatacagtga tggaaacacc tac 33

<210> SEQ ID NO 660
<211> LENGTH: 11
<212> TYPE: PRT
<213> ORGANISM: Artificial Sequence
<220> FEATURE:
<223> OTHER INFORMATION: Synthetic

<400> SEQUENCE: 660

Gln Ser Leu Val Tyr Ser Asp Gly Asn Thr Tyr
1 5 10

<210> SEQ ID NO 661
<211> LENGTH: 9
<212> TYPE: DNA
<213> ORGANISM: Artificial Sequence
<220> FEATURE:
<223> OTHER INFORMATION: Synthetic

<400> SEQUENCE: 661 aaggtttct 9

<210> SEQ ID NO 662
<211> LENGTH: 3
<212> TYPE: PRT
<213> ORGANISM: Artificial Sequence
<220> FEATURE:
<223> OTHER INFORMATION: Synthetic

<400> SEQUENCE: 662

Lys Val Ser
1

<210> SEQ ID NO 663
<211> LENGTH: 27
<212> TYPE: DNA
<213> ORGANISM: Artificial Sequence
<220> FEATURE:
<223> OTHER INFORMATION: Synthetic

<400> SEQUENCE: 663
atgcaaggta cacactggcc gtacact 27

<210> SEQ ID NO 664
<211> LENGTH: 9
<212> TYPE: PRT
<213> ORGANISM: Artificial Sequence
<220> FEATURE:
<223> OTHER INFORMATION: Synthetic

<400> SEQUENCE: 664

Met Gln Gly Thr His Trp Pro Tyr Thr
1 5

<210> SEQ ID NO 665
<211> LENGTH: 381
<212> TYPE: DNA
<213> ORGANISM: Artificial Sequence
<220> FEATURE:
<223> OTHER INFORMATION: Synthetic

<400> SEQUENCE: 665
caggttcagc tggtgcagtc tggacctgag gtgaagaacc ctggggcctc agtgaaggtc 60
tcctgcaagg cttctggtta cacctttacc acctatggta tcagttgggt acgacaggcc 120

```
cctggacaag ggcttgagtg gatgggatgg atcagcggtt acaatggtaa aacaaacgat    180

gcacagaagt tccaggacag agtcgccatg accacagaca catccacgag cacagcctac    240

atggagctga ggagcctgag atctgacgac acggccattt attactgttc gagagatcgt    300

ttagtagtac cacctgccct taattattac tactacgtta tggacgtctg ggccaaggg    360

accacggtca ccgtctcctc a                                               381


<210> SEQ ID NO 666
<211> LENGTH: 127
<212> TYPE: PRT
<213> ORGANISM: Artificial Sequence
<220> FEATURE:
<223> OTHER INFORMATION: Synthetic

<400> SEQUENCE: 666

Gln Val Gln Leu Val Gln Ser Gly Pro Glu Val Lys Asn Pro Gly Ala
1               5                   10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Asp Ala Gln Lys Phe
    50                  55                  60

Gln Asp Arg Val Ala Met Thr Thr Asp Thr Ser Thr Ser Thr Ala Tyr
65                  70                  75                  80

Met Glu Leu Arg Ser Leu Arg Ser Asp Asp Thr Ala Ile Tyr Tyr Cys
                85                  90                  95

Ser Arg Asp Arg Leu Val Val Pro Pro Ala Leu Asn Tyr Tyr Tyr Tyr
            100                 105                 110

Val Met Asp Val Trp Gly Gln Gly Thr Thr Val Thr Val Ser Ser
        115                 120                 125


<210> SEQ ID NO 667
<211> LENGTH: 336
<212> TYPE: DNA
<213> ORGANISM: Artificial Sequence
<220> FEATURE:
<223> OTHER INFORMATION: Synthetic

<400> SEQUENCE: 667

gatgttgtga tgactcagtc tccactctcc ctgcccgtca cccttggaca gccggcctcc     60

atctcctgca ggtctagtca aagcctcgta tacagtgatg gaaacaccta cttgaattgg    120

tttcagcaga ggccaggtca atctccaagg cgcctaattt ataaggtttc taaccgggac    180

tctggggtcc cagacagatt cagcggcagt gggtcaggca ctgatttcac actgaaaatc    240

agcagggtgg aggctgagga tgttggggtt tattactgca tgcaaggtac acactggccg    300

tacacttttg gccaggggac caagctggag atcaaa                              336


<210> SEQ ID NO 668
<211> LENGTH: 112
<212> TYPE: PRT
<213> ORGANISM: Artificial Sequence
<220> FEATURE:
<223> OTHER INFORMATION: Synthetic

<400> SEQUENCE: 668

Asp Val Val Met Thr Gln Ser Pro Leu Ser Leu Pro Val Thr Leu Gly
1               5                   10                  15
```

```
Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110


<210> SEQ ID NO 669
<211> LENGTH: 381
<212> TYPE: DNA
<213> ORGANISM: Artificial Sequence
<220> FEATURE:
<223> OTHER INFORMATION: Synthetic

<400> SEQUENCE: 669

caggttcagc tggtgcagtc tggagctgag gtgaagaagc ctggggcctc agtgaaggtc      60

tcctgcaagg cttctggtta cacctttacc acctatggta tcagctgggt gcgacaggcc     120

cctggacaag ggcttgagtg gatgggatgg atcagcggtt acaatggtaa aacaaactat     180

gcacagaagc tccagggcag agtcaccatg accacagaca catccacgag cacagcctac     240

atggagctga ggagcctgag atctgacgac acggccgtgt attactgttc gagagatcgt     300

ttagtagtac cacctgccct taattattac tactacgtta tggacgtctg ggggcaaggg     360

accacggtca ccgtctcctc a                                               381


<210> SEQ ID NO 670
<211> LENGTH: 127
<212> TYPE: PRT
<213> ORGANISM: Artificial Sequence
<220> FEATURE:
<223> OTHER INFORMATION: Synthetic

<400> SEQUENCE: 670

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ser Arg Asp Arg Leu Val Val Pro Pro Ala Leu Asn Tyr Tyr Tyr Tyr
            100                 105                 110

Val Met Asp Val Trp Gly Gln Gly Thr Thr Val Thr Val Ser Ser
        115                 120                 125


<210> SEQ ID NO 671
```

<211> LENGTH: 336
<212> TYPE: DNA
<213> ORGANISM: Artificial Sequence
<220> FEATURE:
<223> OTHER INFORMATION: Synthetic

<400> SEQUENCE: 671
gatgttgtga tgactcagtc tccactctcc ctgcccgtca cccttggaca gccggcctcc 60
atctcctgca ggtctagtca aagcctcgta tacagtgatg gaaacaccta cttgaattgg 120
tttcagcaga ggccaggcca atctccaagg cgcctaattt ataaggtttc taaccgggac 180
tctggggtcc cagacagatt cagcggcagt gggtcaggca ctgatttcac actgaaaatc 240
agcagggtgg aggctgagga tgttggggtt tattactgca tgcaaggtac acactggccg 300
tacacttttg gccaggggac caagctggag atcaaa 336

<210> SEQ ID NO 672
<211> LENGTH: 112
<212> TYPE: PRT
<213> ORGANISM: Artificial Sequence
<220> FEATURE:
<223> OTHER INFORMATION: Synthetic

<400> SEQUENCE: 672

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val Tyr Ser
20 25 30

Asp Gly Asn Thr Tyr Leu Asn Trp Phe Gln Gln Arg Pro Gly Gln Ser
35 40 45

Pro Arg Arg Leu Ile Tyr Lys Val Ser Asn Arg Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Gly
85 90 95

Thr His Trp Pro Tyr Thr Phe Gly Gln Gly Thr Lys Leu Glu Ile Lys
100 105 110

<210> SEQ ID NO 673
<211> LENGTH: 381
<212> TYPE: DNA
<213> ORGANISM: Artificial Sequence
<220> FEATURE:
<223> OTHER INFORMATION: Synthetic

<400> SEQUENCE: 673
caggttcagc tggtgcagtc tggacctgag gtgaagaacc ctggggcctc agtgaaggtc 60
tcctgcaagg cttctggtta cacctttacc acctatggta tcagttgggt acgacaggcc 120
cctggacaag ggcttgagtg gatgggatgg atcagcggtt acaatggtaa aacaaacgat 180
gcacagaagt tccaggacag agtcgccatg accacagaca catccacgag cacagcctac 240
atggagctga ggagcctgag atctgacgac acggccattt attactgttc gagagatcgt 300
ttagtagtac cacctgccct ttattattac tactacgtta tggacgtctg gggccaaggg 360
accacggtca ccgtctcctc a 381

<210> SEQ ID NO 674
<211> LENGTH: 127
<212> TYPE: PRT

```
<213> ORGANISM: Artificial Sequence
<220> FEATURE:
<223> OTHER INFORMATION: Synthetic

<400> SEQUENCE: 674

Gln Val Gln Leu Val Gln Ser Gly Pro Glu Val Lys Asn Pro Gly Ala
1               5                   10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Asp Ala Gln Lys Phe
    50                  55                  60

Gln Asp Arg Val Ala Met Thr Thr Asp Thr Ser Thr Ser Thr Ala Tyr
65                  70                  75                  80

Met Glu Leu Arg Ser Leu Arg Ser Asp Asp Thr Ala Ile Tyr Tyr Cys
                85                  90                  95

Ser Arg Asp Arg Leu Val Val Pro Pro Ala Leu Tyr Tyr Tyr Tyr Tyr
            100                 105                 110

Val Met Asp Val Trp Gly Gln Gly Thr Thr Val Thr Val Ser Ser
        115                 120                 125


<210> SEQ ID NO 675
<211> LENGTH: 24
<212> TYPE: DNA
<213> ORGANISM: Artificial Sequence
<220> FEATURE:
<223> OTHER INFORMATION: Synthetic

<400> SEQUENCE: 675

ggttacacct ttaccaccta tggt                                            24


<210> SEQ ID NO 676
<211> LENGTH: 8
<212> TYPE: PRT
<213> ORGANISM: Artificial Sequence
<220> FEATURE:
<223> OTHER INFORMATION: Synthetic

<400> SEQUENCE: 676

Gly Tyr Thr Phe Thr Thr Tyr Gly
1               5


<210> SEQ ID NO 677
<211> LENGTH: 24
<212> TYPE: DNA
<213> ORGANISM: Artificial Sequence
<220> FEATURE:
<223> OTHER INFORMATION: Synthetic

<400> SEQUENCE: 677

atcagcggtt acaatggtaa aaca                                            24


<210> SEQ ID NO 678
<211> LENGTH: 8
<212> TYPE: PRT
<213> ORGANISM: Artificial Sequence
<220> FEATURE:
<223> OTHER INFORMATION: Synthetic

<400> SEQUENCE: 678

Ile Ser Gly Tyr Asn Gly Lys Thr
1               5
```

<210> SEQ ID NO 679
<211> LENGTH: 60
<212> TYPE: DNA
<213> ORGANISM: Artificial Sequence
<220> FEATURE:
<223> OTHER INFORMATION: Synthetic

<400> SEQUENCE: 679
tcgagagatc gtttagtagt accacctgcc ctttattatt actactacgt tatggacgtc 60

<210> SEQ ID NO 680
<211> LENGTH: 20
<212> TYPE: PRT
<213> ORGANISM: Artificial Sequence
<220> FEATURE:
<223> OTHER INFORMATION: Synthetic

<400> SEQUENCE: 680

Ser Arg Asp Arg Leu Val Val Pro Pro Ala Leu Tyr Tyr Tyr Tyr Tyr
1 5 10 15

Val Met Asp Val
20

<210> SEQ ID NO 681
<211> LENGTH: 336
<212> TYPE: DNA
<213> ORGANISM: Artificial Sequence
<220> FEATURE:
<223> OTHER INFORMATION: Synthetic

<400> SEQUENCE: 681
gatgttgtga tgactcagtc tccactctcc ctgcccgtca cccttggaca gccggcctcc 60
atctcctgca ggtctagtca aagcctcgta tacagtgatg gaaacaccta cttgaattgg 120
tttcagcaga ggccaggtca atctccaagg cgcctaattt ataaggtttc taaccgggac 180
tctggggtcc cagacagatt cagcggcagt gggtcaggca ctgatttcac actgaaaatc 240
agcagggtgg aggctgagga tgttggggtt tattactgca tgcaaggtac acactggccg 300
tacacttttg gccaggggac caagctggag atcaaa 336

<210> SEQ ID NO 682
<211> LENGTH: 112
<212> TYPE: PRT
<213> ORGANISM: Artificial Sequence
<220> FEATURE:
<223> OTHER INFORMATION: Synthetic

<400> SEQUENCE: 682

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val Tyr Ser
20 25 30

Asp Gly Asn Thr Tyr Leu Asn Trp Phe Gln Gln Arg Pro Gly Gln Ser
35 40 45

Pro Arg Arg Leu Ile Tyr Lys Val Ser Asn Arg Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Gly
85 90 95

Thr His Trp Pro Tyr Thr Phe Gly Gln Gly Thr Lys Leu Glu Ile Lys
100 105 110

<210> SEQ ID NO 683
<211> LENGTH: 33
<212> TYPE: DNA
<213> ORGANISM: Artificial Sequence
<220> FEATURE:
<223> OTHER INFORMATION: Synthetic

<400> SEQUENCE: 683
caaagcctcg tatacagtga tggaaacacc tac 33

<210> SEQ ID NO 684
<211> LENGTH: 11
<212> TYPE: PRT
<213> ORGANISM: Artificial Sequence
<220> FEATURE:
<223> OTHER INFORMATION: Synthetic

<400> SEQUENCE: 684

Gln Ser Leu Val Tyr Ser Asp Gly Asn Thr Tyr
1 5 10

<210> SEQ ID NO 685
<211> LENGTH: 9
<212> TYPE: DNA
<213> ORGANISM: Artificial Sequence
<220> FEATURE:
<223> OTHER INFORMATION: Synthetic

<400> SEQUENCE: 685 aaggtttct 9

<210> SEQ ID NO 686
<211> LENGTH: 3
<212> TYPE: PRT
<213> ORGANISM: Artificial Sequence
<220> FEATURE:
<223> OTHER INFORMATION: Synthetic

<400> SEQUENCE: 686

Lys Val Ser
1

<210> SEQ ID NO 687
<211> LENGTH: 27
<212> TYPE: DNA
<213> ORGANISM: Artificial Sequence
<220> FEATURE:
<223> OTHER INFORMATION: Synthetic

<400> SEQUENCE: 687
atgcaaggta cacactggcc gtacact 27

<210> SEQ ID NO 688
<211> LENGTH: 9
<212> TYPE: PRT
<213> ORGANISM: Artificial Sequence
<220> FEATURE:
<223> OTHER INFORMATION: Synthetic

<400> SEQUENCE: 688

Met Gln Gly Thr His Trp Pro Tyr Thr
1 5

<210> SEQ ID NO 689
<211> LENGTH: 381
<212> TYPE: DNA
<213> ORGANISM: Artificial Sequence
<220> FEATURE:
<223> OTHER INFORMATION: Synthetic

<400> SEQUENCE: 689
caggttcagc tggtgcagtc tggacctgag gtgaagaacc ctggggcctc agtgaaggtc 60
tcctgcaagg cttctggtta cacctttacc acctatggta tcagttgggt acgacaggcc 120
cctggacaag ggcttgagtg gatgggatgg atcagcggtt acaatggtaa aacaaacgat 180
gcacagaagt tccaggacag agtcgccatg accacagaca catccacgag cacagcctac 240
atggagctga ggagcctgag atctgacgac acggccattt attactgttc gagagatcgt 300
ttagtagtac cacctgccct ttattattac tactacgtta tggacgtctg gggccaaggg 360
accacggtca ccgtctcctc a 381

<210> SEQ ID NO 690
<211> LENGTH: 127
<212> TYPE: PRT
<213> ORGANISM: Artificial Sequence
<220> FEATURE:
<223> OTHER INFORMATION: Synthetic

<400> SEQUENCE: 690

Gln Val Gln Leu Val Gln Ser Gly Pro Glu Val Lys Asn Pro Gly Ala
1 5 10 15

Ser Val Lys Val Ser Cys Lys Ala Ser Gly Tyr Thr Phe Thr Thr Tyr
20 25 30

Gly Ile Ser Trp Val Arg Gln Ala Pro Gly Gln Gly Leu Glu Trp Met
35 40 45

Gly Trp Ile Ser Gly Tyr Asn Gly Lys Thr Asn Asp Ala Gln Lys Phe
50 55 60

Gln Asp Arg Val Ala Met Thr Thr Asp Thr Ser Thr Ser Thr Ala Tyr
65 70 75 80

Met Glu Leu Arg Ser Leu Arg Ser Asp Asp Thr Ala Ile Tyr Tyr Cys
85 90 95

Ser Arg Asp Arg Leu Val Val Pro Pro Ala Leu Tyr Tyr Tyr Tyr Tyr
100 105 110

Val Met Asp Val Trp Gly Gln Gly Thr Thr Val Thr Val Ser Ser
115 120 125

<210> SEQ ID NO 691
<211> LENGTH: 336
<212> TYPE: DNA
<213> ORGANISM: Artificial Sequence
<220> FEATURE:
<223> OTHER INFORMATION: Synthetic

<400> SEQUENCE: 691
gatgttgtga tgactcagtc tccactctcc ctgcccgtca cccttggaca gccggcctcc 60
atctcctgca ggtctagtca aagcctcgta tacagtgatg gaaacaccta cttgaattgg 120
tttcagcaga ggccaggtca atctccaagg cgcctaattt ataaggtttc taaccgggac 180
tctggggtcc cagacagatt cagcggcagt gggtcaggca ctgatttcac actgaaaatc 240
agcagggtgg aggctgagga tgttggggtt tattactgca tgcaaggtac acactggccg 300
tacacttttg gccaggggac caagctggag atcaaa 336

<210> SEQ ID NO 692
<211> LENGTH: 112
<212> TYPE: PRT
<213> ORGANISM: Artificial Sequence
<220> FEATURE:
<223> OTHER INFORMATION: Synthetic

<400> SEQUENCE: 692

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110
```

<210> SEQ ID NO 693
<211> LENGTH: 381
<212> TYPE: DNA
<213> ORGANISM: Artificial Sequence
<220> FEATURE:
<223> OTHER INFORMATION: Synthetic

<400> SEQUENCE: 693

```
caggttcagc tggtgcagtc tggagctgag gtgaagaagc ctggggcctc agtgaaggtc     60

tcctgcaagg cttctggtta cacctttacc acctatggta tcagctgggt gcgacaggcc    120

cctggacaag ggcttgagtg gatgggatgg atcagcggtt acaatggtaa aacaaactat    180

gcacagaagc tccagggcag agtcaccatg accacagaca catccacgag cacagcctac    240

atggagctga ggagcctgag atctgacgac acggccgtgt attactgttc gagagatcgt    300

ttagtagtac cacctgccct ttattattac tactacgtta tggacgtctg ggggcaaggg    360

accacggtca ccgtctcctc a                                              381
```

<210> SEQ ID NO 694
<211> LENGTH: 127
<212> TYPE: PRT
<213> ORGANISM: Artificial Sequence
<220> FEATURE:
<223> OTHER INFORMATION: Synthetic

<400> SEQUENCE: 694

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Lys Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80
```

Met Glu Leu Arg Ser Leu Arg Ser Asp Asp Thr Ala Val Tyr Tyr Cys
85 90 95

Ser Arg Asp Arg Leu Val Val Pro Pro Ala Leu Tyr Tyr Tyr Tyr Tyr
100 105 110

Val Met Asp Val Trp Gly Gln Gly Thr Thr Val Thr Val Ser Ser
115 120 125

<210> SEQ ID NO 695
<211> LENGTH: 336
<212> TYPE: DNA
<213> ORGANISM: Artificial Sequence
<220> FEATURE:
<223> OTHER INFORMATION: Synthetic

<400> SEQUENCE: 695
gatgttgtga tgactcagtc tccactctcc ctgcccgtca cccttggaca gccggcctcc 60
atctcctgca ggtctagtca aagcctcgta tacagtgatg gaaacaccta cttgaattgg 120
tttcagcaga ggccaggcca atctccaagg cgcctaattt ataaggtttc taaccgggac 180
tctggggtcc cagacagatt cagcggcagt gggtcaggca ctgatttcac actgaaaatc 240
agcagggtgg aggctgagga tgttggggtt tattactgca tgcaaggtac acactggccg 300
tacacttttg gccaggggac caagctggag atcaaa 336

<210> SEQ ID NO 696
<211> LENGTH: 112
<212> TYPE: PRT
<213> ORGANISM: Artificial Sequence
<220> FEATURE:
<223> OTHER INFORMATION: Synthetic

<400> SEQUENCE: 696

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val Tyr Ser
20 25 30

Asp Gly Asn Thr Tyr Leu Asn Trp Phe Gln Gln Arg Pro Gly Gln Ser
35 40 45

Pro Arg Arg Leu Ile Tyr Lys Val Ser Asn Arg Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Gly
85 90 95

Thr His Trp Pro Tyr Thr Phe Gly Gln Gly Thr Lys Leu Glu Ile Lys
100 105 110

<210> SEQ ID NO 697
<211> LENGTH: 384
<212> TYPE: DNA
<213> ORGANISM: Artificial Sequence
<220> FEATURE:
<223> OTHER INFORMATION: Synthetic

<400> SEQUENCE: 697
caggtgcacc tggtggagtc tggggggaggc ttggtcaagc ctggagggtc cctgagactc 60
tcctgtgcag cctctggatt caccttcagt gaccactaca tgagctggat ccgccaggct 120
ccagggaagg ggctggagtg gatttcatac attagtaatg atggtggtac caaatactat 180
gtggactctg tggagggccg attcatcatt tccagggaca acgccaagaa ctcattgtat 240
ctacatatga acagcctcag agccgacgac acggccgtgt attactgtgc gagagatcag 300
ggatatattg gctacgactc gtattattac tattcctacg gtatggacgt ctggggccaa 360
gggaccacgg tcaccgtcgc ctca 384

<210> SEQ ID NO 698
<211> LENGTH: 128
<212> TYPE: PRT
<213> ORGANISM: Artificial Sequence
<220> FEATURE:
<223> OTHER INFORMATION: Synthetic

<400> SEQUENCE: 698

Gln Val His Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp His
20 25 30

Tyr Met Ser Trp Ile Arg Gln Ala Pro Gly Lys Gly Leu Glu Trp Ile
35 40 45

Ser Tyr Ile Ser Asn Asp Gly Gly Thr Lys Tyr Tyr Val Asp Ser Val
50 55 60

Glu Gly Arg Phe Ile Ile Ser Arg Asp Asn Ala Lys Asn Ser Leu Tyr
65 70 75 80

Leu His Met Asn Ser Leu Arg Ala Asp Asp Thr Ala Val Tyr Tyr Cys
85 90 95

Ala Arg Asp Gln Gly Tyr Ile Gly Tyr Asp Ser Tyr Tyr Tyr Tyr Ser
100 105 110

Tyr Gly Met Asp Val Trp Gly Gln Gly Thr Thr Val Thr Val Ala Ser
115 120 125

<210> SEQ ID NO 699
<211> LENGTH: 24
<212> TYPE: DNA
<213> ORGANISM: Artificial Sequence
<220> FEATURE:
<223> OTHER INFORMATION: Synthetic

<400> SEQUENCE: 699
ggattcacct tcagtgacca ctac 24

<210> SEQ ID NO 700
<211> LENGTH: 8
<212> TYPE: PRT
<213> ORGANISM: Artificial Sequence
<220> FEATURE:
<223> OTHER INFORMATION: Synthetic

<400> SEQUENCE: 700

Gly Phe Thr Phe Ser Asp His Tyr
1 5

<210> SEQ ID NO 701
<211> LENGTH: 24
<212> TYPE: DNA
<213> ORGANISM: Artificial Sequence
<220> FEATURE:
<223> OTHER INFORMATION: Synthetic

<400> SEQUENCE: 701
attagtaatg atggtggtac caaa 24

<210> SEQ ID NO 702
<211> LENGTH: 8
<212> TYPE: PRT
<213> ORGANISM: Artificial Sequence
<220> FEATURE:
<223> OTHER INFORMATION: Synthetic

<400> SEQUENCE: 702

Ile Ser Asn Asp Gly Gly Thr Lys
1 5

<210> SEQ ID NO 703
<211> LENGTH: 63
<212> TYPE: DNA
<213> ORGANISM: Artificial Sequence
<220> FEATURE:
<223> OTHER INFORMATION: Synthetic

<400> SEQUENCE: 703
gcgagagatc agggatatat tggctacgac tcgtattatt actattccta cggtatggac 60
gtc 63

<210> SEQ ID NO 704
<211> LENGTH: 21
<212> TYPE: PRT
<213> ORGANISM: Artificial Sequence
<220> FEATURE:
<223> OTHER INFORMATION: Synthetic

<400> SEQUENCE: 704

Ala Arg Asp Gln Gly Tyr Ile Gly Tyr Asp Ser Tyr Tyr Tyr Tyr Ser
1 5 10 15

Tyr Gly Met Asp Val
20

<210> SEQ ID NO 705
<211> LENGTH: 321
<212> TYPE: DNA
<213> ORGANISM: Artificial Sequence
<220> FEATURE:
<223> OTHER INFORMATION: Synthetic

<400> SEQUENCE: 705
aaaattgtgt tgacgcagtc tccaggcacc ctgcctttgt ttccagggga aagagccacc 60
ctctcctgta gggccagtca gagtgttaac aacaaattct tagcctggta ccagcagaaa 120
tctggccagg ctcccaggct cctcatctat ggtgcatcca gcagggccac tggcatccca 180
gacaggttca gtggcagtgg gtctgggacc gacttcactc tcaccatcag cggactggag 240
cctgaagatt ttgaagtgta ttattgtcaa gtatatggta actcactcac tttcggcgga 300
gggaccaagg tggagatcaa g 321

<210> SEQ ID NO 706
<211> LENGTH: 107
<212> TYPE: PRT
<213> ORGANISM: Artificial Sequence
<220> FEATURE:
<223> OTHER INFORMATION: Synthetic

<400> SEQUENCE: 706

Lys Ile Val Leu Thr Gln Ser Pro Gly Thr Leu Pro Leu Phe Pro Gly
1 5 10 15

Glu Arg Ala Thr Leu Ser Cys Arg Ala Ser Gln Ser Val Asn Asn Lys

```
            20                  25                  30

Phe Leu Ala Trp Tyr Gln Gln Lys Ser Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Gly Leu Glu
65                  70                  75                  80

Pro Glu Asp Phe Glu Val Tyr Tyr Cys Gln Val Tyr Gly Asn Ser Leu
                85                  90                  95

Thr Phe Gly Gly Gly Thr Lys Val Glu Ile Lys
            100                 105


<210> SEQ ID NO 707
<211> LENGTH: 21
<212> TYPE: DNA
<213> ORGANISM: Artificial Sequence
<220> FEATURE:
<223> OTHER INFORMATION: Synthetic

<400> SEQUENCE: 707

cagagtgtta acaacaaatt c                                                 21


<210> SEQ ID NO 708
<211> LENGTH: 7
<212> TYPE: PRT
<213> ORGANISM: Artificial Sequence
<220> FEATURE:
<223> OTHER INFORMATION: Synthetic

<400> SEQUENCE: 708

Gln Ser Val Asn Asn Lys Phe
 1               5


<210> SEQ ID NO 709
<211> LENGTH: 9
<212> TYPE: DNA
<213> ORGANISM: Artificial Sequence
<220> FEATURE:
<223> OTHER INFORMATION: Synthetic

<400> SEQUENCE: 709

ggtgcatcc                                                                9


<210> SEQ ID NO 710
<211> LENGTH: 3
<212> TYPE: PRT
<213> ORGANISM: Artificial Sequence
<220> FEATURE:
<223> OTHER INFORMATION: Synthetic

<400> SEQUENCE: 710

Gly Ala Ser
 1


<210> SEQ ID NO 711
<211> LENGTH: 24
<212> TYPE: DNA
<213> ORGANISM: Artificial Sequence
<220> FEATURE:
<223> OTHER INFORMATION: Synthetic

<400> SEQUENCE: 711

caagtatatg gtaactcact cact                                              24
```

<210> SEQ ID NO 712
<211> LENGTH: 8
<212> TYPE: PRT
<213> ORGANISM: Artificial Sequence
<220> FEATURE:
<223> OTHER INFORMATION: Synthetic

<400> SEQUENCE: 712

Gln Val Tyr Gly Asn Ser Leu Thr
1 5

<210> SEQ ID NO 713
<211> LENGTH: 384
<212> TYPE: DNA
<213> ORGANISM: Artificial Sequence
<220> FEATURE:
<223> OTHER INFORMATION: Synthetic

<400> SEQUENCE: 713
caggtgcagc tggtggagtc tgggggaggc ttggtcaagc ctggagggtc cctgagactc 60
tcctgtgcag cctctggatt caccttcagt gaccactaca tgagctggat ccgccaggct 120
ccagggaagg ggctggagtg gatttcatac attagtaatg atggtggtac caaatactat 180
gtggactctg tggagggccg attcatcatt tccagggaca acgccaagaa ctcattgtat 240
ctacatatga acagcctcag agccgacgac acggccgtgt attactgtgc gagagatcag 300
ggatatattg gctacgactc gtattattac tattcctacg gtatggacgt ctggggccaa 360
gggaccacgg tcaccgtctc ctca 384

<210> SEQ ID NO 714
<211> LENGTH: 128
<212> TYPE: PRT
<213> ORGANISM: Artificial Sequence
<220> FEATURE:
<223> OTHER INFORMATION: Synthetic

<400> SEQUENCE: 714

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp His
20 25 30

Tyr Met Ser Trp Ile Arg Gln Ala Pro Gly Lys Gly Leu Glu Trp Ile
35 40 45

Ser Tyr Ile Ser Asn Asp Gly Gly Thr Lys Tyr Tyr Val Asp Ser Val
50 55 60

Glu Gly Arg Phe Ile Ile Ser Arg Asp Asn Ala Lys Asn Ser Leu Tyr
65 70 75 80

Leu His Met Asn Ser Leu Arg Ala Asp Asp Thr Ala Val Tyr Tyr Cys
85 90 95

Ala Arg Asp Gln Gly Tyr Ile Gly Tyr Asp Ser Tyr Tyr Tyr Tyr Ser
100 105 110

Tyr Gly Met Asp Val Trp Gly Gln Gly Thr Thr Val Thr Val Ser Ser
115 120 125

<210> SEQ ID NO 715
<211> LENGTH: 321
<212> TYPE: DNA
<213> ORGANISM: Artificial Sequence
<220> FEATURE:
<223> OTHER INFORMATION: Synthetic

<400> SEQUENCE: 715
gaaattgtgt tgacgcagtc tccaggcacc ctgcctttgt ttccagggga aagagccacc 60
ctctcctgta gggccagtca gagtgttaac aacaaattct tagcctggta ccagcagaaa 120
tctggccagg ctcccaggct cctcatctat ggtgcatcca gcagggccac tggcatccca 180
gacaggttca gtggcagtgg gtctgggacc gacttcactc tcaccatcag cggactggag 240
cctgaagatt ttgaagtgta ttattgtcaa gtatatggta actcactcac tttcggcgga 300
gggaccaagg tggagatcaa a 321

<210> SEQ ID NO 716
<211> LENGTH: 107
<212> TYPE: PRT
<213> ORGANISM: Artificial Sequence
<220> FEATURE:
<223> OTHER INFORMATION: Synthetic

<400> SEQUENCE: 716

Glu Ile Val Leu Thr Gln Ser Pro Gly Thr Leu Pro Leu Phe Pro Gly
1 5 10 15

Glu Arg Ala Thr Leu Ser Cys Arg Ala Ser Gln Ser Val Asn Asn Lys
20 25 30

Phe Leu Ala Trp Tyr Gln Gln Lys Ser Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Gly Leu Glu
65 70 75 80

Pro Glu Asp Phe Glu Val Tyr Tyr Cys Gln Val Tyr Gly Asn Ser Leu
85 90 95

Thr Phe Gly Gly Gly Thr Lys Val Glu Ile Lys
100 105

<210> SEQ ID NO 717
<211> LENGTH: 384
<212> TYPE: DNA
<213> ORGANISM: Artificial Sequence
<220> FEATURE:
<223> OTHER INFORMATION: Synthetic

<400> SEQUENCE: 717
caggtgcagc tggtggagtc tgggggaggc ttggtcaagc ctggagggtc cctgagactc 60
tcctgtgcag cctctggatt caccttcagt gaccactaca tgagctggat ccgccaggct 120
ccagggaagg ggctggagtg ggtttcatac attagtaatg atggtggtac caaatactac 180
gcagactctg tgaagggccg attcaccatc tccagggaca acgccaagaa ctcactgtat 240
ctgcaaatga acagcctgag agccgaggac acggccgtgt attactgtgc gagagatcag 300
ggatatattg gctacgactc gtattattac tattcctacg gtatggacgt ctgggggcaa 360
gggaccacgg tcaccgtctc ctca 384

<210> SEQ ID NO 718
<211> LENGTH: 128
<212> TYPE: PRT
<213> ORGANISM: Artificial Sequence
<220> FEATURE:
<223> OTHER INFORMATION: Synthetic

<400> SEQUENCE: 718

```
Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp His
            20                  25                  30

Tyr Met Ser Trp Ile Arg Gln Ala Pro Gly Lys Gly Leu Glu Trp Val
        35                  40                  45

Ser Tyr Ile Ser Asn Asp Gly Gly Thr Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Gly Tyr Ile Gly Tyr Asp Ser Tyr Tyr Tyr Tyr Ser
            100                 105                 110

Tyr Gly Met Asp Val Trp Gly Gln Gly Thr Thr Val Thr Val Ser Ser
        115                 120                 125
```

<210> SEQ ID NO 719
<211> LENGTH: 321
<212> TYPE: DNA
<213> ORGANISM: Artificial Sequence
<220> FEATURE:
<223> OTHER INFORMATION: Synthetic

<400> SEQUENCE: 719

```
gaaattgtgt tgacgcagtc tccaggcacc ctgtctttgt ctccagggga aagagccacc      60

ctctcctgca gggccagtca gagtgttaac aacaaattct tagcctggta ccagcagaaa     120

cctggccagg ctcccaggct cctcatctat ggtgcatcca gcagggccac tggcatccca     180

gacaggttca gtggcagtgg gtctgggaca gacttcactc tcaccatcag cagactggag     240

cctgaagatt ttgcagtgta ttactgtcaa gtatatggta actcactcac tttcggcgga     300

gggaccaagg tggagatcaa a                                               321
```

<210> SEQ ID NO 720
<211> LENGTH: 107
<212> TYPE: PRT
<213> ORGANISM: Artificial Sequence
<220> FEATURE:
<223> OTHER INFORMATION: Synthetic

<400> SEQUENCE: 720

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Asn Asn Lys
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Val Tyr Gly Asn Ser Leu
                85                  90                  95

Thr Phe Gly Gly Gly Thr Lys Val Glu Ile Lys
            100                 105
```

<210> SEQ ID NO 721

<211> LENGTH: 378
<212> TYPE: DNA
<213> ORGANISM: Artificial Sequence
<220> FEATURE:
<223> OTHER INFORMATION: Synthetic

<400> SEQUENCE: 721
caaattctgc tggtgcaatc tggacctgag gtgaaggagc ctggggcctc agtgaaggtc 60
tcctgcaagg cttctggtta cacctttacc aactacgcta tcagctgggt gcgacaggtc 120
cctggacaag ggcttgagtg gatgggatgg gtcagcgctt acaatggtca cacaaactat 180
gcacatgaag tccagggcag agtcaccatg accacagaca catccacgac cacagcctac 240
atggagctga ggagcctgag atctgacgac acggccatgt attactgtgc gagagggggt 300
gtagtcgtgc cagttgctcc ccacttctac aacggtatgg acgtctgggg ccaagggacc 360
acggtcaccg tctcctca 378

<210> SEQ ID NO 722
<211> LENGTH: 126
<212> TYPE: PRT
<213> ORGANISM: Artificial Sequence
<220> FEATURE:
<223> OTHER INFORMATION: Synthetic

<400> SEQUENCE: 722

Gln Ile Leu Leu Val Gln Ser Gly Pro Glu Val Lys Glu Pro Gly Ala
1 5 10 15

Ser Val Lys Val Ser Cys Lys Ala Ser Gly Tyr Thr Phe Thr Asn Tyr
20 25 30

Ala Ile Ser Trp Val Arg Gln Val Pro Gly Gln Gly Leu Glu Trp Met
35 40 45

Gly Trp Val Ser Ala Tyr Asn Gly His Thr Asn Tyr Ala His Glu Val
50 55 60

Gln Gly Arg Val Thr Met Thr Thr Asp Thr Ser Thr Thr Thr Ala Tyr
65 70 75 80

Met Glu Leu Arg Ser Leu Arg Ser Asp Asp Thr Ala Met Tyr Tyr Cys
85 90 95

Ala Arg Gly Gly Val Val Val Pro Val Ala Pro His Phe Tyr Asn Gly
100 105 110

Met Asp Val Trp Gly Gln Gly Thr Thr Val Thr Val Ser Ser
115 120 125

<210> SEQ ID NO 723
<211> LENGTH: 24
<212> TYPE: DNA
<213> ORGANISM: Artificial Sequence
<220> FEATURE:
<223> OTHER INFORMATION: Synthetic

<400> SEQUENCE: 723
ggttacacct ttaccaacta cgct 24

<210> SEQ ID NO 724
<211> LENGTH: 8
<212> TYPE: PRT
<213> ORGANISM: Artificial Sequence
<220> FEATURE:
<223> OTHER INFORMATION: Synthetic

<400> SEQUENCE: 724

Gly Tyr Thr Phe Thr Asn Tyr Ala 1 5

<210> SEQ ID NO 725
<211> LENGTH: 24
<212> TYPE: DNA
<213> ORGANISM: Artificial Sequence
<220> FEATURE:
<223> OTHER INFORMATION: Synthetic

<400> SEQUENCE: 725
gtcagcgctt acaatggtca caca 24

<210> SEQ ID NO 726
<211> LENGTH: 8
<212> TYPE: PRT
<213> ORGANISM: Artificial Sequence
<220> FEATURE:
<223> OTHER INFORMATION: Synthetic

<400> SEQUENCE: 726

Val Ser Ala Tyr Asn Gly His Thr
1 5

<210> SEQ ID NO 727
<211> LENGTH: 57
<212> TYPE: DNA
<213> ORGANISM: Artificial Sequence
<220> FEATURE:
<223> OTHER INFORMATION: Synthetic

<400> SEQUENCE: 727
gcgagagggg gtgtagtcgt gccagttgct ccccacttct acaacggtat ggacgtc 57

<210> SEQ ID NO 728
<211> LENGTH: 19
<212> TYPE: PRT
<213> ORGANISM: Artificial Sequence
<220> FEATURE:
<223> OTHER INFORMATION: Synthetic

<400> SEQUENCE: 728

Ala Arg Gly Gly Val Val Val Pro Val Ala Pro His Phe Tyr Asn Gly
1 5 10 15

Met Asp Val

<210> SEQ ID NO 729
<211> LENGTH: 336
<212> TYPE: DNA
<213> ORGANISM: Artificial Sequence
<220> FEATURE:
<223> OTHER INFORMATION: Synthetic

<400> SEQUENCE: 729
gatattgtga tgactcagtt tccactctcc ctgcccgtca cccctggaga gccggcctcc 60
atctcctgca ggtctagtca gagcctcctg catattaatg aatacaacta tttggattgg 120
tacctaaaga agccagggca gtctccacag ctcctgatct atttgggttt taatcgggcc 180
tccggggtcc ctgacaggtt cagtggcagt ggatcaggca cagattttac actgaaaatc 240
agcagagtgg aggctgagga tgttggggtc tattactgca tgcaagctct tcaaactccg 300
tggacgttcg gccaagggac caaggtggaa atcaaa 336

<210> SEQ ID NO 730
<211> LENGTH: 112

<212> TYPE: PRT
<213> ORGANISM: Artificial Sequence
<220> FEATURE:
<223> OTHER INFORMATION: Synthetic

<400> SEQUENCE: 730

Asp Ile Val Met Thr Gln Phe Pro Leu Ser Leu Pro Val Thr Pro Gly
1 5 10 15

Glu Pro Ala Ser Ile Ser Cys Arg Ser Ser Gln Ser Leu Leu His Ile
20 25 30

Asn Glu Tyr Asn Tyr Leu Asp Trp Tyr Leu Lys Lys Pro Gly Gln Ser
35 40 45

Pro Gln Leu Leu Ile Tyr Leu Gly Phe Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro Trp Thr Phe Gly Gln Gly Thr Lys Val Glu Ile Lys
100 105 110

<210> SEQ ID NO 731
<211> LENGTH: 33
<212> TYPE: DNA
<213> ORGANISM: Artificial Sequence
<220> FEATURE:
<223> OTHER INFORMATION: Synthetic

<400> SEQUENCE: 731
cagagcctcc tgcatattaa tgaatacaac tat 33

<210> SEQ ID NO 732
<211> LENGTH: 11
<212> TYPE: PRT
<213> ORGANISM: Artificial Sequence
<220> FEATURE:
<223> OTHER INFORMATION: Synthetic

<400> SEQUENCE: 732

Gln Ser Leu Leu His Ile Asn Glu Tyr Asn Tyr
1 5 10

<210> SEQ ID NO 733
<211> LENGTH: 9
<212> TYPE: DNA
<213> ORGANISM: Artificial Sequence
<220> FEATURE:
<223> OTHER INFORMATION: Synthetic

<400> SEQUENCE: 733 ttgggtttt 9

<210> SEQ ID NO 734
<211> LENGTH: 3
<212> TYPE: PRT
<213> ORGANISM: Artificial Sequence
<220> FEATURE:
<223> OTHER INFORMATION: Synthetic

<400> SEQUENCE: 734

Leu Gly Phe
1

<210> SEQ ID NO 735
<211> LENGTH: 27
<212> TYPE: DNA
<213> ORGANISM: Artificial Sequence
<220> FEATURE:
<223> OTHER INFORMATION: Synthetic

<400> SEQUENCE: 735
atgcaagctc ttcaaactcc gtggacg 27

<210> SEQ ID NO 736
<211> LENGTH: 9
<212> TYPE: PRT
<213> ORGANISM: Artificial Sequence
<220> FEATURE:
<223> OTHER INFORMATION: Synthetic

<400> SEQUENCE: 736

Met Gln Ala Leu Gln Thr Pro Trp Thr
1 5

<210> SEQ ID NO 737
<211> LENGTH: 378
<212> TYPE: DNA
<213> ORGANISM: Artificial Sequence
<220> FEATURE:
<223> OTHER INFORMATION: Synthetic

<400> SEQUENCE: 737
caggttcagc tggtgcagtc tggacctgag gtgaaggagc ctggggcctc agtgaaggtc 60
tcctgcaagg cttctggtta cacctttacc aactacgcta tcagctgggt gcgacaggtc 120
cctggacaag ggcttgagtg gatgggatgg gtcagcgctt acaatggtca cacaaactat 180
gcacatgaag tccagggcag agtcaccatg accacagaca catccacgac cacagcctac 240
atggagctga ggagcctgag atctgacgac acggccatgt attactgtgc gagagggggt 300
gtagtcgtgc cagttgctcc ccacttctac aacggtatgg acgtctgggg ccaagggacc 360
acggtcaccg tctcctca 378

<210> SEQ ID NO 738
<211> LENGTH: 126
<212> TYPE: PRT
<213> ORGANISM: Artificial Sequence
<220> FEATURE:
<223> OTHER INFORMATION: Synthetic

<400> SEQUENCE: 738

Gln Val Gln Leu Val Gln Ser Gly Pro Glu Val Lys Glu Pro Gly Ala
1 5 10 15

Ser Val Lys Val Ser Cys Lys Ala Ser Gly Tyr Thr Phe Thr Asn Tyr
20 25 30

Ala Ile Ser Trp Val Arg Gln Val Pro Gly Gln Gly Leu Glu Trp Met
35 40 45

Gly Trp Val Ser Ala Tyr Asn Gly His Thr Asn Tyr Ala His Glu Val
50 55 60

Gln Gly Arg Val Thr Met Thr Thr Asp Thr Ser Thr Thr Thr Ala Tyr
65 70 75 80

Met Glu Leu Arg Ser Leu Arg Ser Asp Asp Thr Ala Met Tyr Tyr Cys
85 90 95

Ala Arg Gly Gly Val Val Val Pro Val Ala Pro His Phe Tyr Asn Gly
100 105 110

```
Met Asp Val Trp Gly Gln Gly Thr Thr Val Thr Val Ser Ser
        115                 120                 125


<210> SEQ ID NO 739
<211> LENGTH: 336
<212> TYPE: DNA
<213> ORGANISM: Artificial Sequence
<220> FEATURE:
<223> OTHER INFORMATION: Synthetic

<400> SEQUENCE: 739

gatattgtga tgactcagtc tccactctcc ctgcccgtca cccctggaga gccggcctcc      60

atctcctgca ggtctagtca gagcctcctg catattaatg aatacaacta tttggattgg     120

tacctaaaga agccagggca gtctccacag ctcctgatct atttgggttt taatcgggcc     180

tccggggtcc ctgacaggtt cagtggcagt ggatcaggca cagattttac actgaaaatc     240

agcagagtgg aggctgagga tgttggggtc tattactgca tgcaagctct tcaaactccg     300

tggacgttcg gccaagggac caaggtggaa atcaaa                               336


<210> SEQ ID NO 740
<211> LENGTH: 112
<212> TYPE: PRT
<213> ORGANISM: Artificial Sequence
<220> FEATURE:
<223> OTHER INFORMATION: Synthetic

<400> SEQUENCE: 740

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ile
            20                  25                  30

Asn Glu Tyr Asn Tyr Leu Asp Trp Tyr Leu Lys Lys Pro Gly Gln Ser
        35                  40                  45

Pro Gln Leu Leu Ile Tyr Leu Gly Phe Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110


<210> SEQ ID NO 741
<211> LENGTH: 378
<212> TYPE: DNA
<213> ORGANISM: Artificial Sequence
<220> FEATURE:
<223> OTHER INFORMATION: Synthetic

<400> SEQUENCE: 741

caggttcagc tggtgcagtc tggagctgag gtgaagaagc ctggggcctc agtgaaggtc      60

tcctgcaagg cttctggtta cacctttacc aactacgcta tcagctgggt gcgacaggcc     120

cctggacaag ggcttgagtg gatgggatgg gtcagcgctt acaatggtca cacaaactat     180

gcacagaagc tccagggcag agtcaccatg accacagaca catccacgag cacagcctac     240

atggagctga ggagcctgag atctgacgac acggccgtgt attactgtgc gagagggggt     300

gtagtcgtgc cagttgctcc ccacttctac aacggtatgg acgtctgggg gcaagggacc     360

acggtcaccg tctcctca                                                   378
```

<210> SEQ ID NO 742
<211> LENGTH: 126
<212> TYPE: PRT
<213> ORGANISM: Artificial Sequence
<220> FEATURE:
<223> OTHER INFORMATION: Synthetic

<400> SEQUENCE: 742

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
            20                  25                  30

Ala Ile Ser Trp Val Arg Gln Ala Pro Gly Gln Gly Leu Glu Trp Met
        35                  40                  45

Gly Trp Val Ser Ala Tyr Asn Gly His Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Val Val Val Pro Val Ala Pro His Phe Tyr Asn Gly
            100                 105                 110

Met Asp Val Trp Gly Gln Gly Thr Thr Val Thr Val Ser Ser
        115                 120                 125
```

<210> SEQ ID NO 743
<211> LENGTH: 336
<212> TYPE: DNA
<213> ORGANISM: Artificial Sequence
<220> FEATURE:
<223> OTHER INFORMATION: Synthetic

<400> SEQUENCE: 743

```
gatattgtga tgactcagtc tccactctcc ctgcccgtca cccctggaga gccggcctcc     60

atctcctgca ggtctagtca gagcctcctg catattaatg aatacaacta tttggattgg    120

tacctgcaga agccagggca gtctccacag ctcctgatct atttgggttc taatcgggcc    180

tccggggtcc ctgacaggtt cagtggcagt ggatcaggca cagattttac actgaaaatc    240

agcagagtgg aggctgagga tgttggggtt tattactgca tgcaagctct tcaaactccg    300

tggacgttcg gccaagggac caaggtggaa atcaaa                              336
```

<210> SEQ ID NO 744
<211> LENGTH: 112
<212> TYPE: PRT
<213> ORGANISM: Artificial Sequence
<220> FEATURE:
<223> OTHER INFORMATION: Synthetic

<400> SEQUENCE: 744

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ile
            20                  25                  30

Asn Glu Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60
```

```
Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110


<210> SEQ ID NO 745
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(8)
<223> OTHER INFORMATION: Xaa = Any amino acid

<400> SEQUENCE: 745

Xaa Xaa Xaa Xaa Xaa Xaa Xaa Xaa
 1               5


<210> SEQ ID NO 746
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(8)
<223> OTHER INFORMATION: Xaa - Any amino acid

<400> SEQUENCE: 746

Xaa Xaa Xaa Xaa Xaa Xaa Xaa Xaa
 1               5


<210> SEQ ID NO 747
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(20)
<223> OTHER INFORMATION: Xaa = Any amino acid

<400> SEQUENCE: 747

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa
            20


<210> SEQ ID NO 748
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(12)
<223> OTHER INFORMATION: Xaa = Any amino acid

<400> SEQUENCE: 748

Xaa Xaa Xaa Xaa Xaa Xaa Xaa Xaa Xaa Xaa Xaa Xaa
 1               5                  10
```

<210> SEQ ID NO 749
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(3)
<223> OTHER INFORMATION: Xaa = Any amino acid

<400> SEQUENCE: 749

Xaa Xaa Xaa
 1

<210> SEQ ID NO 750
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(9)
<223> OTHER INFORMATION: Xaa = Any amino acid

<400> SEQUENCE: 750

Xaa Xaa Xaa Xaa Xaa Xaa Xaa Xaa Xaa
 1               5

<210> SEQ ID NO 751
<211> LENGTH: 330
<212> TYPE: PRT
<213> ORGANISM: Artificial Sequence
<220> FEATURE:
<223> OTHER INFORMATION: Synthetic

<400> SEQUENCE: 751

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu

```
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 752
<211> LENGTH: 327
<212> TYPE: PRT
<213> ORGANISM: Artificial Sequence
<220> FEATURE:
<223> OTHER INFORMATION: Synthetic

<400> SEQUENCE: 752

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
```

```
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 753
<211> LENGTH: 327
<212> TYPE: PRT
<213> ORGANISM: Artificial Sequence
<220> FEATURE:
<223> OTHER INFORMATION: Synthetic

<400> SEQUENCE: 753

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
```

-continued

```
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 754
<211> LENGTH: 2076
<212> TYPE: DNA
<213> ORGANISM: Homo sapiens

<400> SEQUENCE: 754

atgggcaccg tcagctccag gcggtcctgg tggccgctgc cactgctgct gctgctgctg     60

ctgctcctgg gtcccgcggg cgcccgtgcg caggaggacg aggacggcga ctacgaggag    120

ctggtgctag ccttgcgttc cgaggaggac ggcctggccg aagcacccga gcacggaacc    180

acagccacct tccaccgctg cgccaaggat ccgtggaggt tgcctggcac ctacgtggtg    240

gtgctgaagg aggagaccca cctctcgcag tcagagcgca ctgcccgccg cctgcaggcc    300

caggctgccc gccggggata cctcaccaag atcctgcatg tcttccatgg ccttcttcct    360

ggcttcctgg tgaagatgag tggcgacctg ctggagctgg ccttgaagtt gccccatgtc    420

gactacatcg aggaggactc ctctgtcttt gcccagagca tcccgtggaa cctggagcgg    480

attacccctc cacggtaccg ggcggatgaa taccagcccc ccgacggagg cagcctggtg    540

gaggtgtatc tcctagacac cagcatacag agtgaccacc gggaaatcga gggcagggtc    600

atggtcaccg acttcgagaa tgtgcccgag gaggacggga cccgcttcca cagacaggcc    660

agcaagtgtg acagtcatgg cacccacctg gcaggggtgg tcagcggccg ggatgccggc    720

gtggccaagg gtgccagcat gcgcagcctg cgcgtgctca actgccaagg gaagggcacg    780

gttagcggca ccctcatagg cctggagttt attcggaaaa gccagctggt ccagcctgtg    840

gggccactgg tggtgctgct gcccctggcg ggtgggtaca gccgcgtcct caacgccgcc    900

tgccagcgcc tggcgagggc tggggtcgtg ctggtcaccg ctgccggcaa cttccgggac    960

gatgcctgcc tctactcccc agcctcagct cccgaggtca tcacagttgg ggccaccaat   1020

gcccaggacc agccggtgac cctggggact ttggggacca actttggccg ctgtgtggac   1080

ctctttgccc caggggagga catcattggt gcctccagcg actgcagcac ctgctttgtg   1140

tcacagagtg ggacatcaca ggctgctgcc cacgtggctg gcattgcagc catgatgctg   1200

tctgccgagc cggagctcac cctggccgag ttgaggcaga gactgatcca cttctctgcc   1260

aaagatgtca tcaatgaggc ctggttccct gaggaccagc gggtactgac ccccaacctg   1320

gtggccgccc tgccccccag cacccatggg gcaggttggc agctgttttg caggactgtg   1380

tggtcagcac actcggggcc tacacggatg gccacagcca tcgcccgctg cgccccagat   1440

gaggagctgc tgagctgctc cagtttctcc aggagtggga agcggcgggg cgagcgcatg   1500

gaggcccaag gggcaagct ggtctgccgg gcccacaacg cttttggggg tgagggtgtc   1560

tacgccattg ccaggtgctg cctgctaccc caggccaact gcagcgtcca cacagctcca   1620
```

-continued

```
ccagctgagg ccagcatggg gacccgtgtc cactgccacc aacagggcca cgtcctcaca   1680

ggctgcagct cccactggga ggtggaggac cttggcaccc acaagccgcc tgtgctgagg   1740

ccacgaggtc agcccaacca gtgcgtgggc cacagggagg ccagcatcca cgcttcctgc   1800

tgccatgccc caggtctgga atgcaaagtc aaggagcatg gaatcccggc ccctcaggag   1860

caggtgaccg tggcctgcga ggagggctgg accctgactg gctgcagtgc cctccctggg   1920

acctcccacg tcctgggggc ctacgccgta gacaacacgt gtgtagtcag gagccgggac   1980

gtcagcacta caggcagcac cagcgaagag gccgtgacag ccgttgccat ctgctgccgg   2040

agccggcacc tggcgcaggc ctcccaggag ctccag                               2076


<210> SEQ ID NO 755
<211> LENGTH: 692
<212> TYPE: PRT
<213> ORGANISM: Homo sapiens

<400> SEQUENCE: 755

Met Gly Thr Val Ser Ser Arg Arg Ser Trp Trp Pro Leu Pro Leu Leu
 1               5                  10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
```

```
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Ile Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Glu Ala Val
            660                 665                 670

Thr Ala Val Ala Ile Cys Cys Arg Ser Arg His Leu Ala Gln Ala Ser
        675                 680                 685

Gln Glu Leu Gln
    690
```

<210> SEQ ID NO 756

<211> LENGTH: 692
<212> TYPE: PRT
<213> ORGANISM: Macaca mulata

<400> SEQUENCE: 756

```
Met Gly Thr Val Ser Ser Arg Arg Ser Trp Trp Pro Leu Pro Leu Pro
 1               5                  10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Asp Ala Pro Glu His Gly Ala Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Arg Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His His Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Ala Arg Tyr Arg Ala Asp Glu Tyr Gln Pro Pro Lys Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Ser Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Gly Leu Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Phe Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Arg Ser Gly
    370                 375                 380

Thr Ser Gln Ala Ala Ala His Val Ala Gly Ile Ala Ala Met Met Leu
```

```
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Arg Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Gln Asp
465                 470                 475                 480

Glu Glu Leu Leu Ser Cys Ser Ser Phe Ser Arg Ser Gly Lys Arg Arg
                485                 490                 495

Gly Glu Arg Ile Glu Ala Gln Gly Gly Lys Arg Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Val Asn Cys Ser Val His Thr Ala Pro Pro Ala Gly Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Ile Val
    610                 615                 620

Ala Cys Glu Asp Gly Trp Thr Leu Thr Gly Cys Ser Pro Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Lys Glu Ala Val
            660                 665                 670

Ala Ala Val Ala Ile Cys Cys Arg Ser Arg His Leu Val Gln Ala Ser
        675                 680                 685

Gln Glu Leu Gln
    690


<210> SEQ ID NO 757
<211> LENGTH: 694
<212> TYPE: PRT
<213> ORGANISM: Mus muscular

<400> SEQUENCE: 757

Met Gly Thr His Cys Ser Ala Trp Leu Arg Trp Pro Leu Leu Pro Leu
 1               5                  10                  15

Leu Pro Pro Leu Leu Leu Leu Leu Leu Leu Leu Cys Pro Thr Gly Ala
            20                  25                  30

Gly Ala Gln Asp Glu Asp Gly Asp Tyr Glu Glu Leu Met Leu Ala Leu
        35                  40                  45

Pro Ser Gln Glu Asp Gly Leu Ala Asp Glu Ala Ala His Val Ala Thr
    50                  55                  60
```

```
Ala Thr Phe Arg Arg Cys Ser Lys Glu Ala Trp Arg Leu Pro Gly Thr
65                  70                  75                  80

Tyr Ile Val Val Leu Met Glu Glu Thr Gln Arg Leu Gln Ile Glu Gln
                85                  90                  95

Thr Ala His Arg Leu Gln Thr Arg Ala Ala Arg Arg Gly Tyr Val Ile
            100                 105                 110

Lys Val Leu His Ile Phe Tyr Asp Leu Phe Pro Gly Phe Leu Val Lys
        115                 120                 125

Met Ser Ser Asp Leu Leu Gly Leu Ala Leu Lys Leu Pro His Val Glu
    130                 135                 140

Tyr Ile Glu Glu Asp Ser Phe Val Phe Ala Gln Ser Ile Pro Trp Asn
145                 150                 155                 160

Leu Glu Arg Ile Ile Pro Ala Trp His Gln Thr Glu Glu Asp Arg Ser
                165                 170                 175

Pro Asp Gly Ser Ser Gln Val Glu Val Tyr Leu Leu Asp Thr Ser Ile
            180                 185                 190

Gln Gly Ala His Arg Glu Ile Glu Gly Arg Val Thr Ile Thr Asp Phe
        195                 200                 205

Asn Ser Val Pro Glu Glu Asp Gly Thr Arg Phe His Arg Gln Ala Ser
    210                 215                 220

Lys Cys Asp Ser His Gly Thr His Leu Ala Gly Val Val Ser Gly Arg
225                 230                 235                 240

Asp Ala Gly Val Ala Lys Gly Thr Ser Leu His Ser Leu Arg Val Leu
                245                 250                 255

Asn Cys Gln Gly Lys Gly Thr Val Ser Gly Thr Leu Ile Gly Leu Glu
            260                 265                 270

Phe Ile Arg Lys Ser Gln Leu Ile Gln Pro Ser Gly Pro Leu Val Val
        275                 280                 285

Leu Leu Pro Leu Ala Gly Gly Tyr Ser Arg Ile Leu Asn Ala Ala Cys
    290                 295                 300

Arg His Leu Ala Arg Thr Gly Val Val Leu Val Ala Ala Ala Gly Asn
305                 310                 315                 320

Phe Arg Asp Asp Ala Cys Leu Tyr Ser Pro Ala Ser Ala Pro Glu Val
                325                 330                 335

Ile Thr Val Gly Ala Thr Asn Ala Gln Asp Gln Pro Val Thr Leu Gly
            340                 345                 350

Thr Leu Gly Thr Asn Phe Gly Arg Cys Val Asp Leu Phe Ala Pro Gly
        355                 360                 365

Lys Asp Ile Ile Gly Ala Ser Ser Asp Cys Ser Thr Cys Phe Met Ser
    370                 375                 380

Gln Ser Gly Thr Ser Gln Ala Ala Ala His Val Ala Gly Ile Val Ala
385                 390                 395                 400

Arg Met Leu Ser Arg Glu Pro Thr Leu Thr Leu Ala Glu Leu Arg Gln
                405                 410                 415

Arg Leu Ile His Phe Ser Thr Lys Asp Val Ile Asn Met Ala Trp Phe
            420                 425                 430

Pro Glu Asp Gln Gln Val Leu Thr Pro Asn Leu Val Ala Thr Leu Pro
        435                 440                 445

Pro Ser Thr His Glu Thr Gly Gly Gln Leu Leu Cys Arg Thr Val Trp
    450                 455                 460

Ser Ala His Ser Gly Pro Thr Arg Thr Ala Thr Ala Thr Ala Arg Cys
465                 470                 475                 480

Ala Pro Glu Glu Glu Leu Leu Ser Cys Ser Ser Phe Ser Arg Ser Gly
```

```
                485                 490                 495

Arg Arg Arg Gly Asp Trp Ile Glu Ala Ile Gly Gly Gln Gln Val Cys
            500                 505                 510

Lys Ala Leu Asn Ala Phe Gly Gly Glu Gly Val Tyr Ala Val Ala Arg
        515                 520                 525

Cys Cys Leu Val Pro Arg Ala Asn Cys Ser Ile His Asn Thr Pro Ala
    530                 535                 540

Ala Arg Ala Gly Leu Glu Thr His Val His Cys His Gln Lys Asp His
545                 550                 555                 560

Val Leu Thr Gly Cys Ser Phe His Trp Glu Val Glu Asp Leu Ser Val
                565                 570                 575

Arg Arg Gln Pro Ala Leu Arg Ser Arg Arg Gln Pro Gly Gln Cys Val
            580                 585                 590

Gly His Gln Ala Ala Ser Val Tyr Ala Ser Cys Cys His Ala Pro Gly
        595                 600                 605

Leu Glu Cys Lys Ile Lys Glu His Gly Ile Ser Gly Pro Ser Glu Gln
    610                 615                 620

Val Thr Val Ala Cys Glu Ala Gly Trp Thr Leu Thr Gly Cys Asn Val
625                 630                 635                 640

Leu Pro Gly Ala Ser Leu Thr Leu Gly Ala Tyr Ser Val Asp Asn Leu
                645                 650                 655

Cys Val Ala Arg Val His Asp Thr Ala Arg Ala Asp Arg Thr Ser Gly
            660                 665                 670

Glu Ala Thr Val Ala Ala Ala Ile Cys Cys Arg Ser Arg Pro Ser Ala
        675                 680                 685

Lys Ala Ser Trp Val Gln
    690


<210> SEQ ID NO 758
<211> LENGTH: 653
<212> TYPE: PRT
<213> ORGANISM: Homo sapiens

<400> SEQUENCE: 758

Glu Phe Arg Cys His Asp Gly Lys Cys Ile Ser Arg Gln Phe Val Cys
 1               5                  10                  15

Asp Ser Asp Arg Asp Cys Leu Asp Gly Ser Asp Glu Ala Ser Cys Pro
            20                  25                  30

Val Leu Thr Cys Gly Pro Ala Ser Phe Gln Cys Asn Ser Ser Thr Cys
        35                  40                  45

Ile Pro Gln Leu Trp Ala Cys Asp Asn Asp Pro Asp Cys Glu Asp Gly
    50                  55                  60

Ser Asp Glu Trp Pro Gln Arg Cys Arg Gly Leu Tyr Val Phe Gln Gly
65                  70                  75                  80

Asp Ser Ser Pro Cys Ser Ala Phe Glu Phe His Cys Leu Ser Gly Glu
                85                  90                  95

Cys Ile His Ser Ser Trp Arg Cys Asp Gly Gly Pro Asp Cys Lys Asp
            100                 105                 110

Lys Ser Asp Glu Glu Asn Cys Ala Val Ala Thr Cys Arg Pro Asp Glu
        115                 120                 125

Phe Gln Cys Ser Asp Gly Asn Cys Ile His Gly Ser Arg Gln Cys Asp
    130                 135                 140

Arg Glu Tyr Asp Cys Lys Asp Met Ser Asp Glu Val Gly Cys Val Asn
145                 150                 155                 160
```

-continued

```
Val Thr Leu Cys Glu Gly Pro Asn Lys Phe Lys Cys His Ser Gly Glu
                165                 170                 175

Cys Ile Thr Leu Asp Lys Val Cys Asn Met Ala Arg Asp Cys Arg Asp
            180                 185                 190

Trp Ser Asp Glu Pro Ile Lys Glu Cys Gly Thr Asn Glu Cys Leu Asp
        195                 200                 205

Asn Asn Gly Gly Cys Ser His Val Cys Asn Asp Leu Lys Ile Gly Tyr
    210                 215                 220

Glu Cys Leu Cys Pro Asp Gly Phe Gln Leu Val Ala Gln Arg Arg Cys
225                 230                 235                 240

Glu Asp Ile Asp Glu Cys Gln Asp Pro Asp Thr Cys Ser Gln Leu Cys
                245                 250                 255

Val Asn Leu Glu Gly Gly Tyr Lys Cys Gln Cys Glu Glu Gly Phe Gln
            260                 265                 270

Leu Asp Pro His Thr Lys Ala Cys Lys Ala Val Gly Ser Ile Ala Tyr
        275                 280                 285

Leu Phe Phe Thr Asn Arg His Glu Val Arg Lys Met Thr Leu Asp Arg
    290                 295                 300

Ser Glu Tyr Thr Ser Leu Ile Pro Asn Leu Arg Asn Val Val Ala Leu
305                 310                 315                 320

Asp Thr Glu Val Ala Ser Asn Arg Ile Tyr Trp Ser Asp Leu Ser Gln
                325                 330                 335

Arg Met Ile Cys Ser Thr Gln Leu Asp Arg Ala His Gly Val Ser Ser
            340                 345                 350

Tyr Asp Thr Val Ile Ser Arg Asp Ile Gln Ala Pro Asp Gly Leu Ala
        355                 360                 365

Val Asp Trp Ile His Ser Asn Ile Tyr Trp Thr Asp Ser Val Leu Gly
    370                 375                 380

Thr Val Ser Val Ala Asp Thr Lys Gly Val Lys Arg Lys Thr Leu Phe
385                 390                 395                 400

Arg Glu Asn Gly Ser Lys Pro Arg Ala Ile Val Val Asp Pro Val His
                405                 410                 415

Gly Phe Met Tyr Trp Thr Asp Trp Gly Thr Pro Ala Lys Ile Lys Lys
            420                 425                 430

Gly Gly Leu Asn Gly Val Asp Ile Tyr Ser Leu Val Thr Glu Asn Ile
        435                 440                 445

Gln Trp Pro Asn Gly Ile Thr Leu Asp Leu Leu Ser Gly Arg Leu Tyr
    450                 455                 460

Trp Val Asp Ser Lys Leu His Ser Ile Ser Ser Ile Asp Val Asn Gly
465                 470                 475                 480

Gly Asn Arg Lys Thr Ile Leu Glu Asp Glu Lys Arg Leu Ala His Pro
                485                 490                 495

Phe Ser Leu Ala Val Phe Glu Asp Lys Val Phe Trp Thr Asp Ile Ile
            500                 505                 510

Asn Glu Ala Ile Phe Ser Ala Asn Arg Leu Thr Gly Ser Asp Val Asn
        515                 520                 525

Leu Leu Ala Glu Asn Leu Leu Ser Pro Glu Asp Met Val Leu Phe His
    530                 535                 540

Asn Leu Thr Gln Pro Arg Gly Val Asn Trp Cys Glu Arg Thr Thr Leu
545                 550                 555                 560

Ser Asn Gly Gly Cys Gln Tyr Leu Cys Leu Pro Ala Pro Gln Ile Asn
                565                 570                 575

Pro His Ser Pro Lys Phe Thr Cys Ala Cys Pro Asp Gly Met Leu Leu
```

```
            580                 585                 590

Ala Arg Asp Met Arg Ser Cys Leu Thr Glu Ala Glu Ala Ala Val Ala
        595                 600                 605

Thr Gln Glu Thr Ser Thr Val Arg Leu Lys Val Ser Ser Thr Ala Val
    610                 615                 620

Arg Thr Gln His Thr Thr Thr Arg Pro Val Pro Asp Thr Ser Arg Leu
625                 630                 635                 640

Pro Gly Ala Thr Pro Gly Leu Thr Thr Val Glu Ile Val
                645                 650


<210> SEQ ID NO 759
<211> LENGTH: 753
<212> TYPE: PRT
<213> ORGANISM: Homo sapiens

<400> SEQUENCE: 759

Met Glu Arg Arg Ala Trp Ser Leu Gln Cys Thr Ala Phe Val Leu Phe
 1               5                  10                  15

Cys Ala Trp Cys Ala Leu Asn Ser Ala Lys Ala Lys Arg Gln Phe Val
            20                  25                  30

Asn Glu Trp Ala Ala Glu Ile Pro Gly Gly Pro Glu Ala Ala Ser Ala
        35                  40                  45

Ile Ala Glu Glu Leu Gly Tyr Asp Leu Leu Gly Gln Ile Gly Ser Leu
    50                  55                  60

Glu Asn His Tyr Leu Phe Lys His Lys Asn His Pro Arg Arg Ser Arg
65                  70                  75                  80

Arg Ser Ala Phe His Ile Thr Lys Arg Leu Ser Asp Asp Asp Arg Val
                85                  90                  95

Ile Trp Ala Glu Gln Gln Tyr Glu Lys Glu Arg Ser Lys Arg Ser Ala
            100                 105                 110

Leu Arg Asp Ser Ala Leu Asn Leu Phe Asn Asp Pro Met Trp Asn Gln
        115                 120                 125

Gln Trp Tyr Leu Gln Asp Thr Arg Met Thr Ala Ala Leu Pro Lys Leu
    130                 135                 140

Asp Leu His Val Ile Pro Val Trp Gln Lys Gly Ile Thr Gly Lys Gly
145                 150                 155                 160

Val Val Ile Thr Val Leu Asp Asp Gly Leu Glu Trp Asn His Thr Asp
                165                 170                 175

Ile Tyr Ala Asn Tyr Asp Pro Glu Ala Ser Tyr Asp Phe Asn Asp Asn
            180                 185                 190

Asp His Asp Pro Phe Pro Arg Tyr Asp Pro Thr Asn Glu Asn Lys His
        195                 200                 205

Gly Thr Arg Cys Ala Gly Glu Ile Ala Met Gln Ala Asn Asn His Lys
    210                 215                 220

Cys Gly Val Gly Val Ala Tyr Asn Ser Lys Val Gly Gly Ile Arg Met
225                 230                 235                 240

Leu Asp Gly Ile Val Thr Asp Ala Ile Glu Ala Ser Ser Ile Gly Phe
                245                 250                 255

Asn Pro Gly His Val Asp Ile Tyr Ser Ala Ser Trp Gly Pro Asn Asp
            260                 265                 270

Asp Gly Lys Thr Val Glu Gly Pro Gly Arg Leu Ala Gln Lys Ala Phe
        275                 280                 285

Glu Tyr Gly Val Lys Gln Gly Arg Gln Gly Lys Gly Ser Ile Phe Val
    290                 295                 300
```

```
Trp Ala Ser Gly Asn Gly Gly Arg Gln Gly Asp Asn Cys Asp Cys Asp
305                 310                 315                 320

Gly Tyr Thr Asp Ser Ile Tyr Thr Ile Ser Ile Ser Ser Ala Ser Gln
                325                 330                 335

Gln Gly Leu Ser Pro Trp Tyr Ala Glu Lys Cys Ser Ser Thr Leu Ala
            340                 345                 350

Thr Ser Tyr Ser Ser Gly Asp Tyr Thr Asp Gln Arg Ile Thr Ser Ala
        355                 360                 365

Asp Leu His Asn Asp Cys Thr Glu Thr His Thr Gly Thr Ser Ala Ser
    370                 375                 380

Ala Pro Leu Ala Ala Gly Ile Phe Ala Leu Ala Leu Glu Ala Asn Pro
385                 390                 395                 400

Asn Leu Thr Trp Arg Asp Met Gln His Leu Val Val Trp Thr Ser Glu
                405                 410                 415

Tyr Asp Pro Leu Ala Asn Asn Pro Gly Trp Lys Lys Asn Gly Ala Gly
            420                 425                 430

Leu Met Val Asn Ser Arg Phe Gly Phe Gly Leu Leu Asn Ala Lys Ala
        435                 440                 445

Leu Val Asp Leu Ala Asp Pro Arg Thr Trp Arg Ser Val Pro Glu Lys
    450                 455                 460

Lys Glu Cys Val Val Lys Asp Asn Asp Phe Glu Pro Arg Ala Leu Lys
465                 470                 475                 480

Ala Asn Gly Glu Val Ile Ile Glu Ile Pro Thr Arg Ala Cys Glu Gly
                485                 490                 495

Gln Glu Asn Ala Ile Lys Ser Leu Glu His Val Gln Phe Glu Ala Thr
            500                 505                 510

Ile Glu Tyr Ser Arg Arg Gly Asp Leu His Val Thr Leu Thr Ser Ala
        515                 520                 525

Ala Gly Thr Ser Thr Val Leu Leu Ala Glu Arg Glu Arg Asp Thr Ser
    530                 535                 540

Pro Asn Gly Phe Lys Asn Trp Asp Phe Met Ser Val His Thr Trp Gly
545                 550                 555                 560

Glu Asn Pro Ile Gly Thr Trp Thr Leu Arg Ile Thr Asp Met Ser Gly
                565                 570                 575

Arg Ile Gln Asn Glu Gly Arg Ile Val Asn Trp Lys Leu Ile Leu His
            580                 585                 590

Gly Thr Ser Ser Gln Pro Glu His Met Lys Gln Pro Arg Val Tyr Thr
        595                 600                 605

Ser Tyr Asn Thr Val Gln Asn Asp Arg Arg Gly Val Glu Lys Met Val
    610                 615                 620

Asp Pro Gly Glu Glu Gln Pro Thr Gln Glu Asn Pro Lys Glu Asn Thr
625                 630                 635                 640

Leu Val Ser Lys Ser Pro Ser Ser Ser Ser Val Gly Gly Arg Arg Asp
                645                 650                 655

Glu Leu Glu Glu Gly Ala Pro Ser Gln Ala Met Leu Arg Leu Leu Gln
            660                 665                 670

Ser Ala Phe Ser Lys Asn Ser Pro Pro Lys Gln Ser Pro Lys Lys Ser
        675                 680                 685

Pro Ser Ala Lys Leu Asn Ile Pro Tyr Glu Asn Phe Tyr Glu Ala Leu
    690                 695                 700

Glu Lys Leu Asn Lys Pro Ser Gln Leu Lys Asp Ser Glu Asp Ser Leu
705                 710                 715                 720

Tyr Asn Asp Tyr Val Asp Val Phe Tyr Asn Thr Lys Pro Tyr Lys His
```

```
                725                 730                 735

Arg Asp Asp Arg Leu Leu Gln Ala Leu Val Asp Ile Leu Asn Glu Glu
            740                 745                 750

Asn


<210> SEQ ID NO 760
<211> LENGTH: 785
<212> TYPE: PRT
<213> ORGANISM: Homo sapiens

<400> SEQUENCE: 760

Met Pro Lys Gly Arg Gln Lys Val Pro His Leu Asp Ala Pro Leu Gly
 1               5                  10                  15

Leu Pro Thr Cys Leu Trp Leu Glu Leu Ala Gly Leu Phe Leu Leu Val
            20                  25                  30

Pro Trp Val Met Gly Leu Ala Gly Thr Gly Gly Pro Asp Gly Gln Gly
        35                  40                  45

Thr Gly Gly Pro Ser Trp Ala Val His Leu Glu Ser Leu Glu Gly Asp
    50                  55                  60

Gly Glu Glu Glu Thr Leu Glu Gln Gln Ala Asp Ala Leu Ala Gln Ala
65                  70                  75                  80

Ala Gly Leu Val Asn Ala Gly Arg Ile Gly Glu Leu Gln Gly His Tyr
                85                  90                  95

Leu Phe Val Gln Pro Ala Gly His Arg Pro Ala Leu Glu Val Glu Ala
            100                 105                 110

Ile Arg Gln Gln Val Glu Ala Val Leu Ala Gly His Glu Ala Val Arg
        115                 120                 125

Trp His Ser Glu Gln Arg Leu Leu Arg Arg Ala Lys Arg Ser Val His
    130                 135                 140

Phe Asn Asp Pro Lys Tyr Pro Gln Gln Trp His Leu Asn Asn Arg Arg
145                 150                 155                 160

Ser Pro Gly Arg Asp Ile Asn Val Thr Gly Val Trp Glu Arg Asn Val
                165                 170                 175

Thr Gly Arg Gly Val Thr Val Val Val Val Asp Asp Gly Val Glu His
            180                 185                 190

Thr Ile Gln Asp Ile Ala Pro Asn Tyr Ser Pro Glu Gly Ser Tyr Asp
        195                 200                 205

Leu Asn Ser Asn Asp Pro Asp Pro Met Pro His Pro Asp Val Glu Asn
    210                 215                 220

Gly Asn His His Gly Thr Arg Cys Ala Gly Glu Ile Ala Ala Val Pro
225                 230                 235                 240

Asn Asn Ser Phe Cys Ala Val Gly Val Ala Tyr Gly Ser Arg Ile Ala
                245                 250                 255

Gly Ile Arg Val Leu Asp Gly Pro Leu Thr Asp Ser Met Glu Ala Val
            260                 265                 270

Ala Phe Asn Lys His Tyr Gln Ile Asn Asp Ile Tyr Ser Cys Ser Trp
        275                 280                 285

Gly Pro Asp Asp Asp Gly Lys Thr Val Asp Gly Pro His Gln Leu Gly
    290                 295                 300

Lys Ala Ala Leu Gln His Gly Val Ile Ala Gly Arg Gln Gly Phe Gly
305                 310                 315                 320

Ser Ile Phe Val Val Ala Ser Gly Asn Gly Gly Gln His Asn Asp Asn
                325                 330                 335

Cys Asn Tyr Asp Gly Tyr Ala Asn Ser Ile Tyr Thr Val Thr Ile Gly
```

```
            340                 345                 350

Ala Val Asp Glu Glu Gly Arg Met Pro Phe Tyr Ala Glu Glu Cys Ala
        355                 360                 365

Ser Met Leu Ala Val Thr Phe Ser Gly Gly Asp Lys Met Leu Arg Ser
    370                 375                 380

Ile Val Thr Thr Asp Trp Asp Leu Gln Lys Gly Thr Gly Cys Thr Glu
385                 390                 395                 400

Gly His Thr Gly Thr Ser Ala Ala Ala Pro Leu Ala Ala Gly Met Ile
                405                 410                 415

Ala Leu Met Leu Gln Val Arg Pro Cys Leu Thr Trp Arg Asp Val Gln
            420                 425                 430

His Ile Ile Val Phe Thr Ala Thr Arg Tyr Glu Asp Arg Arg Ala Glu
        435                 440                 445

Trp Val Thr Asn Glu Ala Gly Phe Ser His Ser His Gln His Gly Phe
    450                 455                 460

Gly Leu Leu Asn Ala Trp Arg Leu Val Asn Ala Ala Lys Ile Trp Thr
465                 470                 475                 480

Ser Val Pro Tyr Leu Ala Ser Tyr Val Ser Pro Val Leu Lys Glu Asn
                485                 490                 495

Lys Ala Ile Pro Gln Ser Pro Arg Ser Leu Glu Val Leu Trp Asn Val
            500                 505                 510

Ser Arg Met Asp Leu Glu Met Ser Gly Leu Lys Thr Leu Glu His Val
        515                 520                 525

Ala Val Thr Val Ser Ile Thr His Pro Arg Arg Gly Ser Leu Glu Leu
    530                 535                 540

Lys Leu Phe Cys Pro Ser Gly Met Met Ser Leu Ile Gly Ala Pro Arg
545                 550                 555                 560

Ser Met Asp Ser Asp Pro Asn Gly Phe Asn Asp Trp Thr Phe Ser Thr
                565                 570                 575

Val Arg Cys Trp Gly Glu Arg Ala Arg Gly Thr Tyr Arg Leu Val Ile
            580                 585                 590

Arg Asp Val Gly Asp Glu Ser Phe Gln Val Gly Ile Leu Arg Gln Trp
        595                 600                 605

Gln Leu Thr Leu Tyr Gly Ser Val Trp Ser Ala Val Asp Ile Arg Asp
    610                 615                 620

Arg Gln Arg Leu Leu Glu Ser Ala Met Ser Gly Lys Tyr Leu His Asp
625                 630                 635                 640

Asp Phe Ala Leu Pro Cys Pro Pro Gly Leu Lys Ile Pro Glu Glu Asp
                645                 650                 655

Gly Tyr Thr Ile Thr Pro Asn Thr Leu Lys Thr Leu Val Leu Val Gly
            660                 665                 670

Cys Phe Thr Val Phe Trp Thr Val Tyr Tyr Met Leu Glu Val Tyr Leu
        675                 680                 685

Ser Gln Arg Asn Val Ala Ser Asn Gln Val Cys Arg Ser Gly Pro Cys
    690                 695                 700

His Trp Pro His Arg Ser Arg Lys Ala Lys Glu Glu Gly Thr Glu Leu
705                 710                 715                 720

Glu Ser Val Pro Leu Cys Ser Ser Lys Asp Pro Asp Glu Val Glu Thr
                725                 730                 735

Glu Ser Arg Gly Pro Pro Thr Thr Ser Asp Leu Leu Ala Pro Asp Leu
            740                 745                 750

Leu Glu Gln Gly Asp Trp Ser Leu Ser Gln Asn Lys Ser Ala Leu Asp
        755                 760                 765
```

```
Cys Pro His Gln His Leu Asp Val Pro His Gly Lys Glu Glu Gln Ile
    770                 775                 780

Cys
785


<210> SEQ ID NO 761
<211> LENGTH: 692
<212> TYPE: PRT
<213> ORGANISM: Macaca fascicularis

<400> SEQUENCE: 761

Met Gly Thr Val Ser Ser Arg Arg Ser Trp Trp Pro Leu Pro Leu Pro
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Asp Ala Pro Glu His Gly Ala Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Arg Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His His Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Ala Arg Tyr Arg Ala Asp Glu Tyr Gln Pro Pro Lys Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Ser Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Gly Leu Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Phe Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
```

```
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Arg Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Arg Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Gln Asp
465                 470                 475                 480

Glu Glu Leu Leu Ser Cys Ser Ser Phe Ser Arg Ser Gly Lys Arg Arg
                485                 490                 495

Gly Glu Arg Ile Glu Ala Gln Gly Gly Lys Arg Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Val Asn Cys Ser Val His Thr Ala Pro Pro Ala Gly Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Ile Val
    610                 615                 620

Ala Cys Glu Asp Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Glu Ala Val
            660                 665                 670

Ala Ala Val Ala Ile Cys Cys Arg Ser Arg His Leu Val Gln Ala Ser
        675                 680                 685

Gln Glu Leu Gln
    690


<210> SEQ ID NO 762
<211> LENGTH: 698
<212> TYPE: PRT
<213> ORGANISM: Mesocricetus auratus

<400> SEQUENCE: 762

Met Gly Thr Ser Cys Ser Ala Arg Pro Arg Trp Leu Leu Ser Pro Leu
 1               5                  10                  15
```

```
Leu Leu Leu Leu Leu Leu Leu Arg Tyr Met Gly Ala Ser Ala Gln Asp
            20                  25                  30

Glu Asp Ala Glu Tyr Glu Glu Leu Met Leu Thr Leu Gln Ser Gln Asp
        35                  40                  45

Asp Gly Leu Ala Asp Glu Thr Asp Glu Ala Pro Gln Gly Ala Thr Ala
    50                  55                  60

Ala Phe His Arg Cys Pro Glu Glu Ala Trp Arg Val Pro Gly Thr Tyr
65                  70                  75                  80

Ile Val Met Leu Ala Glu Glu Ala Gln Trp Val His Ile Glu Gln Thr
                85                  90                  95

Met His Arg Leu Gln Thr Gln Ala Ala Arg Arg Gly Tyr Val Ile Lys
            100                 105                 110

Ile Gln His Ile Phe Tyr Asp Phe Leu Pro Ala Phe Val Val Lys Met
        115                 120                 125

Ser Ser Asp Leu Leu Asp Leu Ala Leu Lys Leu Pro His Val Lys Tyr
    130                 135                 140

Ile Glu Glu Asp Ser Leu Val Phe Ala Gln Ser Ile Pro Trp Asn Leu
145                 150                 155                 160

Asp Arg Ile Ile Pro Ala Gly Arg Gln Ala Gln Glu Tyr Ser Ser Ser
                165                 170                 175

Arg Lys Val Pro Ser Gly Ser Gly Gln Val Glu Val Tyr Leu Leu Asp
            180                 185                 190

Thr Ser Ile Gln Ser Asp His Arg Glu Ile Glu Gly Arg Val Thr Val
        195                 200                 205

Thr Asp Phe Asn Ser Val Pro Glu Glu Asp Gly Thr Arg Phe His Arg
    210                 215                 220

Gln Ala Ser Lys Cys Asp Ser His Gly Thr His Leu Ala Gly Val Val
225                 230                 235                 240

Ser Gly Arg Asp Ala Gly Val Ala Lys Gly Thr Ile Leu His Gly Leu
                245                 250                 255

Arg Val Leu Asn Cys Gln Gly Lys Gly Ile Val Ser Gly Ile Leu Thr
            260                 265                 270

Gly Leu Glu Phe Ile Trp Lys Ser Gln Leu Met Gln Pro Ser Gly Pro
        275                 280                 285

Gln Val Val Leu Leu Pro Leu Ala Gly Arg Tyr Ser Arg Val Leu Asn
    290                 295                 300

Thr Ala Cys Gln His Leu Ala Arg Thr Gly Val Val Leu Val Ala Ala
305                 310                 315                 320

Ala Gly Asn Phe Arg Asp Asp Ala Cys Leu Tyr Ser Pro Ala Ser Ala
                325                 330                 335

Pro Glu Val Ile Thr Val Gly Ala Thr Asp Val Gln Asp Gln Pro Val
            340                 345                 350

Thr Leu Gly Thr Leu Gly Thr Asn Phe Gly Arg Cys Val Asp Leu Phe
        355                 360                 365

Ala Pro Gly Lys Asp Ile Ile Gly Ala Ser Ser Asp Cys Ser Ala Cys
    370                 375                 380

Phe Met Ser Gln Ser Gly Thr Ser Gln Ala Ala Ala His Val Ala Gly
385                 390                 395                 400

Ile Val Ala Met Met Leu Thr Leu Glu Pro Glu Leu Thr Leu Thr Glu
                405                 410                 415

Leu Arg Gln Arg Leu Ile His Phe Ser Thr Lys Asp Ala Ile Asn Met
            420                 425                 430

Ala Trp Phe Pro Glu Asp Gln Arg Val Leu Thr Pro Asn Leu Val Ala
```

```
        435                 440                 445

Thr Leu Pro Pro Ser Thr His Gly Thr Gly Gly Gln Leu Leu Cys Arg
    450                 455                 460

Thr Val Trp Ser Ala His Ser Gly Pro Thr Arg Ala Ala Thr Ala Thr
465                 470                 475                 480

Ala Arg Cys Ala Pro Gly Glu Glu Leu Leu Ser Cys Ser Ser Phe Ser
                485                 490                 495

Arg Ser Gly Arg Arg Arg Gly Asp Arg Ile Glu Ala Ala Gly Thr Gln
            500                 505                 510

Gln Val Cys Lys Ala Leu Asn Ala Phe Gly Gly Glu Gly Val Tyr Ala
        515                 520                 525

Val Ala Arg Cys Cys Leu Leu Pro Arg Ala Asn Cys Ser Ile His Thr
    530                 535                 540

Thr Pro Ala Ala Arg Thr Ser Leu Glu Thr His Ala His Cys His Gln
545                 550                 555                 560

Lys Asp His Val Leu Thr Gly Cys Ser Leu His Trp Glu Val Glu Gly
                565                 570                 575

Ile Gly Val Gln Pro Leu Ala Val Leu Arg Ser Arg His Gln Pro Gly
            580                 585                 590

Gln Cys Thr Gly His Arg Glu Ala Ser Val His Ala Ser Cys Cys His
        595                 600                 605

Ala Pro Gly Leu Glu Cys Lys Ile Lys Glu His Gly Ile Ser Gly Pro
    610                 615                 620

Ala Glu Gln Val Thr Val Ala Cys Glu Ala Gly Trp Thr Leu Thr Gly
625                 630                 635                 640

Cys Asn Val Leu Pro Gly Ala Phe Ile Thr Leu Gly Ala Tyr Ala Val
                645                 650                 655

Asp Asn Thr Cys Val Ala Arg Ser Arg Val Thr Asp Thr Ala Gly Arg
            660                 665                 670

Thr Gly Glu Glu Ala Thr Val Ala Ala Ala Ile Cys Cys Arg Asn Arg
        675                 680                 685

Pro Ser Ala Lys Ala Ser Trp Val His Gln
    690                 695


<210> SEQ ID NO 763
<211> LENGTH: 691
<212> TYPE: PRT
<213> ORGANISM: Rattus norvegicus

<400> SEQUENCE: 763

Met Gly Ile Arg Cys Ser Thr Trp Leu Arg Trp Pro Leu Ser Pro Gln
 1               5                  10                  15

Leu Leu Leu Leu Leu Leu Leu Cys Pro Thr Gly Ser Arg Ala Gln Asp
            20                  25                  30

Glu Asp Gly Asp Tyr Glu Glu Leu Met Leu Ala Leu Pro Ser Gln Glu
        35                  40                  45

Asp Ser Leu Val Asp Glu Ala Ser His Val Ala Thr Ala Thr Phe Arg
    50                  55                  60

Arg Cys Ser Lys Glu Ala Trp Arg Leu Pro Gly Thr Tyr Val Val Val
65                  70                  75                  80

Leu Met Glu Glu Thr Gln Arg Leu Gln Val Glu Gln Thr Ala His Arg
                85                  90                  95

Leu Gln Thr Trp Ala Ala Arg Arg Gly Tyr Val Ile Lys Val Leu His
            100                 105                 110
```

```
Val Phe Tyr Asp Leu Phe Pro Gly Phe Leu Val Lys Met Ser Ser Asp
        115                 120                 125

Leu Leu Gly Leu Ala Leu Lys Leu Pro His Val Glu Tyr Ile Glu Glu
    130                 135                 140

Asp Ser Leu Val Phe Ala Gln Ser Ile Pro Trp Asn Leu Glu Arg Ile
145                 150                 155                 160

Ile Pro Ala Trp Gln Gln Thr Glu Glu Asp Ser Ser Pro Asp Gly Ser
                165                 170                 175

Ser Gln Val Glu Val Tyr Leu Leu Asp Thr Ser Ile Gln Ser Gly His
            180                 185                 190

Arg Glu Ile Glu Gly Arg Val Thr Ile Thr Asp Phe Asn Ser Val Pro
        195                 200                 205

Glu Glu Asp Gly Thr Arg Phe His Arg Gln Ala Ser Lys Cys Asp Ser
    210                 215                 220

His Gly Thr His Leu Ala Gly Val Val Ser Gly Arg Asp Ala Gly Val
225                 230                 235                 240

Ala Lys Gly Thr Ser Leu His Ser Leu Arg Val Leu Asn Cys Gln Gly
                245                 250                 255

Lys Gly Thr Val Ser Gly Thr Leu Ile Gly Leu Glu Phe Ile Arg Lys
            260                 265                 270

Ser Gln Leu Ile Gln Pro Ser Gly Pro Leu Val Val Leu Leu Pro Leu
        275                 280                 285

Ala Gly Gly Tyr Ser Arg Ile Leu Asn Thr Ala Cys Gln Arg Leu Ala
    290                 295                 300

Arg Thr Gly Val Val Leu Val Ala Ala Ala Gly Asn Phe Arg Asp Asp
305                 310                 315                 320

Ala Cys Leu Tyr Ser Pro Ala Ser Ala Pro Glu Val Ile Thr Val Gly
                325                 330                 335

Ala Thr Asn Ala Gln Asp Gln Pro Val Thr Leu Gly Thr Leu Gly Thr
            340                 345                 350

Asn Phe Gly Arg Cys Val Asp Leu Phe Ala Pro Gly Lys Asp Ile Ile
        355                 360                 365

Gly Ala Ser Ser Asp Cys Ser Thr Cys Tyr Met Ser Gln Ser Gly Thr
    370                 375                 380

Ser Gln Ala Ala Ala His Val Ala Gly Ile Val Ala Met Met Leu Asn
385                 390                 395                 400

Arg Asp Pro Ala Leu Thr Leu Ala Glu Leu Arg Gln Arg Leu Ile Leu
                405                 410                 415

Phe Ser Thr Lys Asp Val Ile Asn Met Ala Trp Phe Pro Glu Asp Gln
            420                 425                 430

Arg Val Leu Thr Pro Asn Arg Val Ala Thr Leu Pro Pro Ser Thr Gln
        435                 440                 445

Glu Thr Gly Gly Gln Leu Leu Cys Arg Thr Val Trp Ser Ala His Ser
    450                 455                 460

Gly Pro Thr Arg Thr Ala Thr Ala Thr Ala Arg Cys Ala Pro Glu Glu
465                 470                 475                 480

Glu Leu Leu Ser Cys Ser Ser Phe Ser Arg Ser Gly Arg Arg Arg Gly
                485                 490                 495

Asp Arg Ile Glu Ala Ile Gly Gly Gln Gln Val Cys Lys Ala Leu Asn
            500                 505                 510

Ala Phe Gly Gly Glu Gly Val Tyr Ala Val Ala Arg Cys Cys Leu Leu
        515                 520                 525

Pro Arg Val Asn Cys Ser Ile His Asn Thr Pro Ala Ala Arg Ala Gly
```

```
    530                 535                 540

Pro Gln Thr Pro Val His Cys His Gln Lys Asp His Val Leu Thr Gly
545                 550                 555                 560

Cys Ser Phe His Trp Glu Val Glu Asn Leu Arg Ala Gln Gln Gln Pro
                565                 570                 575

Leu Leu Arg Ser Arg His Gln Pro Gly Gln Cys Val Gly His Gln Glu
            580                 585                 590

Ala Ser Val His Ala Ser Cys Cys His Ala Pro Gly Leu Glu Cys Lys
        595                 600                 605

Ile Lys Glu His Gly Ile Ala Gly Pro Ala Glu Gln Val Thr Val Ala
    610                 615                 620

Cys Glu Ala Gly Trp Thr Leu Thr Gly Cys Asn Val Leu Pro Gly Ala
625                 630                 635                 640

Ser Leu Pro Leu Gly Ala Tyr Ser Val Asp Asn Val Cys Val Ala Arg
                645                 650                 655

Ile Arg Asp Ala Gly Arg Ala Asp Arg Thr Ser Glu Glu Ala Thr Val
            660                 665                 670

Ala Ala Ala Ile Cys Cys Arg Ser Arg Pro Ser Ala Lys Ala Ser Trp
        675                 680                 685

Val His Gln
    690


<210> SEQ ID NO 764
<211> LENGTH: 447
<212> TYPE: PRT
<213> ORGANISM: Artificial Sequence
<220> FEATURE:
<223> OTHER INFORMATION: synthetic

<400> SEQUENCE: 764

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Asn Tyr
            20                  25                  30

Ala Met Asn Trp Val Arg Gln Ala Pro Gly Lys Gly Leu Asp Trp Val
        35                  40                  45

Ser Thr Ile Ser Gly Ser Gly Gly Thr Thr Asn Tyr Ala Asp Ser Val
    50                  55                  60

Lys Gly Arg Phe Ile Ile Ser Arg Asp Ser Ser Lys His Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Asn Trp Gly Asn Phe Asp Leu Trp Gly Arg Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
```

```
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445


<210> SEQ ID NO 765
<211> LENGTH: 220
<212> TYPE: PRT
<213> ORGANISM: Artificial Sequence
<220> FEATURE:
<223> OTHER INFORMATION: synthetic

<400> SEQUENCE: 765

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Arg
            20                  25                  30

Ser Asn Asn Arg Asn Phe Leu Gly Trp Tyr Gln Gln Lys Pro Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
```

-continued

```
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

METHODS FOR REDUCING REMNANT CHOLESTEROL AND OTHER LIPOPROTEIN FRACTIONS BY ADMINISTERING AN INHIBITOR OF PROPROTEIN CONVERTASE SUBTILISIN KEXIN-9 (PCSK9)

CROSS-REFERENCE TO RELATED APPLICATIONS

This application claims the benefit under 35 U.S.C. § 119(e) of U.S. provisional application Nos. 61/828,753, filed on May 30, 2013; 61/901,705, filed on Nov. 8, 2013; 61/919,836, filed on Dec. 23, 2013; 61/935,358, filed on Feb. 4, 2014; 61/953,959, filed on Mar. 17, 2014; and 61/991,738, filed on May 12, 2014, the disclosures of which are herein incorporated by reference in their entireties.

FIELD OF THE INVENTION

The present invention relates to the field of therapeutic treatments of diseases and disorders which are associated with elevated levels of lipoproteins. More specifically, the invention relates to the administration of PCSK9 inhibitors to reduce the levels of serum remnant cholesterol and other lipoprotein subfractions in a patient.

BACKGROUND

Remnant cholesterol (also referred to as remnant lipoprotein) is a category of cholesterol that comprises non-HDL and non-LDL cholesterol. Remnant lipoproteins are products of VLDL lipolysis, and include $VLDL_3$ and intermediate-density lipoproteins (IDL, the direct precursor to LDL formation). Serum remnant cholesterol level has been identified as a predictive risk factor for coronary artery disease. In addition to remnant cholesterol, there are several subfractions of low density lipoprotein cholesterol (LDL-C) that may have relevance with regard to cardiovascular health. In particular, LDL-C is composed of a continuum of LDL particles of different densities and states of lipidation. Therapeutic reduction of serum remnant cholesterol and other lipoprotein subfraction levels may be a means for treating or reducing the risk of cardiovascular disorders.

PCSK9 is a proprotein convertase belonging to the proteinase K subfamily of the secretory subtilase family. The use of PCSK9 inhibitors (anti-PCSK9 antibodies) to reduce serum total cholesterol, LDL cholesterol and serum triglycerides is described in U.S. Pat. Nos. 8,062,640, 8,357,371, and US Patent Application Publication No. 2013/0064834.

BRIEF SUMMARY OF THE INVENTION

The present invention provides methods for reducing various lipoproteins and lipoprotein fractions in the serum of a patient. The patient can be a patient with hypercholesterolemia or at risk of developing hypercholesterolemia, or who has or is at risk of developing a cardiovascular disease.

The methods of the present invention comprise selecting a patient with an elevated serum level of a particular lipoprotein or lipoprotein fraction, and administering to the patient a pharmaceutical composition comprising an inhibitor of proprotein convertase subtilisin kexin-9 (PCSK9). According to certain aspects of the invention, the patient is selected on the basis of having an elevated serum remnant cholesterol level. According to certain other aspects of the invention, the patient is selected on the basis of having an elevated serum very low-density lipoprotein cholesterol level (e.g., elevated serum VLDL-C, $VLDL_1$-C, $VLDL_2$-C, $VLDL_{1+2}$-C, $VLDL_3$-C, etc.). According to yet other aspects of the invention, the patient is selected on the basis of having an elevated serum intermediate-density lipoprotein cholesterol (IDL-C) level. According to certain other aspects of the invention, the patient is selected on the basis of having an elevated serum level of one or more low-density lipoprotein cholesterol (LDL-C) subfraction (e.g., elevated serum $LDL_1$-C, $LDL_2$-C, $LDL_3$-C, $LDL_4$-C, $LDL_{3+4}$-C, etc.). According to certain aspects of the present invention, the patient is additionally or alternatively selected on the basis of having an elevated serum level of Lp(a).

The patient may also be selected on the basis of exhibiting additional risk factors for such diseases and disorders in which a reduction in lipoprotein levels would be beneficial or risk-lowering. For example, patients with hypercholesterolemia (e.g., heFH, nonFH, etc.) may be good candidates for treatment with the therapeutic methods of the present invention.

PCSK9 inhibitors which may be administered in accordance with the methods of the present invention include, e.g., anti-PCSK9 antibodies or antigen-binding fragments thereof. Specific exemplary anti-PCSK9 antibodies which may be used in the practice of the methods of the present invention include any antibodies or antigen-binding fragments as set forth in U.S. Pat. No. 8,062,640, and/or disclosed herein.

The PCSK9 inhibitor may be administered to a subject subcutaneously or intravenously. Furthermore, the PCSK9 inhibitor may be administered to a patient who is on a therapeutic statin regimen at the time of therapeutic intervention.

Other embodiments of the present invention will become apparent from a review of the ensuing detailed description.

BRIEF DESCRIPTION OF THE FIGURES

FIG. 7 depicts the results for Study A, FIG. 8 depicts the results for Study B, and FIG. 9 depicts the results for Study C.

FIG. 10 depicts the results for Study A, FIG. 11 depicts the results for Study B, and FIG. 12 depicts the results for Study C.

DETAILED DESCRIPTION

Figure 1:
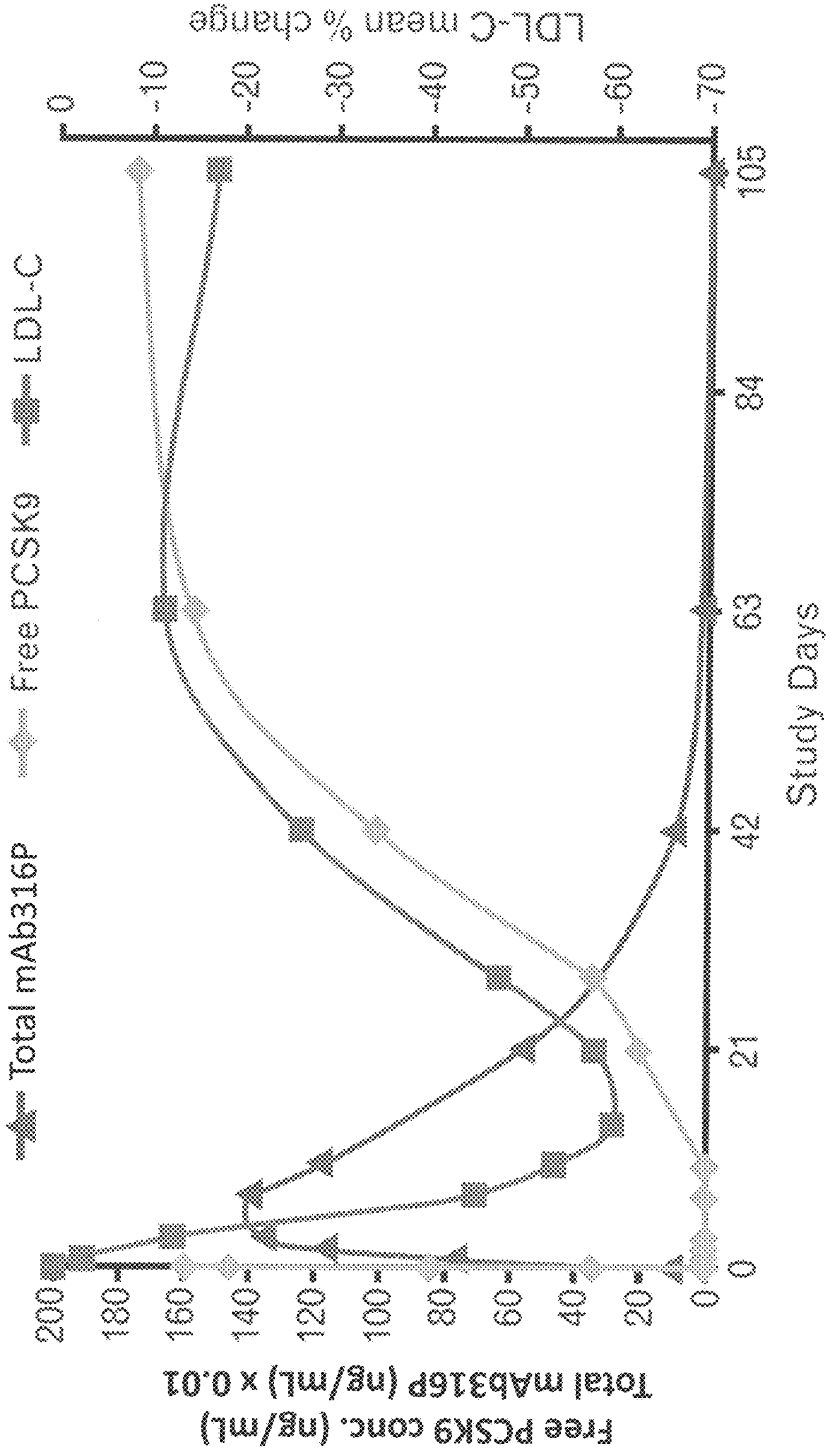
FIG. 1 shows the dynamic relationship between mAb316P, free (unbound) PCSK9, and LDL-C levels following a single dose of mAb316P 150 mg SC in health subjects who were not receiving background statin therapy.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice of the present invention, the preferred methods and materials are now described. All publications mentioned herein are incorporated herein by reference to describe in their entirety.

Methods for Reducing Remnant Cholesterol and Other Lipoprotein Fractions

The present invention provides methods for reducing serum remnant cholesterol and other lipoprotein fractions in a patient. The methods of the invention comprise selecting a patient who exhibits an elevated serum level of one or more of remnant cholesterol (also referred to as "remnant lipoprotein cholesterol," "remnant lipoproteins," or RLP-C), very low density lipoprotein cholesterol (VLDL-C), intermediate density lipoprotein cholesterol (IDL-C), triglycerides (TG), and or Lp(a). In certain embodiments, the methods of the invention comprise selecting a patient who exhibits elevated serum $VLDL_1$, $VLDL_2$, $VLDL_{1+2}$, $VLDL_3$, $LDL_1$, $LDL_2$, $LDL_3$, $LDL_4$, $LDL_{3+4}$, and/or other combinations thereof. The methods of the present invention further comprise administering to the patient a pharmaceutical composition comprising a PCSK9 inhibitor.

As used herein, the expressions "remnant cholesterol," "remnant lipoproteins," "RLP," and the like, means the cholesterol content of triglyceride-rich lipoproteins, composed of VLDLs and IDLs in the fasting state and of these two lipoproteins together with chylomicron remnants in the nonfasting state. Remnant cholesterol can be calculated as: total cholesterol minus HDL-C minus LDL-C (i.e., non-[HDL-C+LDL-C]). Remnant cholesterol includes $VLDL_3$ and IDL.

Other lipoprotein fractions include, e.g., $LDL_1$-C ("large buoyant" LDL), $LDL_2$-C, $LDL_3$-C and $LDL_4$-C ("small dense" LDL). The serum levels of these lipoproteins may be ascertained by standard lipoprotein subfractionation techniques such as, e.g., vertical auto profile (VAP) testing, ion mobility, etc.

In the context of the present invention, "elevated serum lipoprotein" (e.g., elevated serum remnant cholesterol, elevated serum VLDL-C, elevated serum $VLDL_1$-C, elevated serum $VLDL_2$-C, elevated serum $VLDL_{1+2}$-C, elevated serum $VLDL_3$-C, elevated serum IDL-C, elevated serum $LDL_1$-C, elevated serum $LDL_2$-C, elevated serum $LDL_3$-C, elevated serum $LDL_4$-C, elevated serum $LDL_{3+4}$-C, etc.) means a serum level of the respective lipoprotein greater than about 8 mg/dL. In certain embodiments, a patient is considered to exhibit an elevated serum lipoprotein if the level of the particular lipoprotein measured in the serum of a patient is greater than about 9 mg/dL, 10 mg/dL, 11 mg/dL, 12 mg/dL, 13 mg/dL, 14 mg/dL, 15 mg/dL, 16 mg/dL, 17 mg/dL, 18 mg/dL, 19 mg/dL, 20 mg/dL, 25 mg/dL, 30 mg/dL, 35 mg/dL, 40 mg/dL, 45 mg/dL, 50 mg/dL. The serum lipoprotein level can be measured in a patient post-prandial. In some embodiments, the lipoprotein level is measured after a period of time of fasting (e.g., after fasting for 6 hrs, 8 hrs, 10 hrs, 12 hrs or more). Any clinically acceptable diagnostic method can be used in the context of the present invention to measure serum lipoprotein in a patient.

According to the present invention, a reduction in serum remnant cholesterol or other lipoprotein subfraction (e.g., VLDL-C, $VLDL_1$-C, $VLDL_2$-C, $VLDL_{1+2}$-C, $VLDL_3$-C, IDL-C, $IDL_1$-C, $IDL_2$-C, $IDL_{1+2}$-C, $LDL_1$-C, $LDL_2$-C, $LDL_{2a}$-C, $LDL_{2b}$-C, $LDL_{1+2a}$-C, $LDL_3$-C, $LDL_{3a}$-C, $LDL_{3b}$-C, $LDL_4$-C, $LDL_{4a}$-C, $LDL_{4b}$-C, $LDL_{4c}$-C, $LDL_{4a+4b+4c+3b}$-C, $LDL_{3+4}$-C, etc.) means that the serum lipoprotein/lipoprotein subfraction level in the patient after receiving a pharmaceutical composition of the invention is reduced by about 5%, 10%, 15%, 20%, 25%, 30%, 35%, 40%, 45%, 50%, 55%, 60%, 65%, 70%, 75%, 80%, or more, from baseline. As used herein, "baseline level," when referring to a particular lipoprotein or lipoprotein subfraction, means the level of lipoprotein/lipoprotein subfraction measured in the serum of a subject prior to receiving a pharmaceutical composition of the present invention. The reduction in serum lipoprotein/lipoprotein subfraction resulting from administration of a pharmaceutical composition of the invention may be achieved and/or observed at 1 day, 2 days, 3 days, 4 days, 5 days, 6 days, 1 week, 2 weeks, 4 weeks, 6 weeks, 8 weeks, 10 weeks, 12 weeks, 14 weeks, 16 weeks, 18 weeks, 20 weeks, 22 weeks, or longer, following the initiation of a therapeutic regimen comprising administration of one or more doses of a pharmaceutical composition comprising a PCSK9 inhibitor, examples of which are disclosed elsewhere herein.

For example, the present invention includes methods for reducing serum remnant cholesterol in a patient by selecting a patient with elevated serum remnant cholesterol, and administering to the patient a pharmaceutical composition comprising a PCSK9 inhibitor, wherein serum remnant cholesterol is reduced in the patient by at least about 35% to about 45% from baseline following administration of the pharmaceutical composition.

The present invention also includes methods for reducing serum VLDL-C in a patient by selecting a patient with elevated serum VLDL-C, and administering to the patient a pharmaceutical composition comprising a PCSK9 inhibitor, wherein serum VLDL-C is reduced in the patient by at least about 20% to about 28% from baseline following administration of the pharmaceutical composition.

The present invention also includes methods for reducing serum $VLDL_{1+2}$-C in a patient by selecting a patient with elevated serum $VLDL_{1+2}$-C, and administering to the patient a pharmaceutical composition comprising a PCSK9 inhibitor, wherein serum $VLDL_{1+2}$-C is reduced in the patient by at least about 20% to about 32% from baseline following administration of the pharmaceutical composition.

The present invention also includes methods for reducing serum $VLDL_3$-C in a patient by selecting a patient with elevated serum $VLDL_3$-C, and administering to the patient a pharmaceutical composition comprising a PCSK9 inhibitor, wherein serum $VLDL_3$-C is reduced in the patient by at least about 20% to about 27% from baseline following administration of the pharmaceutical composition.

The present invention also includes methods for reducing serum IDL-C in a patient by selecting a patient with elevated serum IDL-C, and administering to the patient a pharmaceutical composition comprising a PCSK9 inhibitor, wherein serum IDL-C is reduced in the patient by at least about 50% to about 56% from baseline following administration of the pharmaceutical composition.

The present invention also includes methods for reducing serum $LDL_1$-C in a patient by selecting a patient with elevated serum $LDL_1$-C, and administering to the patient a pharmaceutical composition comprising a PCSK9 inhibitor, wherein serum $LDL_1$-C is reduced in the patient by at least about 65% to about 78% from baseline following administration of the pharmaceutical composition.

The present invention also includes methods for reducing serum $LDL_2$-C in a patient by selecting a patient with elevated serum $LDL_2$-C, and administering to the patient a pharmaceutical composition comprising a PCSK9 inhibitor, wherein serum $LDL_2$-C is reduced in the patient by at least about 75% to about 85% from baseline following administration of the pharmaceutical composition.

The present invention also includes methods for reducing serum $LDL_{3+4}$-C in a patient by selecting a patient with elevated serum $LDL_{3+4}$-C, and administering to the patient a pharmaceutical composition comprising a PCSK9 inhibitor, wherein serum $LDL_{3+4}$-C is reduced in the patient by at least about 45% to about 70% from baseline following administration of the pharmaceutical composition.

The present invention also includes methods for reducing apolipoprotein (apo) CII and/or CIII in a patient by selecting a patient with hypercholesterolemia, and administering to the patient a pharmaceutical composition comprising a PCSK9 inhibitor. According to certain embodiments, the patient has non-familial hypercholesterolemia (non-FH); in certain other embodiments, the patient has heterozygous familial hypercholesterolemia (he-FH). According to certain embodiments of this aspect of the invention, apo CII is reduced in the patient by at least about 9% to about 30% from baseline, and apo CIII is reduced in the patient by at least about 20% to about 25%, following administration of the pharmaceutical composition.

The present invention also includes methods for reducing serum Lp(a) in a patient by selecting a patient with elevated serum Lp(a), and administering to the patient a pharmaceutical composition comprising a PCSK9 inhibitor, wherein serum Lp(a) is reduced in the patient by at least about 10% to about 40% (e.g., about 25%, about 30% or about 35%) from baseline following administration of the pharmaceutical composition.

The present invention also includes methods for reducing lipoprotein particle concentration in a patient by selecting a patient with hypercholesterolemia and/or elevated serum lipoprotein particle concentration, and administering to the patient a pharmaceutical composition comprising a PCSK9 inhibitor. The methods according to this aspect of the invention are useful for, inter alia, reducing the concentration of low-density lipoprotein particles (LDL-P), intermediate density lipoprotein particles (IDL-P), and very low-density lipoprotein particles (VLDL-P), including methods for reducing the serum concentrations of, e.g., small VLDL-P (diameter 29 to 42 mm); medium VLDL-P (diameter 42 to 60 nm); large VLDL-P (diameter>60 nM); small LDL-P (diameter 18 to 20.5 nm); large LDL-P (diameter 20.5 to 23 nm); and IDL-P (diameter 23 to 29 nm).

Patient Population

The methods of the present invention are useful for reducing serum remnant cholesterol and other lipoprotein fractions (e.g., VLDL-C, $VLDL_1$-C, $VLDL_2$-C, $VLDL_{1+2}$-C, $VLDL_3$-C, IDL-C, $LDL_1$-C, $LDL_2$-C, $LDL_3$-C, $LDL_4$-C, $LDL_{3+4}$-C, etc.) in a patient. In some instances the patient is otherwise healthy except for exhibiting elevated levels of one or more of the aforementioned serum lipoproteins. For example, the patient may not exhibit any other risk factor of cardiovascular, thrombotic or other diseases or disorders at the time of treatment. In other instances, however, the patient is selected on the basis of being diagnosed with, or at risk of developing, a disease or disorder that is caused by or correlated with elevated serum remnant cholesterol or with elevated serum levels of other lipoproteins or lipoprotein fractions. For example, at the time of, or prior to administration of the pharmaceutical composition of the present invention, the patient may be diagnosed with or identified as being at risk of developing a cardiovascular disease or disorder, such as, e.g., coronary artery disease, acute myocardial infarction, asymptomatic carotid atherosclerosis, stroke, peripheral artery occlusive disease, etc. The cardiovascular disease or disorder, in some instances, is hypercholesterolemia. For example, a patient may be selected for treatment with the methods of the present invention if the patient is diagnosed with or identified as being at risk of developing a hypercholesterolemia condition such as, e.g., heterozygous Familial Hypercholesterolemia (heFH), homozygous Familial Hypercholesterolemia (hoFH), Autosomal Dominant Hypercholesterolemia (ADH, e.g., ADH associated with one or more gain-of-function mutations in the PCSK9 gene), as well as incidences of hypercholesterolemia that are distinct from Familial Hypercholesterolemia (nonFH).

In other instances, at the time of, or prior to administration of the pharmaceutical composition of the present invention, the patient may be diagnosed with or identified as being at risk of developing an arterial disorder such as cerebrovascular occlusive disease, peripheral vascular disease, peripheral arterial disorder, etc. In certain embodiments, the patient is selected on the basis of being diagnosed with or at risk of developing a combination of two or more of the abovementioned diseases or disorders.

In yet other instances, the patient who is to be treated with the methods of the present invention is selected on the basis of one or more factors selected from the group consisting of age (e.g., older than 40, 45, 50, 55, 60, 65, 70, 75, or 80 years), race, gender (male or female), exercise habits (e.g., regular exerciser, non-exerciser), other preexisting medical conditions (e.g., type-II diabetes, high blood pressure, etc.), and current medication status (e.g., currently taking statins [e.g., cerivastatin, atorvastatin, simvastatin, pitavastatin, rosuvastatin, fluvastatin, lovastatin, pravastatin, etc.], beta blockers, niacin, etc.). The present invention also includes methods for reducing serum remnant cholesterol and/or other lipoprotein fraction levels in patients who are intolerant of, non-responsive to, or inadequately responsive to conventional statin therapy. Potential patients can be selected/screened on the basis of one or more of these factors (e.g., by questionnaire, diagnostic evaluation, etc.) before being treated with the methods of the present invention.

PCSK9 Inhibitors

The methods of the present invention comprise administering to a patient a therapeutic composition comprising a PCSK9 inhibitor. As used herein, a "PCSK9 inhibitor" is any agent which binds to or interacts with human PCSK9 and inhibits the normal biological function of PCSK9 in vitro or in vivo. Non-limiting examples of categories of PCSK9 inhibitors include small molecule PCSK9 antagonists, peptide-based PCSK9 antagonists (e.g., "peptibody" molecules), and antibodies or antigen-binding fragments of antibodies that specifically bind human PCSK9.

The term "human proprotein convertase subtilisin/kexin type 9" or "human PCSK9" or "hPCSK9", as used herein, refers to PCSK9 having the nucleic acid sequence shown in SEQ ID NO:754 and the amino acid sequence of SEQ ID NO:755, or a biologically active fragment thereof.

The term "antibody", as used herein, is intended to refer to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-PCSK9 antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody", as used herein, is intended to include antibodies having variable and constant regions derived from human germline immunoglobulin sequences. The human antibodies of the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" PCSK9, as used in the context of the present invention, includes antibodies that bind PCSK9 or portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human PCSK9, however, have cross-reactivity to other antigens, such as PCSK9 molecules from other (non-human) species.

The anti-PCSK9 antibodies useful for the methods of the present invention may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes methods involving the use of antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. The use of antibodies and antigen-binding fragments obtained in this general manner are encompassed within the present invention.

The present invention also includes methods involving the use of anti-PCSK9 antibodies comprising variants of any of the HCVR, LCVR, and/or CDR amino acid sequences disclosed herein having one or more conservative substitutions. For example, the present invention includes the use of anti-PCSK9 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

According to certain embodiments, the anti-PCSK9 antibody used in the methods of the present invention is an antibody with pH-dependent binding characteristics. As used herein, the expression "pH-dependent binding" means that the antibody or antigen-binding fragment thereof exhibits "reduced binding to PCSK9 at acidic pH as compared to neutral pH" (for purposes of the present disclosure, both expressions may be used interchangeably). For the example, antibodies "with pH-dependent binding characteristics" includes antibodies and antigen-binding fragments thereof that bind PCSK9 with higher affinity at neutral pH than at acidic pH. In certain embodiments, the antibodies and antigen-binding fragments of the present invention bind PCSK9 with at least 3, 5, 10, 15, 20, 25, 30, 35, 40, 45, 50, 55, 60, 65, 70, 75, 80, 85, 90, 95, 100, or more times higher affinity at neutral pH than at acidic pH.

According to this aspect of the invention, the anti-PCSK9 antibodies with pH-dependent binding characteristics may possess one or more amino acid variations relative to the parental anti-PCSK9 antibody. For example, an anti-PCSK9 antibody with pH-dependent binding characteristics may contain one or more histidine substitutions or insertions, e.g., in one or more CDRs of a parental anti-PCSK9 antibody. Thus, according to certain embodiments of the present invention, methods are provided comprising administering an anti-PCSK9 antibody which comprises CDR amino acid sequences (e.g., heavy and light chain CDRs) which are identical to the CDR amino acid sequences of a parental anti-PCSK9 antibody, except for the substitution of one or more amino acids of one or more CDRs of the parental antibody with a histidine residue. The anti-PCSK9 antibodies with pH-dependent binding may possess, e.g., 1, 2, 3, 4, 5, 6, 7, 8, 9, or more histidine substitutions, either within a single CDR of a parental antibody or distributed throughout multiple (e.g., 2, 3, 4, 5, or 6) CDRs of a parental anti-PCSK9 antibody. For example, the present invention includes the use of anti-PCSK9 antibodies with pH-dependent binding comprising one or more histidine substitutions in HCDR1, one or more histidine substitutions in HCDR2, one or more histidine substitutions in HCDR3, one or more histidine substitutions in LCDR1, one or more histidine substitutions in LCDR2, and/or one or more histidine substitutions in LCDR3, of a parental anti-PCSK9 antibody.

As used herein, the expression "acidic pH" means a pH of 6.0 or less (e.g., less than about 6.0, less than about 5.5, less than about 5.0, etc.). The expression "acidic pH" includes pH values of about 6.0, 5.95, 5.90, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

Preparation of Human Antibodies

Methods for generating human antibodies in transgenic mice are known in the art. Any such known methods can be used in the context of the present invention to make human antibodies that specifically bind to human PCSK9.

Using VELOCIMMUNE™ technology (see, for example, U.S. Pat. No. 6,596,541, Regeneron Pharmaceuticals) or any other known method for generating monoclonal antibodies, high affinity chimeric antibodies to PCSK9 are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. The antibodies are characterized and selected for desirable characteristics, including affinity, selectivity, epitope, etc, using standard procedures known to those skilled in the art. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

In general, the antibodies that can be used in the methods of the present invention possess high affinities, as described above, when measured by binding to antigen either immobilized on solid phase or in solution phase. The mouse constant regions are replaced with desired human constant regions to generate the fully human antibodies of the invention. While the constant region selected may vary according to specific use, high affinity antigen-binding and target specificity characteristics reside in the variable region.

Specific examples of human antibodies or antigen-binding fragments of antibodies that specifically bind PCSK9 which can be used in the context of the methods of the present invention include any antibody or antigen-binding fragment which comprises the three heavy chain CDRs (HCDR1, HCDR2 and HCDR3) contained within a heavy chain variable region (HCVR) having an amino acid sequence selected from the group consisting of SEQ ID NOs: 2, 18, 22, 26, 42, 46, 50, 66, 70, 74, 90, 94, 98, 114, 118, 122, 138, 142, 146, 162, 166, 170, 186, 190, 194, 210, 214, 218, 234, 238, 242, 258, 262, 266, 282, 286, 290, 306, 310, 314, 330, 334, 338, 354, 358, 362, 378, 382, 386, 402, 406, 410, 426, 430, 434, 450, 454, 458, 474, 478, 482, 498, 502, 506, 522, 526, 530, 546, 550, 554, 570, 574, 578, 594, 598, 602, 618, 622, 626, 642, 646, 650, 666, 670, 674, 690, 694, 698, 714, 718, 722, 738 and 742, or a substantially similar sequence thereof having at least 90%, at least 95%, at least 98% or at least 99% sequence identity. The antibody or antigen-binding fragment may comprise the three light chain CDRs (LCVR1, LCVR2, LCVR3) contained within a light chain variable region (LCVR) having an amino acid sequence selected from the group consisting of SEQ ID NOs: 10, 20, 24, 34, 44, 48, 58, 68, 72, 82, 92, 96, 106, 116, 120, 130, 140, 144, 154, 164, 168, 178, 188, 192, 202, 212, 216, 226, 236, 240, 250, 260, 264, 274, 284, 288, 298, 308, 312, 322, 332, 336, 346, 356, 360, 370, 380, 384, 394, 404, 408, 418, 428, 432, 442, 452, 456, 466, 476, 480, 490, 500, 504, 514, 524, 528, 538, 548, 552, 562, 572, 576, 586, 596, 600, 610, 620, 624, 634, 644, 648, 658, 668, 672, 682, 692, 696, 706, 716, 720, 730, 740 and 744, or a substantially similar sequence thereof having at least 90%, at least 95%, at least 98% or at least 99% sequence identity.

In certain embodiments of the present invention, the antibody or antigen-binding fragment thereof comprises the six CDRs (HCDR1, HCDR2, HCDR3, LCDR1, LCDR2 and LCDR3) from the heavy and light chain variable region amino acid sequence pairs (HCVR/LCVR) selected from the group consisting of SEQ ID NOs: 2/10, 18/20, 22/24, 26/34, 42/44, 46/48, 50/58, 66/68, 70/72, 74/82, 90/92, 94/96, 98/106, 114/116, 118/120, 122/130, 138/140, 142/144, 146/154, 162/164, 166/168, 170/178, 186/188, 190/192, 194/202, 210/212, 214/216, 218/226, 234/236, 238/240, 242/250, 258/260, 262/264, 266/274, 282/284, 286/288, 290/298, 306/308, 310/312, 314/322, 330/332, 334/336, 338/346, 354/356, 358/360, 362/370, 378/380, 382/384, 386/394, 402/404, 406/408, 410/418, 426/428, 430/432, 434/442, 450/452, 454/456, 458/466, 474/476, 478/480, 482/490, 498/500, 502/504, 506/514, 522/524, 526/528, 530/538, 546/548, 550/552, 554/562, 570/572, 574/576, 578/586, 594/596, 598/600, 602/610, 618/620, 622/624, 626/634, 642/644, 646/648, 650/658, 666/668, 670/672, 674/682, 690/692, 694/696, 698/706, 714/716, 718/720, 722/730, 738/740 and 742/744.

In certain embodiments of the present invention, the anti-PCSK9 antibody, or antigen-binding fragment thereof, that can be used in the methods of the present invention has HCDR1/HCDR2/HCDR3/LCDR1/LCDR2/LCDR3 amino acid sequences selected from SEQ ID NOs: 76/78/80/84/86/88 (mAb316P) and 220/222/224/228/230/232 (mAb300N) (See US Patent App. Publ No. 2010/0166768).

In certain embodiments of the present invention, the antibody or antigen-binding fragment thereof comprises HCVR/LCVR amino acid sequence pairs selected from the group consisting of SEQ ID NOs: 2/10, 18/20, 22/24, 26/34, 42/44, 46/48, 50/58, 66/68, 70/72, 74/82, 90/92, 94/96, 98/106, 114/116, 118/120, 122/130, 138/140, 142/144, 146/154, 162/164, 166/168, 170/178, 186/188, 190/192, 194/202, 210/212, 214/216, 218/226, 234/236, 238/240, 242/250, 258/260, 262/264, 266/274, 282/284, 286/288, 290/298, 306/308, 310/312, 314/322, 330/332, 334/336, 338/346, 354/356, 358/360, 362/370, 378/380, 382/384, 386/394, 402/404, 406/408, 410/418, 426/428, 430/432, 434/442, 450/452, 454/456, 458/466, 474/476, 478/480, 482/490, 498/500, 502/504, 506/514, 522/524, 526/528, 530/538, 546/548, 550/552, 554/562, 570/572, 574/576, 578/586, 594/596, 598/600, 602/610, 618/620, 622/624, 626/634, 642/644, 646/648, 650/658, 666/668, 670/672, 674/682, 690/692, 694/696, 698/706, 714/716, 718/720, 722/730, 738/740 and 742/744.

Pharmaceutical Compositions and Methods of Administration

The present invention includes methods which comprise administering a PCSK9 inhibitor to a patient, wherein the PCSK9 inhibitor is contained within a pharmaceutical composition. The pharmaceutical compositions of the invention are formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Dosage

The amount of PCSK9 inhibitor (e.g., anti-PCSK9 antibody) administered to a subject according to the methods of the present invention is, generally, a therapeutically effective amount. As used herein, the phrase "therapeutically effective amount" means a dose of PCSK9 inhibitor that results in a detectable reduction (at least about 5%, 10%, 15%, 20%, 25%, 30%, 35%, 40%, 45%, 50%, 55%, 60%, 65%, 70%, 75%, or more from baseline) in one or more parameters selected from the group consisting of remnant cholesterol (RLP-C), VLDL-C, $VLDL_1$-C, $VLDL_2$-C, $VLDL_{1+2}$-C, $VLDL_3$-C, IDL-C, $LDL_1$-C, $LDL_2$-C, $LDL_3$-C, $LDL_4$-C, $LDL_{3+4}$-C. Alternatively, animal models can be used to establish whether a particular amount of a candidate PCSK9 inhibitor is a therapeutically effective amount.

In the case of an anti-PCSK9 antibody, a therapeutically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 75 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-PCSK9 antibody.

The amount of anti-PCSK9 antibody contained within the individual doses may be expressed in terms of milligrams of antibody per kilogram of patient body weight (i.e., mg/kg). For example, the anti-PCSK9 antibody may be administered to a patient at a dose of about 0.0001 to about 10 mg/kg of patient body weight.

Combination Therapies

The methods of the present invention, according to certain embodiments, may comprise administering a pharmaceutical composition comprising an anti-PCSK9 antibody to a patient who is on a therapeutic regimen for the treatment of hypercholesterolemia at the time of, or just prior to, administration of the pharmaceutical composition of the invention. For example, a patient who has previously been diagnosed with hypercholesterolemia may have been prescribed and is taking a stable therapeutic regimen of another drug prior to and/or concurrent with administration of a pharmaceutical composition comprising an anti-PCSK9 antibody. The prior or concurrent therapeutic regimen may comprise, e.g., (1) an agent which induces a cellular depletion of cholesterol synthesis by inhibiting 3-hydroxy-3-methylglutaryl (HMG)-coenzyme A (CoA) reductase, such as a statin (e.g., cerivastatin, atorvastatin, simvastatin, pitavastatin, rosuvastatin, fluvastatin, lovastatin, pravastatin, etc.); (2) an agent which inhibits cholesterol uptake and or bile acid re-absorption; (3) an agent which increase lipoprotein catabolism (such as niacin); and/or (4) activators of the LXR transcription factor that plays a role in cholesterol elimination such as 22-hydroxycholesterol. In certain embodiments, the patient, prior to or concurrent with administration of an anti-PCSK9 antibody is on a fixed combination of therapeutic agents such as ezetimibe plus simvastatin; a statin with a bile resin (e.g., cholestyramine, colestipol, colesevelam); niacin plus a statin (e.g., niacin with lovastatin); or with other lipid lowering agents such as omega-3-fatty acid ethyl esters (for example, omacor).

Administration Regimens

According to certain embodiments of the present invention, multiple doses of a PCSK9 inhibitor (i.e., a pharmaceutical composition comprising a PCSK9 inhibitor) may be administered to a subject over a defined time course. The methods according to this aspect of the invention comprise sequentially administering to a subject multiple doses of a PCSK9 inhibitor. As used herein, "sequentially administering" means that each dose of PCSK9 inhibitor is administered to the subject at a different point in time, e.g., on different days separated by a predetermined interval (e.g., hours, days, weeks or months). The present invention includes methods which comprise sequentially administering to the patient a single initial dose of a PCSK9 inhibitor, followed by one or more secondary doses of the PCSK9 inhibitor, and optionally followed by one or more tertiary doses of the PCSK9 inhibitor.

The terms "initial dose," "secondary doses," and "tertiary doses," refer to the temporal sequence of administration of the individual doses of a pharmaceutical composition comprising a PCSK9 inhibitor. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the PCSK9 inhibitor, but generally may differ from one another in terms of frequency of administration. In certain embodiments, however, the amount of PCSK9 inhibitor contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

According to exemplary embodiments of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of antigen-binding molecule which is administered to a patient prior to the administration of the very next dose in the sequence with no intervening doses.

The methods according to this aspect of the invention may comprise administering to a patient any number of secondary and/or tertiary doses of a PCSK9 inhibitor. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2, 4, 6, 8 or more weeks after the immediately preceding dose. Similarly, in embodiments involving multiple tertiary doses, each tertiary dose may be administered at the same frequency as the other tertiary doses. For example, each tertiary dose may be administered to the patient 1 to 2, 4, 6, 8 or more weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

The present invention includes administration regimens comprising an up-titration option (also referred to herein as "dose modification"). As used herein, an "up-titration option" means that, after receiving a particular number of doses of a PCSK9 inhibitor, if a patient has not achieved a specified reduction in one or more defined therapeutic parameters, the dose of the PCSK9 inhibitor is thereafter increased. For example, in the case of a therapeutic regimen comprising administration of 75 mg doses of an anti-PCSK9 antibody to a patient at a frequency of once every two weeks, if after 8 weeks (i.e., 5 doses administered at Week 0, Week 2 and Week 4, Week 6 and Week 8), the patient has not achieved a serum LDL-C concentration of less than 70 mg/dL, then the dose of anti-PCSK9 antibody is increased to e.g., 150 mg administered once every two weeks thereafter (e.g., starting at Week 10 or Week 12, or later).

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Generation of Human Antibodies to Human PCSK9

Human anti-PCSK9 antibodies were generated as described in U.S. Pat. No. 8,062,640. The exemplary PCSK9 inhibitor used in the following Example is the human anti-PCSK9 antibody designated "mAb316P" (also referred to in the scientific literature as "alirocumab"). mAb316P has the following amino acid sequence characteristics: heavy chain variable region (HCVR) comprising SEQ ID NO:90; light chain variable domain (LCVR) comprising SEQ ID NO:92; heavy chain complementarity determining region 1 (HCDR1) comprising SEQ ID NO:76; HCDR2 comprising SEQ ID NO:78; HCDR3 comprising SEQ ID NO:80; light chain complementarity determining region 1 (LCDR1) comprising SEQ ID NO:84; LCDR2 comprising SEQ ID NO:86; and LCDR3 comprising SEQ ID NO:88.

Example 2: Dynamics Between Anti-PCSK9 Antibody Levels and Low-Density Lipoprotein Cholesterol (LDL-C) Levels Introduction Descriptive analyses of pharmacokinetic and pharmacodynamic data from Phase I and II studies of mAb316P were conducted to characterize relationships between mAb316P, PCSK9 and LDL-C levels. Three different clinical trials were included in this analysis:

(1) Single-Dose Study:

Phase I, single-dose study in healthy subjects not receiving background statin therapy in which subjects received single subcutaneous (SC) doses of mAb316P 50, 100, 150, and 250 mg, or placebo.

(2) Multiple-Dose Study:

A Phase I study in cohorts of heterozygous familial hypercholesterolemia (HeFH) and non-familial hypercholesterolemia (FH) patients receiving atorvastatin therapy and non-FH patients receiving diet alone. Patients receiving atorvastatin were randomized to mAb316P (50, 100, or 150 mg) or placebo administered SC on Days 1, 29, and 43. Non-FH patients receiving diet alone were randomized to mAb316P 150 mg or placebo administered SC on Days 1 and 29.

(3) Phase II Study:

A 12-week study in hypercholesterolemic patients receiving atorvastatin therapy: patients randomized to mAb316P 50, 100, or 150 mg SC every 2 weeks (Q2W), 200 or 300 mg SC every 4 weeks (Q4W), or placebo.

Results

Figure 2:
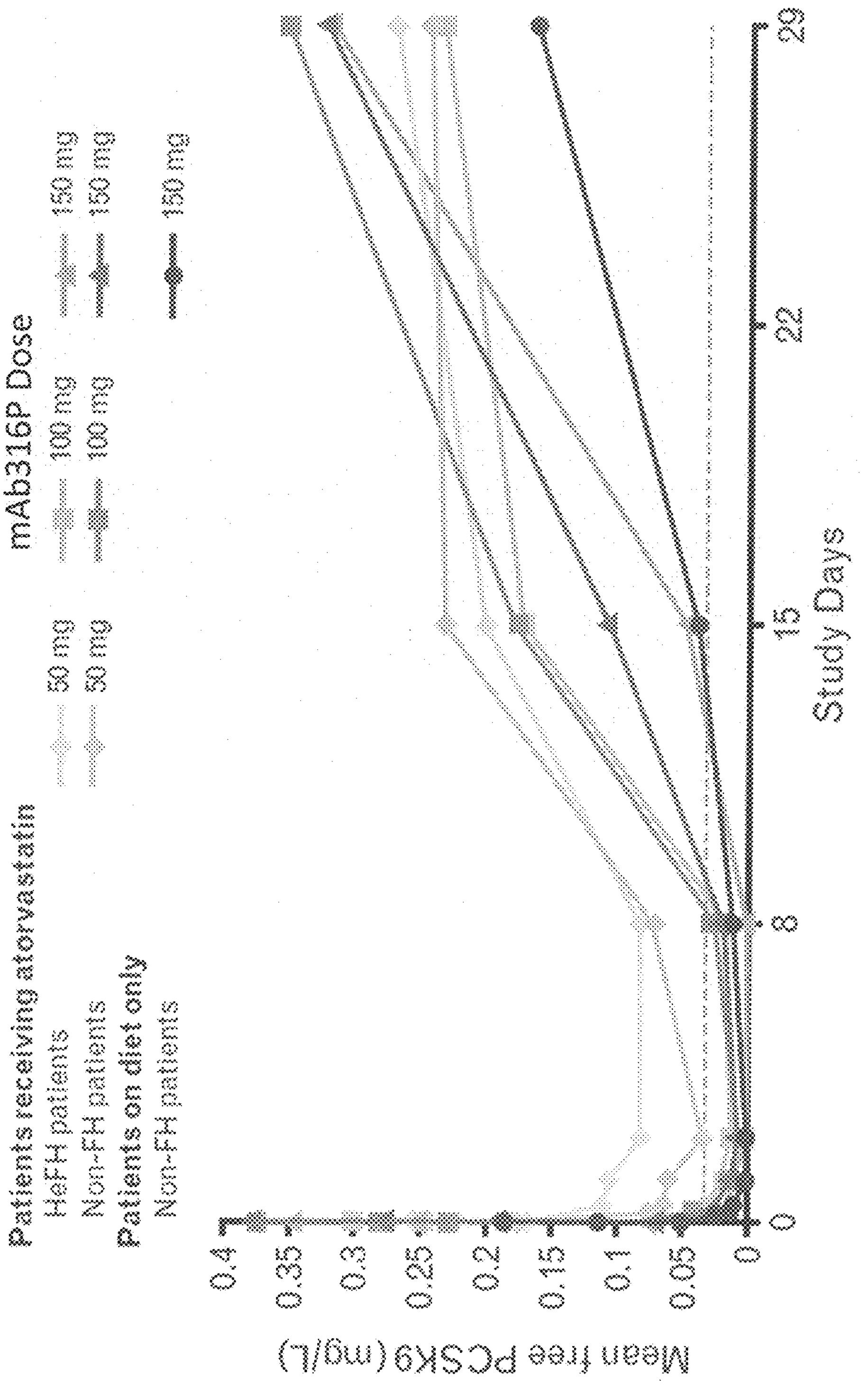
FIG. 2 shows the mean concentration of free mAb316P in HeFH and non-FH patients receiving mAb316P 50, 100, or 150 mg SC plus atorvastatin or mAb316P 150 mg SC plus diet only. Dotted line indicates quantitation limit for free PCSK9 (0.0312 mg/dL)
Figure 3:
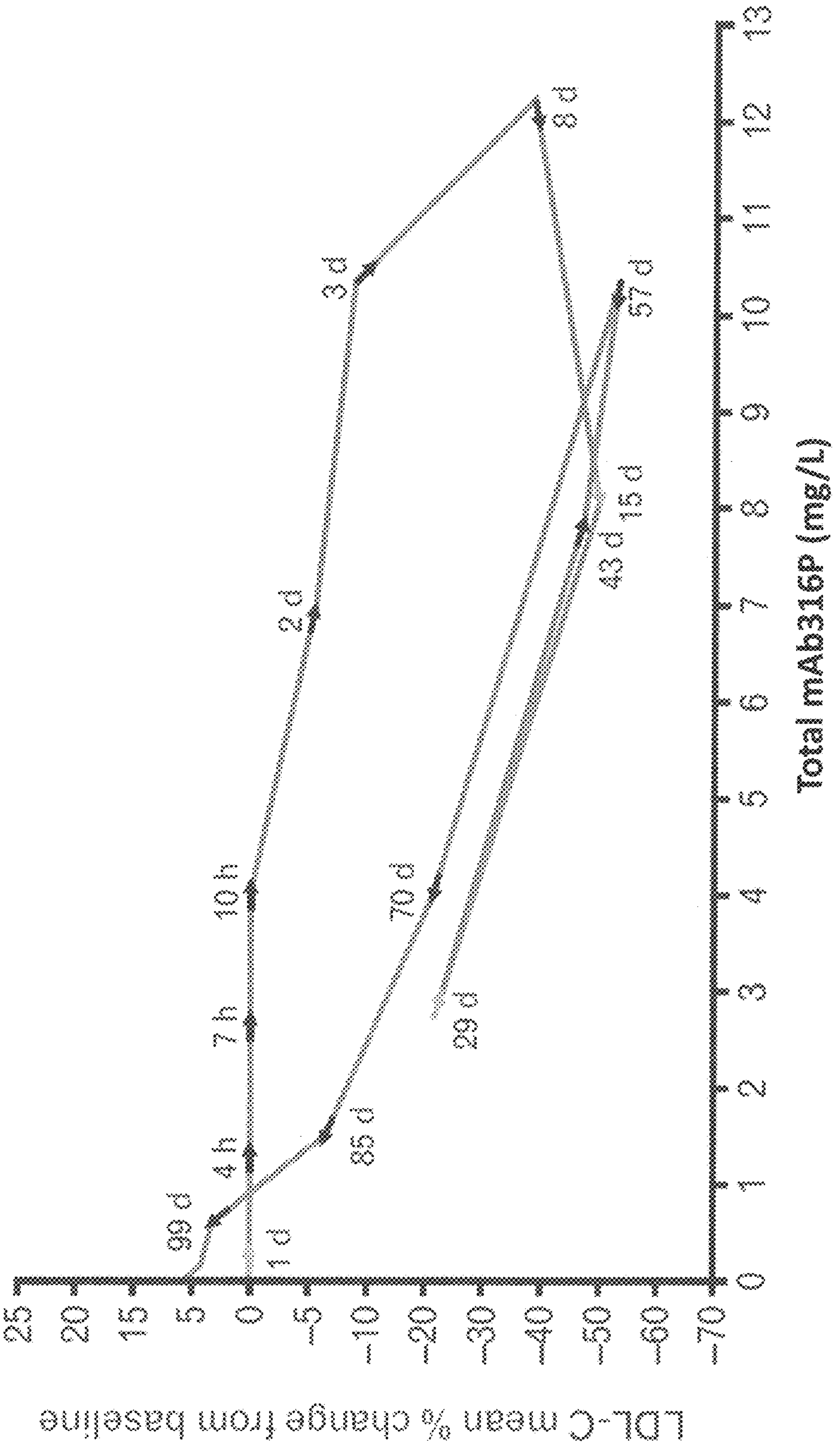
FIG. 3 shows the mean percentage change in LDL-C from baseline versus mean total mAb316P concentration (mg/dL) in patients (HeFH and non-FH combined; n–21 receiving mAb316P 150 mg SC on Study Days 1, 29, and 43. Points indicate sampling times; h, hour; d, day. The hysteresis curve moves in a clockwise direction over time, as indicated by the arrows, demonstrating the temporal relationship between mAb316P concentration and change in LDL-C.

Single administration of mAb316P 150 mg SC rapidly bound to and rapidly reduced circulating free PCSK9 levels; this was followed by a drop in LDL-C. The return of free PCSK9 towards starting levels was noted to precede the return of LDL-C levels (FIG. 1). Free PCSK9 levels reached nadir by Day 3 following administration of mAb316P 50, 100, or 150 mg SC in HeFH or non-FH patients (FIG. 2). The return of free PCSK9 to starting levels was slower in the patients who received mAb316P plus diet alone versus patients who received mAb316P plus atorvastatin (FIG. 2). The greatest mean LDL-C reductions were recorded on Day 8 for the 50 mg and 100 mg doses and Day 15 for the 150 mg dose; this delay relative to free PCSK9 concentrations may possibly be due to the time required for the production of new LDL-C receptors. A representative hysteresis curve showing the relationship between total mAb316P and LDL-C following administration of the 150 mg dose is shown in FIG. 3.

Figure 4:
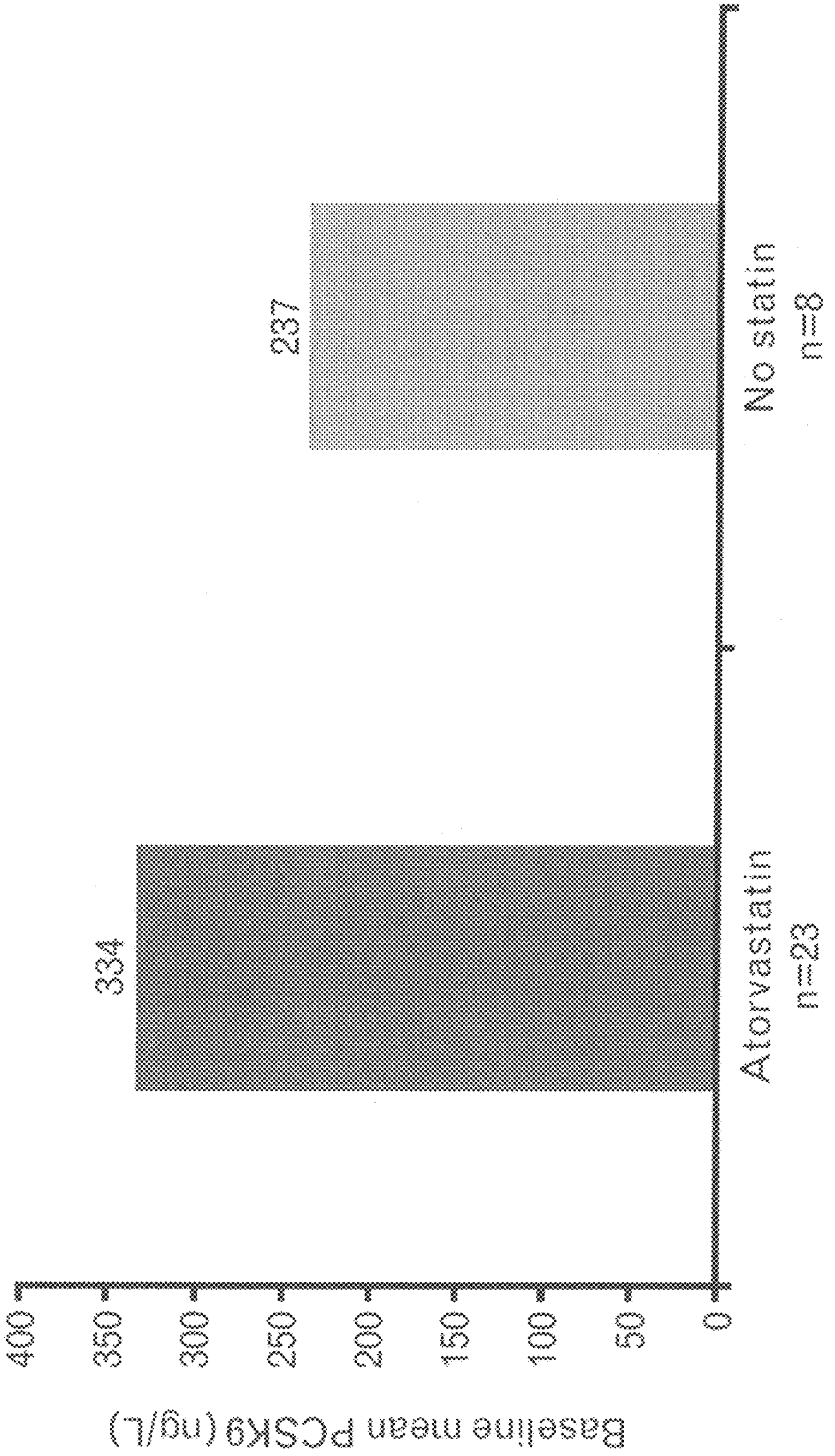
FIG. 4 shows mean baseline free PCSK9 levels in non-FH patients receiving atorvastatin or diet alone (no statin).
Figure 5:
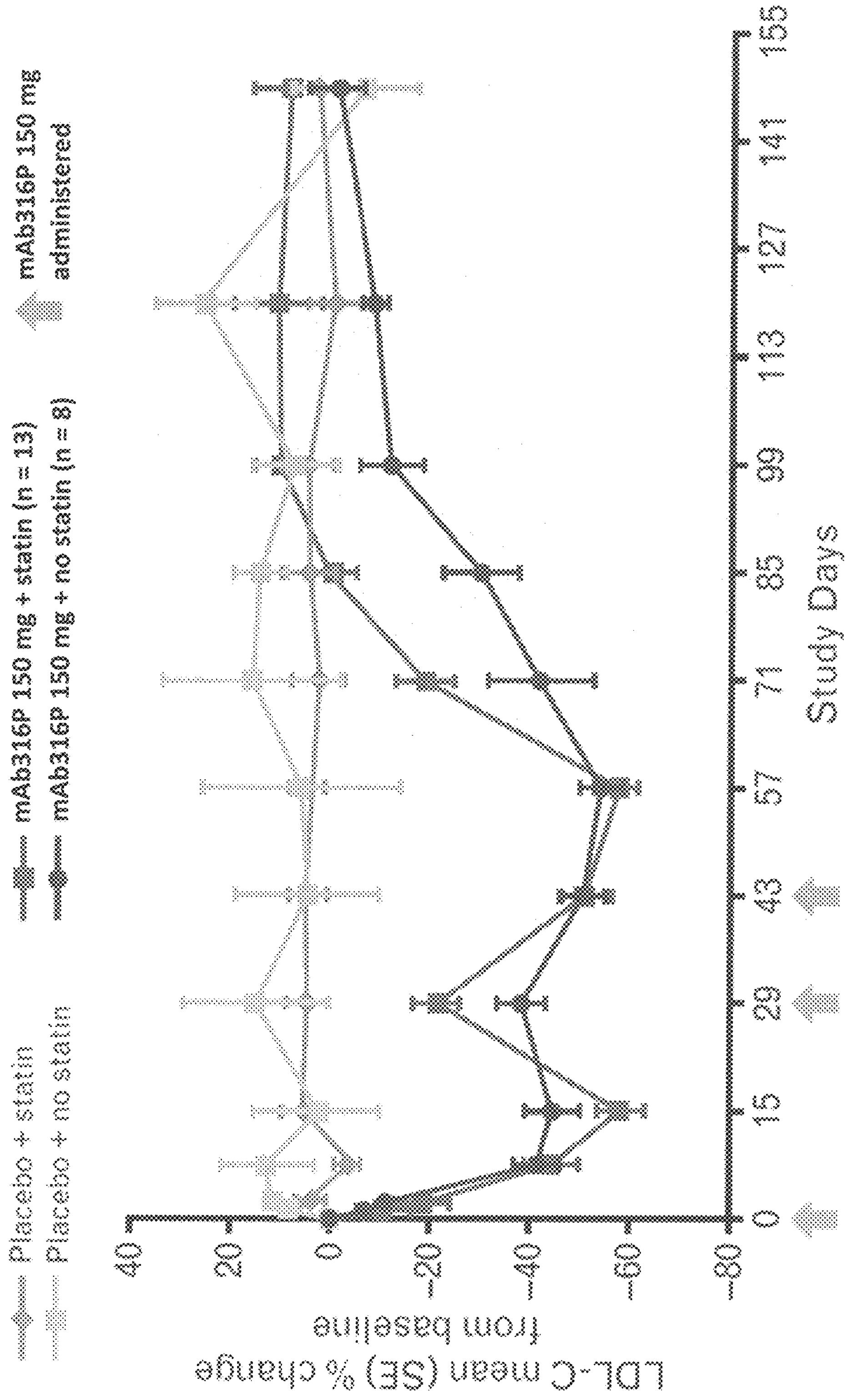
FIG. 5 shows LDL-C efficacy curves for patients receiving mAb316P 150 mg SC or placebo±atorvastatin.

Higher baseline free PCSK9 levels were observed in patients taking statins as compared with diet alone (FIG. 4). There was increased target-mediated clearance of mAb316P with concurrent statin therapy (due to higher free PCSK9 levels, likely reflective of an increase in production rate) compared with mAb316P and diet therapy alone. This appeared to affect the duration of LDL-C lowering over a 4-week dosing interval (Days 1 to 29), which was reduced with concurrent statin therapy versus diet only; however, this effect was not seen over the 2-week dosing interval (Days 29 to 43) (FIG. 5).

Figure 6:
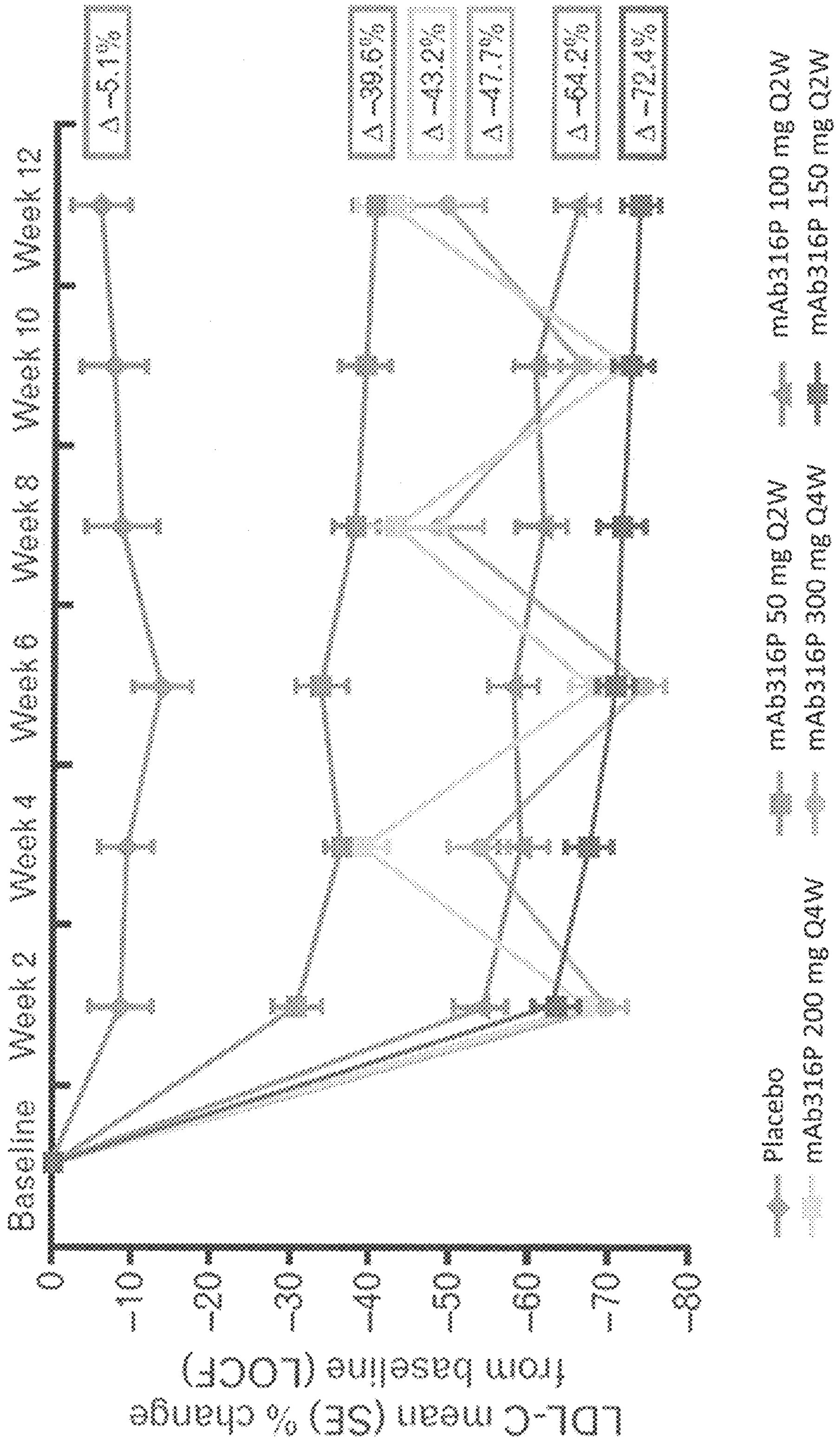
FIG. 6 shows the mean percentage change in LDL-C from baseline over time in hypercholesterolemic patients on concomitant statin therapy following administration of mAb316P 50 mg, 100 mg, or 150 mg Q2W, 200 mg or 300 mg Q4W, or placebo. Delta symbol (Δ) corresponds to LOCF means.

In hypercholesterolemic (non-FH) patients receiving concomitant statin therapy, mAb316P Q2W resulted in uniformly strong LDL-C lowering at 12 weeks. Patients on Q2W dosing regimens exhibited lower variability in the LDL-C response at Week 12 versus Q4W dosing (FIG. 6); coefficient of variation 16% versus 49% for 150 mg Q2W and 300 mg Q4W, respectively.

Conclusions

Dynamics were apparent between mAb316P, free PCSK9 and LDL-C levels. mAb316P treatment resulted in reductions in free PCSK9 levels within 3 days of dosing and peak reductions in LDL-$C_{8-15}$ days after dosing.

The clearance of mAb316P was accelerated by its binding to free PCSK9 (target-mediated clearance). Lower levels of free PCSK9 resulted in a longer duration of efficacy through lower target-mediated clearance. Previous studies have shown that administration of statins increases the production of free PCSK9. In the studies analyzed herein, patients who received mAb316P plus diet alone had lower baseline free PCSK9 levels and higher mAb316P blood concentrations compared with patients who received mAb316P plus atorvastatin therapy.

In patients receiving concomitant statin therapy, mAb316P administered Q2W achieved lower variation in LDL-C lowering at the end of the dosing interval as compared with Q4W dosing regimens. In Q4W dosing, patient-to-patient differences in target-mediated clearance (among other factors) appeared to contribute to differences in the duration of maximum LDL-C between Weeks 2 and 4 post dose and therefore wider differences in achieved efficacy 4 weeks after dosing. These differences were not observed when doses were administered Q2W.

Example 3A: An Anti-PCSK9 Antibody Reduces Cholesterol Concentrations of Serum Remnant Lipoprotein Fractions, Very Low Density Lipoproteins, Triglycerides, and Lipoprotein(a) [Lp(a)]

Introduction

Increased very low-density lipoproteins (VLDL) levels form part of a pattern of atherogenic dyslipidemia, which predisposes to premature atherosclerosis. Remnant lipoproteins are products of VLDL lipolysis, and include $VLDL_3$ and intermediate-density lipoproteins (IDL, the direct precursor to LDL formation).

Lipoprotein(a) [Lp(a)] consists of apolipoprotein(a) [apo (a)] covalently bound to the apo B component of a cholesterol-rich lipoprotein which is approximately the same size as a low-density lipoprotein (LDL) particle. Lp(a) metabolism is under mostly genetic regulation, in that more than 90% of its plasma concentration is influenced by quantitative and qualitative polymorphisms at the apo(a) gene (LPA). Elevated Lp(a) levels are considered to be an independent risk factor for cardiovascular disease, with risk continuing to increase as levels rise. Although elevated Lp(a) may promote atherosclerosis through intimal deposition of cholesterol, it may also promote thrombosis due to a high homology with plasminogen, although it lacks protease activity. In patients undergoing coronary angiography, Lp(a) concentrations>30 mg/dL have been shown to be associated with an increased risk of angiographic stenosis and major coronary events. Furthermore, Lp(a) levels and genotype have been shown to be associated with aortic-valve calcification, suggesting it may play a role in causation.

The objective of this Example was to test the hypothesis that mAb316P, a fully human monoclonal antibody to proprotein convertase subtilisin/kexin type 9 (PCSK9), reduces serum levels of VLDL and lipoprotein remnants, contributing to its ability to reduce serum LDL-C and non-HDL-C, and to confirm the Lp(a) lowering activity of mAb316P in patients.

Three multicenter, double-blind, parallel-group, placebo-controlled trials were conducted in patients with primary hypercholesterolemia (Study A, n=183; Study B, n=92) or heterozygous familial hypercholesterolemia (Study C, n=77). A summary of the designs and dosing for the three trials is shown in Table 1.

TABLE 1

Summary of Designs and Dosing for mAb316P Clinical Trials

| | Study | | |
|---|---|---|---|
| | A | B | C |
| Duration | 12 weeks | 8 weeks | 12 weeks |
| Patients | hypercholesterolemia (n = 183) | hypercholesterolemia (n = 92) | heterozygous familial hypercholesterolemeia (n = 77) |
| mAb316P Doses | 200-300 mg Q4W 50-100 mg Q2W 150 mg Q2W (n = 31) | 150 mg Q2W + ATV 10 to 80 mg 150 mg Q2W + ATV 10 to 80 mg (total n = 61) | 150, 200, 300 mg Q4W 150 mg Q2W (n = 16) |
| Placebo | n = 31 | Placebo + ATV 10 to 80 mg (n = 31) | n = 15 |
| Pooled Analysis Population | mAb316P 150 mg Q2W (n = 108) | | Placebo (n = 77) |

In Study B, all patients received atorvastatin (ATV) 10 mg prior to randomization, which was uptitrated to ATV 80 mg at the start of randomized treatment in the placebo and one mAb316P arm.

Patients on background atorvastatin or statins+/−ezetimibe received mAb316P 50-300 mg administered subcutaneously (SC) either every 2 or 4 weeks (Q2W, Q4W), depending on the study. The mAb316P 150 mg Q2W dose was common to all three trials.

In post hoc analyses, lipoproteins were subfractionated by vertical auto profile (VAP) testing. The VAP method is a single, direct ultracentrifugation test that separates the lipoprotein fractions according to their densities in a vertical rotor, which allows high resolution of each lipoprotein class and subclass. The bottom of the tube is punctured and the cholesterol in each layer is measured with a spectrophotometer after the addition of an enzymatic cholesterol reagent. Percent changes in VLDL-C, $VLDL_{1+2}$-C (a measure of cholesterol in "large, buoyant" VLDL particles), triglycerides (TG), $VLDL_3$-C, IDL-C and total remnant lipoprotein cholesterol levels (RLP-C; $VLDL_3$-C+IDL-C) in patients treated with mAb316P 150 mg Q2W vs. placebo were analyzed at week 12 (Study A), week 8 (Study B) and week 6 (Study C) using ANCOVA.

In addition, baseline and on-treatment Lp(a) levels were assessed in patients from the three different Phase 2 studies receiving mAb316P 150 mg Q2W or placebo. In all Phase 2 studies Lp(a) levels were measured at the same laboratory and using the same method. Data on Lp(a) levels at baseline and end of treatment (Week 8/12 on-treatment value or the last available on-treatment value carried forward) from the modified intention-to-treat populations of the three studies were pooled, and percentage changes from baseline for mAb316P 150 mg Q2W and placebo were compared using analysis of covariance with treatment group and study as fixed effects and baseline Lp(a) as covariate. P-values associated with these exploratory analyses are provided for descriptive purposes only and were not adjusted for multiplicity. The relationship between the percentage changes from baseline in Lp(a) and LDL-C was assessed using linear regression, and the Spearman's correlation coefficient was calculated.

Results/Conclusions

Figure 7:
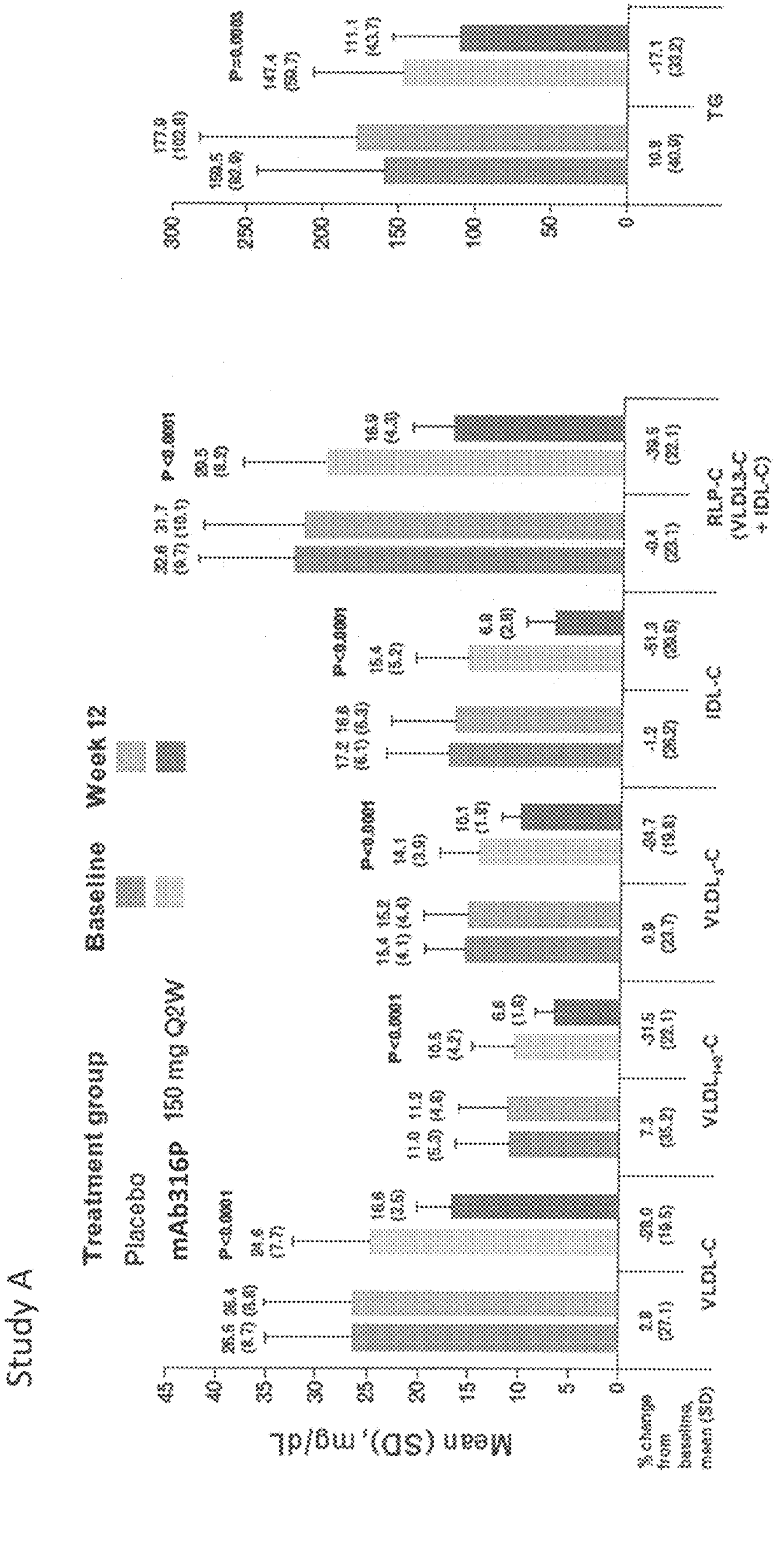
FIGS. 7-9 show the mean (SD) levels of cholesterol in VLDL and serum remnant lipoprotein subfractions and triglycerides before and after treatment for placebo and mAb316P 150 mg Q2W in three different clinical studies (A, B, and C, as summarized in Table 1 herein).
Figure 8:
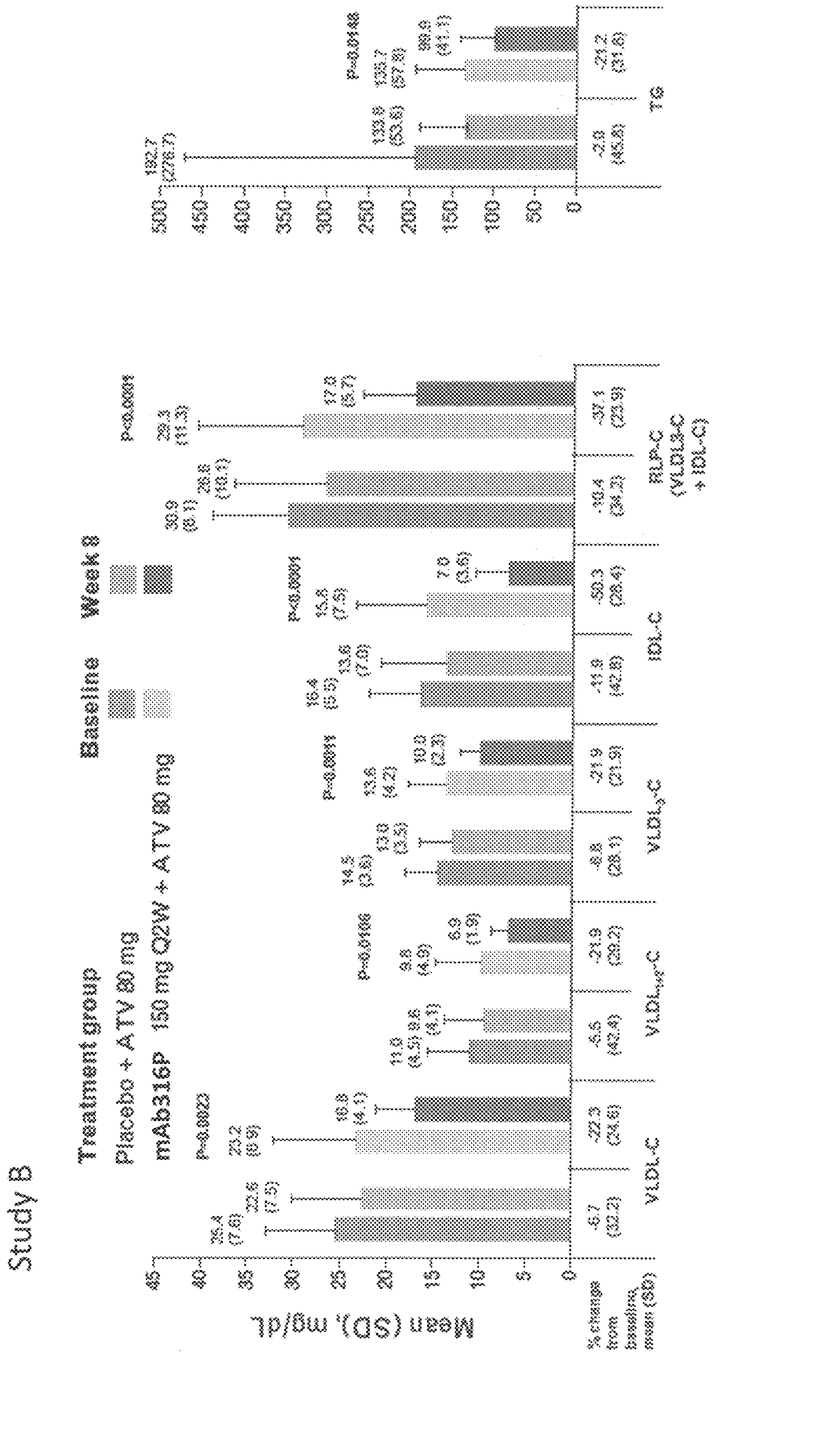
Figure 9:
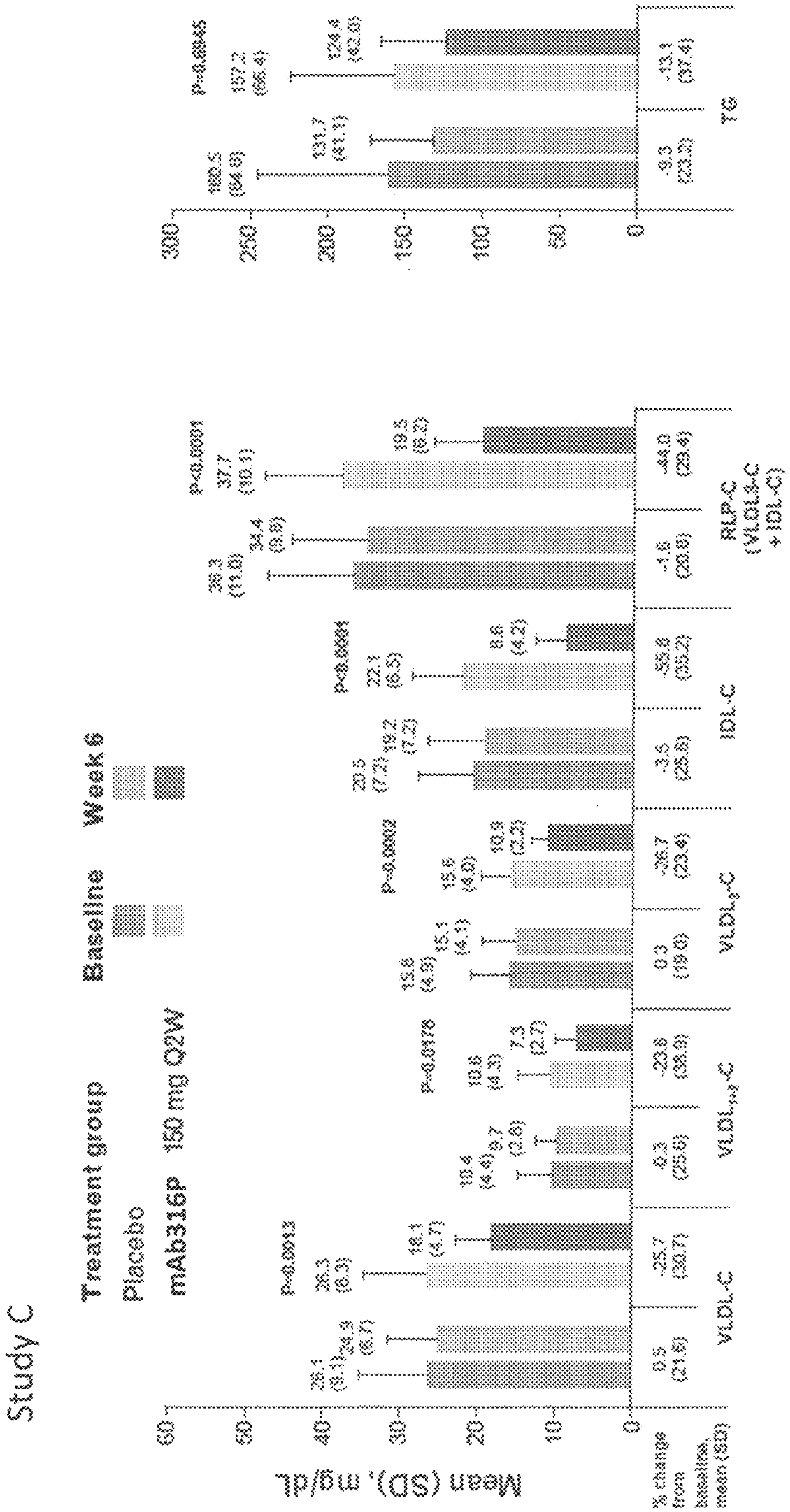

In the 3 studies, reductions in TG, VLDL-C, and in the cholesterol content of remnant lipoprotein were observed with mAb316P vs. placebo. Results are summarized in Table 2 and FIGS. 7-9.

TABLE 2

| | Baseline (mg/dL) | Endpoint (mg/dL) | Percent Change | p-value (s) |
|---|---|---|---|---|
| VLDL | 23.24 to 26.31 | 16.62 to 18.12 | −22.33 to −27.95 | 0.0023 to <0.0001 |
| $VLDL_{1+2}$-C | 9.79 to 10.59 | 6.59 to 7.31 | −21.87 to −31.45 | 0.0178 to <0.0001 |
| $VLDL_3$ | 13.55 to 15.62 | 10.03 to 10.88 | −21.9 to −26.66 | 0.0011 to <0.0001 |
| TG | 135.72 to 157.19 | 99.9 to 124.44 | −13.07 to −21.19 | 0.6945 to 0.0003 |
| IDL | 15.38 to 22.06 | 6.79 to 8.62 | −50.28 to −55.75 | <0.0001 |
| RLPC | 29.34 to 37.69 | 16.86 to 19.5 | −37.05 to −44.04 | <0.0001 |

The entire spectrum of atherogenic lipoproteins (LDL-C, IDL-C, VLDL-C and RLP subfractions) was reduced by mAb316P, against a background of lipid lowering therapy (statins±ezetimibe), in heFH/non-FH patients. This Example therefore illustrates that mAb316P significantly reduced serum TG and VLDL-C, in addition to significant reductions in cholesterol concentrations of remnant lipoprotein fractions separable by VAP, including $VLDL_3$-C and IDL-C.

Baseline and on-treatment Lp(a) data were available for 102 of the 108 patients who received mAb316P 150 mg Q2W and 74 of the 77 patients who received placebo in the Pooled Analysis Population. Baseline values are shown in Table 3.

TABLE 3

| Baseline Lp(a) Levels in Patients Included in the Pooled Analysis | | |
|---|---|---|
| | Placebo (n = 74) | mAb316P 150 mg Q2W (n = 102) |
| Lp(a) values in mg/dL | | |
| Overall Population, median (IQR) | 19.0 (6.0-77.0) | 29.5 (8.0-70.0) |
| Range | 1.5-299.0 | 1.5-181.0 |
| Number of Patients Subdivided by Baseline Lp(a) | | |
| ≤50 mg/dL, n (%) | 49 (66.2) | 68 (66.7) |
| >50 mg/dL, n (%) | 25 (33.8) | 36 (35.3) |

*Patients from the mITT population with Lp(a) data available at baseline and end of treatment (Week 8/12 on-treatment value or the last available on-treatment value carried forward).

As shown in Table 3, 36 (35%) patients treated with mAb316P and 25 (33%) patients treated with placebo had baseline Lp(a) >50 mg/dL, considered as the high-risk cut-point by the EAS guidelines.

Absolute and percentage median reductions from baseline in Lp(a) are summarized in Table 4.

TABLE 4

| Lp(a) Change From Baseline | | | | | |
|---|---|---|---|---|---|
| | | Patients Subdivided by Baseline Lp(a) | | | |
| All Patients | | ≤50 mg/dL | | >50 mg/dL | |
| pooled placebo treated (n = 74) | pooled mAb316P treated (n = 102) | pooled placebo treated (n = 49) | pooled mAb316P treated (n = 68) | pooled placebo treated (n = 25) | pooled mAb316P treated (n = 34) |
| Median Lp(a) Change From Baseline, mg/dL (IQR; LOCF) | | | | | |
| −0.5 (−5.0-2.0) | −9.0 (−19.0-−2.0)* | 0.0 (−3.0-1.5) | −3.5 (−11.5-−1.5)* | −5.0 (−11.0-6.0) | −26.5 (−39.0-−16.0)* |
| Median Lp(a) Percent Change From Baseline, (IQR; LOCF) | | | | | |
| −0.3% (−16.7-11.5) | −30.3% (−50.0-−19.4)* | 0.0% (−16.7-16.7) | −36.1% (−51.1-−17.4)* | −4.4% (−9.4-7.1) | −27.0% (−32.6-−19.6)* |

*P < 0.0001 vs placebo.

As shown in Table 4, the median percentage reduction from baseline in Lp(a) was −30.3% with mAb316P 150 mg Q2W versus −0.3% with placebo (P<0.0001). The absolute median reductions in Lp(a) from baseline were substantially greater in patients with the higher baseline Lp(a). In summary, an analysis of data pooled from three Phase 2 trials conducted with mAb316P 150 mg Q2W demonstrated significant reductions in Lp(a) versus placebo, including in patients with baseline Lp(a)>50 mg/dL. In those patients considered at higher cardiovascular disease risk due to elevated Lp(a), the percentage reductions in Lp(a) appeared to be of similar magnitude resulting in greater absolute reductions in Lp(a).

Example 3B: An Anti-PCSK9 Antibody Reduces Apolipoprotein CII and CIII Levels in Serum

Introduction

Apoprotein (apo) CIII inhibits lipoprotein lipase (LPL)-mediated catabolism of VLDL triglycerides. Apo CII appears to have a more complex relationship with VLDL and LPL activity that may depend on baseline triglyceride levels. Apo CII is, in general, an important activator of LPL LPL hydrolyzes the triglyceride mass of VLDL and its remnants. In this Example, the ability of an anti-PCSK9 antibody, mAb316P, to reduce VLDL-C and remnants by impacting serum levels of apoproteins CII and CIII was investigated.

Three multicenter, double-blind, parallel-group, placebo-controlled trials were conducted in patients with primary (non-familial) hypercholesterolemia (non-FH) (Study A, n=183; Study B, n=92) or heterozygous familial hypercholesterolemia (heFH) (Study C, n=77). Patients (who were receiving atorvastatin or statins+/−ezetimibe) were treated with mAb316P 50-150 mg every 2 wks (Q2W) or 150-300 mg every 4 wks (Q4W) depending on the study. The mAb316P 150 mg Q2W dose was common to all three trials. (See Example 3A, Table 1).

In post hoc analyses, apo CII and CIII concentrations were measured via immunoassay. (using reagent kits from Randox Laboratories Limited, UK [apo CII, Cat. No. LP3866; apo CIII, Cat. No. LP3865] and an Architect Ci8200 analyzer [Abbott Laboratories, IL]). The immunoassay methods were based on the reaction of a sample containing human apo CII (or apo CIII) and specific antiserum to apo CII (or CIII) to form an insoluble complex whose concentration can be measured turbidimetrically at 340 nm. Both assays were validated for analytical performance.

Percent change from baseline in apo CII and apo CIII in the placebo group was compared with patients treated with mAb316P, analyzed at week 12 (Study A), week 8 (Study B) and week 6 (Study C) using analysis of covariance. Study C had a Week 12 endpoint; however, 6-week data were used due to reduced number of patients with available stored samples at 12 weeks (n=17) compared with 6 weeks (n=75).

Results

Figure 13:
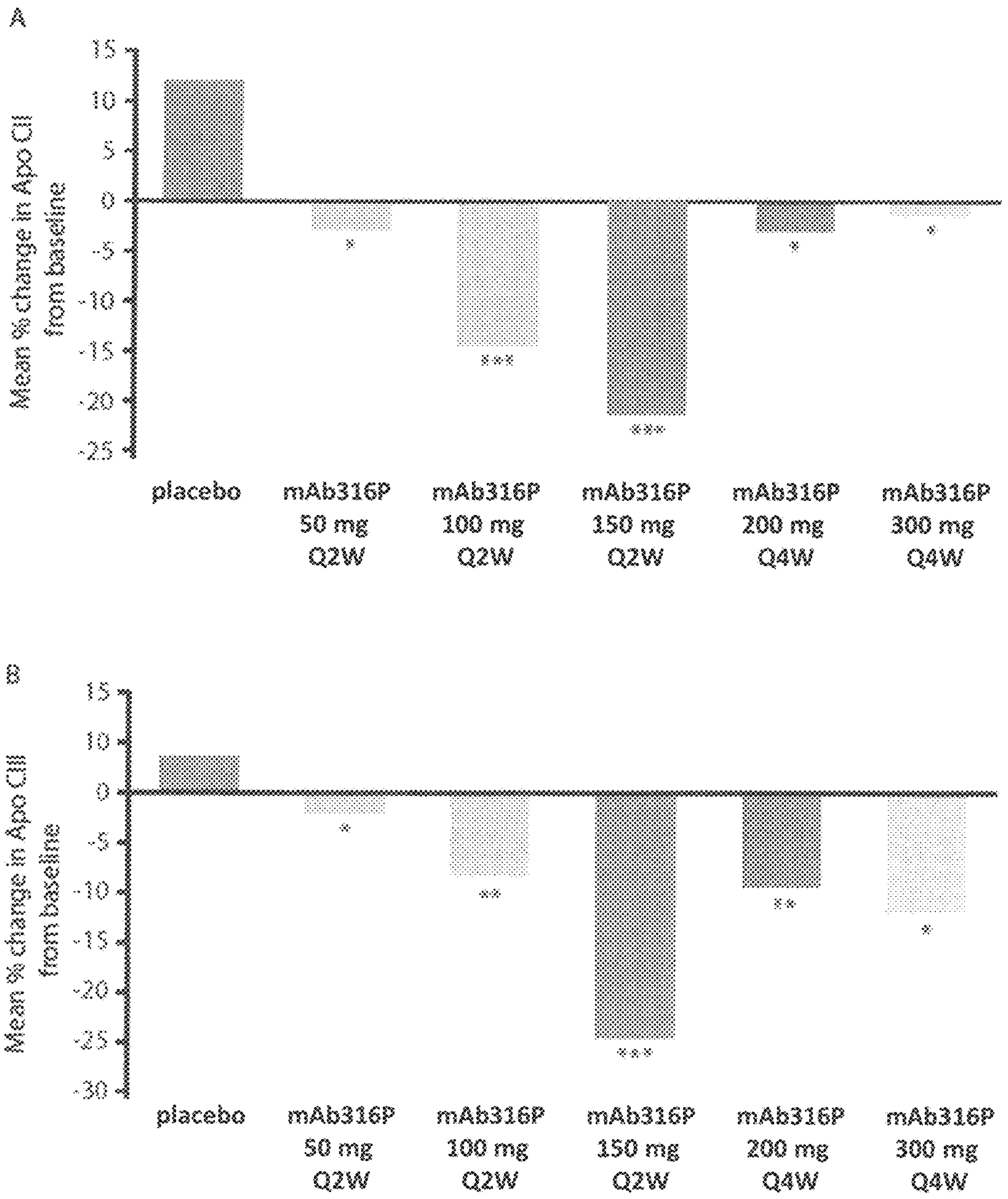
FIG. 13, panels A and B, show the dose response changes in apo CII and apo CIII, respectively, for all doses in Study A (as summarized in Table 1 herein).

Percent change in apo CII and CIII from baseline by treatment group for mAb316P 150 mg Q2W in Studies A, B and C are shown in Table 5. Values shown are mean (SD), except for apo CIII, where values are median (IQR). Data are from Week 12 (study A), Week 8 (study B) and Week 6 (study C). FIG. 13 shows the dose response changes in apo CII (panel A) and CIII (panel B) for study A.

TABLE 5

| | Apo CII % change | P-value versus placebo | Apo CIII % change | P-value versus placebo |
|---|---|---|---|---|
| Study A | | | | |
| Placebo | 12.0 (33.0) | | 3.76 (−5.5 to 27.6) | |
| mAb316P 150 mg Q2W | −21.4 (26.5) | <0.00001 | −24.7 (−28.4 to −2.9) | <0.00001 |
| Study B | | | | |
| Placebo | −10.6 (30.2) | | −7.0 (29.8 to 7.3) | |
| mAb316P 150 mg Q2W + atorvastatin 10 mg | −10.0 (22.7) | 0.98 | −4.9 (−24.4 to 1.0) | 0.4426 |
| mAb316P 150 mg Q2W + atorvastatin 80 mg | −29.3 (19.29) | 0.0067 | −22.9 (−28 to −14.0) | 0.0165 |
| Study C | | | | |
| Placebo | 1.6 (15.5) | | −3.3 (−15.3 to 5.6) | |
| mAb316P 150 mg Q2W | −9.4 (28.1) | 0.0794 | −20.2 (−29.0 to 2.5) | 0.019 |

mAb316P reduced apo CII and CIII at all doses, but a clear dose response was observed (Table 5, FIG. 13). In all three studies, mAb316P reduced apo CII in patients from baseline (Table 5). The mean reductions from baseline at Week 12 (study A), Week 8 (study B) and Week 6 (study C) were 21.4% (P<0.00001), 29.3% (P=0.0067) and 9.4% (P=0.08), respectively (P-values compared with placebo). Apo CIII was reduced by 24.7% (P<0.00001), 22.9% (P=0.017) and 20.2% (P=0.019), for studies A, B and C, respectively (P-values compared with placebo).

Conclusions

Therapy with anti-PCSK9 antibody mAb316P was associated with significant reductions in serum apo CII and CIII. There was a nearly 1:1 reduction in both apo CII and CIII in patients with non-FH. In patients with heFH, apo CIII decreased approximately two-fold more than apo CII. The reductions in apo CII and CIII may be a manifestation of either increased clearance or reduced production/secretion of VLDL particles, known carriers of these apoproteins.

Example 4: An Anti-PCSK9 Antibody Reduces Cholesterol Concentrations of all Serum Low-Density Lipoprotein Fractions Introduction Low-density lipoprotein cholesterol (LDL-C) is composed of a continuum of LDL particles of different densities and states of lipidation. Analysis of effects of lipid-modifying therapies on LDL particle composition may aid understanding of treatment mode-of-action. The purpose of this Example was to test the hypothesis that mAb316P, a fully human monoclonal antibody to proprotein convertase subtilisin/kexin 9 (PCSK9), reduces LDL-C by decreasing multiple LDL fractions.

Three multicenter, double-blind, parallel-group, placebo-controlled trials were conducted in patients with primary hypercholesterolemia (Study A, n=183; Study B, n=92) or heterozygous familial hypercholesterolemia (Study C, n=77). Patients (who were receiving atorvastatin or statins+/−ezetimibe) were treated with mAb316P 50-150 mg every 2 wks (Q2W) or 150-300 mg every 4 wks (Q4W) depending on the study. The mAb316P 150 mg Q2W dose was common to all three trials. (See Example 3A, Table 1).

In post hoc analyses, lipoproteins were subfractionated by vertical auto profile (VAP) testing. Percent change in $LDL_1$-C ("large buoyant" LDL), $LDL_2$-C, $LDL_3$-C, and $LDL_4$-C ("small, dense" LDL) levels in patients receiving mAb316P 150 mg Q2W vs. placebo from baseline to week 12 for Study A, week 8 for Study B, and week 6 for Study C were assessed using ANCOVA. The $LDL_3$-C and $LDL_4$-C fractions were analyzed individually and in a pooled analysis. This was done because $LDL_4$-C typically exists at substantially lower concentrations than $LDL_{3-4}$-C. There was much more substantial variation in percent reductions in $LDL_4$-C. The sum of $LDL_{3+4}$-C represents a sum of the two smallest and densest LDL-C fractions.

Results/Conclusions

Figure 10:
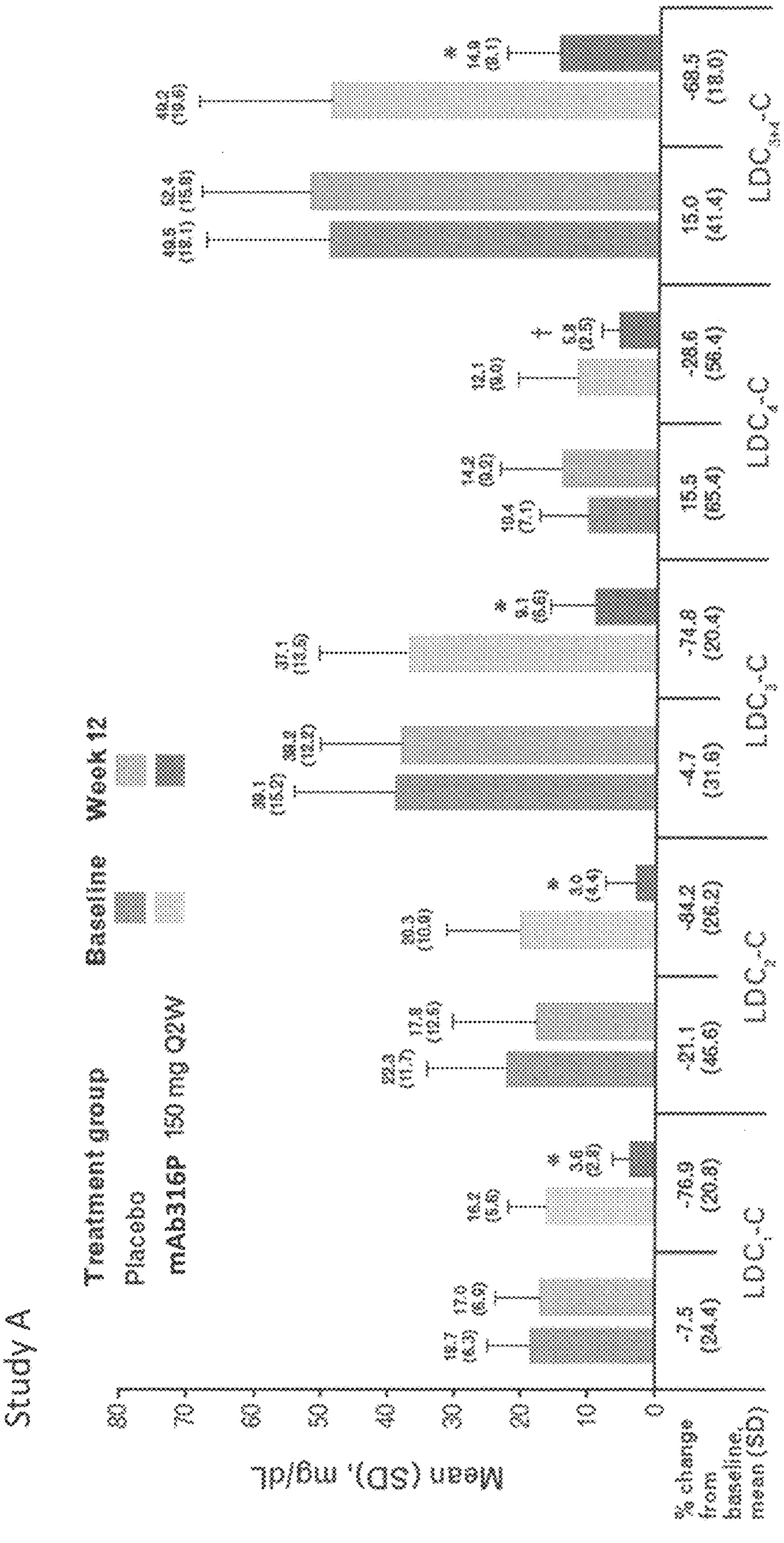
FIGS. 10-12 show the mean (SD) levels of cholesterol in LDL subfractions before and after treatment for placebo and mAb316P 150 mg Q2W in three different clinical studies (A, B, and C, as summarized in Table 1 herein).
Figure 11:
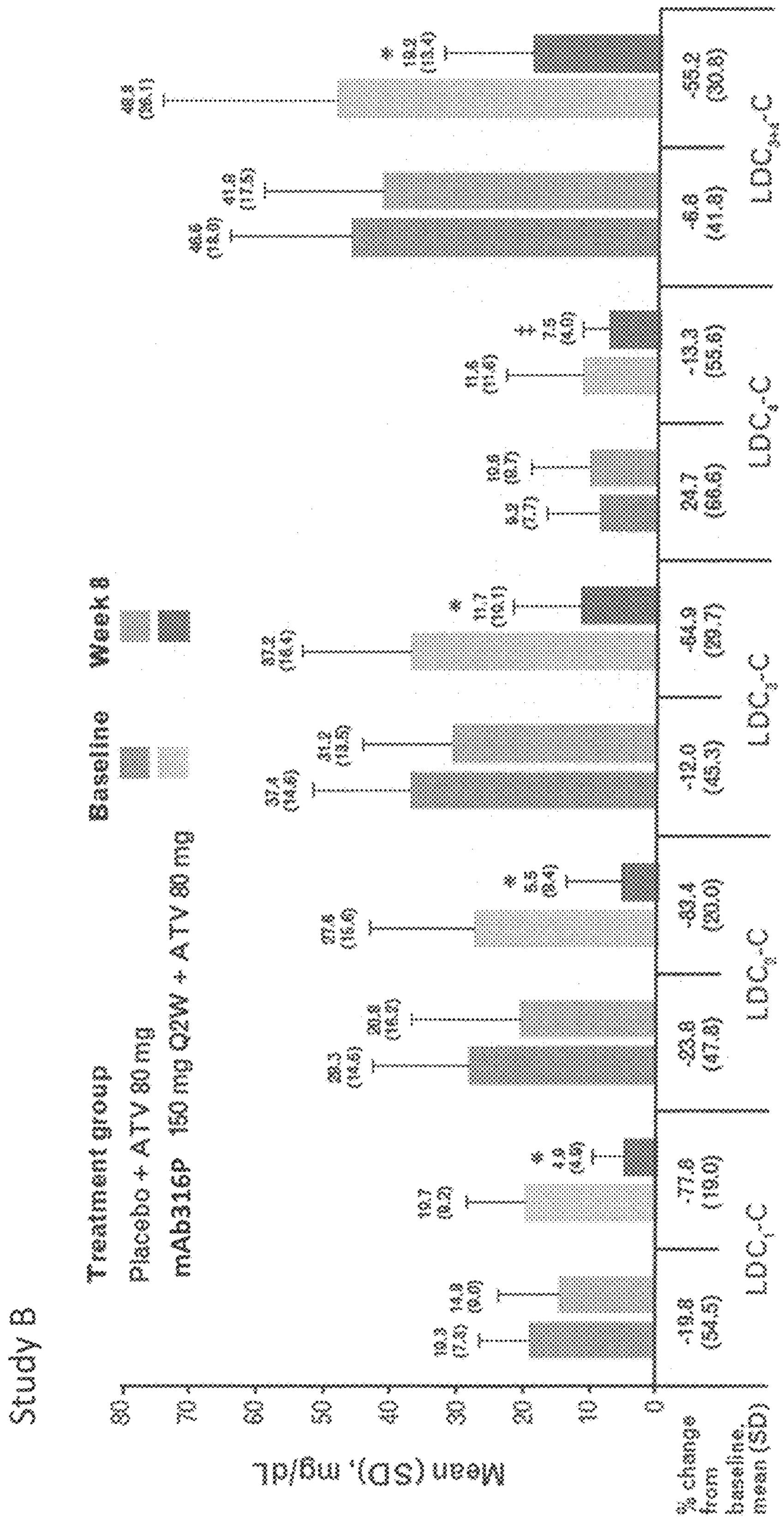
Figure 12:
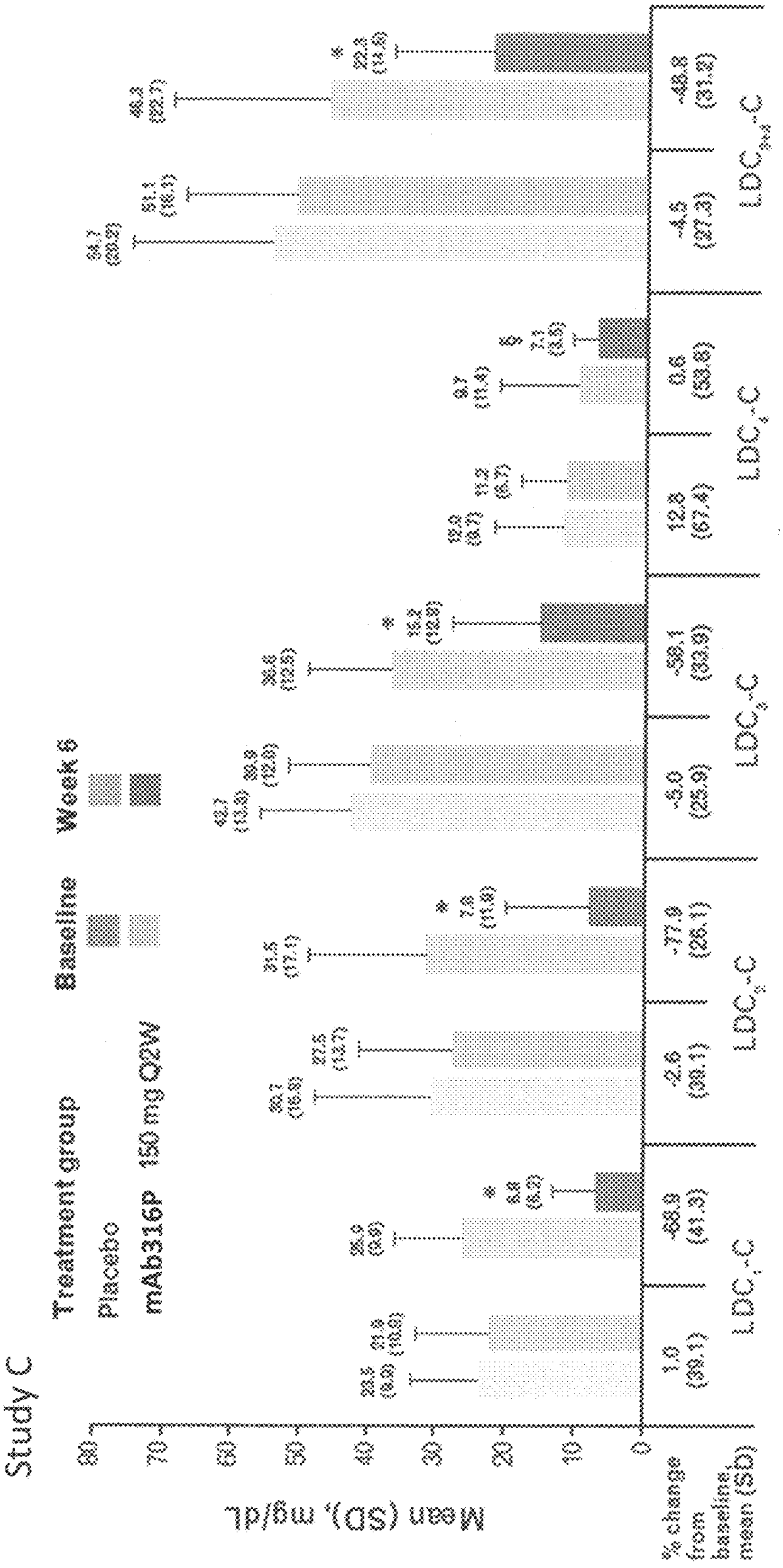

Significant reductions from baseline in cholesterol content of all LDL subfractions separable by VAP were observed in patients receiving mAb316P 150 mg Q2W in the 3 studies, vs. placebo. Results are summarized in Table 6 and FIGS. 10-12.

TABLE 6

| | Baseline (mg/dL) | Endpoint (mg/dL) | Percent Change | p-value |
|---|---|---|---|---|
| $LDL_1$ | 16.18 to 25.92 | 3.56 to 6.81 | −68.87 to −77.84 | <0.0001 |
| $LDL_2$ | 20.29 to 31.46 | 3.04 to 7.84 | −77.85 to −84.17 | <0.0001 |
| $LDL_{34}$ | 46.33 to 49.16 | 14.9 to 22.29 | −48.77 to −68.49 | <0.0001 |

This Example therefore illustrates that therapy with a monoclonal antibody directed against PCSK9 (mAb316P) significantly reduced cholesterol concentrations in LDL fractions separable by VAP. The previously demonstrated LDL-C reductions with mAb316P were confirmed across the spectrum of LDL-C sub-fractions.

Example 5: Effects of an Anti-PCSK9 Antibody on Lipoprotein Particle Concentrations Background The cholesterol content of low-density lipoprotein particles (LDL-P) and high-density lipoprotein particles (HDL-P) can vary greatly among individuals. For example, one individual may have larger, cholesterol-rich LDL-P, and another will have smaller, cholesterol-poor LDL-P. Therefore measurements of serum levels of low-density lipoprotein cholesterol (LDL-C) and high-density lipoprotein cholesterol (HDL-C) often do not correlate with circulating LDL-P and HDL-P number.

Epidemiological studies have demonstrated that atherosclerotic cardiovascular disease risk tracks with both LDL-C and LDL-P. However, in patient populations where these measures are discordant (e.g., patients with diabetes or metabolic syndrome), risk has been shown to track more consistently with LDL-P than LDL-C. Consequently, multiple expert panels and consensus statements have advocated the adjunctive use of LDL-P as a target of therapy in the management of high-risk patients.

Nuclear magnetic resonance (NMR) technology can accurately measure the number of circulating lipoprotein particles to identify patients with discordantly high LDL-P levels that require intensification of therapy.

The anti-PCSK9 antibody mAb316P, has been shown to reduce LDL-C by up to 72.4% in patients on stable doses of atorvastatin over 12 weeks with similar rates of adverse events between placebo and mAb316P-treatment groups. mAb316P reduced apolipoprotein B by up to 56% proportionally with the changes in LDL-C. The effect of mAb316P on lipoprotein particle numbers in hypercholesterolemic patients has heretofore not been reported.

The present Example sets forth an evaluation of the effects of mAb316P on the concentration and size of lipoprotein particles.

Methods

A sub-study of a randomized double-blind Phase II trial was carried out with respect to patients with LDL-C ≥100 mg/dL who received placebo (n=31) or mAb316P 150 mg administered subcutaneously (SC) every 2 weeks (Q2W) (n=28) on top of stable daily atorvastatin (10, 20 or 40 mg daily). Lipid and lipoprotein tests were performed using samples collected after a 12-hour overnight fast. Lipoprotein particle profiles were measured by NMR spectroscopy using the LipoProfile-3 algorithm at LipoScience, Inc. (Raleigh, N.C.). LDL-P and HDL-P subclasses were quantified from the amplitudes of their spectroscopically distinct lipid methyl group NMR signals, and weighted-average LDL and HDL sizes were derived from the sum of the diameter of each subclass multiplied by its relative mass percentage based on the amplitude of its methyl NMR signal.

Diameter range estimates for the subclasses were as follows:

VLDL-P: small VLDL-P=29 to 42 nm; medium VLDL-P=42 to 60 nm; large VLDL-P>60 nm;

LDL-P: small LDL-P=18 to 20.5 nm; large LDL-P=20.5 to 23 nm; intermediate-density lipoprotein particles (IDL-P)=23 to 29 nm;

HDL-P: small HDL-P=7.3 to 8.2 nm; medium HDL-P=8.2 to 9.4 nm; and large HDL-P=9.4 to 14 nm.

Total VLDL-P, LDL-P, and HDL-P equal the sum of the particle number concentrations of the VLDL, LDL, and HDL subclasses, respectively. Endpoints for the analysis were percentage change in the concentration of LDL-P, VLDL-P and HDL-P from baseline to Week 12.

Any variables that were not normally distributed were transformed for all statistical tests, but the untransformed variables are presented in the tables herein. Mean (standard deviation [SD]) are reported for continuous normally distributed variables, while median (interquartile range [IQR]) are reported for any non-normally distributed variables. Count and percentage are reported for categorical variables. To determine if the treatment group was significantly different than placebo, Fisher's exact tests were performed and the associated P-values are reported. To determine if each of the treatment groups were significantly different than placebo, t-tests were performed and the associated P-values are reported. To determine if there was a significant difference in percent change between baseline and Week 12 for the placebo compared to the treatment groups analysis of covariances were performed with the baseline value as a covariate.

Results

Table 7 shows lipoprotein particle concentrations before and after mAb316P 150 mg SC Q2W compared to placebo.

TABLE 7

Lipoprotein particle concentrations (nmol/L) for placebo (n = 31) and mAb316P 150 mg Q2W (n = 28).

| Mean (sd) or median (Q1:Q3) [proportion of total] | | Baseline | Week 12 | % change |
|---|---|---|---|---|
| | | PLACEBO | | |
| LDL | Total LDL | 1422.5 (321.3) | 1383.8 (327.9) | −1.0% |
| | Intermediate density lipoprotein | 110 (51:166.5) | 57 (24.5:144.5) | −15.0% |
| | Large LDL | 546.6 (205.3) | 431.8 (217.4) | −21.8% |
| | Small LDL | 755.3 (304.9) | 847.6 (375.1) | 17.8% |
| VLDL + chylomicron | Total VLDL + chylomicron | 61.9 (47.8:95.6) | 83.9 (45:102.2) | 33.4% |
| | Large VLDL + chylomicron | 3.5 (2.1:8.5) | 4.3 (1.8:9.4) | 14.3% |
| | Medium VLDL | 19.3 (13.1:33.9) | 33.1 (13.1:51.9) | 24.0% |
| | Small VLDL | 35.3 (28.2:47.8) | 37.3 (23.4:56.3) | 21.4% |
| HDL | Total HDL | 32.9 (6.4) | 33.2 (7.4) | 1.4% |
| | Large HDL | 3.8 (2.0) | 3.9 (2.2) | 6.99% |
| | Medium HDL | 9.2 (5.9:14.4) | 8 (5.4:10.2) | −13.9% |
| | Small HDL | 18.8 (5.3) | 21.3 (5.8) | 18.4% |
| | | mAb316P 150 mg Q2W | | |
| LDL | Total LDL | 1320 (304.0) | 475.4 (167.3)† | −63.3%† |
| | Intermediate density lipoprotein | 84.5 (33:115) | 37 (12:66)* | −52.8% |
| | Large LDL | 532.2 (212.9) | 152.4 (107.6)† | −71.3% |
| | Small LDL | 666.5 (333.8) | 279.9 (191.0)† | −54.0% |
| VLDL + chylomicron | Total VLDL + chylomicron | 71.5 (36.9:94.1) | 42.0 (30.5:54.1)† | −36.4%† |
| | Large VLDL + chylomicron | 3.6 (1.8:8.5) | 3.1 (1.7:6.9) | 5.37% |
| | Medium VLDL | 18.3 (10.7:50) | 14.4 (8.2:26.9)† | −38.92% |
| | Small VLDL | 35.7 (25:49.5) | 21.4 (19.9:26.7)* | −33.4% |
| HDL | Total HDL | 32.6 (6.3) | 36.1 (6.5)* | 11.2%* |
| | Large HDL | 4.8 (3.1) | 6.1 (3.5)* | 44.6% |

TABLE 7-continued

| Lipoprotein particle concentrations (nmol/L) for placebo (n = 31) and mAb316P 150 mg Q2W (n = 28). | | | |
|---|---|---|---|
| Mean (sd) or median (Q1:Q3) [proportion of total] | Baseline | Week 12 | % change |
| Medium HDL | 7.8 (5.6:10.7) | 9.8 (6.6:11.3) | 17.65% |
| Small HDL | 19.4 (4.1) | 20.0 (5.7)* | 2.8% |

*P < 0.05;
†P < 0.001 vs. placebo mAb316P reduced mean LDL-P by 63% vs 1% for placebo (P<0.0001) and median VLDL-P by 36% vs an increase of 33% for placebo (P<0.0001). HDL-P levels increased 11% for mAb316P vs 1% for placebo (P<0.05). Changes in all particle subclasses were directionally similar.

Conclusion mAb316P significantly reduced LDL-P and other lipoprotein particles in a manner similar to its previously reported effect on LDL-C and apolipoprotein B.

Example 6: Effects of an Anti-PCSK9 Antibody on Lipoprotein Subfractions as Determined by Ion Mobility Background mAb316P (also known as Alirocumab) has demonstrated significant reductions in low-density lipoprotein cholesterol (LDL-C) in Phase 2 clinical trials. LDL-C tracks closely with cardiovascular disease (CVD) risk and subfractions of LDL, defined by differences in particle size and density, have also been associated with varying degrees of CVD risk. Analysis of lipoprotein subfractions may provide further insight into CVD risk evaluation and the effects of lipid-lowering treatments seen in individual patients.

Methods

A Phase 2 randomized, double-blind, clinical trial was conducted in patients with hypercholesterolemia and LDL-C levels≥100 mg/dL, in which 31 patients received placebo and 27 patients received alirocumab 150 mg every 2 weeks (Q2W) via a 1-mL subcutaneous auto-injection in addition to stable atorvastatin (10-40 mg daily). In the present sub-study, lipoprotein subfractions were determined at baseline and at Week 12 using ion mobility.

Results

Changes in lipoprotein subfractions and lipid parameters from baseline to Week 12 are set forth in Tables 8A (placebo-treated) and 8B (mAb316P-treated).

TABLE 8A

| Placebo | | | |
|---|---|---|---|
| | Baseline | Week 12 | Percent Change |
| Lipoprotein subfractions | | | |
| VLDL + IDL + Total LDL | 1648.44 (453.5) | 1728.88 (434.58) | 8.25 |
| VLDL (large + intermediate + small) | 134.97 (109.01 to 152.85) | 140.48 (106.18 to 193.49) | 6.64 |
| IDL (IDL 1 + 2) | 314.28 (282.74 to 407.95) | 303.35 (277.99 to 376.17) | −3.3 |
| Total LDL | 1172.99 (362.85) | 1233.76 (331.13) | 8.8 |
| Large LDL (LDL 1 + 2a) | 448.23 (173.52) | 419.36 (160.98) | −0.26 |
| Medium LDL (LDL 2b) | 233.2 (105.34) | 228.92 (88.12) | 5.07 |
| Small LDL (LDL 3a) | 195.17 (85.53) | 225.98 (105.1) | 24.39 |
| Very Small LDL (LDL 4a + 4b + 4c + 3b) | 296.4 (91.75) | 359.49 (136.92) | 24.61 |
| HDL (HDL 2b; HDL3 + 2a) | 23532.48 (5392.57) | 24400.97 (5798.21) | 0.06 |
| Lipid parameters | | | |
| LDL-C, mg/dL | 130.2 (27.3) | 120.5 (27.0) | −5.1 |
| HDL-C, mg/dL | 49.0 (10.3) | 48.9 (13.2) | −1.0 |
| TG, mg/dL | 124.0 (92.0 to 187.5) | 127.0 (98.0 to 197.0) | 9.7 |
| Apo-B, mg/dL | 108.3 (19.3) | 109.2 (27.0) | 2.2 |
| Apo-A1, g/L | 1.4 (1.3 to 1.6) | 1.4 (1.3 to 1.7) | 0.0 |
| Lp(a), g/L | 0.2 (0.1 to 0.9) | 0.2 (0.07 to 0.85) | 0.0 |

TABLE 8B

| mAb316P 150 mg Q2W | Baseline | Week 12 | Percent Change (p-value) |
|---|---|---|---|
| Lipoprotein subfractions | | | |
| VLDL + IDL + Total LDL | 1542.82 (435.5) | 767.78 (212.39) | −48.68 (<0.0001) |
| VLDL (large + intermediate + small) | 138.17 (96.41 to 167.8) | 77.2 (51.81 to 95.8) | −51.37 (<0.0001) |
| IDL (IDL 1 + 2) | 309.64 (268.32 to 363.95) | 155.19 (134.05 to 194.5) | −52.29 (<0.0001) |
| Total LDL | 1078.28 (347.61) | 529.35 (171) | −49.84 (<0.0001) |
| Large LDL (LDL 1 + 2a) | 421.08 (130.03) | 152.66 (53.4) | −62.66 (<0.0001) |
| Medium LDL (LDL 2b) | 200.86 (91.4) | 78.67 (40.76) | −58.69 (<0.0001) |
| Small LDL (LDL 3a) | 172.02 (104.89) | 79.24 (38.36) | −48.56 (<0.0001) |
| Very Small LDL (LDL 4a + 4b + 4c + 3b) | 284.31 (101.87) | 218.77 (55.66) | −17.91 (<0.0001) |
| HDL (HDL 2b; HDL3 + 2a) | 23480.25 (5281.63) | 21888.87 (4515.15) | −0.05 (0.0339) |
| Lipid parameters | | | |
| LDL-C, mg/dL | 123.9 (26.7) | 34.2 (15.6) | −72.4 (<0.0001)* |
| HDL-C, mg/dL | 53.3 (16.1) | 55.1 (14.8) | 5.5 (0.570)‡ |
| TG, mg/dL | 140.5 (92.5 to 177.5) | 99.0 (79.0 to 139.0) | −18.9 (0.0006)‡ |
| Apo-B, mg/dL | 101.6 (26.6) | 44.1 (14.1) | −56.1 (<0.0001)‡ |
| Apo-A1, g/L | 1.5 (1.3 to 1.7) | 1.6 (1.4 to 1.7) | 1.4 (0.1524)‡ |
| Lp(a), g/L | 0.3 (0.1 to 0.6) | 0.1 (0.05 to 0.41) | −28.6 (<0.0001)‡ |

*Statistically significant p-value according to the hierarchical procedure.
‡P-values are not adjusted for multiplicity and are for descriptive purposes only.

Tables 8A and 8B illustrate changes in lipoprotein subfractions and lipid parameters in placebo and mAb316P 150 mg Q2W groups, respectively, from baseline to Week 12. Compared with placebo, mAb316P reduced very low-density lipoprotein (VLDL)+intermediate-density lipoprotein (IDL)+total LDL by 48.7% ($p<0.0001$), VLDL by 51.4% ($p<0.0001$), IDL by 52.3% ($p<0.0001$) and total LDL by 49.8% ($p<0.0001$); changes in other subfractions were directionally similar. No significant change was noted for HDL. There was a highly significant difference in percent change reduction in very small LDL versus the other LDL fractions ($p<0.0001$).

Conclusions

As determined by ion mobility, mAb316P significantly reduced LDL subfractions when added to stable atorvastatin therapy, similar to its previously reported effect on LDL-C.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method for reducing in a patient the serum concentration of IDL-C; the method comprising selecting a patient with elevated serum IDL-C, and administering to the patient a pharmaceutical composition comprising a PCSK9 inhibitor;

wherein the patient is otherwise healthy except for exhibiting elevated serum IDL-C; and wherein the PCSK9 inhibitor is an antibody or antigen-binding fragment of an antibody that specifically binds PCSK9 and comprises the heavy and light chain CDRs of a HCVR/LCVR amino acid sequence pair selected from the group consisting of SEQ ID Nos: 90/92 and 218/226.

2. The method of claim 1, wherein the serum IDL-C is reduced in the patient by at least about 50% to about 56% from baseline following administration of the pharmaceutical composition.

3. The method of claim 1, wherein the pharmaceutical composition comprises 20 mg to 200 mg of the PCSK9 inhibitor.

4. The method of claim 3, wherein the pharmaceutical composition comprises 75 mg or 150 mg of the PCSK9 inhibitor.

5. The method of claim 1, wherein the antibody or antigen-binding fragment thereof comprises heavy and light chain CDR amino acid sequences having SEQ ID NOs: 220, 222, 224, 228, 230 and 232.

6. The method of claim 5, wherein the antibody or antigen-binding fragment thereof comprises an HCVR having the amino acid sequence of SEQ ID NO:218 and an LCVR having the amino acid sequence of SEQ ID NO:226.

7. The method of claim 1, wherein the antibody or antigen-binding fragment thereof comprises heavy and light chain CDR amino acid sequences having SEQ ID NOs: 76, 78, 80, 84, 86 and 88.

8. The method of claim 7, wherein the antibody or antigen-binding fragment thereof comprises an HCVR having the amino acid sequence of SEQ ID NO:90 and an LCVR having the amino acid sequence of SEQ ID NO:92.

9. The method of claim 1, wherein the patient is on a therapeutic statin regimen at the time of or just prior to administration of the pharmaceutical composition.

10. The method of claim 9, wherein the therapeutic statin regimen comprises a statin selected from the group consisting of cerivastatin, atorvastatin, simvastatin, pitavastatin, rosuvastatin, fluvastatin, lovastatin and pravastatin.

11. The method of claim 10, wherein the statin is atorvastatin.

12. The method of claim 1, wherein the patient is not on a therapeutic statin regimen at the time of administration of the pharmaceutical composition.

* * * * *